(12) United States Patent
Petrakis

(10) Patent No.: US 8,172,458 B2
(45) Date of Patent: May 8, 2012

(54) TEMPERATURE RESPONSIVE SYSTEMS

(76) Inventor: Dennis N. Petrakis, Palo Alto, CA (US)

( * ) Notice: Subject to any disclaimer, the term of this patent is extended or adjusted under 35 U.S.C. 154(b) by 325 days.

(21) Appl. No.: 12/285,128

(22) Filed: Sep. 29, 2008

(65) Prior Publication Data

US 2009/0041085 A1 Feb. 12, 2009

Related U.S. Application Data

(60) Division of application No. 10/549,705, filed on Jun. 23, 2006, now Pat. No. 7,445,616, which is a continuation-in-part of application No. 09/815,643, filed on Mar. 23, 2001, now Pat. No. 6,682,521.

(30) Foreign Application Priority Data

Mar. 17, 2004 (WO) ................ PCT/US2004/008338

(51) Int. Cl.
*G01K 1/00* (2006.01)
*G01K 1/24* (2006.01)

(52) U.S. Cl. ......... 374/101; 374/187; 374/105; 374/205

(58) Field of Classification Search .............. 374/4, 5, 374/55, 57, 100, 187, 205–207, 101–109, 374/43, 44, 45, 46, 47, 48, 49, 50, 52, 160, 374/141; 222/54; 429/62; 403/381; 600/118; 60/527, 528, 529; 604/890.1, 95.01, 95.03, 604/95.04, 510, 528
See application file for complete search history.

(56) References Cited

U.S. PATENT DOCUMENTS

| | | | |
|---|---|---|---|
| 2,580,414 A | 1/1952 | Duffey | 424/408 |
| 2,601,440 A | 6/1952 | Kerrigan | |
| 3,659,600 A | 5/1972 | Merrill | |
| 3,797,492 A | 3/1974 | Place | 604/890.1 |
| 3,848,389 A * | 11/1974 | Gapp et al. | 411/504 |
| 4,114,559 A * | 9/1978 | Rogen | 116/216 |
| 4,239,040 A | 12/1980 | Hosoya et al. | 604/135 |
| 4,439,197 A | 3/1984 | Honda et al. | |

(Continued)

FOREIGN PATENT DOCUMENTS

FR 2671400 A1 * 7/1992

(Continued)

*Primary Examiner* — Gail Verbitsky
(74) *Attorney, Agent, or Firm* — Richard C. Litman

(57) ABSTRACT

A shape memory material activated device of the present invention uses a shape memory material activator to create a path through a shell wall of the device. The path through the shell wall may release a substance contained in the shell or allow a substance to enter the shell. The path may be created by fracturing, puncturing, exploding, imploding, peeling, tearing, stretching, separating, debonding, abrading or otherwise opening the shell and, may be permanent or reversible. The substance may be released in one location while the device is stationary or along a path while it is traveling, self-powered by the shape memory material activator. In addition, the substance may be delivered to an object upon contact with its surface. The self powering abilities allow these devices to be used as substance delivery devices as well as actuators, transporters, and energy conversion systems with modular characteristics and growth potential. The devices may be armed, prior to the beginning of their service life, to be placed in a state of readiness to release their substances once the path is created. Prior to arming they may be maintained at any temperature, incapable of releasing their substances. The devices according to the present invention may be used as temperature sensors or warning devices, drug delivery devices, and the like.

3 Claims, 62 Drawing Sheets

U.S. PATENT DOCUMENTS

| | | | |
|---|---|---|---|
| 4,448,147 A * | 5/1984 | Dewaegheneire | 116/216 |
| 4,481,952 A | 11/1984 | Pawelec | 600/582 |
| 4,507,115 A | 3/1985 | Kambara et al. | 604/135 |
| 4,522,147 A * | 6/1985 | Kroll et al. | 116/216 |
| 4,627,850 A | 12/1986 | Deters et al. | |
| 4,664,056 A | 5/1987 | Jehanno | |
| 4,706,153 A * | 11/1987 | Sainomoto et al. | 361/42 |
| 4,770,105 A | 9/1988 | Takagi et al. | 104/138.2 |
| 4,829,843 A * | 5/1989 | Suzuki | 74/470 |
| 4,918,919 A * | 4/1990 | McCoy et al. | 60/528 |
| 4,998,827 A * | 3/1991 | Holzer | 374/160 |
| 5,119,555 A | 6/1992 | Johnson | |
| 5,120,175 A * | 6/1992 | Arbegast et al. | 411/501 |
| 5,167,626 A | 12/1992 | Casper et al. | |
| 5,170,801 A | 12/1992 | Casper et al. | 600/582 |
| 5,176,275 A | 1/1993 | Bowie | |
| 5,196,002 A | 3/1993 | Hanover et al. | |
| 5,207,666 A | 5/1993 | Idriss et al. | |
| 5,217,449 A | 6/1993 | Yuda et al. | 604/890.1 |
| 5,245,738 A | 9/1993 | Johnson | |
| 5,316,015 A | 5/1994 | Sinaiko | 600/582 |
| 5,335,994 A * | 8/1994 | Weynant nee Girones | 374/205 |
| 5,368,905 A * | 11/1994 | Ohno | 428/34.1 |
| 5,405,614 A | 4/1995 | D'Angelo et al. | |
| 5,626,581 A | 5/1997 | Staehlin et al. | |
| 5,662,587 A | 9/1997 | Grundfest et al. | |
| 5,735,607 A * | 4/1998 | Shahinpoor et al. | 374/187 |
| 5,771,742 A | 6/1998 | Bokaie et al. | |
| 5,821,664 A | 10/1998 | Shahinpoor | |
| 5,843,700 A | 12/1998 | Kerrod et al. | |
| 5,850,837 A * | 12/1998 | Shiroyama et al. | 128/892 |
| 6,083,639 A * | 7/2000 | McHugh et al. | 429/62 |
| 6,200,317 B1 | 3/2001 | Aalsma et al. | |
| 6,230,649 B1 * | 5/2001 | Yeung | 116/102 |
| 6,237,590 B1 | 5/2001 | Leedom et al. | 128/203.15 |
| 6,318,641 B1 * | 11/2001 | Knebel et al. | 239/5 |
| 6,350,537 B1 * | 2/2002 | Pedicni | 429/27 |
| 6,375,638 B2 | 4/2002 | Nason et al. | |
| 6,425,343 B1 | 7/2002 | Akers et al. | |
| 6,436,078 B1 | 8/2002 | Svedman et al. | |
| 6,561,121 B1 * | 5/2003 | Rose | 116/216 |
| 6,574,958 B1 * | 6/2003 | MacGregor | 60/527 |
| 6,612,739 B2 | 9/2003 | Shahinpoor | |
| 6,648,814 B2 | 11/2003 | Kim et al. | |
| 6,656,158 B2 | 12/2003 | Mahoney et al. | |
| 6,656,159 B2 | 12/2003 | Flaherty | |
| 6,682,521 B2 | 1/2004 | Petrakis | 604/890.1 |
| 6,702,734 B2 | 3/2004 | Kim et al. | |
| 6,723,072 B2 | 4/2004 | Flaherty et al. | |
| 6,837,620 B2 | 1/2005 | Shahinpoor | |
| 6,848,390 B2 * | 2/2005 | Akers et al. | 116/216 |
| 6,851,260 B2 * | 2/2005 | Mernøe | 60/527 |
| 6,893,155 B2 * | 5/2005 | Kaiser et al. | 374/187 |
| 6,911,004 B2 | 6/2005 | Kim et al. | |
| 6,928,812 B2 | 8/2005 | Donakowski et al. | |
| 6,945,693 B2 * | 9/2005 | Kaiser et al. | 374/187 |
| 6,953,455 B2 | 10/2005 | Cho et al. | |
| 6,960,192 B1 | 11/2005 | Flaherty et al. | |
| 7,018,360 B2 | 3/2006 | Flaherty et al. | |
| 7,048,730 B2 | 5/2006 | Petrakis | 604/890.1 |
| 7,119,564 B2 * | 10/2006 | Martens et al. | 324/754 |
| 7,204,199 B2 * | 4/2007 | Ribi et al. | 116/218 |
| 7,226,278 B2 * | 6/2007 | Nason et al. | 417/410.1 |
| 7,316,753 B2 * | 1/2008 | Jung et al. | 148/402 |
| 7,367,186 B2 * | 5/2008 | Clements | 60/527 |
| 7,372,348 B2 * | 5/2008 | Xu et al. | 335/78 |
| 7,393,595 B2 * | 7/2008 | Chandrasekaran et al. | 428/614 |
| 7,631,915 B2 * | 12/2009 | Browne et al. | 296/1.02 |
| 2002/0111535 A1 | 8/2002 | Kim et al. | 600/158 |
| 2003/0065250 A1 | 4/2003 | Chiel et al. | |
| 2003/0128491 A1 | 7/2003 | Ruiz et al. | |
| 2003/0188677 A1 * | 10/2003 | Akers et al. | 116/216 |
| 2003/0216622 A1 | 11/2003 | Meron et al. | |
| 2004/0024382 A1 | 2/2004 | Cho et al. | 604/891.1 |
| 2004/0261411 A1 * | 12/2004 | MacGregor | 60/527 |
| 2005/0055014 A1 | 3/2005 | Coppeta et al. | |
| 2005/0105587 A1 | 5/2005 | Shahinpoor | |
| 2005/0160858 A1 | 7/2005 | Mernoe | |
| 2005/0186273 A1 | 8/2005 | Yum et al. | |
| 2005/0192561 A1 | 9/2005 | Mernoe | |
| 2005/0235732 A1 | 10/2005 | Rush | |
| 2008/0051635 A1 | 2/2008 | Tanaka et al. | 600/160 |
| 2008/0086113 A1 | 4/2008 | Tenney et al. | 604/892.1 |
| 2009/0120106 A1 * | 5/2009 | Chin | 62/49.1 |
| 2010/0208768 A1 * | 8/2010 | Lakner et al. | 374/206 |

FOREIGN PATENT DOCUMENTS

| | | |
|---|---|---|
| JP | 58-135808 | 10/1983 |
| JP | 58-194809 | 11/1983 |
| JP | 60-209-673 | 10/1985 |
| JP | 62-212-877 | 6/1987 |
| JP | 63314115 A | 12/1988 |
| JP | 1080775 | 3/1989 |
| JP | 01320477 A | 12/1989 |
| JP | 02244528 A * | 9/1990 |
| JP | 3100376 | 4/1991 |
| JP | 05212093 A | 8/1993 |
| JP | 5221468 | 8/1993 |
| JP | 5221469 | 8/1993 |
| JP | 08310562 A | 11/1996 |
| JP | 2004257274 | 9/2004 |
| JP | 2004278495 | 10/2004 |
| JP | 2007190361 A | 8/2007 |
| WO | WO 9417379 A1 * | 8/1994 |

* cited by examiner

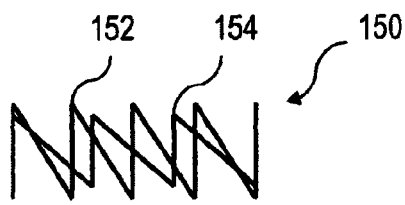
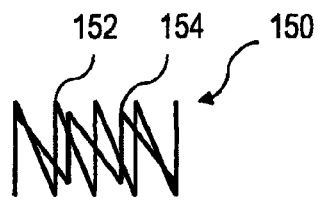
Fig. 20        Fig. 21
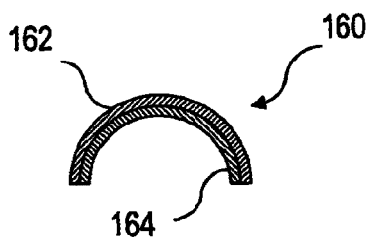
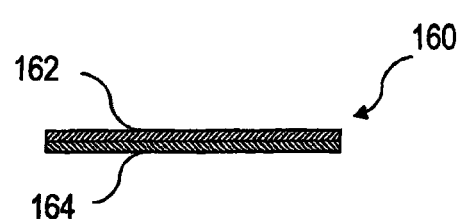
Fig. 22        Fig. 23
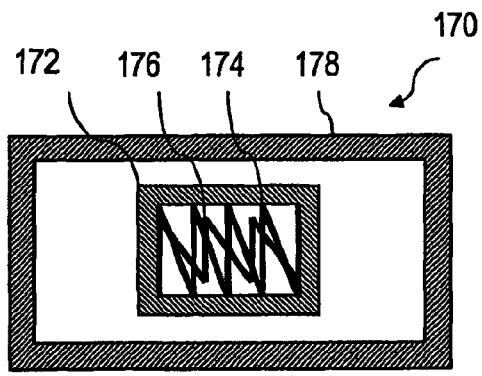
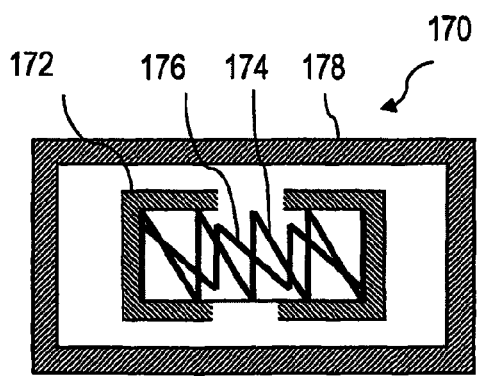
Fig. 24        Fig. 25

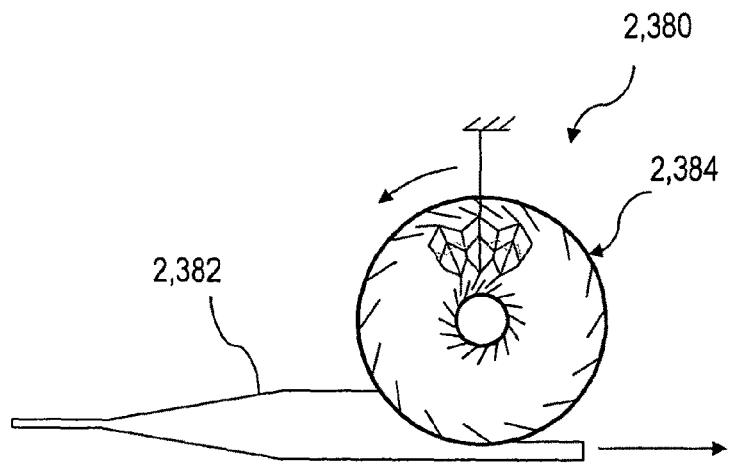
Fig. 136
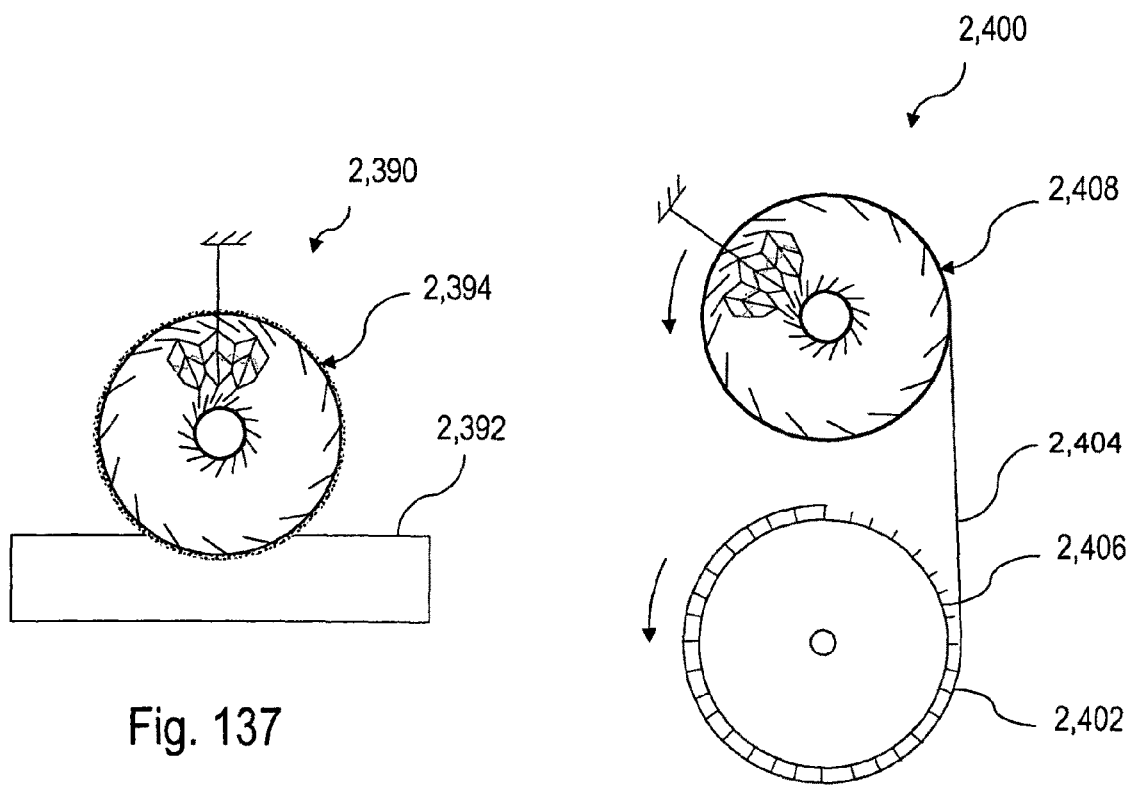
Fig. 137
Fig. 138

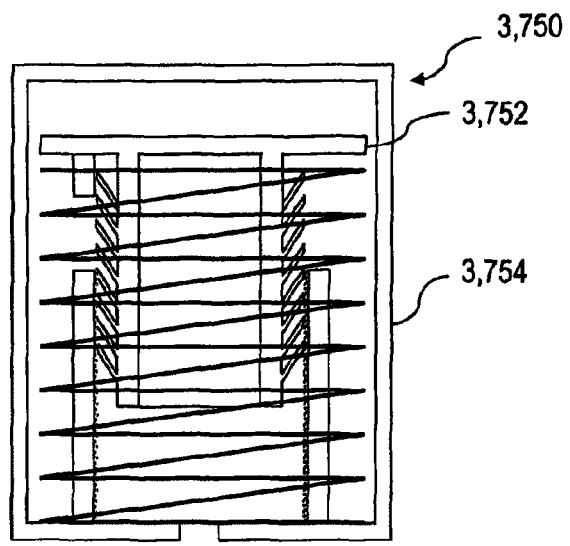
Fig. 189
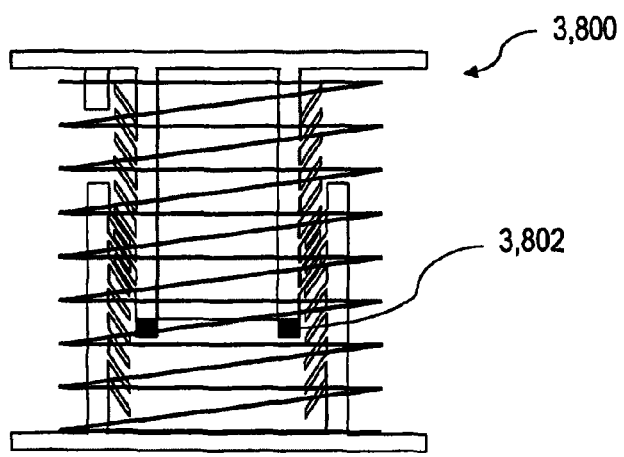
Fig. 190
    
Fig. 191　　Fig. 192　　Fig. 193　　Fig. 194　　Fig. 195

$A_s$: Austenitic Start, Effective
$A_f$: Austenitic Finish, Effective
$A_1$: Austenitic Start, Actual
$A_2$: Austenitic Finish, Actual
$A_x$: Temperature between $A_s$ and $A_f$
$M_s$: Martensitic Start, Effective
$M_f$: Martensitic Finish, Effective
$M_1$: Martensitic Start, Actual
$M_2$: Martensitic Finish, Actual
$M_x$: Temperature between $M_s$ and $M_f$.

TEMPERATURE RESPONSIVE SYSTEMS

CROSS REFERENCE TO RELATED APPLICATIONS

This application is a division of Ser. No. 10/549,705, filed Jun. 23, 2006, now U.S. Pat. No. 7,445,616 which is a continuation-in-part of application Ser. No. 09/815,643, entitled "Temperature Activated Systems", filed on Mar. 23, 2001, and issued on Jan. 27, 2004 as U.S. Pat. No. 6,682,521. This application also claims priority to PCT/US2004/008338, filed Mar. 17, 2004, which claims priority to U.S. Provisional Patent Application Ser. Nos. 60/454,624, entitled "Arming of Thermally Activated Systems", filed on Mar. 17, 2003; 60/479,481, entitled "Pro-Active Systems", filed on Jun. 19, 2003; 60/489,428, entitled "Mobile Systems", filed on Jul. 23, 2003; and 60/408,809, entitled "Conversion Systems", filed on Oct. 2, 2003, all of which are incorporated by reference in their entirety.

FIELD OF THE INVENTION

The invention relates to shape memory material activated devices, and more particularly, the invention relates to shape memory material activated systems, such as, temperature sensors, drug delivery systems, self-powered devices, energy conversion systems, and the like, which employ a shape memory material activator for self-powering and to create a path through a shell.

BRIEF DESCRIPTION OF THE RELATED ART

Temperature warning devices are used as safety devices for products such as pharmaceuticals, foods, and beverages that are subject to loss of potency or strength, chemical alteration or degradation, spoilage, poisoning, and taste or flavor alteration if they are exposed to high temperature or thawed from a frozen condition. Typically, all products have a restricted temperature range outside of which the product begins to change. Many different types of warning devices exist which warn the consumer if the product has reached or exceed its safe temperature limits. Examples of temperature warning devices are described in U.S. Pat. Nos. 5,735,607; 5,531,180; 5,460,117; 5,335,994; and 4,664,056.

Drug delivery devices, such as transdermal patches or implantable drug delivery systems, are available for delivery of drugs to a patient. These drug delivery devices may be manually activated prior to use, such as by the removal of a peelable liner on a transdermal patch. However, it would be desirable to provide on demand activation of a drug delivery device by use of a shape memory material activator.

It would also be desirable to provide a simple and reliable shape memory activated device for use in a variety of applications. Some of these applications may require release of a substance by a mobile, self powered device, mass delivery of a substance over large areas, and ability to maintain the device at any temperature prior to its usage.

SUMMARY OF THE INVENTION

The present invention relates to the creation of a path through a shell wall with the aid of a shape memory material. The path through the shell wall may release a substance contained in the shell or allow a substance to enter the shell. The path may be created while the shell is stationary or self-propelling. The substance may pass through the path instantaneously or over a temperature interval at a specific location or along a course. The shape memory material may stay dormant, unable to create a path at any temperature, until arming takes place. The devices according to the present invention may be used as substance delivery devices, temperature sensors or warning devices, drug delivery devices, actuators, energy conversion systems and the like. The path creation is accomplished by the shape memory material by several means such as fracturing, exploding, imploding, puncturing, peeling, tearing, shearing, rupturing, splitting, separating, abrading, squeezing, debonding etc. the shell. The method depends on the type of shell and on how the shape memory material is utilized.

One aspect of the present invention relates to a temperature warning device, drug delivery device, or other device having a shell containing a first substance and an enclosure containing a second substance. Mixing of the substances is achieved by activation of a shape memory material activator. The shape memory material has been deformed in the martensitic state and its $A_s$ to $A_f$ temperature range includes the predetermined temperature which is considered to be the maximum safe temperature of the product. For the temperature warning device, the enclosure is made of either a transparent or opaque material with a transparent window. Once the predetermined temperature has been attained, the shape memory material recovers its shape and in the process applies a stress (tensile, compressive, shear, torsion, or a combination) that results in the creation of a path for the two substances to come in contact. The color of the enclosure fluid changes to indicate this effect and to provide the temperature warning through the transparent window.

In accordance with one aspect of the present invention, a temperature sensor includes a shell containing a substance capable of providing an indication upon release from the shell, and a shape memory material activator for creating a path through the shell to release the substance from the shell in response to exposure to a temperature which is above a maximum or below a minimum safe temperature. The indication may stimulate one or more senses.

In accordance with an additional aspect of the present invention, a shape memory material activated device for opening a shell containing a substance, the device includes a shell containing a substance, and a shape memory material activator configured to create a path through the shell once the shape memory material attains a predetermined temperature or while it changes temperature within a predefined temperature range. The path creation may be repeatable with temperature cycling of the shape memory material. Multiple paths may be created in a plurality of shells, simultaneously or sequentially with changing temperature of the shape memory material. A plurality of device may be grouped together to form a system to collectively produce a combined effect.

In accordance with a further aspect of the invention, a drug delivery system includes a shell containing a drug, and a shape memory material activator for creating a path to deliver the drug from the shell to a patient when a predetermined temperature of the shape memory material activator is achieved.

In accordance with yet a further aspect of the invention, a self-propelled substance delivery device includes a shape memory material and a shell to deliver the substance along its path. Besides delivering a substance while traveling, the self propelled device is capable of traveling to a specific location to create a path and deliver the substance. In addition, the self-propelled device may be utilized as an actuator to perform tasks other than delivering a substance.

In accordance with yet another further aspect of the invention, an energy conversion system comprises a plurality of shape memory material activators utilized to convert thermal energy to mechanical energy in the form of linear or rotary motion. The mechanical energy may be used to create a path through one or more shells or to actuate other devices.

In accordance with a further more aspect of the invention, a shape memory material activated device comprises a shape memory material activator configured to be armed through transformation form a dormant state, incapable of responding to any temperature, to an active state of readiness, capable of responding to a predetermined temperature. Once armed, it may be utilized to create a path through a shell or to actuate other devices once the shape memory material attains a predetermined temperature.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 20 is a schematic side view of a shape memory material coil spring coupled with a bias coil spring;

FIG. 21 is a schematic side view of the shape memory material coil spring coupled with the bias coil spring of FIG. 20 after shape recovery;

FIG. 22 is a schematic side view of a shape memory material leaf spring coupled with a bias leaf spring;

FIG. 23 is a schematic side view of the shape memory material leaf spring coupled with the bias leaf spring of FIG. 22 after shape recovery;

FIG. 24 is a schematic side view of a shape memory material activated device with an internal shape memory material spring and an internal bias spring;

FIG. 25 is a schematic side view of the shape memory material activated device of FIG. 24 after activation;

FIG. 136 is a schematic side view of a shape memory material activated rolling type release device;

FIG. 137 is a schematic side view of a shape memory material activated grinding type release device;

FIG. 138 is a schematic side view of shape memory material activated thermally driven track with a reel of peelable shells;

FIG. 142 is a schematic side view of two counter-rotating circular thermally driven track devices connected with a belt and a lever attached to it;

FIG. 143 is a schematic side view of a planar power distribution energy conversion system;

FIG. 144 is a perspective view of a three dimensional power concentration energy conversion system;

FIGS. 145 and 146 are schematic side views of a self cooling thermally powered device with two cooling reservoirs, in the contacted and expanded positions, respectively;

FIG. 147 is a schematic side view of a self cooling thermally powered device without valves;

FIG. 148 is a schematic side view of a self cooling thermally powered device in the vertical orientation with a single cooling reservoir;

FIGS. 149, 150 and 151 are schematic side views of an arming device, armed by pushing two ends together, in the unarmed, armed, and path creation positions, respectively;

FIG. 152 is a schematic side view of an arming device, armed by pushing two ends together, containing multiple shells;

FIG. 153 is a schematic side view of an arming device, armed by pushing two ends together, containing multiple peelable shells;

FIG. 154 is a schematic side view of an arming device, armed by pushing two ends together, configured with a witness window;

FIGS. 155 and 156 are schematic side views of an arming device, armed by pulling two ends apart, in the unarmed and the path creation position, respectively;

FIG. 157 is a schematic side view of an arming device, armed by rotation, in the unarmed position;

Figure 158:
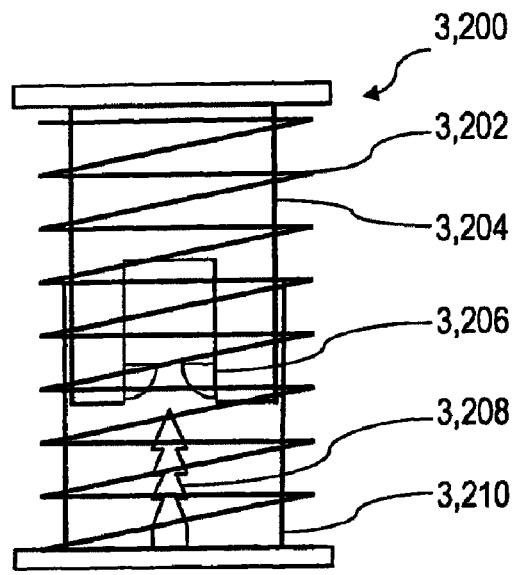
Figure 159:
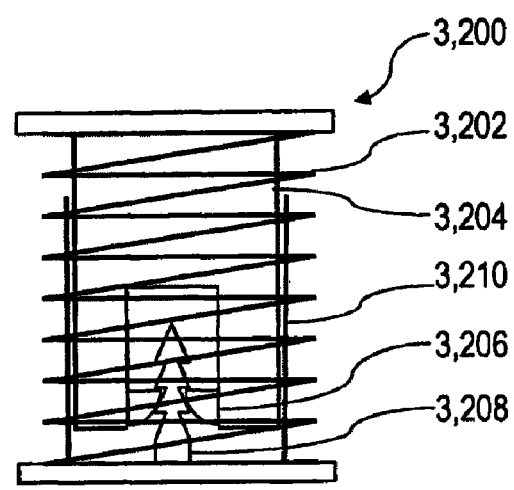
Figure 160:
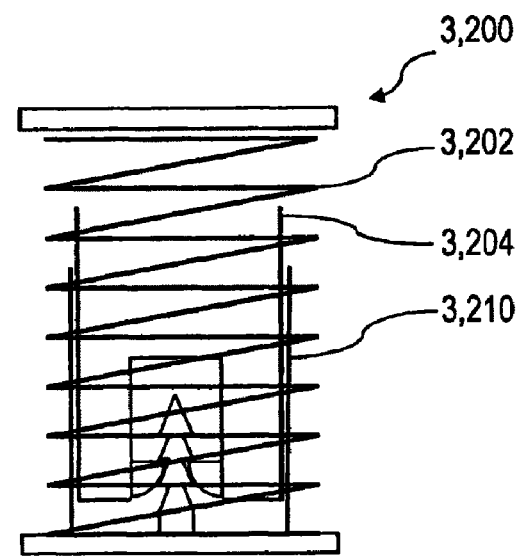
Figure 161:
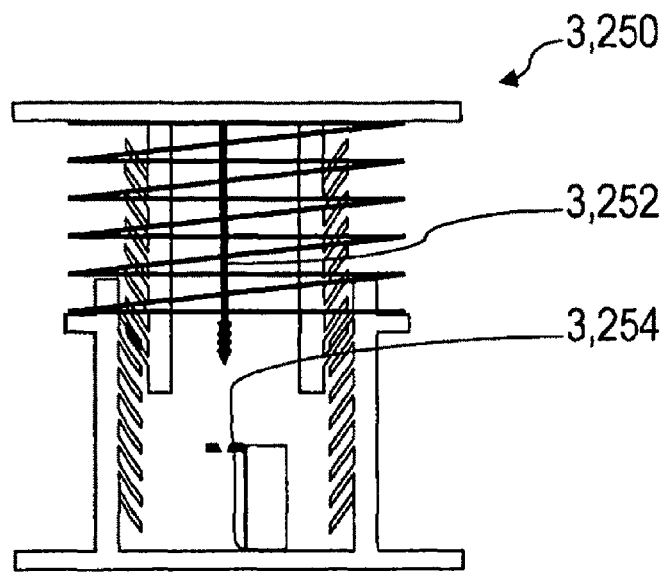
Figure 162:
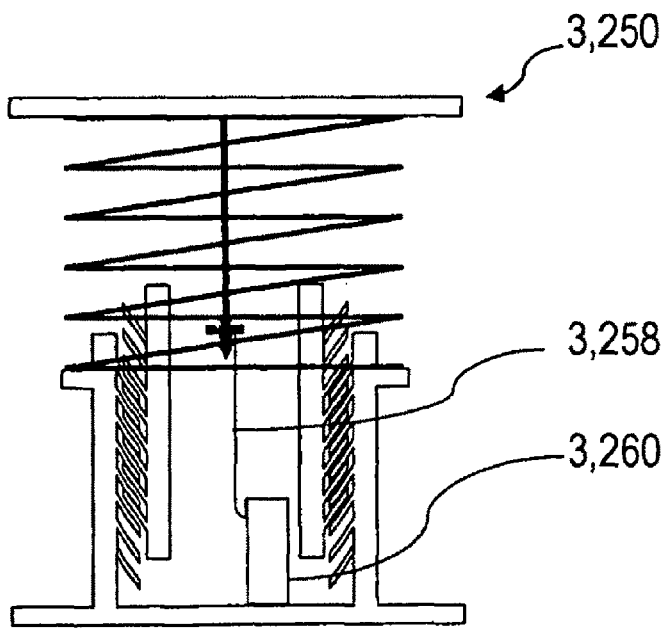
Figure 163:
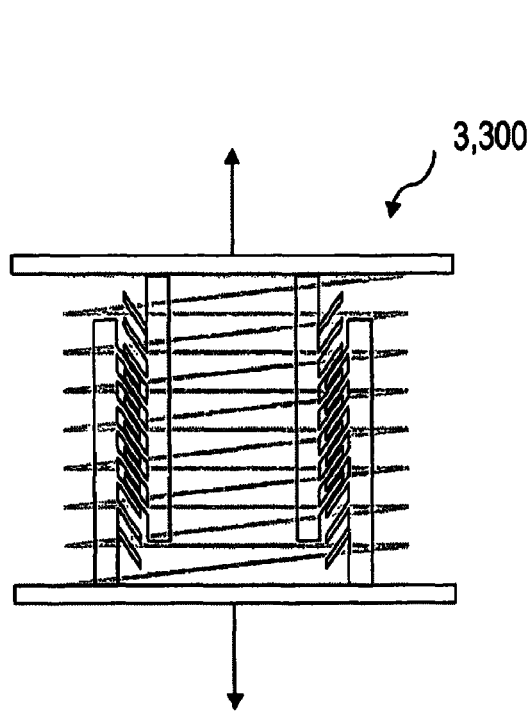
Figure 164:
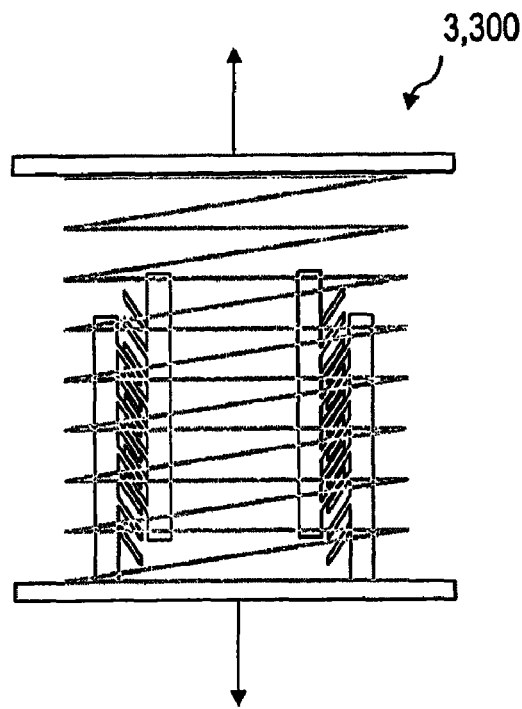
Figure 165:
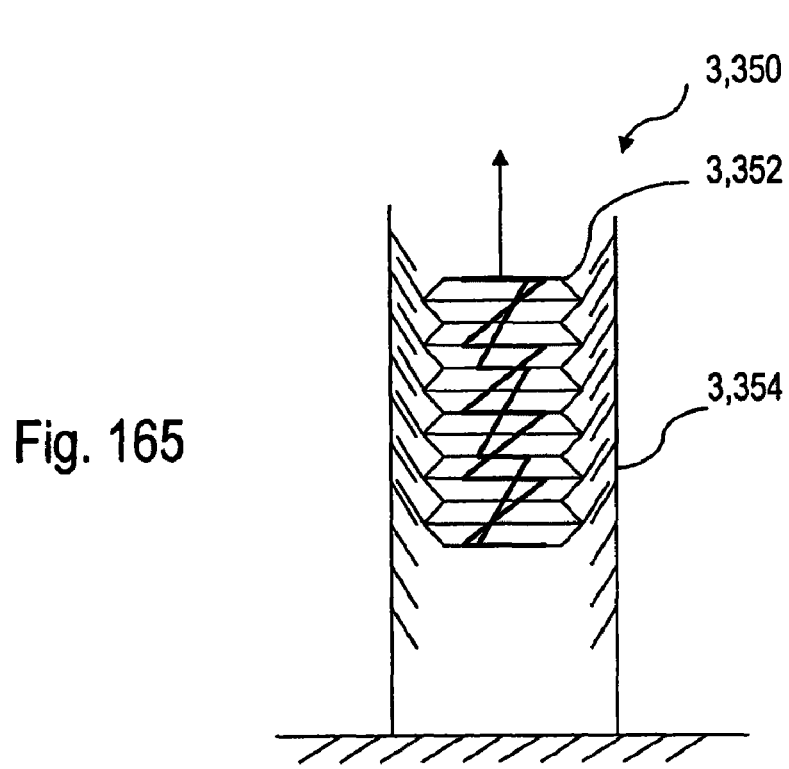
Figure 166:
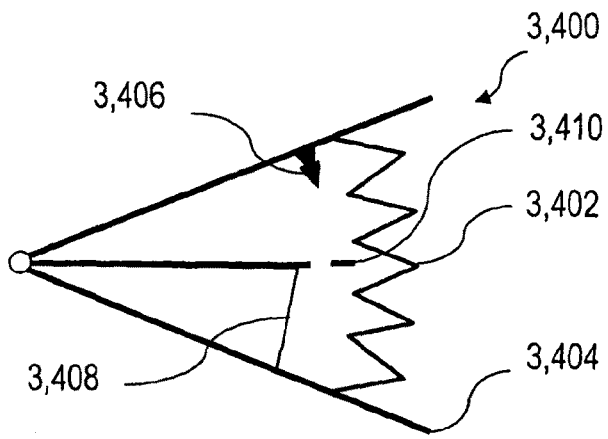
Figure 167:
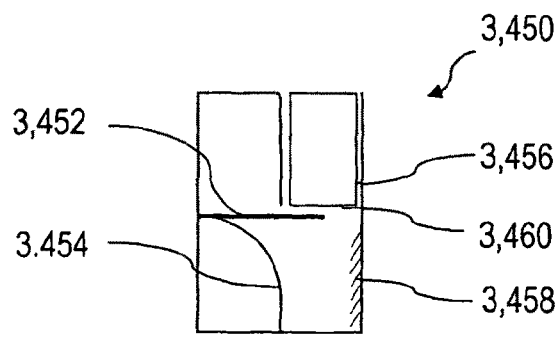
Figure 168:
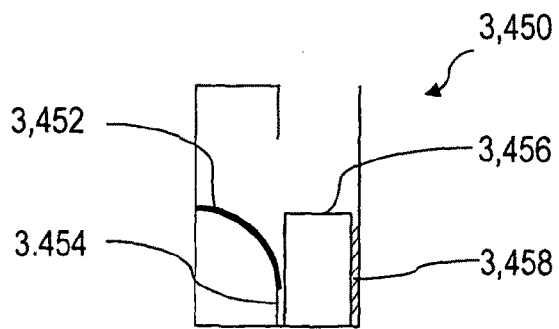
Figure 169:
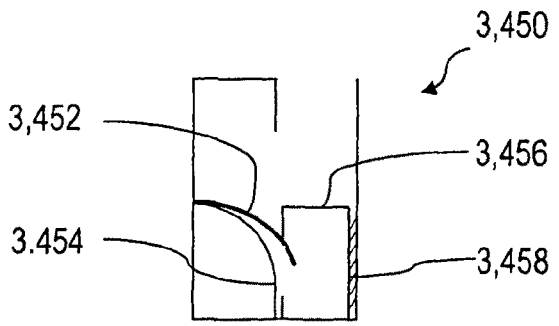
Figure 170:
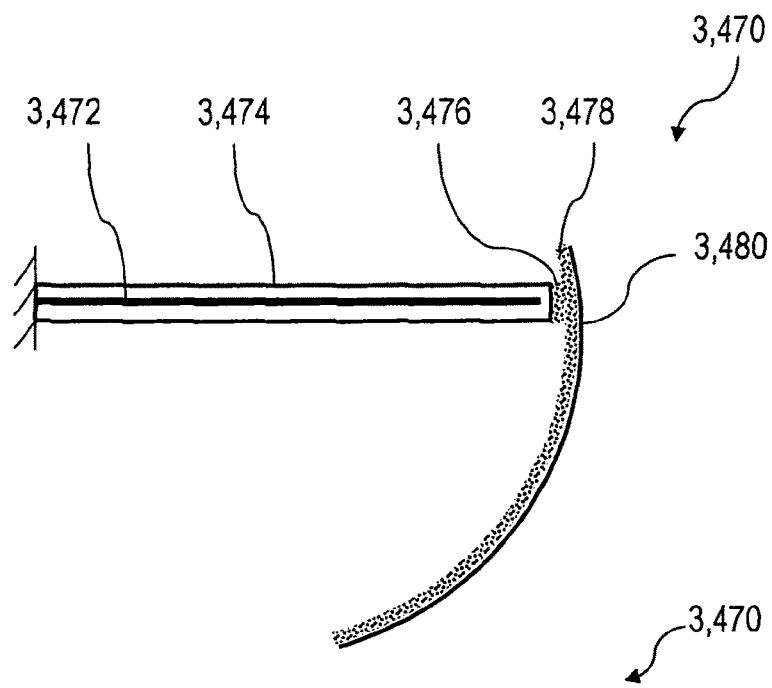
Figure 171:
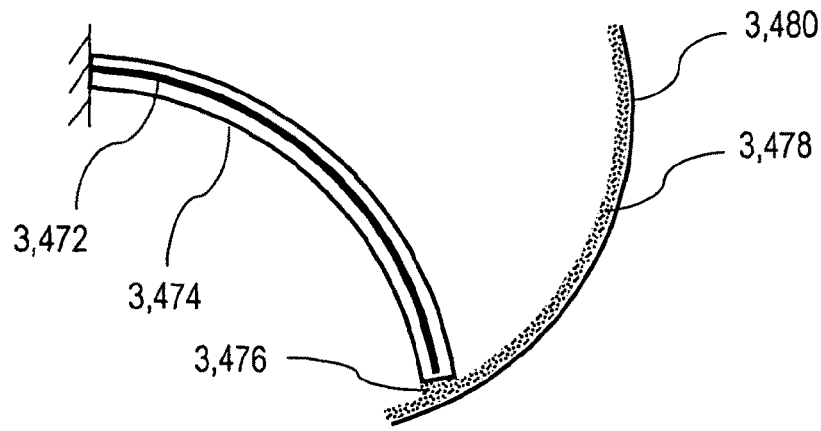
Figure 172:
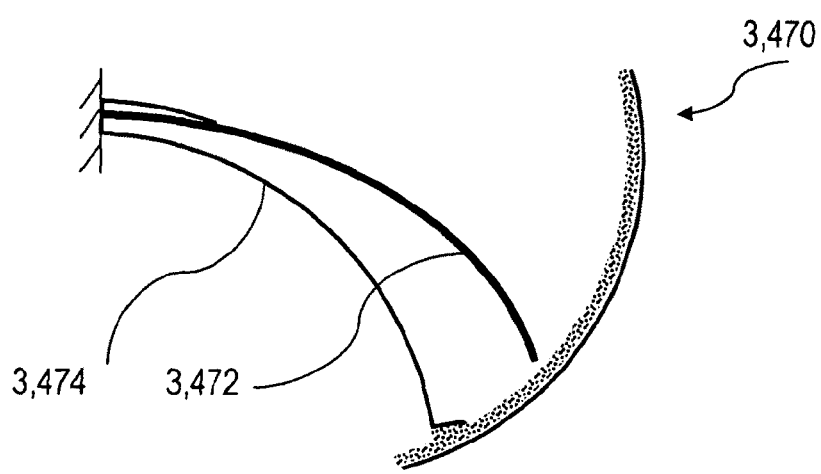
Figure 173:
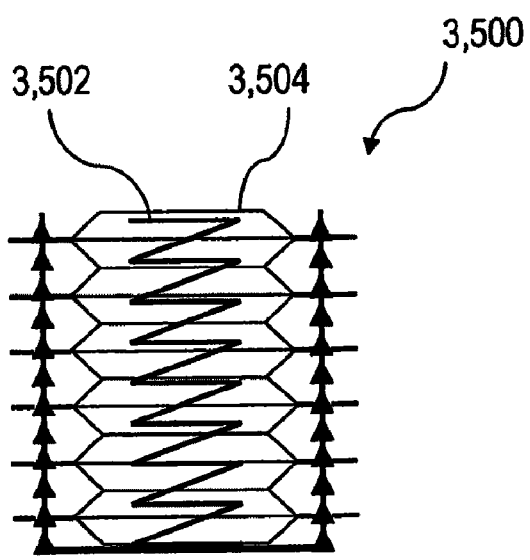
Figure 174:
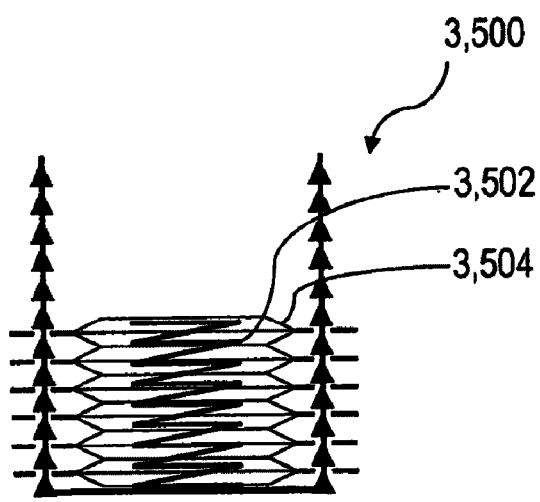
Figure 175:
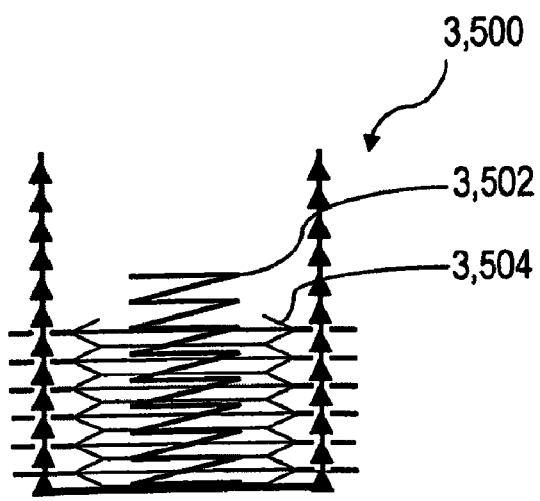
Figure 176:
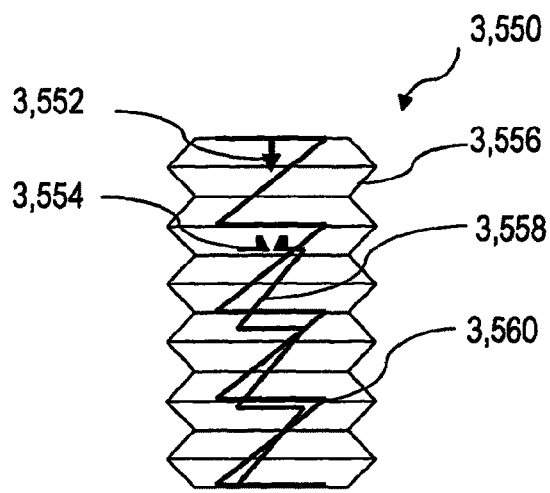
Figure 177:
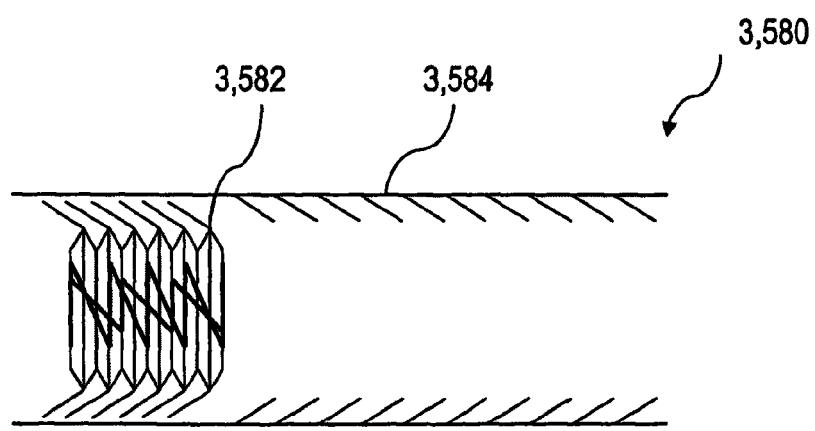
Figure 178:
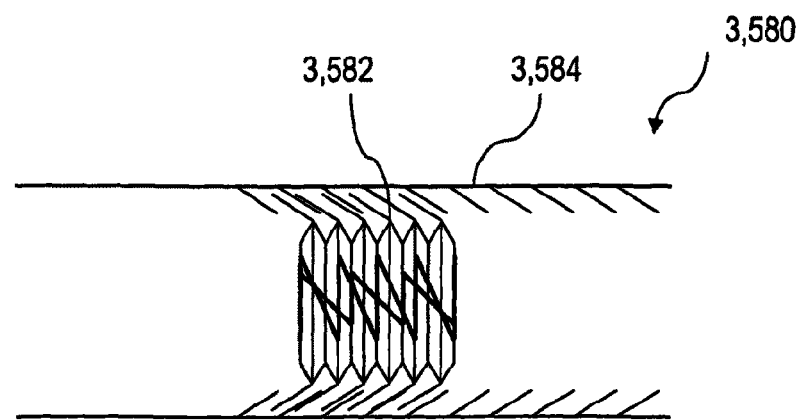
Figure 179:
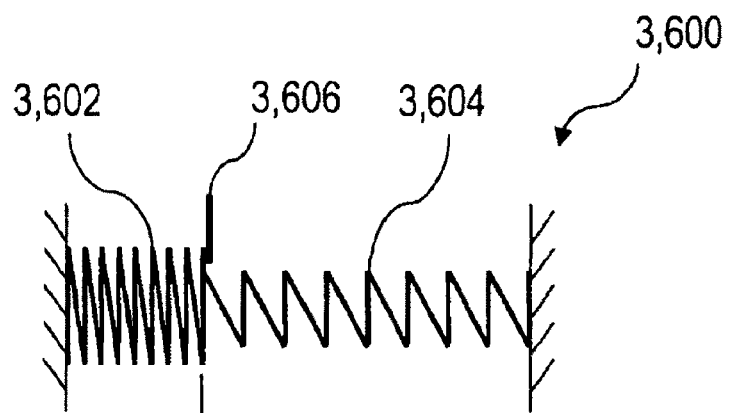
Figure 180:
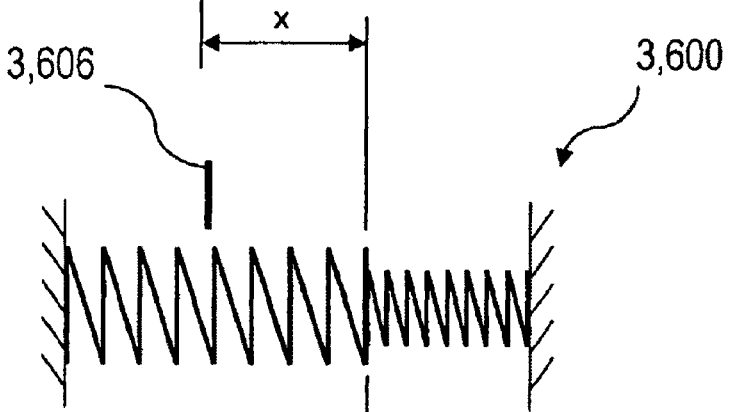
Figure 181:
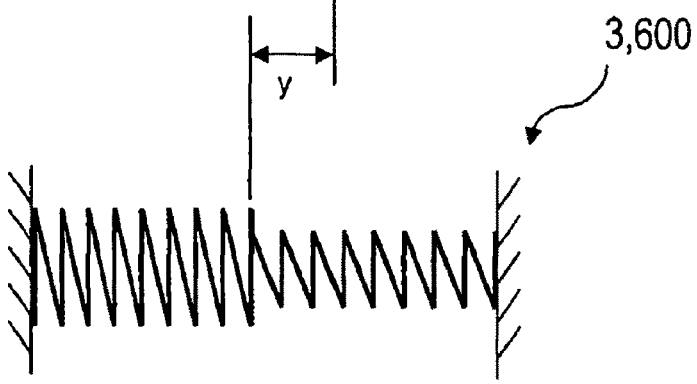
Figure 186:
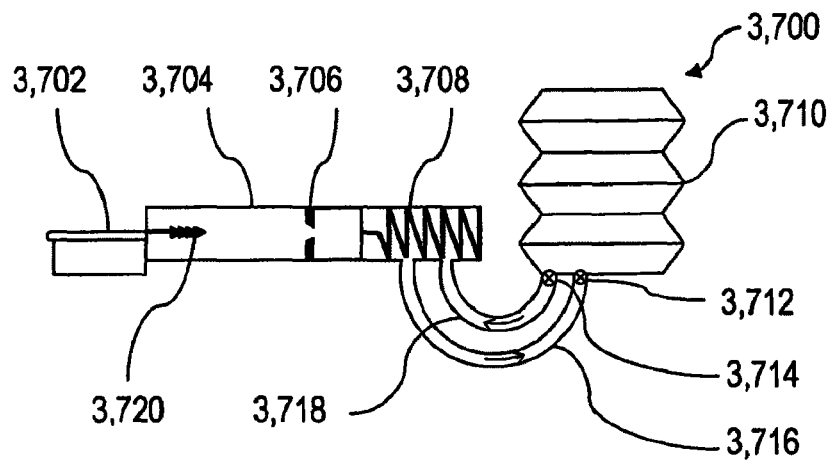
Figure 187:
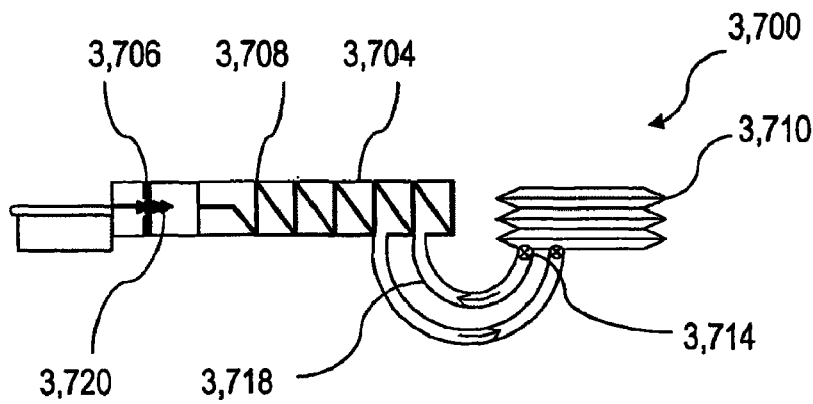
Figure 188:
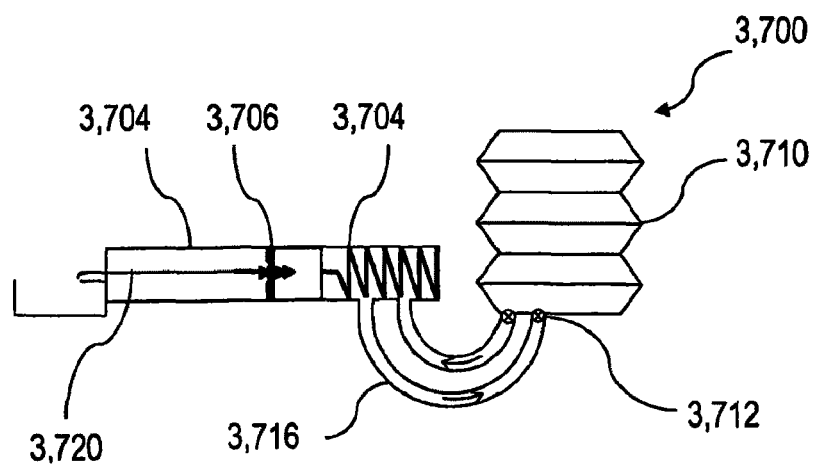
Figure 200:
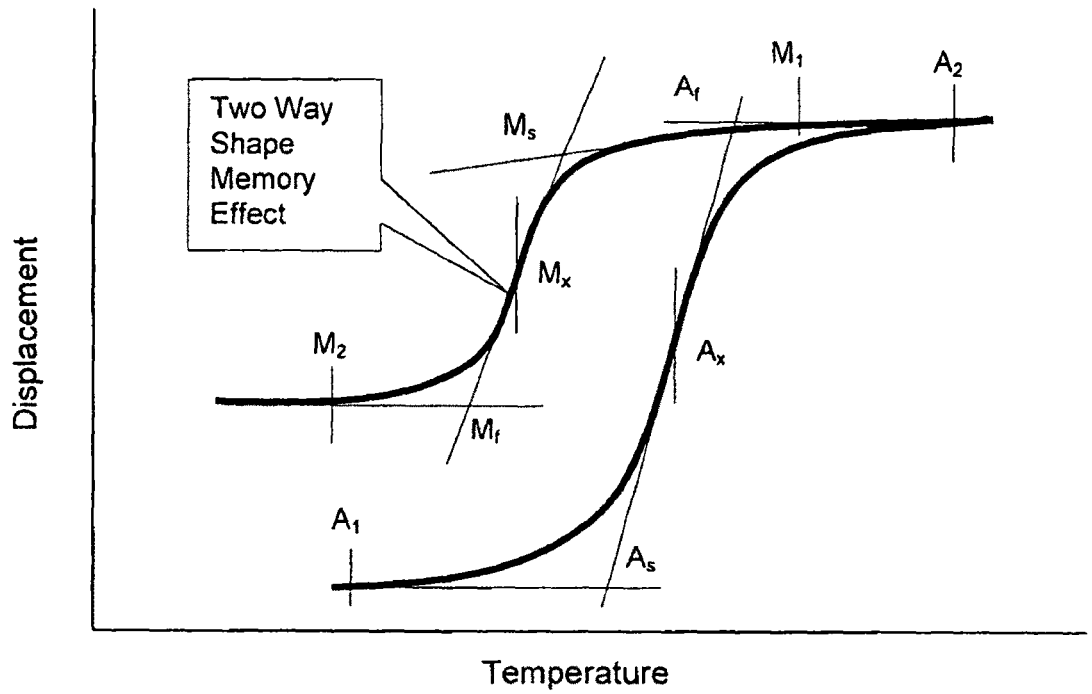

FIGS. 158, 159 and 160 are schematic side views of an arming device, armed by pushing two ends together with centrally located gripping elements, in the unarmed, armed, and path creation positions, respectively;

FIGS. 161 and 162 are schematic side views of an arming device, armed by engaging the pull tab of a peelable shell, in the unarmed and path creation positions, respectively;

FIGS. 163 and 164 are schematic side views of an arming device that releases a force, in the armed and force release positions, respectively;

FIG. 165 is a schematic side view of an arming device that releases a force utilizing a thermally driven track;

FIG. 166 is a schematic side view of an arming device, armed by rotating two parts of the device about a pivot point, in the unarmed position;

FIGS. 167, 168 and 169 are schematic side views of an arming device, armed by pressing the shell in the device, in the unarmed, armed, and path creation positions, respectively;

FIGS. 170, 171 and 172 are schematic side views of an arming device with a deformable shell, in the unarmed, armed, and path creation positions, respectively;

FIGS. 173, 174 and 175 are schematic side views of an arming device with a foldable shell, in the unarmed, armed, and path creation positions, respectively;

FIG. 176 is a schematic side view of a thermally powered device in the unarmed position;

FIGS. 177 and 178 are schematic side views of a thermally driven track in the unarmed and armed positions, respectively;

FIGS. 179, 180 and 181 are schematic side views of an arming device (without a shell) with a bias spring, in the unarmed, armed, and path creation positions, respectively;

FIGS. 182, 183, 184 and 185 are schematic side views of an arming device, that releases a substance with the fall of the temperature, in the unarmed, armed, pull tab engagement, and path creation positions, respectively;

FIGS. 186, 187, and 188 are schematic side views of a hydraulic arming device, in the unarmed, armed, and path creation positions, respectively;

FIG. 189 is a schematic side view of a pneumatically arming device;

FIG. 190 is a schematic side view of a magnetically arming device;

FIGS. 191, 192, 193, 194 and 195 are schematic side views of a double action arming device, with a cylindrical hollow shell, the shape memory material spring in the austenitic and martensitic shapes, the armed device, and the path creation positions, respectively;

FIGS. 196, 197, 198 and 199 are schematic side views of an arming device, with a peelable shell, in the unarmed, armed, fine tuning, and path creation positions, respectively;

FIG. 200 is a typical shape memory material displacement vs temperature graph.

DETAILED DESCRIPTION OF THE PREFERRED EMBODIMENTS

This document describes a series of inventions for devices whose principal operation is to create a path through a shell in order to release or admit one or more substances. The path is created with the direct or indirect aid of a shape memory material. The shape memory material acts as a sensor to detect the release temperature and activate or actuate the device to release the substance. The released substance may be utilized alone or may be mixed with a surrounding substance or substances to produce a new substance or group of substances with different properties for further utilization. Mixing can also take place inside the shell between the contained and the admitted substances. Each substance, contained or admitted in the shell or surrounding the shell, can be at any single or combined state of matter; solid, liquid, or gas, whether classifiable or differentiated as one or not. This includes live organisms such as microbes, plant seeds and the like. Further, the substances contained in the shell may be part of a system whose purpose is to control the release or admission of the substance. An example would be a matrix inside the shell that contains the substance to be released or that is ready to absorb the admitted substance. The shell may contain additional means to manage the release rate. Such examples would be a gas bladder that keeps the contents under pressure and accelerates their release upon creation of the path, or a permeable barrier that controls the release or admission rates of the substances. The surrounding substance can be at any static or dynamic state such as still, agitated or flowing. Examples would be a fluid reservoir inside which the shell is contained, an agitated chemical solution or flowing blood in a mammalian body.

The released substance may or may not be the same or at the same state as the substance contained in the shell. Examples of this would be substances that upon release sublime, melt or volatize. In the first case, the contained substance may be in the solid state but the released substance is in the gas state. In the second case, the contained substance may be in the solid state but the released substance may be in the liquid state. In the third case, the contained substance may be in the liquid state but the released substance may be in the gaseous state. The release rate can be instantaneous at a predetermined temperature, continuous (constant or variable), controlled or integrated over time, or over time and temperature. These systems are mechanical in nature. However, they are capable of becoming electromechanical as will be shown later. Conversion to electromechanical operation enhances the performance of the systems and adds further capabilities.

The ability to release and mix substances at a predetermined temperature or temperature range imparts unique capabilities to these devices. Some of these capabilities are: (1) production a new color upon mixing of two substances; (2) direct or indirect absorption of a substance, externally or internally, by a mammalian body; (3) automatic initiation of a chemical reactions; (4) remote controlled mixing rate or concentration adjustment of a chemical solution; (5) germination of seeds and spores; (6) odor generation; (7) grouping of devices to form massive multi-component delivery systems. Utilization of these capabilities can result in a multitude of new or enhanced applications such as: (1) temperature warning devices and specifically, temperature indicators and time-temperature integrator indicators; (2) on demand drug delivery systems; (3) color changing toys; (4) control of chemical reactions; (5) agricultural and forestry products; (6) fragrance devices; (7) food flavoring and taste enhancers. In addition, multiple devices can be employed as variable scale release systems for specific substances such as drugs, odors, disinfectants, sterilizers, fumigants, battlefield and riot control chemicals and the like. These devices have far more capabilities and potential applications than the ones mentioned herein. Four main applications, temperature indicators, on demand drug delivery systems, odor generation systems, and variable scale release systems will be used as the main examples during the description of the invention. In a number of the examples cited in this document, reference is made to two substances; one contained inside the shell and one outside. The purpose of these examples is to demonstrate the main features and function of the devices. As mentioned above, the devices are capable of containing and releasing or admitting more than one substance. However, the embodiments illustrated for one type of system are capable of use for any of the other types of systems described herein.

This document describes additional concepts to improve the operation and utilization of these devices. Several concepts are presented to control and improve the temperature release of the individual devices. To achieve this, multiple means are employed to control: (1) the beginning of the path creation process and (2) the force required to create the path. In addition, several concepts are presented that offer a selection of release temperatures for individual devices. In these concepts, the device remains inactive, in a dormant state, unable to create a path through the shell when exposed to any temperature environment. By following a simple single action arming process, the device can be placed in an active state of readiness, after which time it would create a path through the shell once the shape memory material activator attains a predetermined temperature. The ability to arm the device provides a choice of placing it in an active state by either the supplier prior to shipping or the user prior to the beginning of its service life.

The inventions described herein utilize shape memory material to act as temperature sensors and to either activate or actuate the device when the predetermined temperature has been attained. Most materials with reasonable shape recoveries and development of adequate stresses during the shape recovery process can be utilized for these devices. Presently, nickel-titanium and copper based alloys adequately meet these criteria and therefore are considered good candidates for these designs. For the sake of consistency, the nickel-titanium class of shape memory alloys known as Nitinol is assumed to be used throughout this document. In addition, throughout the description reference is made to a typical shape memory material Displacement vs Temperature graph shown in FIG. 200.

The inventions described in this document are not restricted to any particular size or fabrication method. They can be scaled up or down without losing their functionality. They can be fabricated by any method or technique without any restriction or limitation to the type of technology utilized.

Temperature warning devices are generally used as safety devices for products such as pharmaceuticals, foods, and beverages that are subject to loss of potency or strength, chemical alteration or degradation, spoilage, poisoning, and taste or flavor alteration if they are exposed to high temperature. Typically, all products have a restricted temperature range outside of which the product begins to change. The temperature warning devices described below warn the consumer if the product has reached or exceed its safe temperature limits. Although the description is primarily concentrated on the high end of the temperature range, these devices can also be used to provide low temperature protection or warnings. The warning provided may be by visual means of a color change, olfactory means of odor generation, gustation means of taste alteration, haptic means of physical touching modification, and auditory means of acoustic signal creation. The acoustic signal is most useful for implant applications as will be seen later. Besides the devices that indicate exposure to a temperature, this invention also includes designs utilizing the same principle of operation for time-temperature integrator indicators.

The substance release devices, when enabled with frictional means, can become self-powered and travel with temperature cycling. They can travel on surfaces, certain media, and on guided tracks. In the process of traveling they can release a substance along their path or at specific locations. In addition, they can release the substance to an object upon contact with its surface. Besides releasing a substance, they are capable of performing additional tasks such as transporting a load or converting thermal energy into mechanical energy. Types of loads that they can transport include detection, diagnostic and robotic equipment for medical applications. Energy conversion increases the capabilities of the substance release devices by extending the operational temperature release range and providing additional methods to create a path through the shell walls to release the substances.

In the concepts described herein, the path created by the shape memory material activator may be temporary or permanent and the substance may be released once or repeatedly with temperature cycling. Further, the substance can be released over time, once a predetermined temperature has been attained, or while the temperature is changing. Any shape memory material of any configuration that can produce work with temperature change is capable of being used as an activator to create a path though a shell wall for substance release.

To standardize the nomenclature and avoid confusion due to multiple applications of these devices, at times the shell contents, whether they are dye, drug, solute, solvent, or any other substance, will be referred to as the "source". Also, the same contents will be referred to as the substance within the shell to distinguish them from the substance which will be the contents of the enclosure surrounding the shell.

Figure 1:
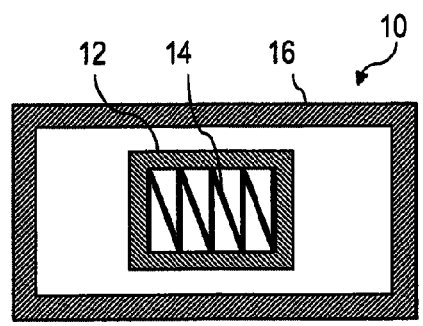
FIG. 1 is a schematic side view of a shape memory material activated device with an internal shape memory material spring.
Figure 2A:
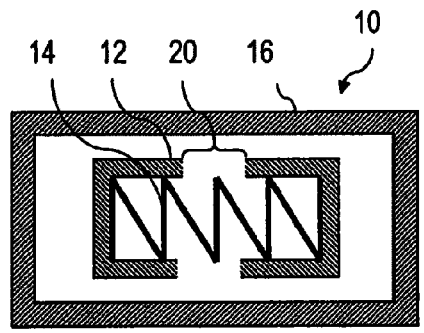
FIG. 2A is a schematic side view of the shape memory material activated device of FIG. 1 after activation.

FIGS. 1 and 2A illustrate a shape memory material activated device 10 including an inner shell 12, a shape memory material spring 14 within the inner shell, and an outer shell or reservoir 16 surrounding the inner shell. According to one embodiment, a first substance is contained within the inner shell 12 and a second substance is contained within the reservoir 16. Initially, the shape memory material is in its martensitic state and has been deformed from its original memory shape to assume the form of a compressed spring, as shown in FIG. 1. Surrounding the shape memory material spring 14 is a first substance in either a solid or a liquid state. Both the shape memory material and the first substance are encapsulated in a moisture impervious material shell 12. During the shape recovery process the shape memory material spring 14 develops sufficiently large stresses to overcome the resistance offered by the shell 12 or encapsulant and creates a path 20 through the shell wall, as shown in FIG. 2A.

For this to take place, a material of the shell 12 must be brittle enough to fracture with minimal plastic deformation. Fracturing allows the first substance from the interior of the shell 12 to be released and, optionally, be mixed/dissolved or otherwise combined with the second substance within the reservoir 16. The color change (if present) is preferably visible through a window of the reservoir and becomes a warning indication that the predetermined temperature has been exceeded. Alternatively, the visible indication may signal another event such as the release of a drug. FIG. 2A shows the inner shell 12 as a capsule that separates or fractures into two pieces upon shape recovery. In this type of design, allowances must be made for any volume increase during the recovery process. This can be accomplished by techniques such as entrapment of gas in the enclosure or by fabricating the enclosure from expandable material.

Figure 2B:
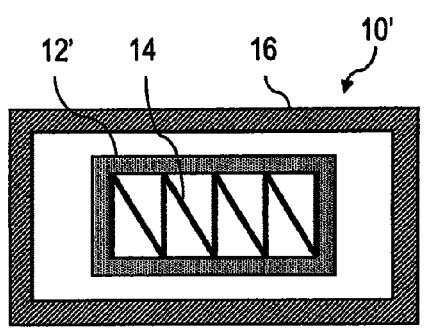
FIG. 2B is a schematic side view of the shape memory activated device of FIG. 1 after activation by stretching.

FIG. 2B illustrates an alternative embodiment of a shell 12' which has been stretched by the shape memory material spring 14 to create multiple small openings or paths through the shell. The paths may be in the form of pores, tears, fissures, or the like that make the shell permeable or semi-permeable to allow a substance to exit or enter the shell. If the openings in the shell are microscopic in size, mixing takes place by diffusion through the shell wall.

The term "shell" as used herein is intended to mean any container or enclosure which is capable of being fractured, opened, severed, stretched, abraded, or otherwise modified to allow a substance to enter or exit the shell. In certain cases where a substance is in the solid form and it its insoluble to its surroundings, there may be no separate shell. In these cases, release of the substance takes place by abrasion or fracturing of the substance to particles of a size releasable to the surrounding environment. The same definition applies to cases where the substance may consist of agglomerated smaller shells.

A temperature at which the device 10 is activated and the mixing of the two substances begins lies between the "Austenitic start" ($A_s$) and the "Austenitic finish" ($A_f$) temperatures of the shape memory material, FIG. 200. By the time the $A_f$ temperature is reached a path has been created through the shell 12 indicating that the shape memory material has recovered its shape either partially or fully. The $A_s$ and $A_f$ temperatures are determined primarily by the chemical composition of the material, its thermo-mechanical processing and the amount of deformation from its shape memory state. The temperature range of operation of the device is equal to the difference between $A_f$ and $A_s$. However, in reality, movement does take place between the temperatures $A_1$ to $A_s$ and $A_f$ to $A_2$. To narrow the $A_1$ to $A_2$ range, sufficient tolerances are allowed between the shape memory material and the inside surface of the shell for partial recovery to take place until temperature $A_x$ is reached. At this temperature, the shape memory material spring 14 is in full contact with the inside surface of the shell 12 and the shape recovery stresses begin to be applied to its inside surface. Conversely, by minimizing the tolerances, recovery begins at $A_s$ and the path is created by the time temperature $A_x$ is reached.

The shell in all the embodiments described herein contains the substance or drug to be released. Once the predetermined temperature is reached, a path is created through the shell that allows the two substances to come into contact. The two substances can be at single or multiple states of matter; solid, liquid, or gas. Additionally, the substances can be live organisms, plant seeds and the like. However, in most of the examples cited herein the enclosure substance is preferably in the liquid state and the shell substance is in either the solid or liquid state. Typically, the shell substance is a dye capable of changing the enclosure's color once the two come in contact.

The path creation through the shell is achieved by activation of the shape memory material activator which creates a path by fracturing, exploding, imploding, puncturing, peeling, tearing, rupturing, splitting, or otherwise opening the shell. The shape memory material has been deformed in the martensitic state and its $A_s$ to $A_f$ temperature range includes the predetermined temperature, which is considered to be the maximum safe temperature of the product. The enclosure is either transparent, or an opaque material with a transparent window. Once the predetermined temperature has been reached, the shape memory material recovers its shape and in the process applies a stress (tensile, compressive, shear, torsion, or a combination) that results in the creation of a path for the two substances to come in contact. The color of the enclosure fluid changes to indicate this effect and to provide the temperature warning through the transparent enclosure or window. The path creation is accomplished by the shape memory material by several means such as: fracturing, exploding, imploding, puncturing, peeling, tearing, shearing, rupturing, splitting, separating, debonding delaminating, squeezing, extruding etc. the shell. The method depends on the type of shell and on how the shape memory material is utilized.

For the temperature warning device of FIGS. 1, 2A and 2B and those described below, the reservoir 16 can be of any shape as long as it does not interfere with the shape recovery of the shape memory material spring 12 and the path creation process. The reservoir 16 can be made of either rigid or flexible materials. Construction of flexible materials will allow the enclosure to conform to different surfaces for bonding. In the case of the flexible enclosure 16, consideration must be given to the fact that the ambient pressure is transferred to the shell 12 though the second substance or fluid in the enclosure. The shell 12 must be able to withstand this pressure and the shape memory material must be able to overcome it. Although the embodiment of FIGS. 1, 2A and 2B has been described as a temperature warning device, it may also be used as a drug delivery device or in other applications. For use of the device 10 as a drug delivery system, the reservoir 16 has to conform to pharmaceutical requirements The actual shape of the deformed shape memory material in the martensitic state does not have to necessarily be in the form of a spring 14, as shown in FIGS. 1, 2A and 2B. Important factors to be considered include the displacement produced and the actual stress generated during the shape recovery process. These factors depend on the geometry of the shape memory material, amount of deformation, chemical composition of the material, thermo-mechanical processing and the forces restricting its recovery process.

The shape memory material can be of any shape as long as during recovery it is able to (a) produce sufficient displacement to come in contact with the inside surface of the shell, and (b) produce sufficient force to create a path through the shell walls. Determining factors for the shape of the shape memory material are (a) the amount of displacement required and (b) the properties and sizes of both the shape memory material and the shell material.

Figure 3:
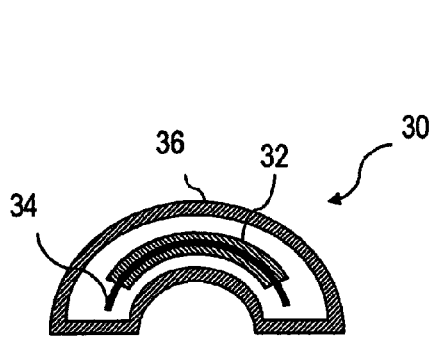
FIG. 3 is a schematic side view of a shape memory material activated device with an internal shape memory leaf spring.

FIG. 3 illustrates an alternative embodiment of a shape memory material activated device 30 having another shape. The device 30 includes an inner shell 32, a shape memory material spring 34, and an outer shell or reservoir 36. The shape memory material spring 34 is in the form of a leaf spring, curved in an initial configuration of FIG. 3, which straightens when exposed to the predetermined temperature. The straightening of the shape memory material spring 34 fractures the shell 32 and creates a single or multiple paths through the shell wall. The device 30 of FIG. 3 illustrates another shape for both the shape memory material spring 34 and the shell 32. The shell 32 is formed of a curved tube shape that can be designed to minimize the volume it occupies.

If the substances contained within the shell 12, 32 and the reservoir 16, 36, prior to mixing or after mixing, react with the shape memory material to the point that either the function of the device or its effectiveness are affected, the shape memory material must be insulated from the substances. This is achieved by containing the shape memory material in a non-reactant material. Alternatively, this may be achieved by placing the shape memory material outside of the shell and/or reservoir as in the embodiments of FIGS. 5, 6, 11, and 19 discussed below.

The shape of the shell 12, 32 depends primarily on the amount of substance it has to contain and the shape and size of the shape memory material. The shell can consist of one or multiple parts. Parts can be held together by several methods including, but not limited to; (a) mechanical pressure such as applied by mechanical fasteners, (b) mechanical interlocking such as interference fitting and thermal fitting, (c) chemical and thermo-chemical such as adhesive bonding, heat sealing and thermal shrinking, (d) any type of welding or weld bonding such as solid state, fusion, ultrasonic, brazing or soldering. Material selection for the shell depends on both intrinsic and extrinsic factors. Intrinsic factors are material properties that must be such as to allow the shape memory material to create a path through the shell walls. Extrinsic factors are; the type of heating to be used to activate the device, i.e. ambient, resistive, etc. and the time required for the device to be activated once the surroundings have reached the predetermined temperature. Again, the material (or materials if more than one is used) must not react with the substances contained in the shell and the enclosure prior to mixing or after mixing to the degree that the effectiveness of the device is compromised.

There are cases where it would be desirable to have the shell degrade over time. If no path has been created through the shell to release its contents, release would be achieved by the degradation process itself. This may arise from the inability, in certain cases, to retrieve the shell once placed in an environment where the temperature does not change appreciably to activate the shape memory material, create the path, and release the substance. The shell can be made of any material that would degrade in the environment that it is placed in. Degradation implies any process such as decay, deterioration, decomposition, disintegration, corrosion of the shell that would result in the release of its contents over time. It involves any combination of environment factors and shell material. Examples of such combinations are, but not limited to: (a) Shells made of wood products such as paper placed in a moist environment. (b) Shells made of organic material that degrade in the presence ultra violent radiation. (c) Shells made of material that have a tendency to corrode in specific environments by initiating and propagating a corrosion process. (d) Shells made of biodegradable material and placed in an environment that would induce biodegradation. Another way to degrade the shell would be a reaction with its own contents. Even though in most cases this is not a desirable effect, there are cases where this might be desirable provided that the degradation is a long term effect that does not interfere with the operation and effectiveness of the device during its intended life span. Degradation, at either a rapid or a slow rate, assures the release of the substance, thereby avoiding any problems of having a device placed in a service environment and remaining inactive.

Figure 4:
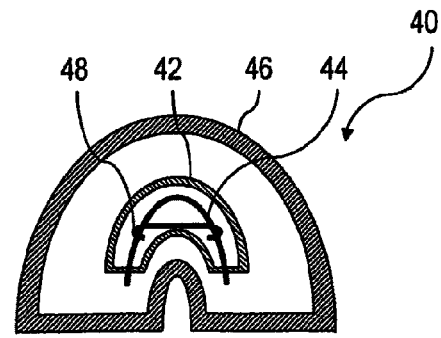
FIG. 4 is a schematic side view of a shape memory material activated device with an internal non-shape material memory leaf spring and a shape memory material release member.

Instead of using a shape memory material to both activate the device and create a path through the shell walls, the shape memory material can be used for the activation process and a regular spring of non-shape memory material or a superelastic material may be used to create the path while the shape memory material is used as a release mechanism. FIG. 4 illustrates an alternative embodiment of a shape memory material activated device 40 having a shell 42, a non-shape memory material spring element 44, an enclosure 46, and a shape memory material release mechanism 48.

Materials considered useful for the non-shape memory spring element 44 include those having spring properties, such as carbon or alloy steel, stainless steels, and beryllium-copper alloys. The spring element 44 is restrained by the release mechanism 48 in a position containing stored mechanical. Examples of restrained positions include (a) compressed coil springs, bent wires or strips (as shown in FIG. 4) and (b) torsion springs.

The spring element 44 of FIG. 4 is held in the restrained position by the shape memory material release mechanism 48 that has been deformed in the martensitic state to form a hook or loop. Alternatively, other restraining methods requiring deformation by stretching or shrinking rather than bending may be used. As the temperature rises above $A_s$, the shape memory material release mechanism 48 recovers its original straight shape. At one point, the spring element 44 is able to overcome the restraining force applied by the shape memory material release mechanism 48 and releases itself, goes to its free state, and in doing so utilizes the stored mechanical energy to create a path by fracturing, cracking, puncturing, peeling, tearing, shearing, delaminating or otherwise forming a path through shell 42. During the path creation process, upon impact with the shell wall it produces an auditory signal that can be utilized as verification of the spring release. Depending on the shape memory material configuration, different restraining methods can be used. FIG. 4 shows a hook type release shape memory material release mechanism provided on a leaf spring. The hook type release mechanism may also be used in a device with a coil type spring, such as the device illustrated in FIGS. 1, 2A and 2B. A number of different release devices, based on the same principle, are discussed later with respect to FIGS. 84-88.

As illustrated in the embodiments of FIGS. 5, 6, 11, and 19, the same effect achieved by placing the shape memory material activator inside the shell can also be achieved by placing it on the outside.

Figure 5:
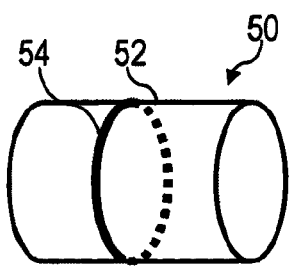
FIG. 5 is a perspective view of a shape memory material activated device with an exterior shape memory ring activator.

FIG. 5 illustrates a device 50 having a substantially cylindrical shell 52 and a ring-shaped, shape memory material activator 54 surrounding the shell. During shape recovery, the ring shaped activator 54 compresses and crushes the shell 52. Also, other shell/shape memory material configurations can be used for this embodiment and the cylindrical shell and ring shaped activator are merely one example.

Figure 6:
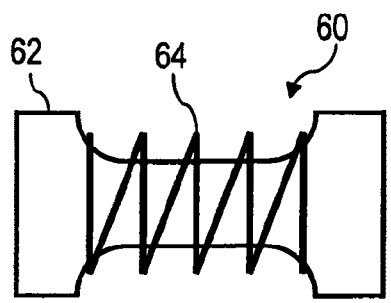
FIG. 6 is a schematic side view of a shape memory material activated device with an exterior shape memory spring activator.

FIG. 6 illustrates a device 60 having an hour glass shaped shell 62 and a spring shaped shape memory material activator 64. According to this embodiment, during shape recovery, the activator 64 expands axially and fractures or otherwise creates a path through the shell 62 by stretching.

Figure 7:
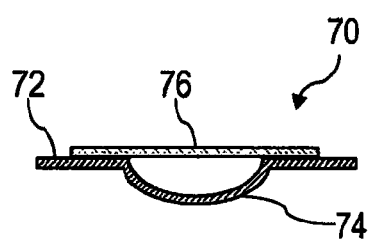
FIG. 7 is a schematic side view of a shape memory material activated device in the form of a popping shell.

FIG. 7 illustrates a popping shell type shape memory material activated device 70. In this concept, the popping shell consists of a shape memory material sheet 72 having a flat austenitic shape and a deformed dimple-like martensitic shape, as shown in FIG. 7. The substance to be released is placed in the dimple 74 of the sheet, sealed by a seal 76. During shape recovery, the material of the popping shell 72 tries to become flat and in the process a path is created, releasing the substance. The path is created either through the seal 76, or between shape memory material sheet 72 and the seal at the interface.

Figure 8:
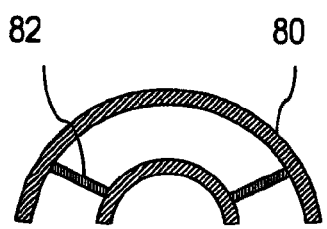
FIG. 8 is a schematic side view of a shape memory material activated device in the form of a shape memory material tube.

FIG. 8 illustrates an example of shape memory material tubular shell. In this concept, the shells incorporate shape memory material tubes that have been deformed in the martensitic state. Upon transformation to the austenitic state, these tubes recover their shapes and create a path by fracturing the end seals when returning to their memory shape. This concept relies on both volume and shape changes to break the end seals and minimizes the part count required to construct the shell.

Figure 9:
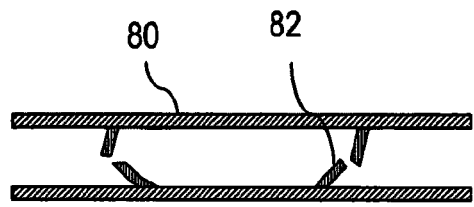
FIG. 9 is a schematic side view of the shape memory material activated device of FIG. 8 after activation.

FIG. 8 shows a bent shape memory material tube 80 which becomes straight upon shape recovery and in the process breaks the end seals 82 and releases its contents. FIG. 9 shows the shape memory material tube 80 after the seals 82 have been broken causing the substance contained in the tube 80 to be released.

In an alternative embodiment, a shape memory material tube may be flattened in the martensitic state to have an oval or other non-circular cross section. The shape memory material tube, upon transformation to the austenitic state, recovers a round cross section and breaks the end seals.

Figure 10:
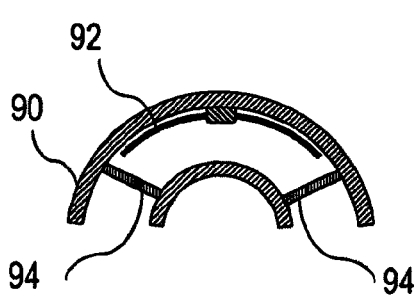
FIG. 10 is a schematic side view of a shape memory material activated device with an interior shape memory material leaf spring.
Figure 11:
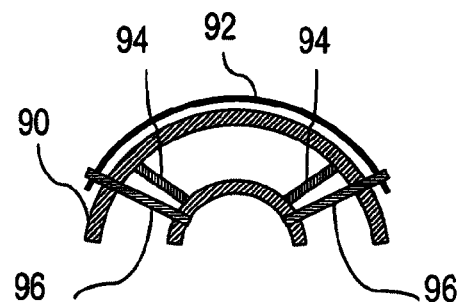
FIG. 11 is a schematic side view of a shape memory material activated device with an exterior shape memory material leaf spring.

FIG. 10 illustrates an embodiment of a non-shape memory material tubular shell 90 with a shape memory material activator 92. This concept utilizes the flexible non-shape memory material tube 90 forming a shell for containing a substance. The shape memory material activator element 92 located either inside (FIG. 10) or outside (FIG. 11) and attached to the tube 90 such that during shape recovery the tube assumes a different shape, i.e. bent to straight, and in the process breaks the end seals 94. In the case of FIG. 11, where the shape memory material activator element 92 is placed on the outside of the tube 90, the shape memory material activator element 92 is attached to the tube by bands 96 or other means.

Figure 12:
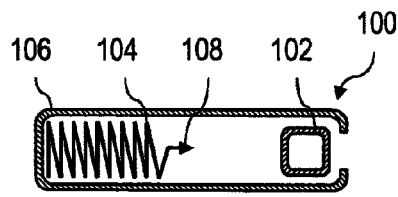
FIG. 12 is a schematic side view of a shape memory material activated device with an impact element.
Figure 13:
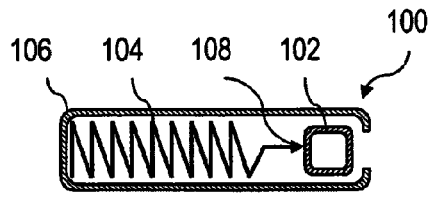
FIG. 13 is a schematic side view of the shape memory material activated device of FIG. 12 after activation.

FIGS. 12 and 13 illustrate an example of the use of shape memory material activators for puncturing or crushing a shell. FIG. 12 shows a shape memory activated device 100 including a shell 102 arranged to be punctured by a shape memory material activator 104 in the form of a coil spring. A cylinder 106 is used as a guide for the spring 104. The shape memory material activator 104 may be provided with a puncturing element 108 if necessary, depending on the force provided by the shape memory activator and the strength of the shell 102.

Figure 14:
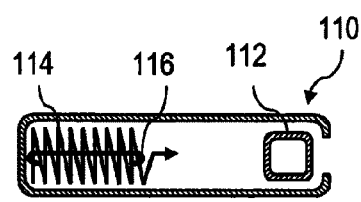
FIG. 14 is a schematic side view of a shape memory material activated device with an impact element and a shape memory material release mechanism.
Figure 15:
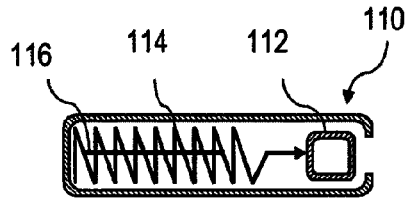
FIG. 15 is a schematic side view of the shape memory material activated device of FIG. 14 after activation.

FIGS. 14 and 15 illustrate the same concept of a shape memory material actuated device 110 in which a shell 112 is punctured or crushed, except that in the device 110, a regular (non-shape memory material) spring 114 is held in compression with a shape memory material release element 116. In both cases the coil spring can be designed to either puncture the shell with a sharp pointed end or to crush it with a blunt end.

Figure 16:
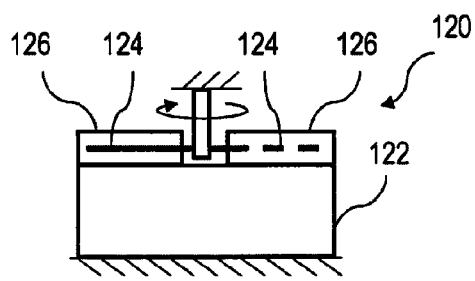
FIG. 16 is a schematic side view of a shape memory material activated device with an external shape memory material activator.

FIG. 16 illustrates a shape memory material activated device 120 which creates a path by twisting the shell. The device 120 includes a twisted shell 122 and two shape memory material elements 124 arranged on paddles 126 attached to the shell. The shear stress generated by the two shape memory material elements 124 become sufficiently large during the shape recovery process to create a path through the shell wall. The paddles 126 can be either rigidly attached to the shell 122 or they can be pivoted and allowed to rotate in order to more efficiently transfer the force generated by the shape memory material elements 124 to the shell. A top view of the device 120 is similar to the release mechanism shown in FIG. 84A.

Figures 17, 18:
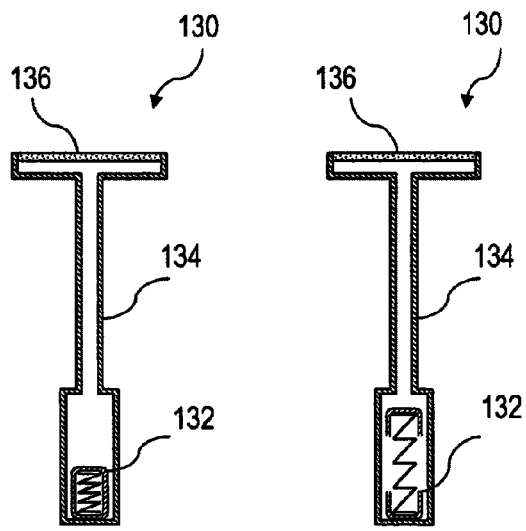
FIG. 17 is a schematic side view of a three dimensional shape memory material activated device.
FIG. 18 is a schematic side view of the three dimensional shape memory material activated device of FIG. 17 after activation.

FIGS. 17 and 18 illustrate a three dimensional shape memory material activated device 130. This concept is utilized to detect bulk temperatures, i.e. other than surface temperatures, and it is primarily applicable to temperature warning devices. The detection mechanism 132, which can be any of the mechanisms described herein, is placed at the bottom of a tube, 134 and a transparent window 136 is attached to the top end of the tube. In this case, the detection mechanism illustrated is similar to the device illustrated in FIGS. 1, 2A and 2B. The tube 134 constitutes a part of the enclosure. The tube 134 can be made of flexible material to accommodate areas inaccessible via line of sight. Once the warning temperature is reached, the shell fractures and a color change is produced which is visible through the clear window 136. Typically, the agitation generated by the fracture of the shell will be sufficient to aid the mixing process. However, in the case of long and narrow tubes 134 this may not be sufficient. In these cases, any gas contained in the shell will form one or more bubbles that will rise to the window 136 and in the process produce further agitation thereby enhancing the mixing process. In the cases where no gas is contained in the shell, gas can be incorporated in the dye if the dye is made of lightly compacted powder. The gas agitation method will work best if the device is vertically oriented.

Figure 19:
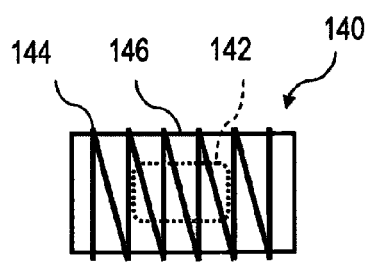
FIG. 19 is a schematic side view of a shape memory material activated device with an indirectly crushed shell.

FIG. 19 illustrates a shape memory material activated device 140 with an indirectly crushed shell 142. The device 140 includes the shell 142, a shape memory material activator 144 in the shape of and external spring, and an enclosure 146. The methods presented so far for creating a path through the shell walls are based on direct application of force on the shell, either from the inside or the outside of the shell. Most of these methods can also be used to apply the force to enclosure 146 and have it transmitted to the shell 142 via the fluid of the enclosure 146 (provided that the enclosure contains a fluid), as shown in FIG. 19. This concept is viable when the following two basic conditions are applied: the enclosure does not fracture prior to the shell and, the shell and its contents are not either incompressible or insufficiently compressible to fracture.

A good example of this concept is the case where the contents of the shell 142 are in solid, loosely packed powder form. This system offers the advantage of reduced cost by having one common enclosure 146 and shell 142 for use at all temperatures and having the shape memory material activator 144, with different $A_s$ temperatures, installed at the end of the assembly process or prior to the application. Also, it avoids the storage and transportation costs associated with maintaining the devices at a temperature lower that the activation temperature prior to application.

According to one alternative embodiment of the inventions described herein, the invention may employ devices similar to the devices described herein except that the shape memory material activator activates at a minimum temperature. In this embodiment, the shape memory material activator has been trained to achieve a two way shape memory effect. The purpose of this reverse system is to detect minimum temperatures and release a substance from a shell when such a minimum temperature has been exceeded. To do so, a shape memory material is selected whose martensitic transformation range $M_s$ to $M_f$ includes the minimum release temperature. Initially, the shape memory material is trained to achieve a two way shape memory effect with the austenitic (recovered) shape being the installation shape and the martensitic (original) shape being the one undertaken once the material is exposed to the predetermined temperature. At this temperature, the shape memory material creates a path through the shell walls and releases the substance from the shell. For single release type devices, the shape memory material is required to exhibit the two way shape memory effect only once, when the service temperature drops below the predetermined temperature. In essence, the shape memory material in the reverse design operates in the reverse temperature cycle. Actuation takes place during cooling from austenite to martensite, whereas in high temperature activation case actuation takes place during heating, from martensite to austenite. The same features used in all of the other designs described herein can also used with the reverse system. The two way shape memory effect, besides being utilized in shell containing devices, can also be incorporated in embodiments presented elsewhere in this specification to be actuated upon cooling below the $M_s$ temperature.

According to another embodiment of path creation during cooling, the shape memory material activator that is trained in a two way shape memory effect is utilized to restrain a non-shape memory material spring. The non-shape memory material spring is deformed elastically and contains stored mechanical energy. During cooling below $M_s$ the shape memory material begins to undergo reverse shape recovery and releases the restrained spring that in turn unleashes the mechanical energy to create a path by an impact force.

A path can also be created when the temperature of the shape memory material element decreases below a predetermined minimum value within the $M_s$ and $M_f$ range without the sole utilization of the two way shape memory effect described above. This is achieved with the incorporation of a bias spring. A bias spring is a non-shape memory material spring that is capable of storing mechanical energy when deformed elastically by the shape memory material undergoing shape recovery. Initially, the shape memory material spring is deformed in the martensitic state, and then the two springs are assembled together such that the bias spring remains in its free state. Once assembled, they are exposed to a temperature above $A_f$ and are maintained at or above this temperature. During the shape recovery process from $A_s$ to above $A_f$, the shape memory material deforms the bias spring elastically. This becomes the installation state, and activation of the device does not begin until the temperature of the shape memory material begins to decrease below $M_s$. As the temperature decreases below $M_s$, the resistance offered by the shape memory material spring begins to decrease and it is overtaken by the force exerted by the bias spring. As the temperature continues to decrease, the bias spring is forcing the shape memory material spring back to its martensitic state while producing a displacement. Once the production of the displacement is restricted by the wall of the shell, a force is generated and, when it reaches a sufficient magnitude, creates a path through the shell wall to release the substance. This force can also be used in alternative designs with enhanced capabilities such as to create a path though a shell wall during cooling ($M_s$ to $M_f$) and close it during heating ($A_s$ to $A_f$) or vice versa, and repeat this operation with temperature cycling. Further, this type of force can be used to create a path through the wall of all the shells described herein, including the peeling of the wall of a shell.

For background information, FIGS. 20 to 24 illustrate mechanisms comprised of shape memory material springs coupled with bias springs. FIG. 20 illustrates an activation mechanism 150 comprising two coil springs, a shape memory material spring 152 and a bias spring 154, positioned inside each other. When a compressive force is required to create a path, the shape memory material spring 152 is deformed by tension in the martensitic state and is assembled with the bias spring 154. During the shape recovery process, as the temperature increases from $A_s$ to $A_f$, the length of the shape memory material spring decreases and places the bias spring in compression. FIG. 21 illustrates the decreased length of both springs; shape memory material 152 and a bias 154 springs after shape recovery. When the temperature drops below M, the shape memory material spring begins to undergo reverse shape recovery, weakens, and when its resistance drops below the magnitude of the force offered by the bias spring, a displacement is produced which when constrained produces a compressive force. If there is no constraint, during reverse recovery the mechanism returns to its martensitic length, illustrated in FIG. 20, once the temperature of the shape memory material spring reaches $M_f$. This compressive force can be utilized to create the path through a shell wall. The nature of this reverse recovery force can be changed from compressive to tensile, simply by deforming the shape memory material spring in compression in the martensitic state prior to coupling it with the bias spring. The advantage of utilizing a bias spring is that path can be created through the shell wall with either a tensile or a compressive force to release or admit a substance during cooling of the shape memory material. Coupling of shape memory material and bias spring is not restricted to parallel positioning only. They can be coupled in series such that if restrained at the two ends, a displacement is produced with temperature change at the point of contact between the two springs. In addition, various types of springs can be combined to create a path through the wall of a shell with falling temperature of the shape memory material spring.

FIG. 22 illustrates an activation mechanism 160 comprising two leaf springs, a shape memory material spring 162 and a bias spring 164. When a leaf spring is required to create the path by producing a force during a shape change from straight to curved, the above process is repeated except that the shape memory material spring 162 is deformed by bending in the martensitic state. Then, it is mated with the bias 164 spring which is permanently bent to the same radius, and the two are heated to a temperature above $A_f$. During the shape recovery process, the shape memory material spring 162 forces the bias spring 164 to deform elastically and to assume a straight shape by the time the $A_f$ temperature is attained, FIG. 23. During cooling, the process is reversed and, if the mechanism is restrained form assuming the martensitic shape, a constrained force is produced. This force can be utilized to create a path through the wall of a shell to release or to admit a substance. The concept of incorporating a bias spring to create a path through the wall of a shell can be used with any type of shape memory material and bias springs.

FIG. 24 illustrates a shape memory material activated device 170 comprising an inner shell 172, a shape memory material spring 174 and a bias spring 176 within the inner shell 172, and an outer shell or reservoir 178 surrounding the inner shell. This device is similar to device 10, with the exception that the path creation takes place during cooling. When the temperature of the shape memory material spring begins to fall below $M_s$, the reverse recovery force, generated from the coupling of the shape memory material spring 174 and the bias spring 176, creates a path through the wall of the shell 172, illustrated in FIG. 25, to release the substance contained in the shell 172 to the reservoir 176. The same concept of utilizing coil springs can be utilized to create a path in more shells such as those described previously in devices 10, 60 and 100.

Besides creating a path directly through the wall of a shell, coupling of leaf springs can also be used to create the path indirectly by releasing an elastically deformed non-shape memory material spring containing stored mechanical energy to create a path through the shell wall. This is the same concept as the one illustrated in FIGS. 4, 14 and 15, with the exception that the restraining element is a coupling of a shape memory material spring and a bias spring, and path creation takes place when the shape memory material spring is cooled bellow $M_s$. Incorporation of a bias springs is not restricted to substance release devices only, it can be utilized in any design requiring actuation with the fall of temperature of the shape memory material spring.

Figure 26:
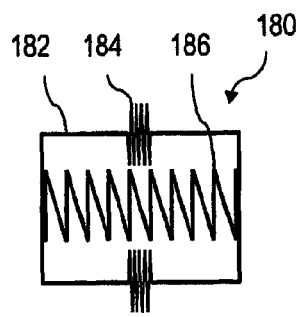
FIGS. 26, 27 and 28 are schematic side views of a shape memory material activated device with a folded wall shell, before during and after activation, respectively.
Figure 29:
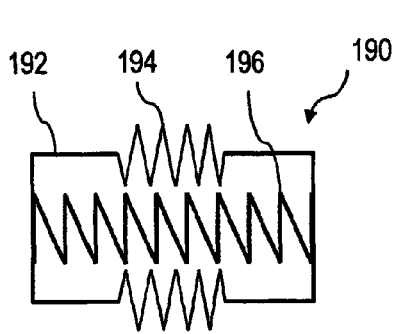
FIG. 29 is a schematic side view of a shape memory material activated device with a simultaneously unfolding wall shell.
Figure 30:
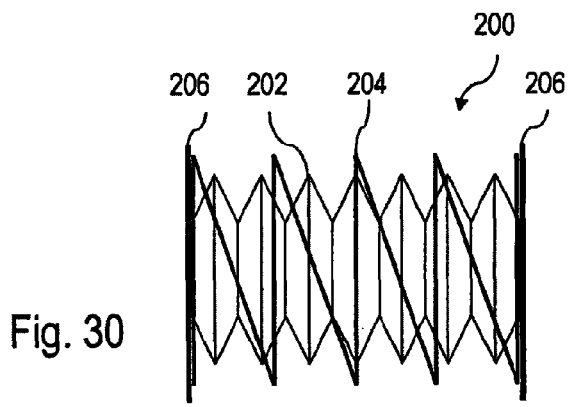
FIG. 30 is a schematic side view of a shape memory material activated device with an accordion type shell.

FIGS. 26, 29 and 30 illustrate alternative embodiments of a shape memory material activated device in which the shape memory material activator does not create a path through the wall of the shell directly. Instead, the path is created by utilizing the shape recovery force to create a new shell surface while the shape memory material activator undergoes a temperature change. The new surface contains pre-existing paths for the shell to release or admit a substance.

FIG. 26 illustrates a shape memory material activated device 180 comprising a shell 182 with part of its wall made up of a folded wall 184 and a shape memory material spring 186 within the shell. Alternatively, the shape memory material spring 186 can be located outside the shell. During the shape recovery process the folded part of the shell wall 184 unfolds to expose new shell surface that contains preexisting paths for the substance to enter or exit the shell. Unfolding can take place by two different methods that depend on the type of shell used. The first one comprises of a sequential unfolding of the folded wall while the second one comprises a simultaneous unfolding.

Figure 27:
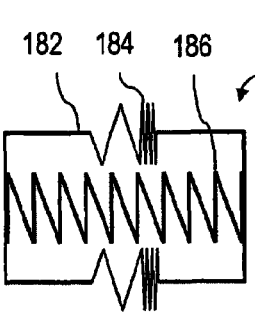
Figure 28:
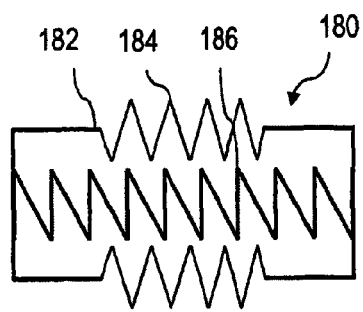

In the first method, unfolding takes place sequentially as the shape memory material spring undergoes shape recovery such that each individual fold opens up after the previous fold has opened up. This is illustrated in FIGS. 27 and 28. FIG. 27 shows a partial unfolding of the shell wall 184 while FIG. 28 shows the final unfolding of the shell wall 184 after the shape recovery of the shape memory material 186 is completed. This concept has the advantage of creating a path by exposing different areas of the shell wall as the temperature increases from $A_s$ to $A_f$. By designing each fold with different degree of permeability, size and number of pores or openings, the release or admission rate of the substance can vary with temperature but remains controlled throughout the transformation range. This type of shell requires that successive folds be held together with increasing contact forces such that increasing shape recovery forces are required to open them up sequentially. Different construction methods can be employed to achieve the sequential unfolding. Such methods may include the use of increased strength adhesives to bond successive folds or mechanical interlocking of successive folds with increasing contact stresses FIG. 29 illustrates an example of a shape memory material activated device 190 comprising a shell 192 with part of its wall made up of a folded wall 194 and a shape memory material spring 196. During the shape recovery process, the shape memory material spring 196 expands and all folds of the folded wall 194 unfold simultaneously until completion of the shape recovery process. The path is created by opening up all folds, whose surfaces contain preexisting paths, at the same rate simultaneously in an accordion fashion. This path creation method provides a smoother rate of release or admittance of the substance with changing temperature while the first method provides more of a stepwise rate increase.

Depending on the particular application, one shell type might be preferred over the other. For example, in some temperature warning systems the accordion type may be preferred in order to provide a more linear indication of time exposure with changing temperature. On the other hand, the sequential method may be preferred in order to provide a substantially increased release with temperature that would accelerate the coloring of the surrounding substance. While in both shell types, the path creation process is the same and both produce the same effect at constant temperature, they differ with respect to the release or admittance rate with changing temperature. The accelerated stepwise release rate of the sequential type qualifies this device as a time-temperature integrator indicator. As an example, at a temperature closer to $A_s$ an "x" amount of a substance may be released at a given time whereas at a temperature closer to $A_f$ and for the same time span a "2x" amount of the same substance may be released.

The unfolding shell provides increased design flexibility. In both shell types, the shape memory material spring can be located either inside or outside the shell. In addition, the shape memory material spring can be of configurations other than a coil spring, such as a leaf or torsion spring. Further, only part of the shell wall can be folded, and folds may not be symmetrical or of equal length. The concept of creating a path through the shell wall by utilizing the mechanical energy stored in an elastically deformed spring that is restrained by a shape memory material element may also be employed with the unfolding shell.

The coiled shape memory material spring can also be used in compression and placed either inside or outside the shell. Instead of opening the folds with increased temperature they are closed. This concept has the advantage that the substance is released out by pressure as the temperature changes and a path is created by converting the shell walls to permeable ones. Alternatively, release can take place through unidirectional flow valves that allow only outward flow and open up only when the contents of the shell are pressurized by the shape memory material spring. This concept is based on the existence of a differential pressure between the substance contained in the shell and the shell's surroundings, and as such it finds applications in environments of increased pressures.

FIG. 30. illustrates an alternative embodiment of a shape memory material activated device 200 comprising an accordion type shell 202 with a shape memory material spring 204 located outside of the accordion shell 202 and two end reaction members 206. During the shape recovery process, the shape memory material spring 204 contracts, reacts on the two end reaction members 206 that in turn squeeze the accordion shell 202, pressurize the substance contained inside and forces it out either though preexisting paths on the shell wall or by converting the shell wall into a permeable one. By placing the shape memory material spring outside of the shell, the shell may be divided into several chambers, each having a wall that requires a force of different magnitude for path creation. In addition, each chamber may contain a different substance. With a multi-chamber shell, the substance in each chamber may be released at a different temperature that lies within the transformation range of the shape memory material.

Release of a substance from an accordion type shell can take place though a predetermined path in a weakened area such that the force exerted by the shape memory material spring creates the path in this specific location. The substance may be squeezed out through a clear path, a valve, a filter or membrane and the like. For viscous substances, a clear opening may suffice. In addition, the substance may be released though several paths in locations away from the shell by connecting multiple passages such as tubes to the shell to carry the substance to different locations. The concept of creating a path by pressurizing or squeezing shell substance is not limited to the accordion type shell. Any shell formed from a cylinder and a piston, such as a syringe, with the piston activated by a shape memory material spring is capable of creating similar paths and releasing the substance in an extrusion fashion. In addition, shells may be made of flexible or malleable material that can change their shapes upon application of a force by the shape memory material spring, contain the substance and release it through a predetermined path. Some of the main advantages of this type of shape memory material activated device include the release of the substance through multiple paths, control of path size though permeable walls such as filters and membranes, and the release of substance only while the temperature of the shape memory material is changing. When the temperature stops changing, even though the shape memory material spring has not attained $A_f$ yet, pressurization of the shell contents stops and no further substance release takes place.

The shape memory material spring, when trained in a two way shape memory effect, can be used to create a path upon cooling to a predetermined temperature. Also, the shape memory material spring can be coupled with a bias spring to make the device operational from either the martensitic or austenitic state.

Figure 31:
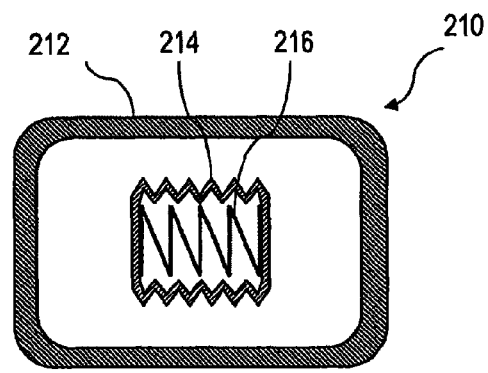
FIG. 31 is a schematic side view of a shape memory material activated device with a bellows type pressurant.

FIG. 31 illustrates a shape memory material activated device 210 comprising a shell 212 with a pressurant housing 214 in the form of a bellows containing a shape memory material spring 216. With this concept, the path is created in an indirect way by utilizing the pressurant housing 214 as an unfolding shell in the form of a bellows that is impervious to the surrounding substance contained in the shell 212. The shape memory material spring 216 may be placed either inside or outside of the pressurant housing 214. The pressurant housing 214 and the shape memory material spring 216 are simultaneously deformed by compression in the martensitic state. The pressurant housing 214 and the memory material spring 216 are utilized as a pressure generator during the shape recovery process and create a path through the wall of the shell 212 to release the substance. The path is created by the forced volumetric expansion of the pressurant housing 214 caused by the shape memory material spring 216 undergoing shape recovery. This expansion exerts a pressure on the shell's 212 wall that is transferred though the substance contained in the shell. The rate at which the substance is released can be instantaneous if the shell walls fracture or separate, or slow if the shell is converted into a permeable one and the substance is exuded out under pressure. In addition, the substance may be forced out through preexisting paths on the shell wall, such as interconnected porosity, by the developing pressure. The type of release rate would depend on the design and construction material of the shell. This concept ha multiple advantages. The same pressure generator can be used with different types of shells, release or admission of the substance takes place only during temperature change. In addition, the pressure generator can be surrounded entirely by the shell substance or it can be mounted on the shell's inside wall such that the shape memory material spring can be inserted from outside prior to placing the device in service. The last attribute allows for shape memory material springs of different activation temperatures to be inserted in the pressurant housing prior to placing the device in service. With this process, the release temperature can be "dialed-in" by the end user and allow for the storage and transportation of the device at any temperature. The pressurant housing of this device is not limited to bellows type only; other types of pressurants capable of pressure generation when activated by a shape memory material and undergo a volume change may be used. Such pressurant housings comprise any closed volume enclosure impermeable to the surrounding substance that can undergo a volume change with a shape recovery force while altering the internal pressure of the shell.

The pressurant concept can be used with a shell to admit a substance by having the bellows contract in response to a temperature change, thereby creating a negative pressure inside the shell. The path in this case is created by a pressure differential between the outside and the inside of the shell such that the shell wall becomes permeable under the existing pressure gradient, drawing the surrounding substance into the shell. Additionally, this device can be activated during the fall of temperature from $M_s$ to $M_f$ if the shape memory material spring is trained in a two way shape memory effect or it is coupled with a bias spring. Irrespective of whether the device is activated during the temperature rise or the fall of the shape memory material, the operating principle remains the same; a change in the temperature of the shape memory material results in a pressure change inside the shell. It is this change in pressure that creates the path through the shell wall to release or admit a substance. The amount of substance released or admitted is controlled by the volume change of the pressurant housing and the minimum pressure differential required to transfer the substance into or out of the shell.

Instead of simply releasing or admitting a substance, this device can be used to release a substance when the temperature of the shape memory material activator changes in one direction, and to admit the surrounding substance when the temperature changes in the opposite direction. This is a two way substance transport system that is repeatable with temperature cycling. With multiple cycling, a solid dye contained inside the shell colors the incoming substance that in turn colors the outside substance when forced out with a reverse temperature change. By repeating this operation with temperature cycling, the outside substance continues to change to a darker color, providing an integrated indication of the time and temperature for multiple exposures above a maximum or below a minimum predetermined temperature.

Additionally, the device may be placed between two adjacent chambers such that it admits a substance from one chamber with temperature change of the shape memory material activator in one direction and releases the substance to the second chamber with temperature change of the shape memory material activator in the opposite direction. While the substance remains inside the shell it can combine with a shell substance to change its physical and or chemical characteristics. Such combinations can produce coloring effects, mixing of drug and the like. Alternatively, the device can be used to transport a given quantity of substance from one chamber to another or to the surrounding environment with temperature cycling. An application of this concept would be the drug delivery to a patient from a reservoir. In this application, the first chamber from which the substance is admitted in the shell constitutes the reservoir and, the second chamber to which the substance is released constitutes the patient's body. The preferred construction of a substance transport device, operating by admission and release of a substance, is to have the part of the shell wall, that is in contact with the substance to be admitted, capable of becoming permeable in the inward direction only and the part that is in contact with the released substance capable of becoming permeable in the outward direction. Besides reversing the permeability direction of the two parts of the shell wall, the molecular size of the substance contained inside the shell may change when combined with the admitted substance. In this case, depending on the molecular size change, a different degree of permeability between the two parts of the shell wall may be sufficient to eliminate the need of reversed permeability. Alternatively, one-way valves can be employed at the walls of the shell for the path creation to take place. The valve in contact with the substance to be admitted allows only inward flow, while the one that is in contact with the released substance allows only outward flow. If valves are use, a permeable or semi-permeable membrane or filter can be incorporated in their opening to control type and the rate of the substance that passes through them.

Figure 32:
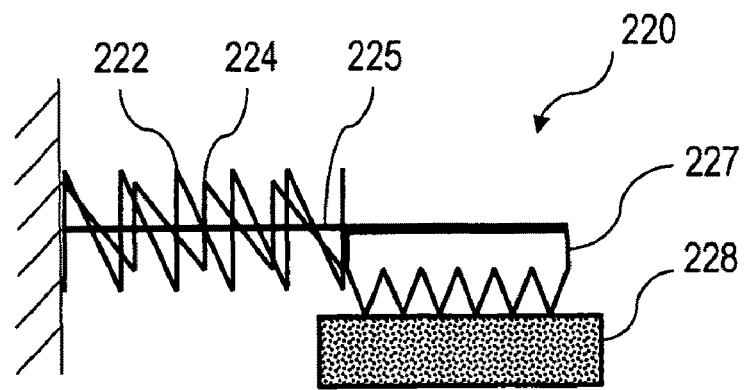
FIG. 32 is a schematic side view of a shape memory material activated device with an abrading element.

FIG. 32 illustrates an alternative embodiment of a shape memory material activated device 220. The device comprises a shape memory material spring 222, a bias spring 224, a support member 225, an abrading element 227 and a shell 228 containing a substance. The substance contained in the shell is a homogeneous or inhomogeneous agglomerated substance composed of such forms as grains, particles, powder of uniform or non-uniform sizes and shapes. The shell 228 may also have a protective layer on the outside to prevent any reaction or mixing with its surroundings. Upon shape recovery, the shape memory material spring 222 forces the abrading element 227 to ride along the support member 225 and abrade part of the agglomerated substance away. The abrading element 227 may have a sharp edge to force its way into the substance and scrape the substance away, or it may be configured with a rough surface to file or grind the substance away. The abrading process continues as long as the temperature changes and the shape memory material spring 222 is undergoing shape recovery. When the temperature of the shape memory material spring 222 reverses direction, the bias spring 224 aids the return of the abrading element 227 to its original position. During the return travel, the abrading element 227 continues to abrade the solid substance and release it to the surroundings. In addition to solid particles, the substance may also be comprised of composite matter such as gas or liquid globules encapsulated in solid casings.

Figure 35:
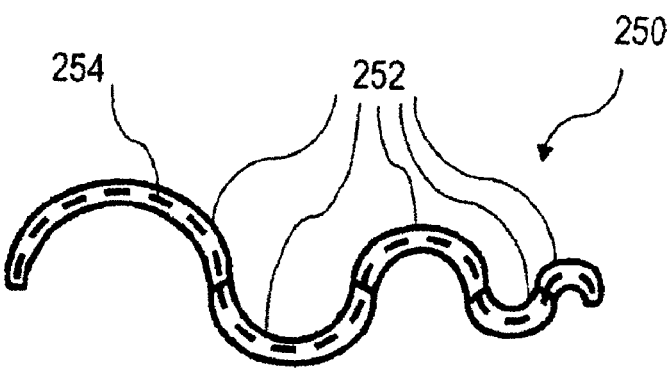
FIG. 35 is a schematic side view of a shape memory material activated device with a shape memory material activator bent in semi-circular segments of constant radii.
Figure 36:
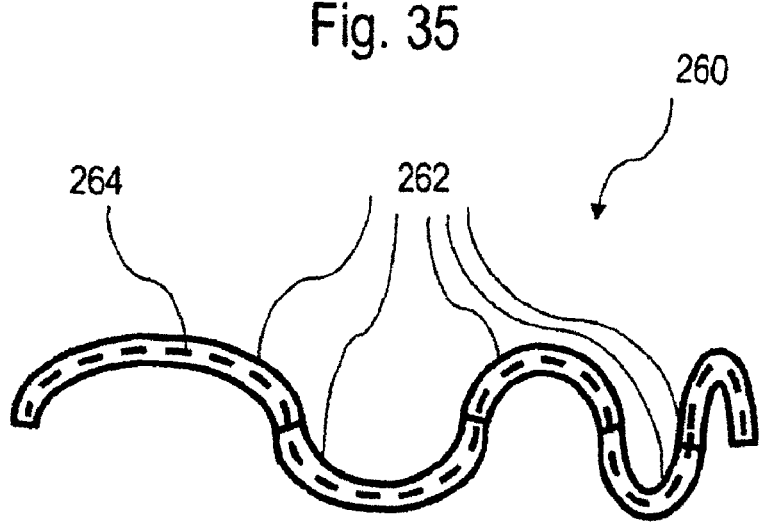
FIG. 36 is a schematic side view of a shape memory material activated device with a shape memory material activator bent in segments of variable radii.

FIGS. 35 and 36 illustrate embodiments of devices capable of releasing single or multiple substances over an extended temperature range. This type of release may be continuous or incremental and it is realized by deforming different parts of the shape memory material by different amounts. The amount of deformation in the martensitic state influences the $A_s$ temperature, and for the most part the entire hysteresis curve is shifted upwards to higher temperatures with increased deformation. Generally, if the deformation is excessive, above 8% for the Nitinol material, the hysteresis curve is expanded mostly by extending the $A_s$-$A_f$ curve upwards (U.S. Pat. No. 4,631,094). By deforming different segments of a shape memory material such as a wire by various amounts, each segment will have its own $A_s$ temperature. By surrounding the shape memory material with a substance and housing it in a shell, release can take place over a large temperature range.

Figure 33:
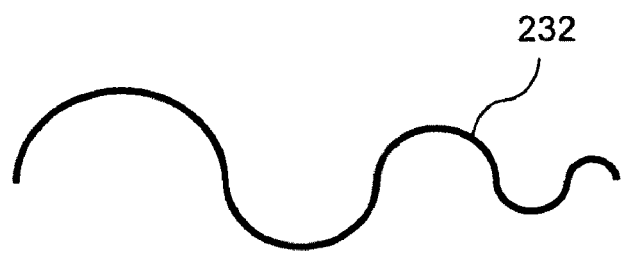
FIG. 33 is a schematic side view of a shape memory material element bent in semi-circular segments of constant radii.
Figure 34:
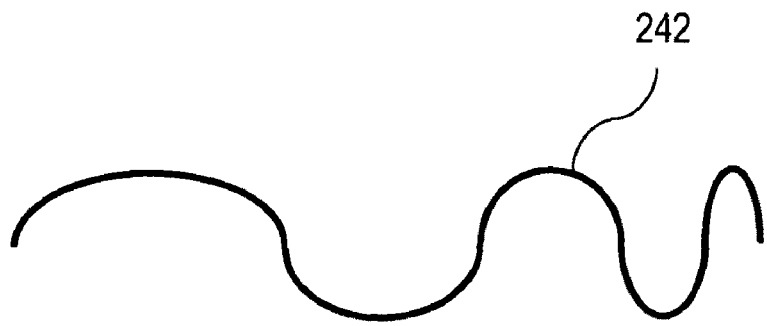
FIG. 34 is a schematic side view of a shape memory material element bent in segments of variable radii.

FIGS. 33 and 34 illustrate two types of deformation that can be induced to shape memory material springs, in wire form, that have straight shapes in the austenitic state. FIG. 32 illustrates a shape memory material spring 232 whose length has been bent to several semicircular segments. Each semicircular segment, defined as the segment between two successive inflection points, has been deformed uniformly by bending it to a single bend radius with successive segments bent to smaller radii. FIG. 33 illustrates another shape memory material spring 242 whose length has been bent to several shapes approximating semicircular segments. However, each segment has been deformed non-uniformly by bending it to a continuously varying radius. The severity of deformation, although variable, generally increases progressively with successive segments.

Shape memory material springs can also be deformed from a bent shape to a straight shape in the martensitic state. In other words, the shapes shown in FIGS. 32 and 33 could be the austenitic state shapes with the martensitic shapes being straight. This may be desirable for specific applications such as ease of assembly or incorporation into another device. One such application would be the assembly of different shells, each having an essentially hollow cylindrical configuration, into a straight shape memory material spring in a similar fashion as the stringing of beads. It should be understood that shape memory materials are not limited to these two modes of variable deformation illustrated in FIGS. 33 and 34.

When the temperature of the shape memory material springs 232 and 242 is raised, the segments subjected to the least amount of deformation will begin the shape recovery process first. Each semicircular segment of the shape memory material spring 232 will begin the shape recovery at a different temperature. In this manner, shape recovery will progress sequentially from segment to segment as the temperature continues to rise. On the other hand, shape recovery in the shape memory material spring 242 will begin simultaneously in several locations of the different segments that have been subjected to the same amount of deformation. While the temperature is raised, varying lengths of each segment will be undergoing shape recovery simultaneously. In the first shape memory material spring 232, the beginning of the shape recovery process would appear to be orderly while in the second one 242 it would appear to be random. However, in both cases the beginning of this process is predetermined by the localized degree of deformation. In the first case, the beginning of shape recovery is sequential and segmented, while in the second one, it is simultaneous and continuous.

FIGS. 35 and 36 illustrate the variable deformation concept that can lead to applications requiring extended release. FIG. 35 illustrates a shape memory material activated device 250 comprising a plurality of shells 252 adjacent to each other and a shape memory material spring 254. FIG. 36 illustrates a shape memory material activated device 260, similar to 250, comprising a plurality of shells 262 adjacent to each other and a shape memory material spring 264. The shape memory material springs 254 and 264 of the two devices have been deformed, from the straight austenitic state, to different configurations in the martensitic state. The two shape memory material springs 254 and 264 have been deformed similarly to 232 and 242, respectively. Initiation of path creation in the first device 250 takes place sequentially between the successive shells as the temperature of the shape memory material spring is raised. Initiation of path creation in the second device 260 takes place simultaneously in different locations of all the shells and continues to move to other locations as the temperature of the shape memory material spring is raised. The determining factor for path initiation in both cases is the amount of localized deformation induced in the martensitic state. As the amount of deformation increases, so does the $A_s$ temperature along with the path initiation. Each shell, of either device, may contain a different substance such that device 250 begins the release of the different substances sequentially as the temperature increases while device 260 begins the release of a predetermined group of different substances simultaneously. The release from each shell may be instantaneous such as in the case of gases and liquids where a single path may be sufficient to release the total substance, or continuous, as in the cases of solids where multiple paths are needed to release the total substance. In the latter case, a single shell of device 260, having its shape memory material spring 264 deformed to variable amounts, will release the substance over a wider temperature range as compared to device 250. For devices comprising a plurality of shells, with the paths in each shell initiated at a single or multiple temperatures, a predetermined release profile over a wide temperature range can be produced.

In fabricating the extended release devices, the substance can be adhered to the shape memory material and the shell can be built around the substance. Some of the methods used to apply the substance are; a powder slurry that is subsequently dried, a gas that is condensed and frozen or a liquid that is frozen. Once the substance is applied, the shell can be build around the substance by methods such as spraying or dipping and drying or curing. It is obvious that no heat should be used that would result in either partial or full shape recovery of the shape memory material activator. Path creation can take place by any of the methods described herein that result in microscopic or macroscopic size openings in the shell wall through which the substance is released.

Instead of a having a single shell with a multi-deformed shape memory material, several shells each containing a different substance can be build around a single multi-deformed shape memory material. With this concept, the path in each shell will be created at a different temperature with the net effect of producing different colors at different temperatures or releasing different types of drugs and quantities. The individual shells may or may not share a common wall. The use of a single multi-deformed shape memory material to produce extended release can replace several individual shells each having their shape memory material deformed by different degrees or each containing a different substance. In addition, a gradually deformed shape memory material with several shells will guarantee continuous release over a large temperature range.

This same concept can be used with a shape memory material trained in two way shape memory effect to create the path upon cooling to below $M_s$. In this case, assembly of the device must take place in the austenitic state after completion of the shape recovery in order to avoid release during heating from $A_s$ to $A_f$. Typically, reverse recovery is limited to nominal shape recovery strains and is not applicable to extended release beyond these limits. The same concept of releasing the substance during cooling can also be used with a bias spring coupled to the shape memory material spring.

Extended release is not limited to a single straight wire deformed by bending, other product forms such as sheet, strip, rod, bar or tube, deformed by other methods such as stretching, compressing, twisting can be used. In addition, the shape memory material may surround the substance to be released, as may be the case of a perforated tube. In this case, as an example, the shape memory material tube is deformed in the martensitic state, diametrically to various degrees of severity along its length, is filled with a substance, and has its perforations and its two ends sealed. Different length segments can be filled with different substances and be separated with dividing materials to form individual shells and to isolate one substance from the next. During heating, the localized strains developed in the shape memory material create paths through the sealed perforations to release the substance. The path initiation process progresses until the most deformed regions undergo shape recovery.

In a second example, a wire that is stretched to various degrees, incrementally or continuously to produce increased amounts of deformation along its length, can be used as a single shape memory material activator to peel the wall and create a path in several shells sequentially with rising temperature. In utilizing the extended release concept, it should be understood that transformation temperatures are affected by the stress applied to the shape memory material while undergoing shape recovery. For example, in the case of the peelable shells, once the part of the shape memory material wire with the lowest $A_s$ temperature begins to undergo shape recovery, a constrained force is developed during the process of peeling and the whole wire is put in tension. As different parts of the wire undergo shape recovery with increasing temperature, the magnitude of the tension varies and influences the transformation temperatures of the balance of the wire. In addition, depending on its magnitude, it may further deform the portions of the wire that have not yet recovered their shapes. Besides stretching a shape memory material wire or rod by varying amounts, different length segments may be stretched by varying amounts while others may be shrunk by varying amounts such that during shape recovery the overall length undergoes multiple expansions and contractions in a predetermined manner. Different modes of deformation can be used to produce shape recoveries to meet specific application requirements.

Figure 37:
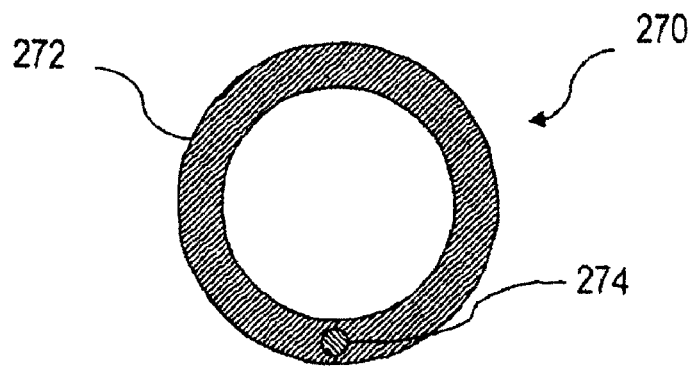
FIG. 37 is a schematic radial cross sectional view of a shape memory material activated device with the shape memory material activator integrated into the wall of the shell.

FIG. 37 illustrates a third example of a shape memory material activated device 270 that releases a substance over a wide temperature range, comprising a shell 272 and a shape memory material spring 274. The shape memory material spring 274 is integrated into the wall of the shell 272 that has a tubular form. The shape memory material spring 274 has been deformed in the martensitic state by varying amounts along its length to enable it to create multiple paths over a wide temperature range. The shape memory material spring 274 is embedded along the length of a sealed axial seam in the shell 272 and it is through this seam that the path is created to release the substance. The view shown in FIG. 37 is a cross sectional view perpendicular to the longitudinal axis of the shell. The shell can be compartmentalized, similarly to devices 250 and 260, to create multiple shells such that the path creation for different compartments takes place at different temperatures. The advantage of this concept is that the length of shape memory material is independent of the shell's diameter and is effectively independent of the quantity of the substance contained in the shell. In devices where the shape memory material is embedded in the shell wall, any possible slippage that may compromise its ability to create a path may be avoided by the introduction of geometric features on the surface of the shape memory material such as projections, indentations or twists that will aid its anchoring.

Extended release offers the advantage of providing an analog type path creation and release with increasing temperature. Assuming "other things being equal", the path creation rate and substance release would depend on the heating rate of the shape memory material as well as the deformation rate change along the length of the shape memory material. Useful applications of this concept include, but are not limited to, dyes and drugs. A dye released can be of a continuously changing color such that the color at any given time is indicative of the temperature of the shape memory material. This type of device offers the advantage of continuous temperature indication with increasing temperature for an extended temperature range, while as a drug release device it offers a controlled release of different drugs, group of drugs or the same drug with varying concentration for an extended temperature range. Further, another advantage that this type of device offers is that release can be controlled in an on-off fashion by the application and removal of heat without the incorporation of switches or valves. Path creation ceases once the temperature of the shape memory material is longer increasing and resumes again with further increase in temperature. This procedure can be repeated several times each time increasing the temperature to a higher level. Extended release of drugs can be used in many applications such as implants and transdermal delivery systems.

The shape memory material used as an activator in these devices can be heated by various methods such as ambient heat, directly or indirectly applied heat and resistive heat. The input of electric energy in the form of resistive heat used to heat these devices can be controlled to allow specific segments of the multi-deformed shape memory material activator to undergo shape recovery and create paths. By resuming the heating to increasingly higher temperatures, more segments undergo shape recovery that results in more path creations and release of more substances.

Variable Volume Shell

FIGS. 38 to 43 illustrate two shape memory material activated devices, 280 and 300 respectively, whose shells change volume with each release cycle. This variable volume shell concept utilizes two variable volume containers such as bellows, one housed inside the other. The inner bellows forms the pressurant housing while the outside one forms the shell. The pressurant housing contains a shape memory material spring coupled with a bias spring, all together comprising a pressure generator, while the shell contains the substance to be released. As the temperature of the shape memory material spring rises and undergoes a shape recovery, it overcomes the resistance offered by the bias spring and in the process applies a pressure to the surrounding substance. The applied pressure is considered positive when the shape memory material spring increases the volume of the pressurant housing, that in turn increases the substance's pressure. It is considered negative when a suction is created by a shrinking pressurant housing when the shape memory material is contracting. The pressure transmitted to the shell walls through the substance contained in the shell creates single or multiple paths through these walls to release or admit the substance. In essence, the shape memory material creates these paths indirectly. The path creation can be permanent or temporary. Permanent paths are intended for a one-time release and are irreversible. Temporary paths are intended for multiple releases and are reversible. Temporary paths include the conversion of the shell wall to a permeable or semi-permeable wall, and the opening of a one way valves. For the substance to be released the valves open outward, while for the substance to be admitted they open inward. Pre-existing paths include permanently permeable or porous walls through which the substance can only flow through under pressure such as is the case during the expansion of the bellows. The direction of substance flow determines the type of variable volume shell. The shell is considered a shrinking shell when the substance flows outward and a growing shell when it flows inward.

Figure 38:
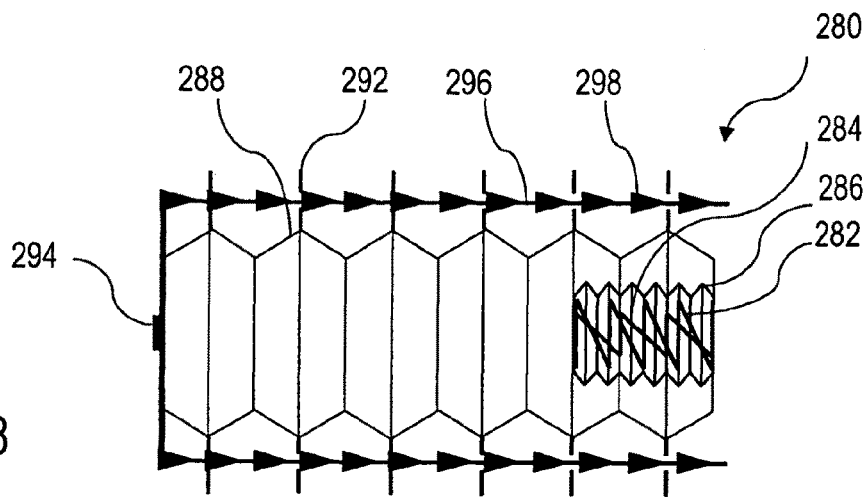
FIGS. 38, 39 and 40 are schematic side views of a shape memory material activated device with a shrinking shell, before activation, after activation and after shrinking, respectively.

The shrinking shell concept is demonstrated in FIG. 38, which illustrates a variable volume shell shape memory material activated device 280 comprising a shape memory material spring 282, a bias spring 284, a pressurant housing 286, a shell 288 with a plurality of fins 292, a valve 294, and a plurality of guide rods 296, each configured with a plurality of teeth 298. The fins 292 are configured with holes to allow them to ride on the guide rods 296, in a curtain fashion, as the shell 288 changes volume. The teeth 298 of the guide rods 296 are configured such as to allow the fins 292 to travel in one direction and to preclude reverse travel. The shape memory material spring 282 and the bias spring 284 are housed inside the pressurant housing 286, which in turn is housed inside the shell 288. As the temperature of the shape memory material spring 282 rises and it undergoes shape recovery, it overcomes the resistance offered by the bias spring 284 and in the process of expanding, forces the pressurant housing 286 to expand also and creates the path to release the substance.

Figure 39:
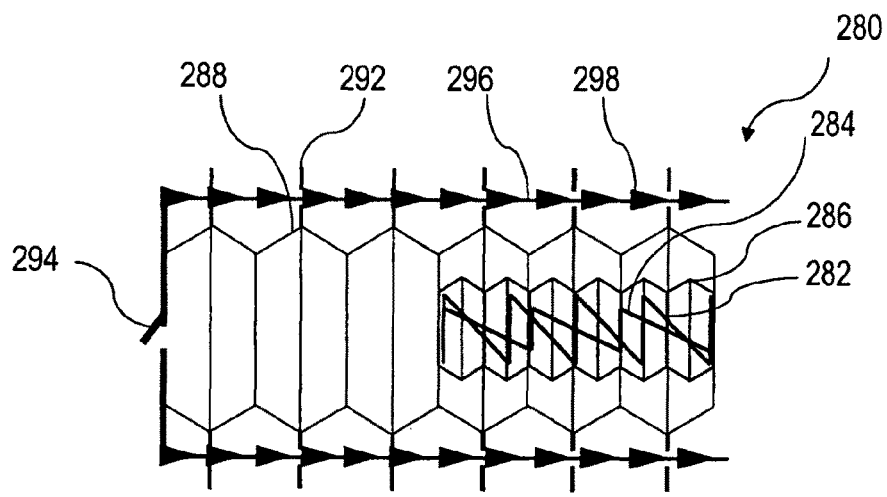

FIG. 39 illustrates the variable volume shell shape memory material activated device 280 while the shape memory material spring 282 is undergoing shape recovery. The pressure exerted on the substance contained in the shell forces the creation of a path to release the substance. In this case, the path is created through the valve 294 that is a one-way valve and allows outward flow only.

Figure 40:
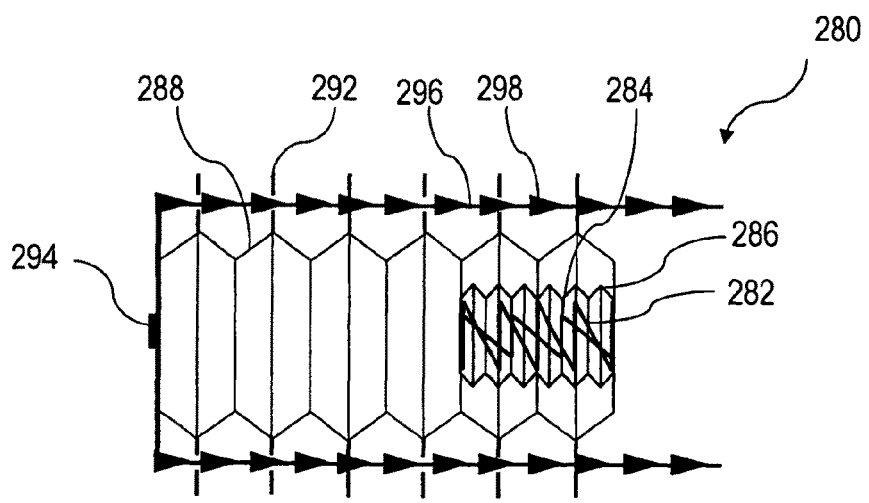

FIG. 40 illustrates the variable volume shell shape memory material activated device 280 while the shape memory material spring 282 is cooling down to the martensitic state and is undergoing reverse shape recovery. During cooling from austenite to martensite, the shape memory material spring 282 is forced to contract by the bias spring 284, and in the process, the pressurant housing 286 is forced to shrink. This reduces the pressure inside the shell 288 relative to the surroundings and in turn it is forced to shrink. Shrinkage is allowed only in the axial direction by the guide rods 296 that function as guides as well as restraints to prevent reverse movement. Each time the heating-cooling cycle is repeated, the shell shrinks by a volume equal to the volume of the released substance. This process continues until the bellows encounters the end and the pressurant housing 286 can no longer expand and contract.

Figure 41:
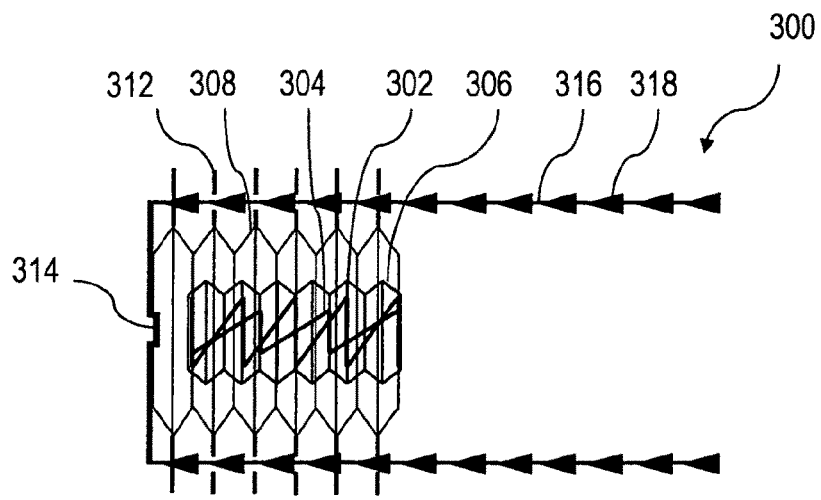
FIGS. 41, 42 and 43 are schematic side views of a shape memory material activated device with a growing shell, before activation, after activation and after growing, respectively.

The growing shell concept is shown in FIG. 41, which illustrates a variable volume shell shape memory material activated device 300 comprising a shape memory material spring 302, a bias spring 304, a pressurant housing 306, a shell 308 with a plurality of fins 312, a valve 314 and a plurality of guide rods 316, each configured with a plurality of teeth 318. This device 300 is similar to device 280 with the exception that the shell grows with temperature cycling as it admits a surrounding substance. The shape memory material spring 302 contracts instead of expanding during shape recovery, shrinks the pressurant housing 306, and creates a path to admit the substance while the shell 308 is restricted from shrinking by the guide rods 316. The teeth 318 of the guide rods 316 are oriented in the opposite direction of the teeth 298 in device 280.

Figure 42:
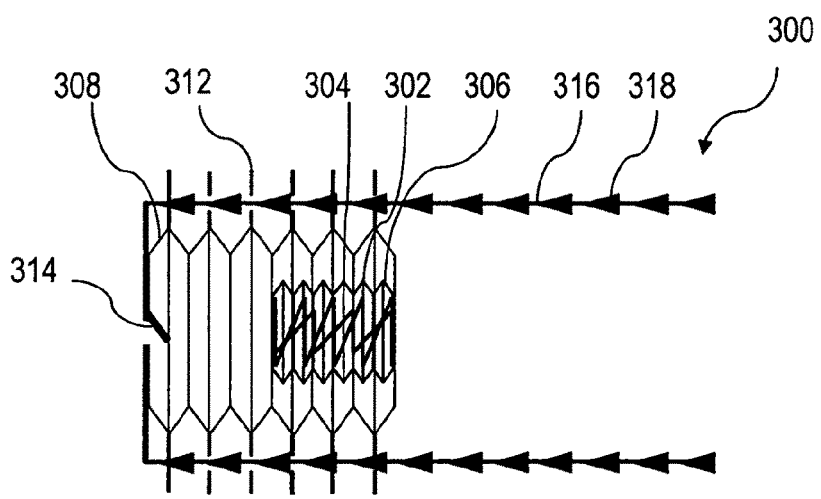

FIG. 42 illustrates the shape memory material activated device 300 while the shape memory material spring 302 is undergoing shape recovery. The suction created by the volume reduction of the pressurant housing 306 forces the creation of a path to admit the surrounding substance. In this case, the path is created through the valve 294, that is a one-way valve and allows inward flow only.

Figure 43:
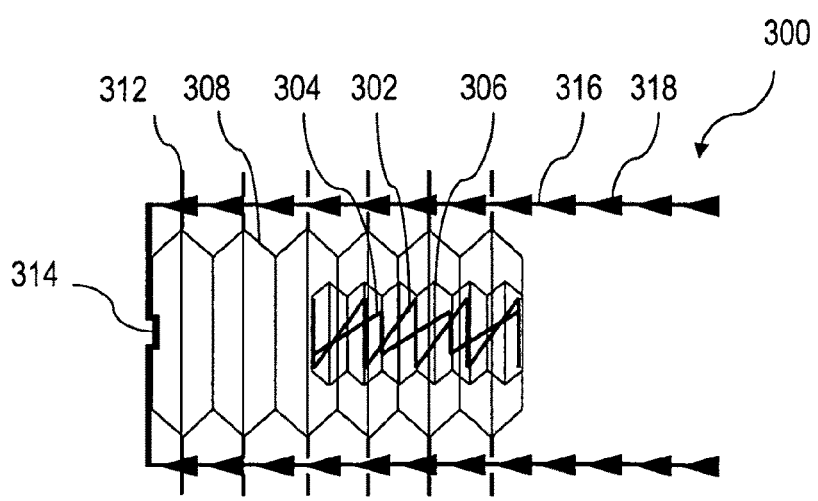

FIG. 43 illustrates the shape memory material activated device 300 while the shape memory material spring 302 is cooling down to the martensitic state, undergoing reverse shape recovery. During cooling from austenite to martensite, the shape memory material spring 302 is forced to expand by the bias spring 304 and in the process, the pressurant housing 306 is forced to expand. This increases the pressure inside the shell 308 relative to the surroundings and in turn it is forced to expand and to close the valve 314. Expansion is allowed only in the axial direction by the guide rods 316 that function as guides as well as restraints to prevent reverse movement. The process of alternate substance admission and shell expansion continues with temperature cycling until the bellows encounters a stop or until the shell is full and it is not capable of further expansion.

The concept of the shrinking and growing shell can be used to release or admit a substance during cooling from the $M_s$ temperature instead of heating from the $A_s$ temperature. This is accomplished simply by reversing the direction of shape recovery in each case. The guide rods, inserted in the holes of the fins, allow the shell to travel axially in one direction and restrict it from traveling in the reverse direction. The conical shape of the teeth allow the fins to slide easily through, from apex to the base, but prevent them from sliding backward. Sliding may entail enlargement of fin holes by stretching while going through the teeth. Instead of using guide rods placed on the outside, a hollow shell with a hollow pressurant housing can be used along with the incorporation of a single center guide rod configured with a plurality of teeth.

In all cases, the bias spring may be eliminated as a separate part if the pressurant housing also serves as the bias spring. This is especially true when the pressurant housing is formed as a bellows that can expand and contract elastically, and in the process, store and release mechanical energy. The mechanical energy is stored during the shape recovery process when the shape memory material spring deforms the pressurant housing elastically, and it is released during cooling when it is utilized to deform the shape memory material spring back to the martensitic shape. Alternatively, in cases where it is not desirable to have the pressurant housing perform as a bias spring, it may be filled with a compressible fluid that would act as a bias spring. Further, the pressurant housing and the bias spring may be combined into one part, made of material such as an elastomer, capable of undergoing volume changes with the application and removal of the shape recovery force. The elastomer may have any shape that will accommodate the shape of the shape memory material spring. For example, a shape memory material tube may be filled with an elastomeric material to act as a couple. The tube may be deformed in the martensitic state, axially or radially, and filled with the elastomeric material. During shape recovery, the shape memory material tube forces the elastomer to change shape, changes the pressure in the shell, creates a path to release or admit the substance. During cooling, along the $M_s$-$M_f$ path, the elastomer acts as a bias spring and deforms the shape memory material back to its starting shape. The term "pressurant" as used herein implies a part or assembly capable of changing its volume with the application of a force such as the one generated by a shape memory material element and in the process change the pressure of its surroundings when placed in a closed volume container such as inside a shell.

Figure 44:
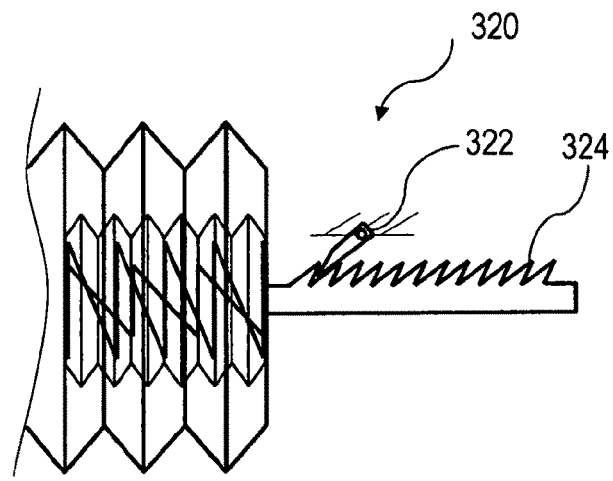
FIG. 44 is a schematic side view of shape memory material activated device with a volume changing shell restrained with ratchet.

The variable volume shell concept can be accomplished by alternative means besides the ones described herein. FIG. 44 illustrates an example of an alternative variable volume shell shape memory material activated device 320 that utilizes restraining means other than the toothed guide rods. This device 320 is similar to devices 280 and 300, with the exception that the guide rods along with the teeth have been replaced with a ratchet 324 and a detent 322 restraining system. The detent 322 is fixed while the ratchet 324 moves along with the shell in one direction only. Alternative guides and restraining concepts include tracks with fins and frictional effects, similar to ones described elsewhere in this specification. Further, a cylinder, having an internal surface configured to allow the shell to travel in one direction only, may be used to house the device and replace the function of the guide rods. In this case, the fins of the shell ride along the inside surface of the cylinder. The morphology of the inside surface of the cylinder may contain features such as knurled marks, gear teeth or circumferential fins, preferentially oriented to allow the shell to travel in one direction with minimal resistance and to prevent its travel in the reverse direction.

Figure 45:
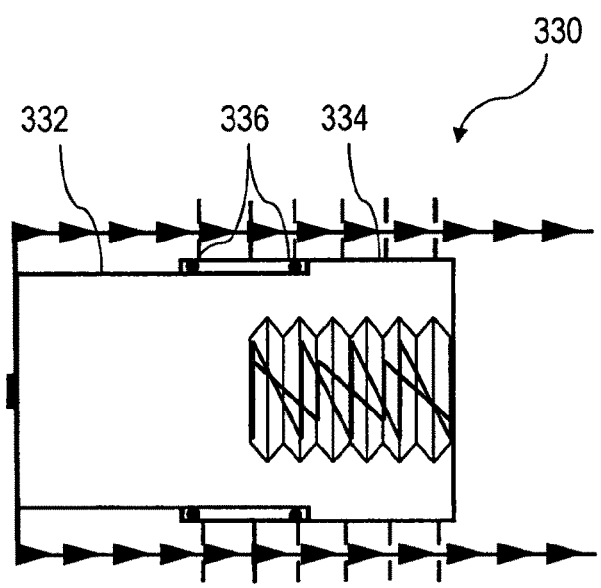
FIG. 45 is a schematic side view of a shape memory material activated device with a shell of two telescoping halves.

The variable volume concept is not restricted to bellows. Any type of container made of a single or multiple parts, whose volume can vary, preferably in one direction, can be utilized as a shell or a pressurant housing. FIG. 45 illustrates another alternative variable volume shell shape memory material activated device 330 whose shell comprises two concentrically located, axially sliding, half shells: an inner half shell 332 and an outer half shell 334 sealed with a plurality of O-rings 336. Only the outer half shell 334 travels, in a telescoping fashion, with temperature cycling. The other shell, the inner half shell, 332 remains stationary at all times.

Figure 46:
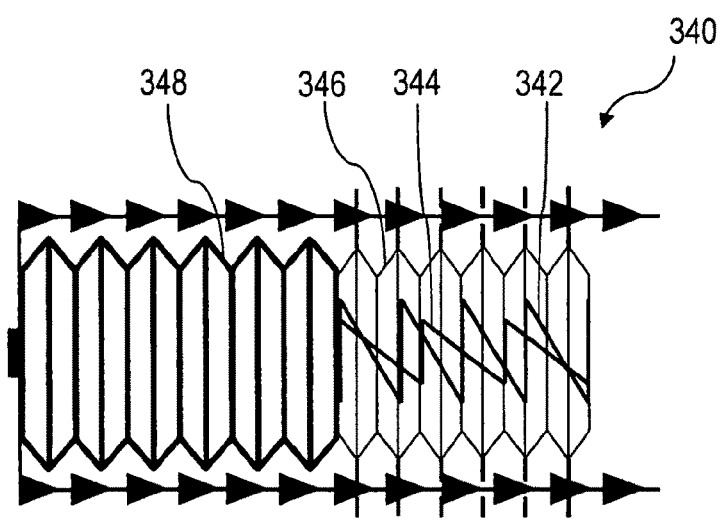
FIG. 46 is a schematic side view of a shape memory material activated device with volume changing shell and with the pressurization means placed outside of the shell.

The pressure generator, comprised of the pressurant housing with the shape memory material and the bias spring, can be placed either inside or outside of the shell. FIG. 46 illustrates device 340, whose pressure generator comprises a shape memory material 342, a bias spring 344 and a pressurant housing 346 all placed outside of the shell. Here the pressurant housing 346 pressurizes the shell 348 from the outside without being in contact with substance. This concept assures release of all the shell contents. One end of the pressurant housing, whether placed inside or outside of the shell, may be open to the outside thereby eliminating any biasing force due to internal pressure. Devices utilizing the open ended pressurant housings make the shape memory material spring and the bias spring accessible from the outside. This allows installation of the springs prior to placing them in service. This is beneficial as the devices may be maintained at any temperature prior to placing them it in service and allows for the selection of shape memory material and bias springs to match the release temperature requirements for a specific application.

Alternatively, the whole device may be be enclosed in a pressurized and hermetically sealed enclosure with only the area encompassing the path creation exposed to the outside. Here the enclosure's pressure determines the amount of substance to be released. The enclosure pressure decreases as more substance is being released and in turn, release per cycle is decreasing. In essence, a variable (decreasing) release is produced with cycling.

The shape memory material spring does not have to be a coil spring. It may be any shape including a simple straight element that is capable of performing repeated work with temperature cycling either by itself or in conjunction with a bias spring. In addition, the shape memory material may comprise part of the whole pressurant housing or be the pressurant housing. Typically, Nitinol alloys recover up to 8% of their strain during the transformation process from martensite to austenite. The amount of substance released with each cycle depends on the volumetric expansion of the pressurant housing. With a linear expansion of a few percent of the total length of the pressurant housing, the contributing volume change factor becomes its diameter. The amount of substance release with each temperature cycle can be optimized through the selection of the shape memory material spring's geometry and size along with the pressurant housing's diameter.

Figure 47:
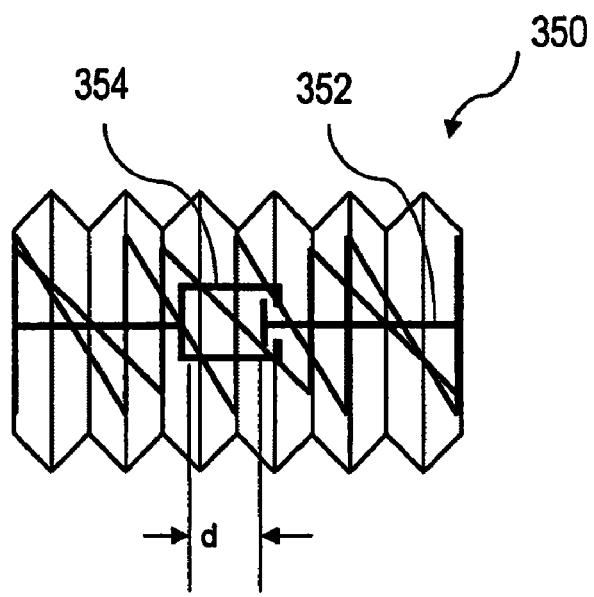
FIG. 47 is a schematic side view of a shape memory material activated device with a controlled volume changing shell.

Alternatively, restraining the pressurant housing by a predetermined amount as it expands and contracts controls the amount of substance released or admitted. FIG. 47 illustrates the concept of the restrained pressurant housing. In addition to the shape memory material spring and the bias spring, the pressurant housing 350 houses two interlocking stops, a male stop 352 and a female stop 354. The two stops move relative to each other in opposite directions with the expansion and contraction of the pressurant housing. However, their movement is limited to a maximum distance "d" that determines the amount of substance to be released. Alternatively, other restraining methods may be use and the distance "d" may be fixed or adjusted by the user prior to placing the device in service.

Figure 48:
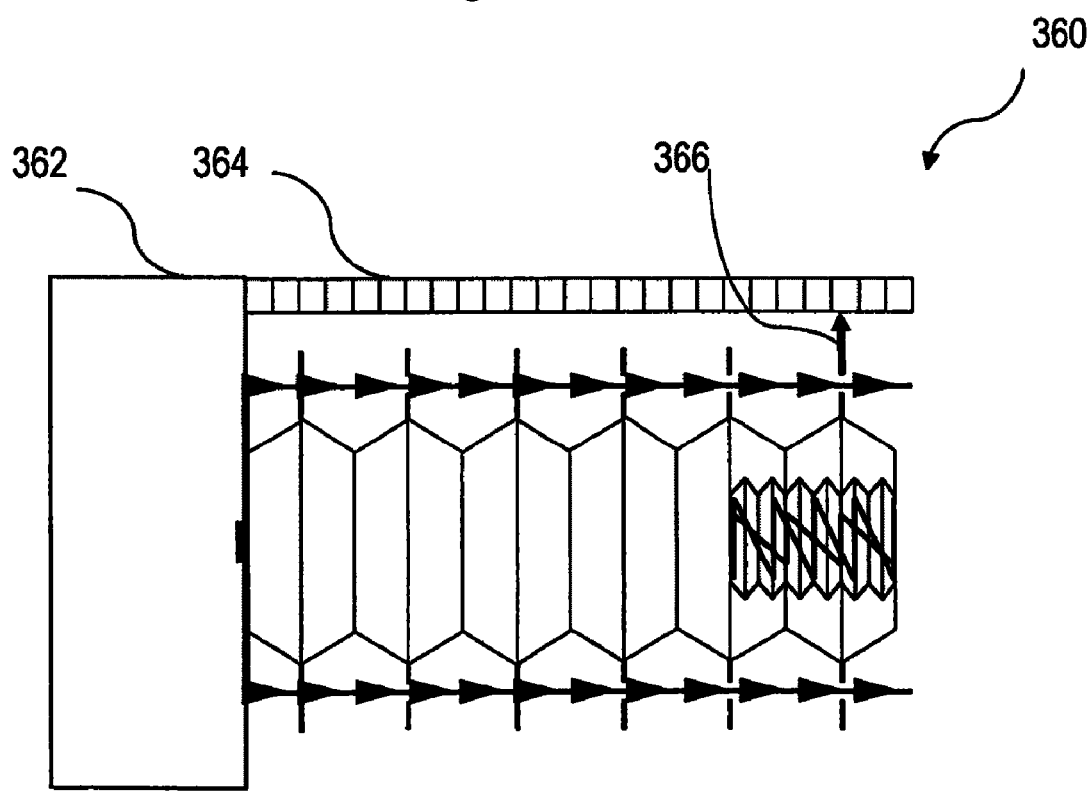
FIG. 48 is a schematic side view of a shape memory material activated device with a volume changing shell and two types of temperature indicators.

As with other devices presented herein, the substance can be released to the surroundings or to an enclosure for further enhancements of the device. Such enhancements include mixing with the substance of the enclosure to produce effects such as color changes that are indicative of the temperature exposure history. Color changes can be detected through a transparent window in the enclosure. Besides color change, temperature exposure history may be indicated with a pointer showing the shell's length change. FIG. 48 illustrates the temperature history indicating elements on a device similar to 280. The indicating elements of device 360 comprise an enclosure 362, a graduated scale 364 and a pointer 366. The enclosure 362 changes color with increasing release of the substance. The color change may be visible though a transparent window of the enclosure. The pointer 366 is mounted on the end fin of the shell and travels along with the shell. As it travels, it indicates the length change of the shell on the graduating scale 364. The length change of the shell indicates the total substance that has been released which, in turn, is indicative of the temperature exposure history of the shape memory material.

One of the main advantages of the volume changing shell concept is the fact that the substance is being released or admitted only while the shape memory material is subjected to a temperature change within a predefined temperature range. During this temperature change, it forces the pressurant housing to change volume resulting in the path creation through the shell's wall. In the case where the path is created during shape recovery, once the $A_f$ temperature is reached the pressurant housing stops changing volume and path creation ceases. The same applies when the path is created during the cooling part of the temperature cycle. Once the $M_f$ temperature is reached, the pressurant housing stops changing volume and path creation ceases. Flow of the substance in or out of the shell is not restricted to valve paths. The substance may flow through paths created by conversion of shell's wall or sections of the wall to permeable or semi-permeable paths. These wall parts may be rendered permeable only during the path creation process when a pressure differential exists between the contents of the shell and its surroundings. Any substance that is detectable by the senses or not can be released though any path created through the shell's wall by a shape memory material activator. Further, a permeable or semi-permeable barrier, such as a filter or membrane, may be incorporated in the opening of the valves. Opening of the valves makes the substance accessible but the accessibility rate is controlled by the barrier.

Medical applications include drug delivery devices such as transdermals and implants. In all cases, the substance is released only while the shape memory material is undergoing shape recovery or reverse shape recovery. This is advantageous as the amount of substance release is independent of the width of the hysteresis. In the case of body temperature activated release, i.e. fever, the amount of release increases as the fever increases, thereby providing the body with more antipyretic drug. In the case of implanted drug delivery systems, the $A_f$ temperature is the limiting release temperature. Release stops at this temperature, irrespective of the heating energy provided to the shape memory material either externally or internally. The width of hysteresis has no influence on the amount released, as no further release takes place once the $A_f$ temperature is reached. For implant devices, this concept offers the advantage that with each temperature cycle, there is a predefined amount of substance released. This amount is independent of energy input, above a minimum level, and independent of the time the shape memory material stays at a given temperature. Also, because the shell contains a finite amount of substance, the drug can not be abused. Once depleted, the shell can not be refilled as the shell guide rods prevent its reverse movement.

Variable shell type temperature indicators provide a cumulative temperature record of exposure of the shape memory material to a predefined temperature range. Exposure may be through the whole temperature range or part of it. The exposure record is indicated by a color change of a substance viewed through the transparent window. The intensity of color changes with increased temperature exposures. The total amount released provides an integrated record of the shape memory material temperature exposure. This device integrates the release with respect to temperature over a predefined range. Besides the change in color intensity with temperature cycling, a new color can also be produced. The new color is produced by utilizing a viscous substance in the shell that is structured in layers of different colors. Once the first layer has been released with temperature cycling, the next layer begins to be released with repeated temperature cycling thereby producing a new color. This process continues to produce a new color each time a complete layers of a specific color has been released. The utilization of multiple colors extends the life of the device by allowing interpretation of temperature exposure by color differentiation in addition to color intensity. In addition to filling the shell with a multicolor substance in layers, the substance may have a color gradient. In all devices, drug delivery, indicators and others, the substance quantity released is independent of the heating or cooling rates of the shape memory material.

Renewable Shell

Figure 49:
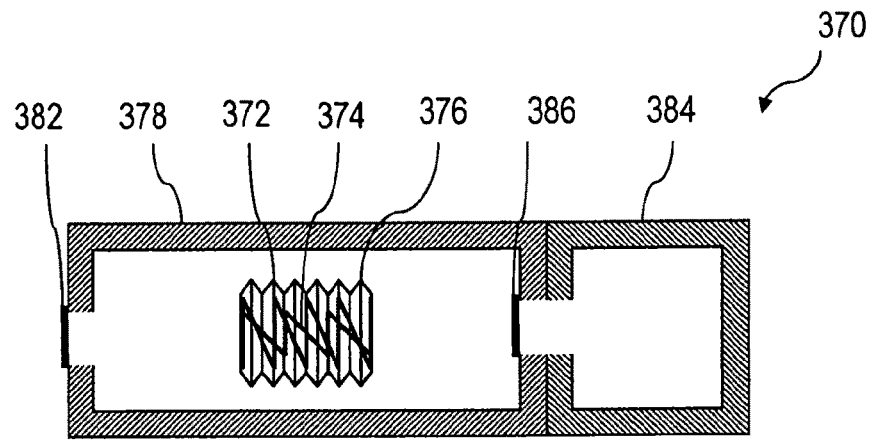
FIGS. 49, 50 and 51 are schematic side views of a shape memory material activated device with a self-refilling shell, before activation, during activation and during refilling, respectively.

FIG. 49 illustrates a shape memory material activated device 370 comprising a shape memory material spring 372 and a bias spring 374 housed in a pressurant housing 376 that is housed in a shell 378 equipped with an outflow valve 382, an inflow valve 386, and a supply reservoir 384. The device 370 is similar in operation to device 280 illustrated in FIG. 38, with the exception that the shell is of fixed volume. This device is capable of refilling the substance contained in the shell 378 after each release and as such, its service life is not limited to a given amount of substance contained in the shell.

Figure 50:
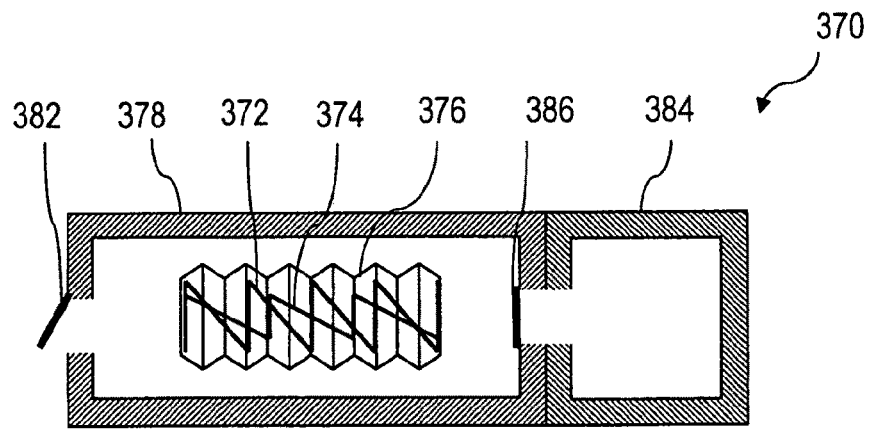

FIG. 50 illustrates the shape memory material activated device 370 while the shape memory material spring 372 is undergoing shape recovery. The pressure exerted on the substance contained in the shell forces the creation of a path to release the substance. In this case, the path is created through the outflow valve 382 that allows one-way flow only.

Figure 51:
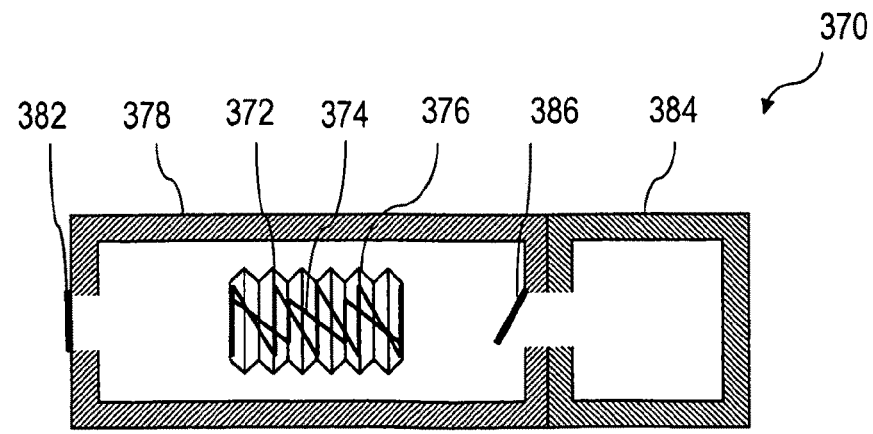

FIG. 51 illustrates the shape memory material activated device 370 while the shape memory material spring 372 is cooling down to the martensitic state and is undergoing reverse shape recovery. During cooling from austenite to martensite, the shape memory material spring 372 is forced to contract by the bias spring 374 and in the process, the pressurant housing 376 is forced to shrink. This reduces the pressure inside the shell 378 relative to the pressure of the supply reservoir 384 and creates a path to admit the substance from the reservoir. The path is created through the inflow valve 386 that allows one-way flow only.

This shell is capable of continuously renewing its substance. With each temperature cycle, it releases the substance to its surroundings or to an enclosure during the first half of the cycle and admits the same or a different substance from the reservoir during the second half of the cycle. To assure continuation of the process of releasing and admitting the substance the supply reservoir, depending on the application, may be refilled by means such as a supply tube, a syringe or a pump.

Figure 52:
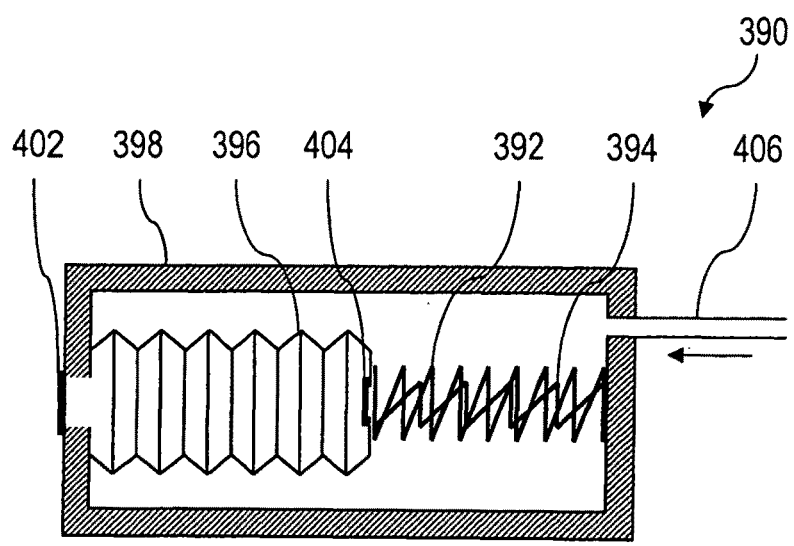
FIGS. 52, 53 and 54 are schematic side views of a shape memory material activated device with a self-refilling bellows type pressurant, before activation, during activation and during refilling, respectively.

FIG. 52 illustrates a shape memory material activated device 390 comprising a shape memory material spring 392, a bias spring 394, a pressurant housing 396 equipped with an outflow valve 402 and an inflow valve 404, all housed in a shell 398 that is connected to a supply line 406. In this case, the pressurant 396 functions mostly as a means for substance transfer and a pressure generator. The outflow valve 402 and the inflow valve 404 attached to opposite ends of the pressurant housing 396 open and close out of phase with the heating and cooling cycle of the shape memory material spring 392, while the shell is being supplied continuously with the same or a different substance by the supply line 406.

Figure 53:
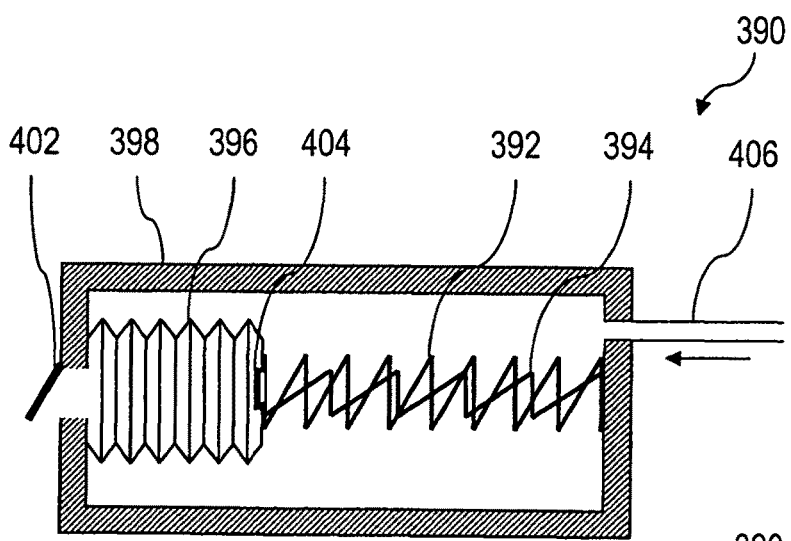

FIG. 53 illustrates the shape memory material activated device 390 while the shape memory material spring 392 is undergoing shape recovery. Initially, the pressurant housing 396 is filled with the shell's substance, during shape recovery its internal pressure increases as the pressurant housing 396 is shrinking and creates a path through the outflow valve 402 to release the substance while its volume is decreasing. The path may also be created by other means such as permeable or semi-permeable shell walls or one-way flow membranes. Release may also take place through pre-existing paths through which the substance flows only when there is a minimum pressure differential between the shell's surroundings and the inside of the pressurant housing. Once the pressure differential drops below the minimum value, or the two pressures equalize, the flow stops.

Figure 54:
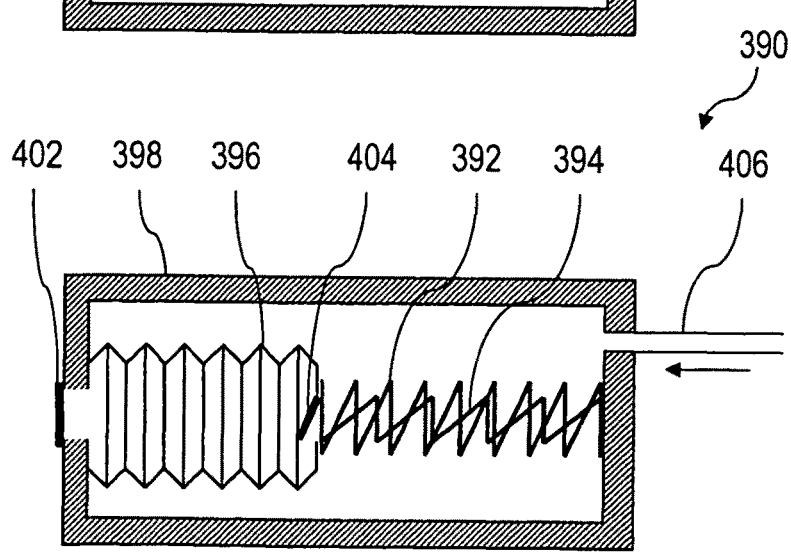

FIG. 54 illustrates the shape memory material activated device 390 while the shape memory material spring 392 is cooling down to the martensitic state and is undergoing reverse shape recovery. During cooling from austenite to martensite, the shape memory material spring 392 is forced to contract by the bias spring 394 and in the process, the pressurant housing 396 is forced to expand. This reduces the pressure inside the pressurant housing 396 relative to the pressure of the shell 398 and creates a path through the inflow valve 404 to admit the substance while its volume is increasing.

In both devices 370 and 390, by reversing the direction of the one-way valves the substance can be admitted into the shell and released into a supply reservoir, thereby reversing the direction of the mass transfer. In addition, the release or admission of the substance can take place during either the heating or the cooling part of the temperature cycle. Simply, in one case the shape memory material expands during heating while in the other it contracts.

Similarly to the variable volume concept, the renewable shell concept presents the advantage of path creation and substance release only when the shape memory material undergoes shape change, either by a shape recovery force or by a biased force. The amount of released substance is controlled by the volume change of the pressurant housing. In addition, the refill substance admitted in the shell may be of changing physical or chemical characteristics, that, when combined with the shell's substance, produces a new color, a modified drug or higher strength drug or some other new feature with each release.

Figure 55:
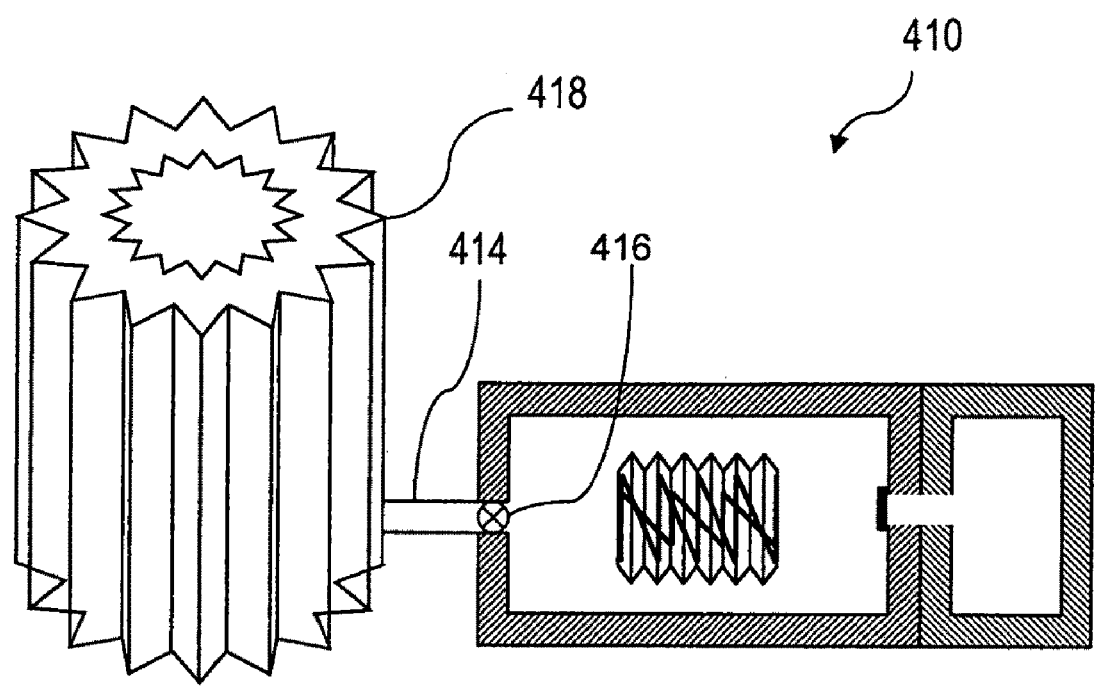
FIG. 55 is a schematic side views of a shape memory material activated device with a self-refilling shell connected to a hollow tube with axial folds (shown in perspective)

Both concepts of variable volume and renewable shell may be used for similar applications. In addition to releasing a substance, either device may be utilized to change the volume and or the pressure of another reservoir. This is a desired benefit in cases where there is a need to change the volume of a reservoir of a given geometry in a predetermined direction or orientation. FIG. 55 illustrates a device 410 where the release of the substance expands a hollow tube with axial folds 418 radially. A renewable shell device similar to 370 coupled with a tube 414 that contains a unidirectional flow valve 416 are utilized for this purpose. As the substance is released into the reservoir, both its outside and inside diameters increase. The radial expansion may be utilized to relieve the pressure around an object or to increase it if the substance's flow is reversed and the reservoir begins to shrink radially. Further, the reservoir may release the substance to its surroundings through permeable walls and the like, enabling the device to act as both a substance release and a mass distribution device.

Time Dependent Temperature Activated Systems

FIGS. 56-68 relate to time dependent temperature warning systems as will be described below. The time dependent temperature warning systems can be used as an indicator of the time that the device has been exposed above or below a predetermined temperature. The time dependent systems may also be used as a drug delivery system, in which case the system is considered as a time compensating drug delivery system.

FIGS. 56-59 illustrate one embodiment of a time dependent device 500 having a shell 502 that consists of two members capable of creating a path upon separation. The first member is a closing part 506 in the form of a conical plug and is in contact with a second part 505, the sealer. A shape memory material activator 508 applies pressure and keeps the two members 505 and 506 in contact along a surface 504. Contact between the two members is maintained until a predetermined temperature is achieved. The device 500 also preferably includes a seal 510 bonded to the sealer 505, made of a material such as an elastomer capable of swelling through absorption of liquid. The device 500 utilizes the same concept as the "shell" described above, i.e. release and/or mixing two substances. However, in the present case, a shape memory material spring 508 is used that is trained in two way shape memory effect. The substance to be released from the shell 502 may be provided within the sealer 505 and/or within the closing member 506. However, for purposes of simplicity in the following discussion, the substance to be released, called the source, will be considered to be contained within the closing member 506.

In the embodiment of FIGS. 56-59, the path created through the shell wall, to release the substance contained within the closing member 506 and/or the sealer 505 at the predetermined temperature, is not permanent. The path is created by the controlled separation of the shell into two parts, the sealer 505 and the closing member 506. The shell opens every time the predetermined temperature is reached, remains open as long as the temperature does not drop below this level, and closes once the temperature drops. While the shell 502 remains open, the substance is released continuously but the release stops when the shell closes. With each opening the drug or other substance may be released to a surrounding reservoir (not shown) in a continuous manner.

Figure 56:
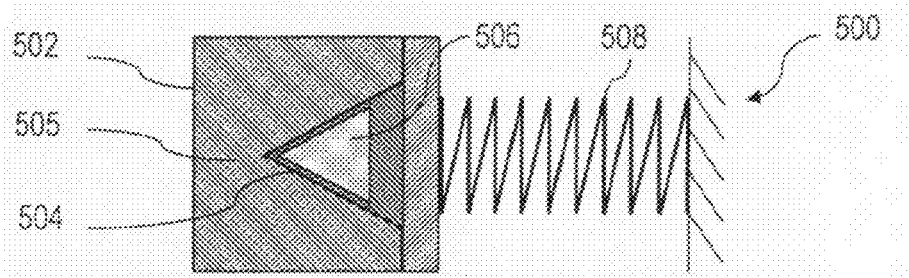
FIG. 56 is a schematic side view of a shape memory material activated time dependent release system in an as installed position.
Figure 57:
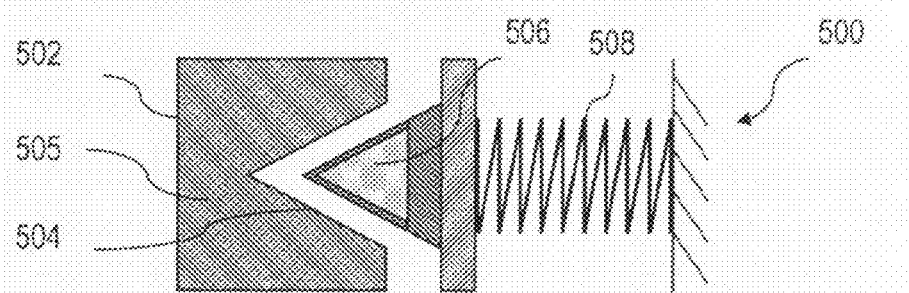
FIG. 57 is a schematic side view of the shape memory material activated time dependent release system of FIG. 56 in an open position.
Figure 58:
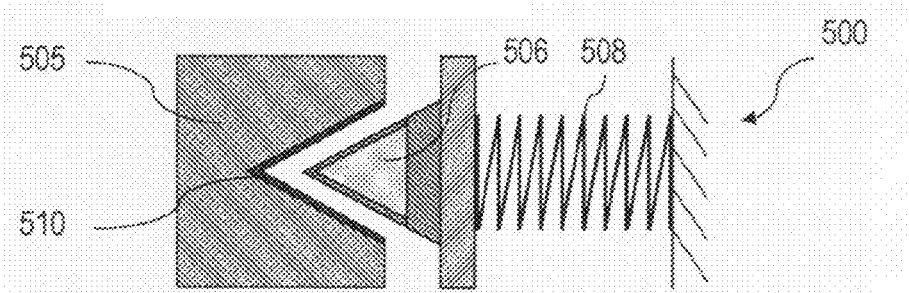
FIG. 58 is a schematic side view of the shape memory material activated time dependent release system of FIG. 56 in an open position with a sealer which has absorbed moisture.

FIG. 56 illustrates the sealer 505, the closing member 506, and the shape memory material activator 508 in a closed position before an initial opening. FIG. 57 illustrates an initial opening of the shell 502 and the creation of a path along the contact surface 504 by the movement of the closing member 506 in response to achieving a predetermined temperature. After opening, the seal 510 provided in the opening 504 comes into contact with the fluid of the enclosure and begins to swell as shown in FIG. 58. When the predetermined temperature for opening is no longer achieved, the closing member 506 moves back and comes into contact with the seal 510 and closes the path, thereby preventing passage of fluid through the opening 504.

According to the embodiment of FIGS. 56-59, if the substance contained in the shell 502 is in the solid state, the surrounding reservoir (not shown) should contain a fluid to dissolve it. On the other hand, if the substance contained in the shell 502 is in liquid state it can be released to either an empty reservoir to be delivered to the patient without further mixing, or to a fluid filled reservoir to be mixed with fluid prior to delivery. Control of the mixing rate in the solid/liquid case is by direct contact whereas in the liquid/liquid case control of the mixing rate is done through a membrane or filter which is part of the sealer's and/or closing member's wall. Because of the continuous release, irrespective of its solid or liquid phase and irrespective of whether it is a dye or a drug, the substance within the shell will be considered as the "source" herein. The shell's liquid source should be under positive pressure relative to its surroundings, with no gas entrapment, to assure wetting of all membrane walls and a constant interface between the two fluids irrespective of orientation. Additionally, pressurization prevents the reverse flow of the substance outside of the shell in the enclosure into the source's housing. Reverse flow can also be prevented with the use of a one way membrane. The principle of osmosis can be utilized to transport the source through the membrane wall provided that the membrane material and liquids of both shell and enclosure are selected such as to satisfy the requirements for osmosis to take place. Pressurization can be accomplished by several means such as the use of a spring as a piston, a gas bladder, a compressed elastomer or a compressed superelastic spring pressuring the dye enclosure. The shape of the shell's solid state source or its liquid state container can be conical (as shown), spherical, or any shape that can be sealed when pressed against an organic material such as an elastomer having springback properties with minimum compression set or creep. Basically, the source forms the male part and the sealer the female part of the device. When in contact with each other there is no open path and no release of the substance from the shell.

Figure 59:
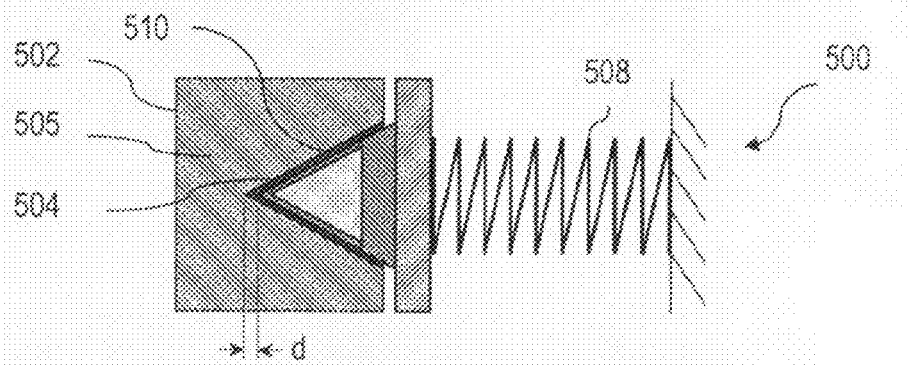
FIG. 59 is a schematic side view of the shape memory material activated time dependent release system of FIG. 56 in a closed position after the sealer has absorbed moisture.

If the seal 510 is made of material that swells with exposure to fluids, the swelling (increase in volume and thereby linear dimensional increase, distance d in FIG. 59) will account for any loss of shape memory with cycling of the shape memory material activator 508.

Figure 60:
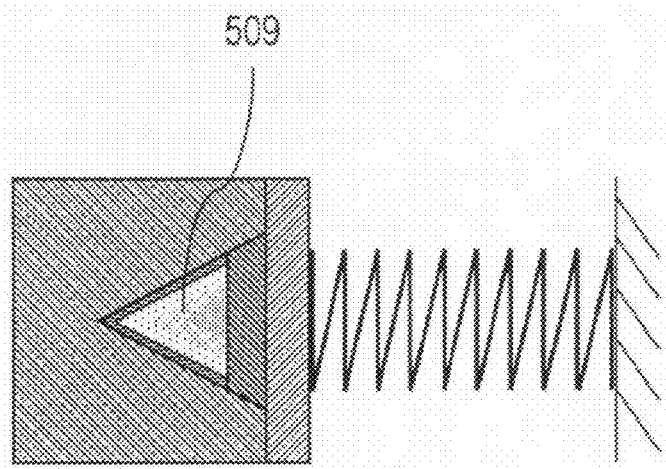
FIG. 60 is a schematic side view of the shape memory material activated time dependent release system of FIG. 56 containing a variable composition source.
Figure 63:
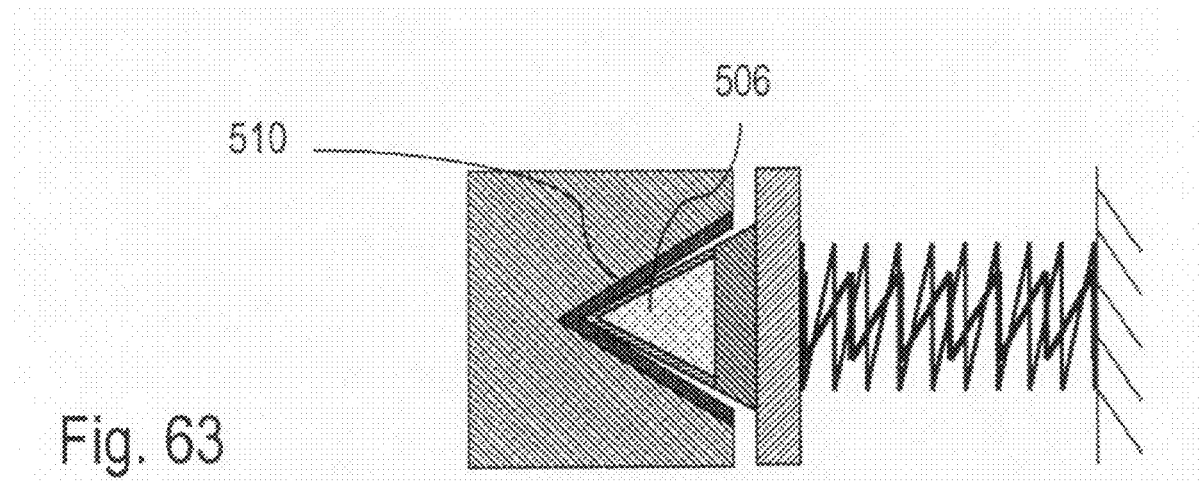
FIG. 63 is a schematic side view of a shape memory material activated time and temperature dependent release system in a partially opened position.
Figure 64:
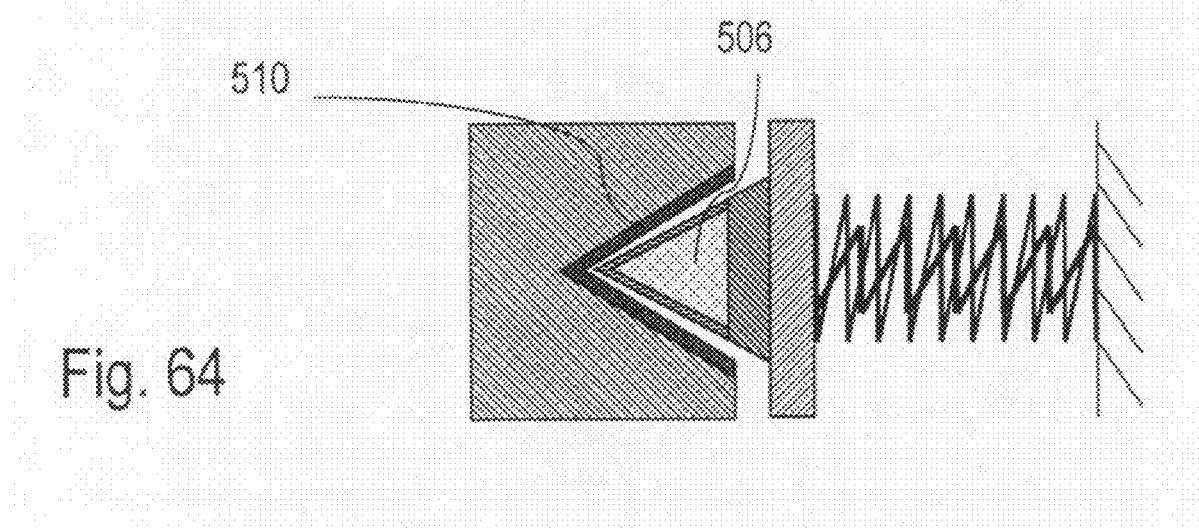
FIG. 64 is a schematic side view of the shape memory material activated time and temperature dependent release system of FIG. 63 in a fully opened position.

If the source is in the solid state and in the form of a cone, sphere, or other shape, it must be dissolved uniformly such that it can be sealed at the end of each cycle. In the case of a time compensating drug delivery system, the solid state drug source can contain a gradient of the active ingredient such that the released drug increases in potency with increased exposure time. In the case of a time integrator indicator the dye can consist of several layers of different colors (with one color being exposed at any given time) so that different colors are produced with increased exposure time. Color change will be indicative of the time exposure above or below the predetermined temperature. FIG. 60 illustrates a device similar to device 500, illustrated in FIG. 56, containing a variable composition source 509. The variation in composition is depicted with the density of the dots in FIG. 60. For better accuracy, the surface of the seal 510 in contact with the source 506 must be sealed so that any absorbed liquid will not continue to dissolve the source. Also, the shape of the drug source must be designed such that the liquid at the interface is displaced during the completion of the cycle, i.e. upon return to the martensitic state. One way this is achieved is to allow for more cushion at the first contact point, i.e. peak of cone or sphere, and decrease the amount of cushioning as the contact continues. An example of this configuration is shown in FIGS. 63 and 64 of which FIG. 63 illustrates a partially recovered position and FIG. 64 illustrates an open position. In other words, it may be preferred to prevent either instantaneous contact or reverse (base to peak) contact.

Figure 61:
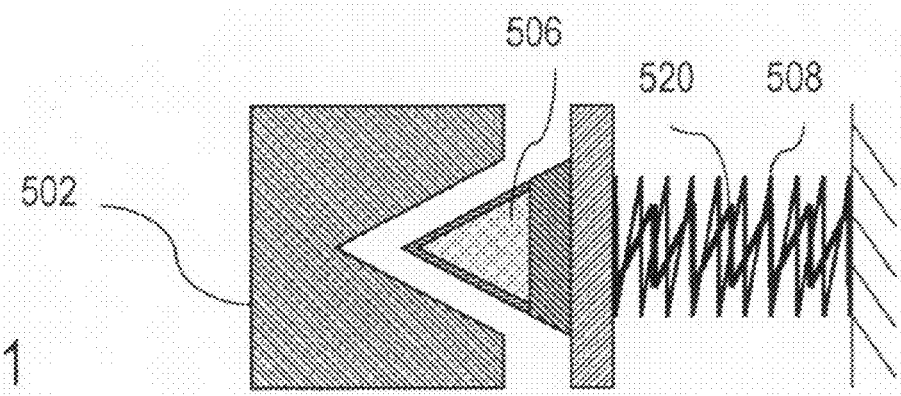
FIG. 61 is a schematic side view of a shape memory material activated time dependent release system with a bias spring.

Instead of using a shape memory material trained in two way shape memory effect, the cycling can also be accomplished with the incorporation of a bias spring 520 along with the shape memory material spring 508, as shown in the embodiment of FIG. 61. The system of FIG. 61 will assure that there is sufficient pressure to keep the source sealed during the shell's closing period by the use of the bias spring 520.

The time integrator indicator devices of FIGS. 56-68 are capable of integrating exposure to a single temperature or temperature range with respect to time. Additionally, they are capable of giving more weight to higher (or lower) temperatures. In other words they are capable of non-linear integration of temperature with time. The time-temperature history can be presented through a color change of the indicator.

The same concept can be used without the swelling effect. In this case the seal must provide the cushioning and sealing, and must exhibit minimal creep in the expected operational temperature range. Again, a bias spring can be used to minimize the amnesia of the shape memory material activator and assure sufficient contact pressure to displace the fluid from the sealer/drug source interface.

Figure 62:
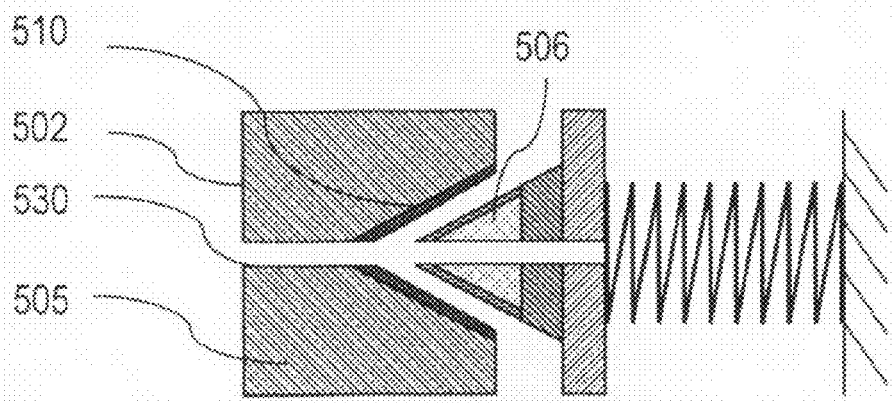
FIG. 62 is a schematic side view of a shape memory material activated time dependent release system with a central hole.

In both cases, swell and no swell of the seal 510, the source 506 can be made the stationary member and the sealer 505 the moving one. In addition, as shown in FIG. 62, one or more holes 530 can be incorporated in both the sealer 505 and the source or closing member 506 to eliminate the possibility of vacuum locking.

The concept used for the time dependent shell described above with respect to FIGS. 56-62 can be extended to become a time and temperature compensating drug delivery system and a time and temperature integrator indicator. This requires one of the two following design changes.

The first change requires selection of the source material, membrane (if one is used) and, enclosure fluid such as to control the release or mixing rates with respect to temperature. In other words, release is both material and temperature dependent. With this system, at a constant temperature above $A_s$ and with increasing time the drug release rate remains constant as time goes by. However, the release rate increases as the temperature increases. If a solid state drug source is used which is built of different strength layers, the release rate will be increasing incrementally, as each layer is dissolved, with either time itself at constant temperature or time and temperature. The strength levels and the rate of change must be calibrated for specific applications, as each application requires different temperatures and times. This concept has only a lower temperature limit. The temperature application range is bounded only at the low end which is the $A_s$ temperature. Above this temperature the path through the shell wall remains open and release or dissolution of the source is continuous. Upper bound is only limited by material capabilities.

The second change requires modification of the geometry of the source such that there is a progressively larger gap, tip to base, between the sealer and the source, as shown in FIGS. 63 and 64. As the temperature increases above $A_s$, the shape recovery progresses and the source or closing member 506 is withdrawn away from the seal 510, the interface area between the source and the fluid of the enclosure increases. This increase results in an increased release (or mixing) rate that is proportional to the increase in the interface area. By varying the geometry of the source (conical, spherical, etc.) the rate of the interface area change is controlled with respect to the withdrawing rate of the source. In return, the degree of linearity and the slope of the $A_s$ to $A_f$ and $M_s$ to $M_f$ segments of the hysteresis curve, as influenced by the bias spring, determine the withdrawal rate of the source. With this concept, at constant temperature above $A_s$ the release rate stays constant (assuming linearity with respect to mixing ratio) but it increases with increasing temperature. Applicability of this concept is limited to the temperature range of the hysteresis curve of the shape memory material as there is no further displacement produced by the shape memory material above $A_f$ and therefore no further temperature compensation takes place. During cooling, the process is reversed except that the $M_s$ to $M_f$ temperature segment of the hysteresis curve determine the return rate of the source.

With this design change, the drug release rate of the time and temperature compensating drug delivery system remains constant with time at a constant temperature but it increases as the temperature increases. The increase can be designed to be either linear or non-linear. The increase in release rate translates into an increase in drug strength. In the case of time and temperature integrator indicator, the mixing rate of the dye remains constant with time at constant temperature and increases the color depth of the enclosure's fluid at a constant rate. The mixing rate of the dye increases with temperature, linearly or non-linearly, and in return it accelerates the increase in color depth accordingly. Additionally, the dye source, if used in the solid state, can be made up of several layers of different colors. Each layer as it is mixed with the enclosure's fluid will produce a new color that will reflect, in a more discerning way, the time and temperature history.

As shown in the embodiments of FIGS. 61, 63, and 64, both the shape memory material activator 508 and the bias spring (s) 520 can be placed in parallel with the shell, either outside or inside, respectively.

Figure 65:
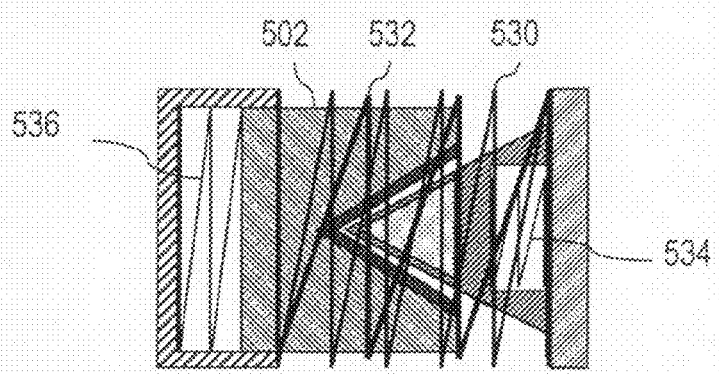
FIG. 65 is a schematic side view of an alternative shape memory material activated time and temperature dependent release system.

As shown in FIG. 65, the shape memory material activator spring 530 is provided outside of the shell 502 and the bias spring 532 is provided outside of the shell. Two additional springs are shown, including a pressurant spring 534 and a compensating spring 536. The pressurant spring 534 is used to keep the liquid source under pressure in order, as mentioned above, to keep the walls of the membrane wet. Alternatively, the pressurant spring 534 can be replaced with a pressurized bladder. The compensating spring 536 is used to compensate for any increase in swelling, minimize the effects of any compression set of the sealing means or minimize any minor effects of any non-uniform dissolution of a solid state source.

Figure 66:
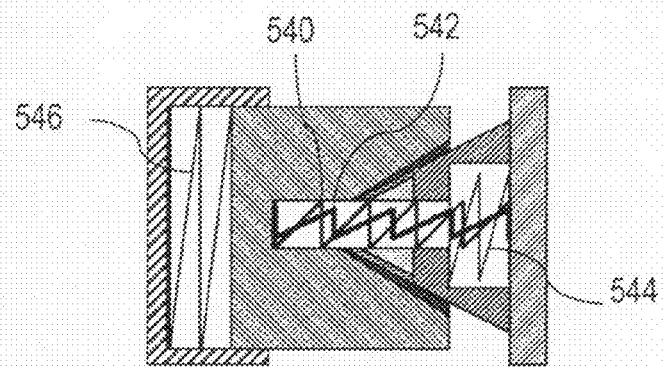
FIG. 66 is a schematic side view of a further alternative shape memory material activated time and temperature dependent release system.

FIG. 66 illustrates an alternative arrangement for the device of FIG. 65 wherein a shape memory material activator spring 540 and a bias spring 542 are provided in a central hole and the pressurant spring 544 and compensating spring 546 are provided as in FIG. 65. Attributes for each concept can be combined to produce a device with more degrees of freedom and more versatility.

Figure 67:
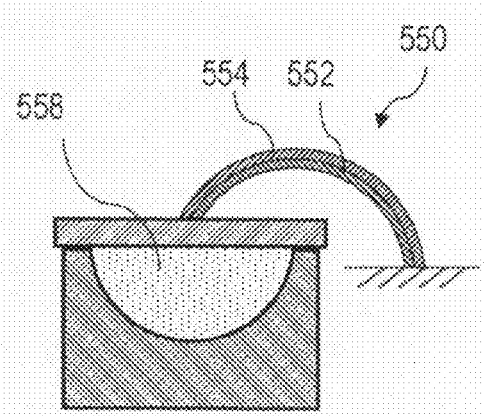
FIGS. 67 and 68 are schematic side views of a dome shaped, shape memory material activated time and temperature dependent release system in a closed and open position.
Figure 68:
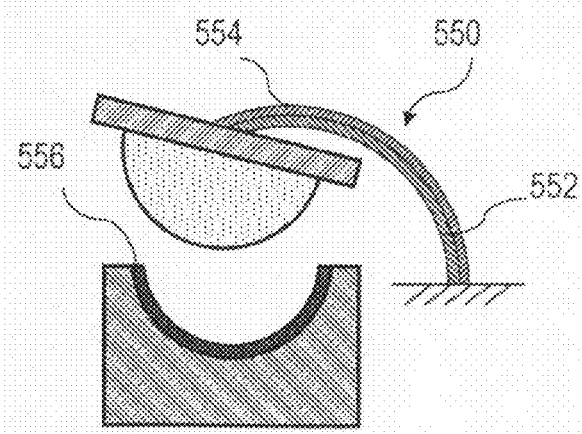

FIGS. 67 and 68 illustrate an alternative embodiment of a shape memory material activated device 550 using leaf springs and a dome shaped closing member. As shown in FIG. 67 a shape memory material leaf spring 552 with an attached or adjacent leaf bias spring 554 can be substituted for the coil springs. Also, in the embodiment of FIGS. 67 and 68, the sealer 556 and the closing member 558 are in the form of dome shaped members.

In all the embodiments discussed herein, the closing member or the shell can be made the moving part and the other part the stationary one simply by exchanging places of the shape memory material and bias springs with the compensating spring.

In all the embodiments described herein, more than one shell, containing the same or different substances, such as drugs of various degrees of potency in the case of a drug delivery system, can be used with a single enclosure. They can all be activated at the same or different temperatures. For shape memory materials to be activated at different temperatures, the chemical composition or the processing of the material including the amount of deformation from the austenitic shape must be different. Multiple shells will allow for several reactions/mixings between the two substances to take place. As an example, in a drug delivery system with multiple shells, shell #1 contains a drug that is to be released at a predetermined temperature while shell #2 contains the same drug of higher potency to be released at a higher predetermined temperature. As a second example, if each shell contains a different color dye, the fluid of the enclosure will obtain a different color at each predetermined temperature. Each color will correspond to a different temperature that will be indicative of a different level of warning.

Additionally, the reverse shape recovery concept described earlier can be utilized to create the path during cooling of the shape memory material instead of heating. In this case, the substance will be released once the temperature falls below $M_s$ producing the same effects as in the case when release takes place when the temperature rises above $A_s$. Finally, it should be understood that if the shape memory material activator is not trained in a two way shape memory effect or no bias spring is utilized, the path creation process will not be reversible and once the shape recovery takes place, the shell will stay open permanently. In this case, the same effects will be produced but would not be repeated with temperature cycling. However, if other features such as pressurization of the shell contents and variable source concentration are maintained, the device is able to produce integrated release with respect to time once the path is created.

Peelable Shell Systems

The devices illustrated in FIGS. 69-77 relate to the use of a shape memory material activator to peel a barrier layer away from a shell creating a path through the shell. The peelable shell devices may be used to enhance the characteristics of the transdermal (patch) and implant type drug delivery systems by converting them from continuous delivery systems to "on demand" drug delivery systems. The peelable shell devices may also be used for temperature warning devices, however, these devices will be described primarily with respect to the delivery of drugs. The operating principle of the peelable shell systems is the same as for the temperature warning devices, the difference being that the shell contains a drug instead of a dye. The drug is released into a reservoir that is specifically designed to transmit it to the patient. The reservoir may contain another drug, in either the solid or liquid state, that is to be mixed with the one that is released.

For purposes of background, there are two types of transdermal drug delivery systems, also known as patches. One that contains the drug in a reservoir and releases it through a rate controlling membrane, and a second one which contains the drug in a polymeric matrix which is applied directly to the skin. In both cases the skin begins to absorb the drug as soon as the protective liner is removed and the patch is adhered to the skin. The device presented herein takes the patch concept one step further and advances it to be qualified as an on demand transdermal drug delivery system. This is accomplished with the addition of a peelable barrier between the drug and an intermediate layer of the transdermal drug delivery system or the drug and the skin. This layer is automatically removed (peeled away) only, after the patch has been applied to the skin and only when and if there is demand for the drug.

Automatic removal of the barrier is achieved with the incorporation of a shape memory material activator in the device. Demand is determined by several ways. In the case of fever, the shape memory material can act either as both a sensor to detect the rise in temperature and as an actuator to remove the barrier layer at a predetermined temperature or simply as an actuator with the sensor being replaced with a separate temperature detection device. In the second case, activation of the shape memory material will require an external energy source to heat it and enable it to undergo the shape recovery process. In other cases such as cardiovascular and hormonal drugs, the shape memory material device is only used as an actuator with the sensing provided by added detectors. When detectors are used, microprocessors can also be incorporated to provide additional features to further enhance the self controlled characteristics of the device.

An added feature of this system is the fact that actuation can also be achieved manually. This is accomplished with the application of heat source such as a hot towel to the device. For this to work, the temperature of the applied heat source must be high enough for the shape memory material activator to undergo shape recovery. On the other hand, this temperature should not be so high as to alter the nature or potency of the drug nor should it change its ability to be absorbed by the skin.

In addition to the peelable layer, in the case of the drug reservoir type transdermal device, the shell can be placed inside the reservoir. Release of the drug into the reservoir takes place at the predetermined temperature. The reservoir may contain another drug or carrier with which it gets mixed prior to the absorption process.

Figure 69:
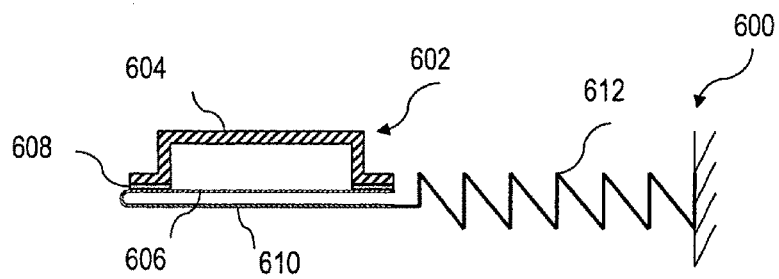
FIG. 69 is a schematic side view of a peelable shape memory material activated time dependent release system.
Figure 70:
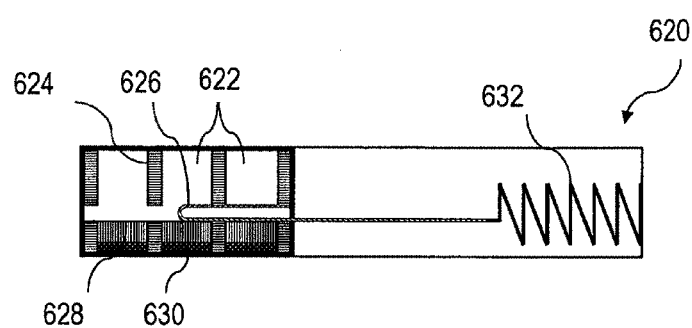
FIG. 70 is a schematic side view of a peelable shape memory material activated time dependent release system in the form of a transdermal patch.

In all cases, multiple shells can be used with each device to enable incremental adjustment of the drug dosage with respect to fever or other parameters. FIGS. 69 and 70 illustrate the basic components and operating principle of the peelable shell device 600. For a temperature warning device, the device 600 utilizes the mixing of two substances to produce a color change once the predetermined temperature of the device is reached. For a drug delivery device, the device 600 releases a drug from the shell. The device 600 consists of a shell 602 formed by a rigid or semi-rigid backing 604 and a protective liner 606. The protective liner 606 is attached to the backing 604 by an adhesive 608. The protective liner 606 is connected by a pull tab 610 to a shape memory material activator 612. The shell 602 for the temperature warning device is positioned within or adjacent an enclosure which may contain a second substance.

The peelable shell drug delivery system consists of substantially the same components as the temperature warning device described above except, the substance delivered from the shell is a drug. The device incorporates a drug containing shell inside a drug reservoir. The shell encapsulates the drug to be released into the reservoir that will deliver it to the patient as a transdermal or implanted system. The reservoir can be either empty to receive the drug contained in the shell or filled with another drug to be mixed with the one released by the shell. The second option provides the advantage of extending a drug's shelf life if mixing is to take place at the time of application instead of the time of manufacturing.

Again, activation of the device 600 takes place when a shape memory material activator 612 peels the protective liner 606 which creates a path through the shell 602 for the drug to be released to the reservoir. The shape memory material can be placed either in the inside or the outside of the shell and must be compatible with the drug or be coated with a coating that is compatible with the drug. For transdermal systems verification of the release can be provided through a transparent window in the reservoir that will exhibit a color change.

As shown in the embodiments of FIGS. 69-77, the path through the shell 602 is created by a peeling process. The shell 602, that may contain a dye or a drug, is formed by two parts; the rigid or semi-rigid backing 606 and the flexible protective liner 606 held together with the adhesive 608. With the incorporation of a shape memory material activator 612 the protective liner 606 is peeled away automatically once a predetermined temperature is exceeded, thereby creating a path for the substance within the shell 602 to be released.

As shown in the embodiments of FIGS. 70-75, the shell can be divided into multiple individual shells with each shell containing the same source such as the same drug of equal or increased strength, or a different drug. As the temperature increases more shells are peeled away. With this incremental process the drug strength or color depth of the enclosure changes with each shell that is peeled away. Each color is indicative of exposure to a specific temperature. In the case of on demand drug delivery systems, the drug can be released for direct absorption by a mammalian body through a rate controlling membrane or it can be mixed with another drug prior to the absorption process. Peeling also includes the process of removing part of the shell wall by tearing or drawing (such as pulling, pushing or rotating) whether the part of the wall is adhered to the shell, scribed, notched, scored, grooved or otherwise prepared for removal. In addition, it includes mechanical unlocking (such as zipping open) of the shell.

FIG. 70 illustrates a transdermal drug delivery device 620 having multiple shells 622 separated by barriers 624. A peelable protective liner 626 is provided between the shells 622 and a rate controlling membrane 628 and is activated by a shape memory material activator 632. An adhesive layer 630 may be used to affix the device 620 to a patient.

Figure 71:
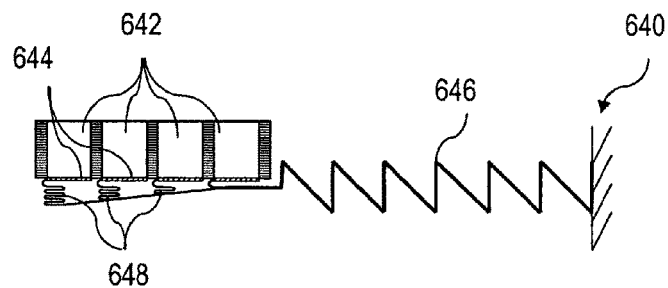
FIG. 71 is a schematic side view of a peelable shape memory material activated time dependent release system with multiple shells.
Figure 72:
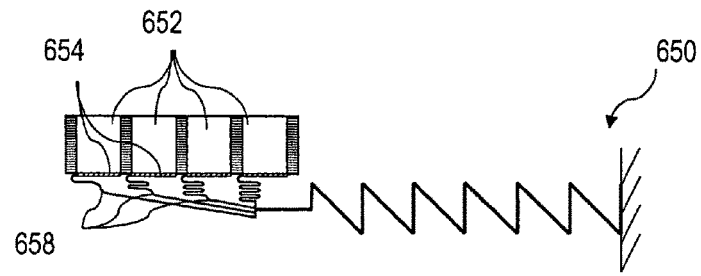
FIG. 72 is a schematic side view of an alternative peelable shape memory material activated time dependent release system with multiple shells.

FIGS. 71 and 72 show a similar concept of multiple shells 642 and a single activator 646 with each shell having its own liner 644. This concept has the advantage of minimizing the overall length of the device and by adjusting the length of the individual tabs the temperature range between peelings can be adjusted accordingly. FIG. 71 shows a device 640 having multiple shells 642 connected in series with individual tabs 648 of varying lengths connected in series such that the shells on a right hand side of the device are peeled first.

FIG. 72 shows a device 650 having multiple shells 652 with individual liners 654 and individual tabs 658 of varying lengths connected in parallel such that the shells on the left hand side of the device are peeled first. With this concept, peeling of each shell is independent of the others in the group.

In the embodiments of FIGS. 71 and 72, the shells are peeled away at equal temperature ranges provided the movement of the shape memory material spring is linear with respect to temperature. The length of the individual tabs may be equal or unequal which results in a peeling sequence of even or uneven temperature ranges. The peeling rate with respect to temperature can also be controlled with the width of the individual shells. In an alternative embodiment, in which tabs are provided of equal length, the shells are peeled simultaneously.

Figure 73:
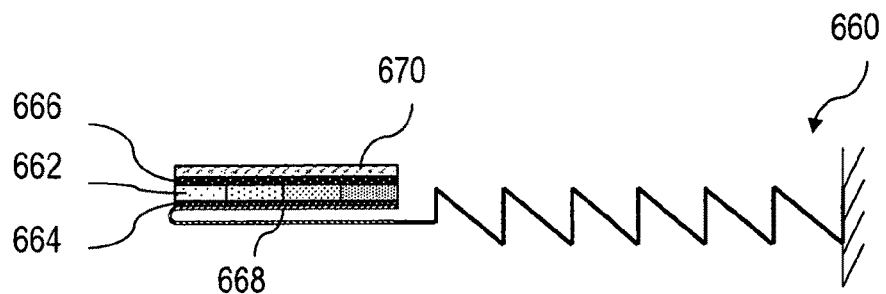
FIG. 73 is a schematic side view of a peelable shape memory material activated time dependent release system for delivery of a powdered substance.

FIG. 73 shows a concept in which the shells are filled with a solid state substance, such as a compacted powder of drug or dye. In a device 660 of FIG. 73, the powder 662 is sandwiched between two adhesive layers 664, 666 and together with the sandwiched source constitutes the shell. The adhesive layer 666 connects the shell to a backing 670. During shape recovery the protective liner 668 on the adhesive layer 664 is peeled away at a rate corresponding to the temperature change exposing the substance 662 to the fluid of the enclosure in continuous fashion. In this case, the substance 662 is a true source. The advantage of this system is the fact that different source strengths or different sources can be used along the length of the strip. This concept is equivalent to time-temperature dependent systems except, it is restricted to a single one half of a temperature cycle, either $A_s$ to $A_f$ or $M_s$ to $M_f$.

The peelable shells can be arranged in different sizes and patterns to accommodate different requirements of temperature spans, types of sources, sequence of releases etc. In addition, the configuration of the peelable protective liners can be varied to accommodate different requirements. Some of the different patterns include shells of different widths, shells arranged in both series and parallel fashion, and shells with circular shaped or blister type drug containing cavities in series and/or parallel.

For transdermal systems the device should be designed such as to prevent any deformation of the shape memory material element during handling and application of the patch in order not to affect its performance. It is recognized that the patch is not applied to rigid flat surfaces and each application is unique in terms of geometry. In order to avoid deformation of the shape memory material during the application process, the shape memory material can be housed separately from the patch in a rigid housing and be connected to the barrier layer with a flexible conduit.

Figure 74:
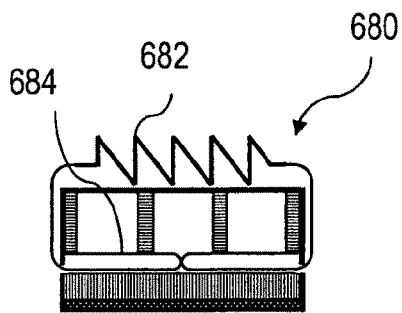
FIGS. 74 and 75 are schematic side views of a peelable shape memory material activated time dependent release system with a peelable liner pulled from two sides.
Figure 75:
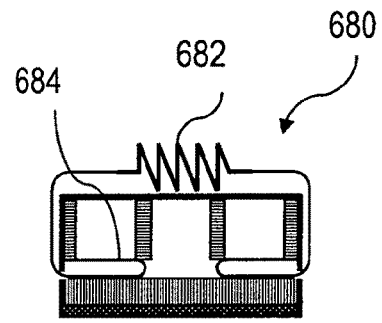

FIGS. 74 and 75 show an alternative embodiment of a transdermal patch device 680 with the shape memory material activator 682 placed on top of the patch. In FIG. 75, the shape memory material activator 682 has pulled the barrier 684 from two sides. However, it should be understood that the barrier may also be pulled from one side of the patch.

Figure 76:
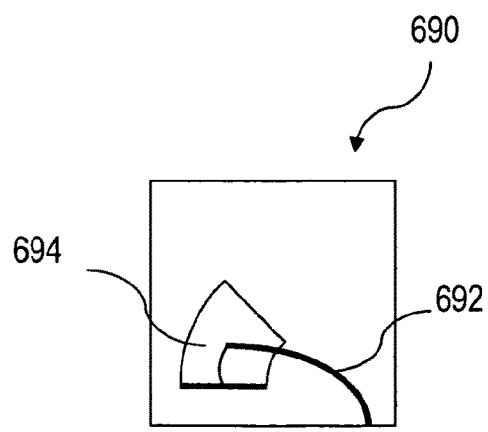
FIGS. 76 and 77 are schematic side views of a peelable shape memory material activated time dependent release system with a rod shaped activator.
Figure 77:
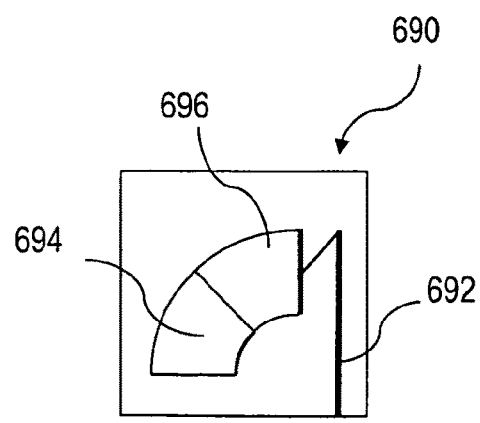

Besides the use of the coiled shape memory material spring as shown in FIGS. 69-75, the peelable shell device may include a leaf spring or other shape memory material activator to peel the liner. FIGS. 76 and 77 show a peelable embodiment of a shape memory material activated device 690 in which the shape memory material activator 692 is in the form of a leaf spring. The shape of the shell 694 and the peelable liner 696 should accommodate the movement of the shape memory material activator 692. As with the shape memory material coil spring, a multi-shell construction can also be used with the leaf spring. In both cases, coil spring or bent wire, shells with different geometry clustered together in different patterns can be used.

It should be understood that even though in all peelable concepts described herein, the path creation took place by pulling the tab of the peelable layer while the shell remained stationary; the same can be achieved by holding the tab stationary and moving the shell by coupling it with the shape memory material. The shape memory material can either push or pull the shell, depending on the orientation of the opening, to crate the path and release the substance.

When the drug delivery device is a device of the type where the drug is provided in a matrix the auto-peelable barrier is placed at the bottom of the matrix. An extra liner, between the peelable barrier and the matrix would help minimize the startling effects of the sudden barrier movement during shape recovery. This layer should be transparent to the drug or contain large holes such that the most of the matrix is in contact with the skin. The matrix may be segmented and each segment having its own barrier. The barriers are removed in a "curtain" fashion with each curtain attached separately to the shape memory material activator. By varying the curtain length, each cell can be exposed to the skin at different temperature. Curtains close to the fixed end of the spring tend to produce smaller movements which necessitates smaller cells. However, by adjusting the curtain length of the individual cells, all cells can have the same size.

Another concept involves two barriers, one stationary and one mobile. Both barriers have alternating strips with cut outs of the same size. Initially, the two barriers are placed out of phase such that the drug matrix is sealed. Upon shape recovery one of the barriers begins to move exposing small areas of the matrix to the skin. At the end of the shape recovery process the strips and cutouts of the two barriers are in phase and maximum exposure is achieved.

In the peelable shell concept, the shape memory material spring is not limited to an outside location only. It can also be placed inside the shell as well. In this case, peeling takes place inside the shell. When ambient heat is used for activation of a peelable shell device this concept presents the advantages that both the shell substance and the shape memory material spring are at the same temperature at all times. This advantage exists for all the types of release devices that, contain the shape memory material inside the shell.

Figure 78:
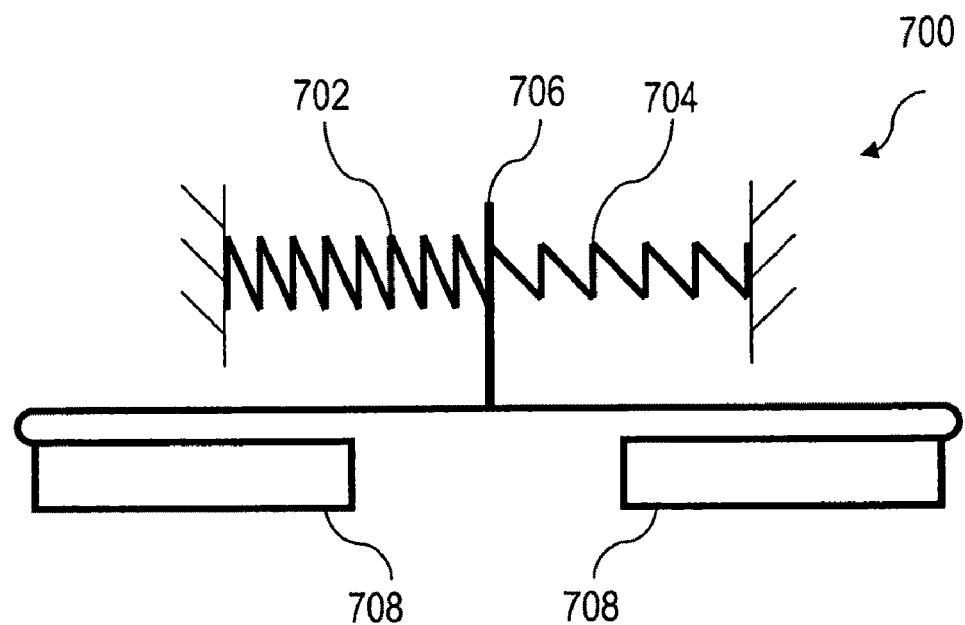
FIG. 78 is a schematic side view of a peelable dual shell shape memory material activated release system for releasing a substance outside of a predetermined temperature range.

FIG. 78 illustrates an embodiment for releasing a substance outside of a predetermined temperature range. Release takes place either above a predefined maximum temperature or below a predefined minimum temperature. This is achieved with a dual shell device 700 comprising a shape memory material spring 702, a bias spring 704, a lever 706 and two peelable shells 708. The peelable layers of the two shells 708 are connected to the lever 706 that is joined to the two springs 702 and 704 at their interface. The lever is free to travel as the interface of the two springs shifts with temperature cycling. When the shape memory material spring undergoes shape recovery and changes length, the interface between the two springs, along with the lever, move in one direction and create a path to release the substance. The path is created in the shell that the lever travels way from by pulling the peelable layer away. When it undergoes reverse shape recovery with temperature reversal, the bias spring moves the lever in the opposite direction such that it pulls the tab of the second shell and creates the path to release the substance. When the device is placed in service, the temperature of the shape memory material spring must be within the hysteresis temperature width. The temperature range within which release will not take place is defined by the width of the hysteresis curve. This concept is not limited to peelable shells only; it can be extended to other shells as well.

An added benefit to peelable shell concept is that besides being a shell capable of releasing a substance, it can also become a temperature indicator without the aid of the released substance. This is achieved by marking or bonding a calibrated temperature strip indicator on the underside of the peelable layer. As this layer is peeled away during shape recovery, the underside is exposed and the temperature strip becomes visible. The highest exposure temperature, if shape recovery is used to create the path, is indicated right at the folding line formed by the peeled portion and the unpeeled portion. This concept can be extended to a peelable temperature indicator without the shell. This is achieved by peeling a layer that is bonded to a substrate that contains a temperature strip indicator. Once the shape recovery begins and the peeling starts, the temperature indicator is exposed continuously with increasing temperature. The latest exposed part is the one corresponding to either the highest or lowest temperature depending whether peeling takes place with rising or falling temperature.

A concept similar to the peelable shell is the sliding cover shell. In this concept, the path to release the substance contained inside the shell is created by the moving of a cover away from a window by a sliding action. The cover may be adhered to the shell and form part of the shell wall. Adhesion can be accomplished by several methods such as bonding, welding, pressure differential, contact stresses, or Van Der Wall forces. Heavy covers may be held in place by gravity without the aid of any adhesion. The cover in turn is connected to the shape memory material spring. Upon shape recovery, the shape memory material spring pulls, pushes or otherwise moves the cover away from the window to release or admit the substance.

Release Rate Control

In all shells described herein, irrespective of how the path is created, a porous barrier such as permeable or semi-permeable membrane may be incorporated between the inside surface of the shell and the substance contained inside the shell. One purpose of this material is to control the transfer rate of the substance as it exits or enters the shell once the path through the shell wall has been created. Another purpose is to control the part of the substance to be released or admitted. An example of this is the release of the volatile part of a substance, in which case the membrane provides the path for the volatile compounds to be released but acts as a barrier to keep the remaining substance inside the shell. A third purpose includes release of a specific substance, among multiple substances contained in the shell, that has the properties to allow it to travel through the membrane. The release rate is mostly controlled by the permeability characteristics of the material and the prevailing pressure differential between the inside contents and the surrounding environment. Pressure differential is achieved with the incorporation of pressurant means to create and maintain a pressure difference for the substances to be released or admitted. Pressurant means may include any of the volume changing devices described herein and the like. In addition, the incorporation of absorptive means inside the shell, such as polymeric matrices, would provide further control by preventing instantaneous release or absorption and stabilizing the existence of any differential pressure. The permeable material can be in the form of a membrane, a coating, film, layer, mesh, screen, strainer, filter etc. Choice of material and design depend on substance to be released or admitted and the desired transfer rate of the substance.

Figure 79:
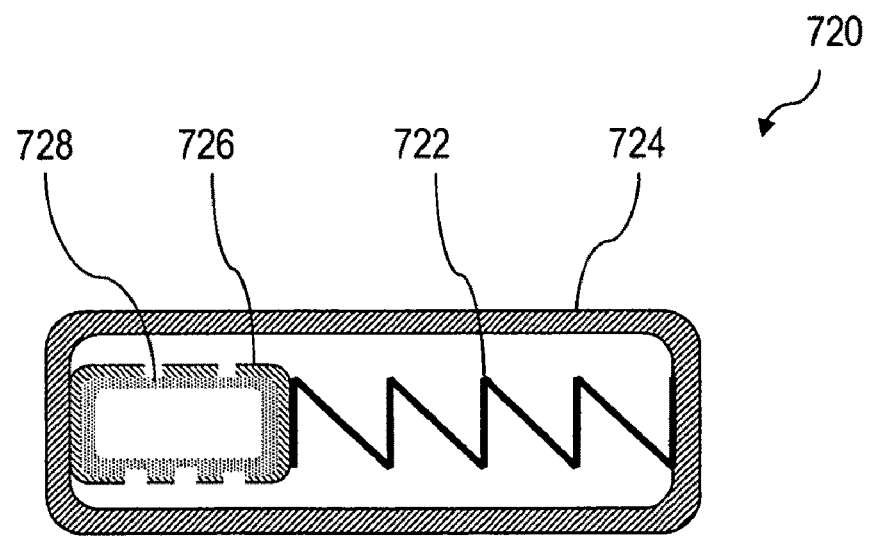
FIG. 79 is a schematic side view of a shape memory material activated device with a membrane between the shell and the substance contained in the shell.

The permeable material can encapsulate the entire substance when the location of the path is indetermined or it can be placed strategically in the location where it is known that the path will be created (predetermined path). Strategic locations are places like the peelable layer of a shell, where the permeable material will provide rate control once the peelable layer is removed. The permeable material may have to be flexible to accommodate any volume changes during the path creation release processes. Further, this jacketing material may not be permeable on its entire surface. By being part permeable and part impermeable, it provides one more degree of freedom to control the transfer or release rate by adjusting the ratio of permeable to impermeable area. This concept of jacketing the substance with a permeable or semi-permeable barrier such as a membrane can be extended to all concepts of release devices presented herein irrespective of how the path is created. FIG. 79 illustrates an example of a shape memory material activated device 720 comprising an enclosure 724 housing a shape memory material spring 722 and a shell 726 containing a substance that is encapsulated by a permeable layer 728. When the shape memory material spring 722 undergoes shape recovery, it stretches the shell 726 to create single or multiple paths through which to release the substance. Irrespective of the path type and size (microscopic or macroscopic), the substance is released through these wall paths at a rate controlled by the permeable layer 728.

Additionally, the path size or rate of exposed area covering the substance can vary with temperature, This can be accomplished with a peelable shell having a pull-away tab that that becomes progressively wider. As the path creation process begins, a small opening is created to release the substance through a permeable layer. As the path creation process continues with increased temperature, the opening, in addition to becoming longer, also becomes progressively wider, allowing for a variable release rate. As the release rate depends on the exposed area, by varying the geometry of the peelable layer, a relationship between temperature and release rate can be established. With this concept, the release rate will stay constant with time but will vary with temperature.

One more degree of freedom of controlling the release rate can be provided by progressively varying the amount of porosity or degree of permeability of the jacketing layer along the path length. The variation can be continuous or incremental. With this concept, the permeability, and therefore the release rate, can increase or decrease with changes in temperature.

Based on the above, there are several ways to control the release rate of the substance and to produce either a constant or a variable rate: (a) wrap the substance with a permeable layer of either constant or variable permeability (b) wrap the substance with a barrier layer that is permeable only in selective areas (c) design the rate of the path opening area to be linear or non-linear with respect to temperature (d) incorporate pressurant means inside or outside the shell.

An alternative placement of the rate control material is outside of the shell to encapsulate the whole device such that all components, including the shell and the shape memory material, are inside. This concept provides the choice of jacketing the same devices with different rate control material to achieve different release rates. In this case, the jacketing material effectively becomes a reservoir that controls the release rate of the substance to the surroundings.

Release Mechanisms

The following description relates to shape memory material activated release mechanisms, such as described above with respect to FIG. 4. It should be understood that the combination of a non-shape memory material mechanical element and a shape memory material release mechanism may be used in place of a shape memory material spring in any of the embodiments described above.

In addition to the embodiments described above, a release mechanism can also be used in the impact shell devices shown in FIGS. 80-83. These embodiments allow for rapid path creation through instantaneous release of stored energy, resulting in more precise temperature control.

Figure 80:
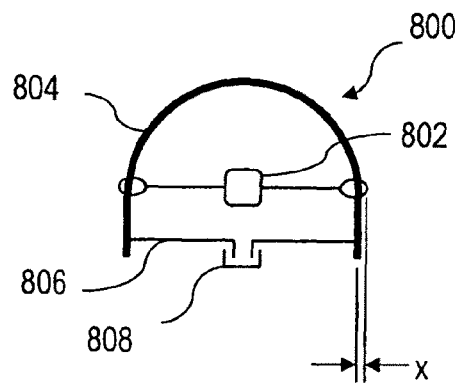
FIG. 80 is a schematic side view of a shape memory material activated release system in the form of an impact shell.

FIG. 80 illustrates a shape memory activated device 800 including a shell 802 and an elastically deformed spring member 804 (such as a wire or strip) to store the energy required to fracture the shell. The spring 804 can be made of either superelastic material or regular spring material. The spring 804 is kept in the bent position with two tension wires 806 (or rods) connected with a release mechanism 808. FIG. 80, shows the shell 802 being loosely suspended between the two ends of the spring 804 with two wires 806 or rods. The loose suspension concept allows the spring to move the distance x and prevents minor forces, generated from $A_1$ to the release temperature, from being transferred to the shell and creating the path prematurely. In addition, it allows the released spring 804 to obtain momentum before it creates the path by fracturing, exploding, imploding, puncturing, peeling, tearing, shearing, rupturing, splitting, separating, debonding, delaminating etc. the shell 802.

Figure 81:
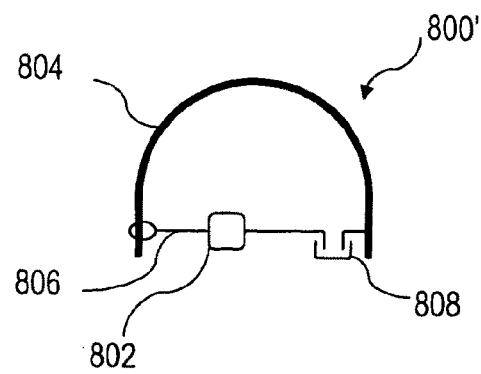
FIG. 81 is a schematic side view of another shape memory material activated release system in the form of an impact shell.

As shown in FIG. 81, the shell 802 may also be positioned in line with the release mechanism 808 along the wires 806 in the device 800.

Figure 82:
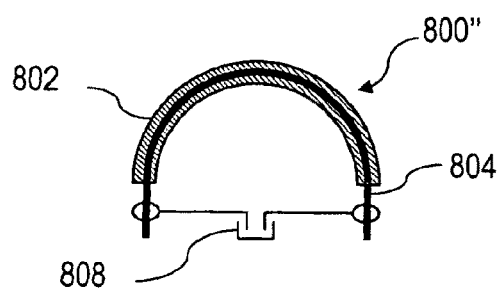
FIG. 82 is a schematic side view of a shape memory material activated release system in the form of an integral impact shell.

As shown in FIG. 82, besides being suspended, the shell 802 can also be an integral part of and surround the bent spring 804 in the device 800. The shell path in the first case is created by tension or shear (depending on shell construction) whereas the second case is created by bending.

Several types of release mechanisms can be employed with this concept. The type depends on temperature-release precision required, space availability, design flexibility, compatibility, ease of path creation etc. Different types of release mechanisms are discussed with respect to FIGS. 84-88. Additional examples of release mechanisms are described in U.S. Provisional Patent Application Ser. No. 60/191,703 which is incorporated herein by reference in its entirety.

Figure 83:
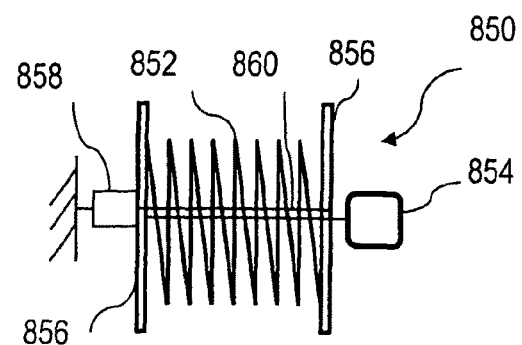
FIG. 83 is a schematic side view of another shape memory material activated release system in the form of an integral impact shell.

FIG. 83 illustrates an impact device 850 in which a compressed coil spring 852 is used to cause the shell 854 to be impacted. Impact is initiated by the release device 858 which releases the tension wire (or rod) 860 and in turn allows the spring 852 which is held under compression between two plates 856 to impact the shell 854. In a different configuration, either or both the shell and the release device can be placed inside the spring. When the shell is placed inside the spring, upon impact the shell is pulled apart in tension as it is tied to both ends of the spring.

A series of concepts for release mechanisms to be used in conjunction with any of the embodiments described herein are described with reference to FIGS. 84-88. Their purpose is to release the stored mechanical energy instantaneously, produce a maximum impact on the shell and improve activation accuracy of the device. The mechanism is inserted between the shape memory material, which activates the mechanism, and the shell that receives the released energy. The incorporation of the release mechanism eliminates the slow application of force by the shape memory material itself during the martensitic to austenitic phase transformation.

Figure 84:
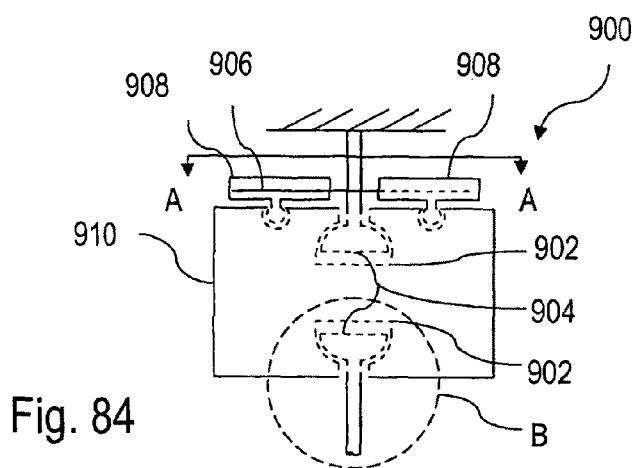
FIG. 84 is a schematic side view of a release mechanism.
Figure 84B:
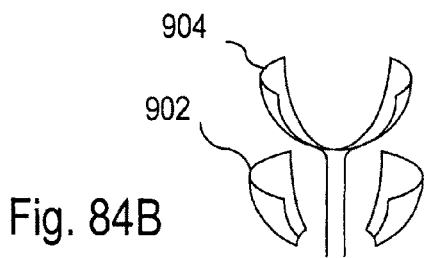
FIGS. 84B, 84C, and 84D are schematic perspective views of the cup assembly in exploded, assembled, and released configurations, respectively.
Figure 84C:
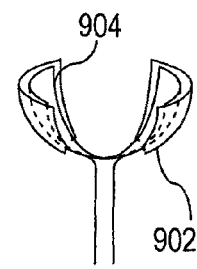
Figure 84A:
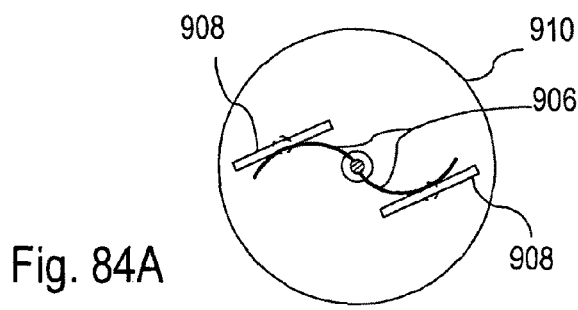
FIG. 84A is a cross sectional view taken along line A-A of FIG. 45.
Figure 84D:
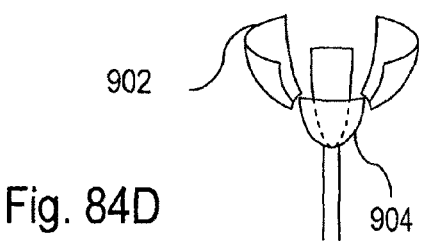

FIG. 84 illustrates a release mechanism 900 which utilizes a body with two hemispherical cavities 902 that are used as sockets for ball joints 904. One ball joint, illustrated in detail in FIGS. 84B, 84C, and 84D is designed with slots such that when the slots of the cavity and the ball (cup in this case) are lined up, the joint is separated, thereby releasing the load. The line up of the cavity and the cup is achieved through the rotation of the body by two shape memory material springs 906 attached to pivoted paddles 908. The springs 906 work as a couple to rotate the body 910, as shown in FIG. 84A. The springs 906 are bent in the martensitic state and become straight in the austenitic state. During the transformation process the springs 906 rotate the body 910 and, when the slots of the cavity and the cup are lined up (FIG. 84D), the restrained spring is released. Depending on the size of the mechanism and the amount of stored energy, one shape memory material spring 906 may be utilized. The friction between the cavity and the cup must be minimized to the point that no rotation is transferred to the cup. If the cup tends to rotate, the rod attached to the cup must be integral with the cup and provisions must be made to restrain it from rotating. For clarity, two slots are shown in the hemispherical cavities 902 and 904 of FIG. 84B. For optimum performance, four or more slots may be incorporated.

Figure 85:
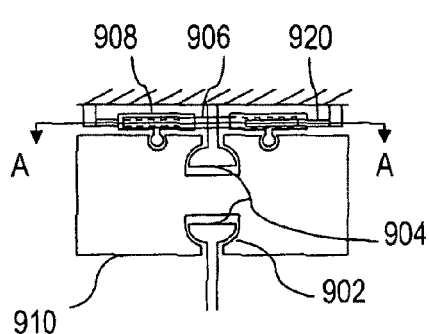
FIG. 85 is a schematic side view of another release mechanism.
Figure 85A:
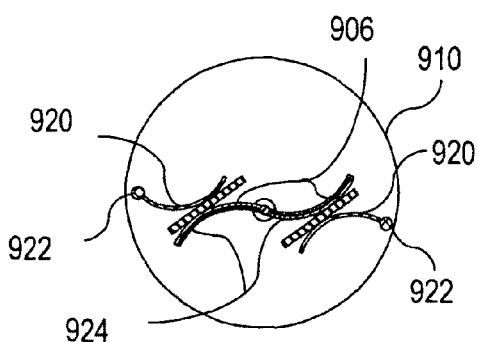
FIG. 85A is a cross sectional view taken along line A-A of FIG. 85.

To allow for the case where the temperature rises above $A_s$ and drops to below $A_s$ before it reaches $A_f$ and release is not achieved, a bias spring 920 attached to posts 922 is incorporated in the embodiment of FIGS. 85 and 85A. The purpose of the bias spring 920 is to return the body 910 back to its original position. This will eliminate the possibility of accidental release though impact in the case where the slots are close to the release position and the temperature drops. For this concept to work, the shape memory material should be trained to achieve a two way shape memory effect.

Without the two way shape memory effect, an additional bias spring 924 integral with or connected to the shape memory material spring 906 should be used. The first bias spring rotates the body back to its original position and the second aids the return of the shape memory material to its original shape.

Figure 86:
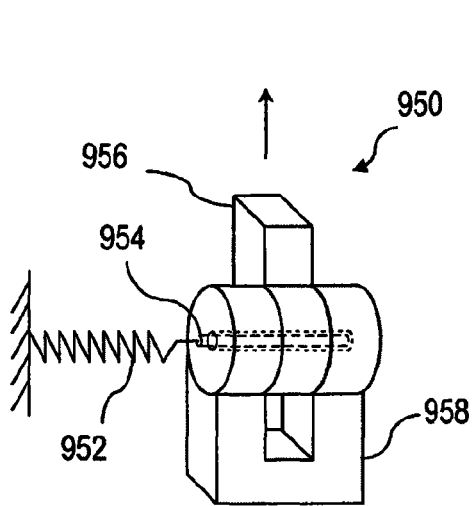
FIGS. 86 and 87 are perspective views of a pull pin release mechanism.
Figure 87:
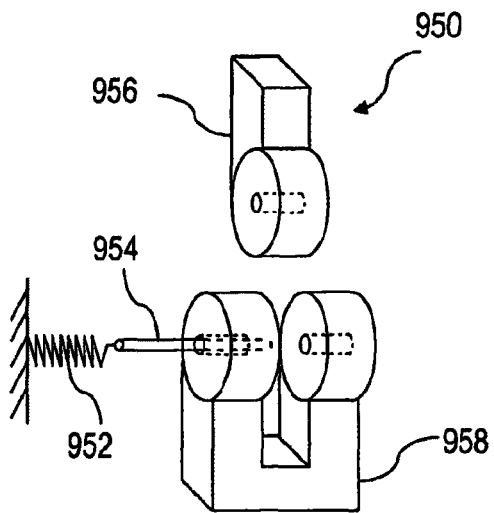

FIGS. 86 and 87 illustrate an instantaneous pin puller release mechanism 950. The pin puller 950 is used to release a single tension member. Unlike the previous release mechanisms, this one employs a shape memory material coil spring 952 to pull a pin 954 and separate two halves 956, 958. A bias coil spring can be used coaxially with the shape memory material spring 952 to return the spring to its original position when the phase transformation is incomplete and no release takes place. There is less of a need for a bias spring in this case since accidentally induced impact forces are not likely to release the hinge member. One advantage of this design is the elimination of the need to anchor the mechanism as no force couples are generated.

Figure 88:
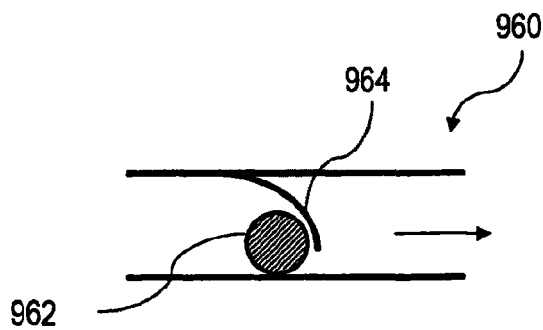
FIG. 88 is a schematic view of a force limited release mechanism.

FIG. 88 illustrates a force limited release system 960. This concept allows a shape memory material element 962 to be released when it develops a certain amount of resistance force against an object 964 such as a restraining leaf spring. As the temperature is increased above $A_s$, the shape memory material element 962 applies an increased force against the restraining spring 964, which in turn begins to deflect and creates more room for the shape memory material element to be released. By controlling the properties, shape and size of the restraining spring 964 for a given shape memory material element 962, the release temperature within the $A_s$ to $A_f$ range can be controlled. If the transformation cycle is not completed and no release takes place, the leaf spring 964 returns the shape memory material element 962 back to its original position. To aid the release process and minimize the possibility of binding, sleeves can be added to the shape memory material element such that the sleeve is in contact with the restraining spring.

When mechanisms as the ones described above (that release stored mechanical energy to activate the device) are used to release a drug, an auditory signal is emitted, the strength of which depends on factors such as material of construction and medium the signal has to travel. This property becomes significant for implants where a manual adjustment of a drug dosage can be detected with device such as a stethoscope. This provides assurance of the drug release and eliminates the uncertainty or the requirement for radiography. Other means for producing auditory signals include pressure difference between shell contents and surroundings, shells with brittle walls and shape recovery with a narrow temperature range that results in an accelerated path creation process.

Thermally Activated Transporter

Figure 89:
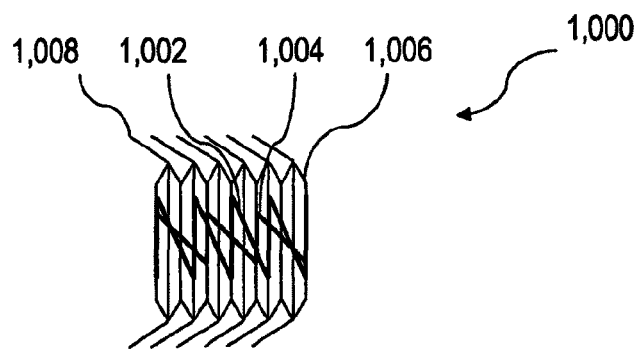
FIG. 89 is a schematic side view of a thermally powered device driven by a shape memory material activator.

The device illustrated in FIG. 89 is a self-propelled thermally powered device driven by a shape memory material activator that, when subjected to temperature cycling, converts thermal energy into mechanical energy and in the process performs multiple functions. Typically, these functions combine motion with force and they can be performed either sequentially or simultaneously with temperature change of shape memory material actuator. They include, but are not limited to, travel from one location to another, transportation of a load, release of a substance, expansion of conduits, and actuation and powering of other devices. The concept on which this device is based is similar to the ones presented earlier for shape memory material activated pressure generators.

When the thermally powered device is left unrestrained, it becomes a self-propelled vehicle that can travel on guided single or multiple tracks, or unguided in different media and on surfaces. The device is capable of traveling on any track, medium or surface, including flat surfaces, that will allow forward movement but will provide traction to prevent reverse movement. The device moves by first thrusting one end forward during the first half of the temperature cycle while the second end provides traction, then, thrusting the second end forward during the second half of the temperature cycle while the first end provides traction. With this sequential movement of the two ends the device expands and contracts with temperature cycling. The order of expansion and contraction with respect to temperature change is determined by the direction of the shape recovery of the shape memory material activator.

FIG. 89 illustrates a thermally powered device 1,000 comprising a shape memory material spring 1,002, a bias spring 1,004 and a variable length body 1,006 with a plurality of fins 1,008. The fins 1,008 are work enablers that allow the thermally powered device 1,000 to interact with its environment and to perform work. They provide the necessary traction means to prevent reverse movement and at the same time facilitate the forward movement. Reversal of travel is prevented by the locking action produced by frictional or traction means. In addition, the work enablers provide stability and aid the direction of travel. The configuration of the work enablers is determined by their functional environment and the type of travel they have to perform such as traveling on a track, on a flat surface or in a specific medium such as a viscous substance or particulate media. In addition, the fins may be configured for non travel functions such as the actuation or activation of a mechanism. The work enablers can be comprised of single or multiple parts configured with flat, cylindrical, conical, spherical, or a combination thereof of geometric features constructed of rigid, flexible or compressible materials. As an example, the forward surface of the work enablers may be made of a non-absorbent material while the aft side is made of an absorbent material. During one half of the temperature cycle, the aft side absorbs the surrounding fluid, becomes stiffer and provides increased traction. During the second half, the work enablers flex towards the body of the device, compress their aft sides against it, and squeezed out the fluid. In addition, the work enablers may be sculpted on the surface of the variable length body to form either depressions such as dents, dimples and cavities or protrusions. In the first case, the work enablers are inwardly projecting and in the second one they are outwardly projecting. Some of the configurations for the work enablers include; fins to enable travel on tracks containing similar fins, detents to enable travel on a ratchet gear system, fins with special surface features to enable travel in viscous fluids or particulate media, and wheels that prevent reverse rotation to enable travel on a flat surface or inside a hollow track. Depending on the type of travel, each of the work enablers may be continuous around the circumference of the variable length body 1,006, or may constitute a circumferential segment. As an example, for a round type variable length body, unguided surface travel can be achieved with conical type work enablers, segments of conical work enablers or just wire extensions. Continuous or segmented work enablers placed around the variable length body allow the device to rotate or tumble while traveling and make travel orientation free with respect to the placement of the work enablers. The fins 1,008 can be either integral or attached to the variable length body 1,006. They can be attached such as to be fixed or they can be pivoted to allow for an adjustable width span to accommodate travel in variable width tracks such as tubes of changing diameter or variable roundness. Generally, the work enablers are preferentially oriented with respect to the direction of travel to provide minimal resistance to forward movement and maximum resistance to backward movement. This is achieved by biasing them such that the aft angle formed between the work enablers and the direction of travel is an acute angle. In addition to multiple configurations of the work enablers, the variable length body can have multiple configurations as well. It can be of any shape that would permit the attachment of the work enablers and will not inhibit the length variability. In addition, its cross section may change from one end to the other to accommodate the travel requirements.

The bias spring 1,004 can be eliminated if the variable length body 1,006 is also used as spring or if the shape memory material spring 1,002 is trained in a two way shape memory effect. Further, the variable length body itself can become the shape memory material spring 1,002 trained in a two way shape memory. In addition, the variable length body 1,006 can be eliminated if the work enables are attached directly to the shape memory material spring 1,002 or the bias spring 1,004. In certain applications, the shape memory material spring or the bias spring may perform the function of the work enablers and as such, the need for the variable length body is eliminated. Further, multiple shape memory material springs with the same hysteresis curves, coupled with bias springs, may be incorporated. Multiple springs with reduced cross sections allow for faster heating and cooling. In addition, they allow for the thermally powered device to travel on a curvilinear path. If two sets of shape memory material springs of unequal length coupled with compatible lengths bias springs are placed inside a variable length body in diametrically opposite locations, the longer shape memory material spring would produce a larger expansion, comparing to the shorter one, and force the thermally powered device to travel on a curved path. Depending on the configuration of the shape memory material and the travel environment, there are times that work enablers are not required. A case for this would be a thermally powered device comprised of shape memory material activator that is configured aerodynamically to minimize the forward resistance and maximize the backward resistance. A similar case exists when the device is traveling in a medium of decreasing density where there is less resistance to forward movement and a higher resistance to backward movement. Depending on the prevailing conditions and the design of the device, a slight backward movement may be tolerated but the net effect is a forward movement with each full temperature cycle.

Figure 90:
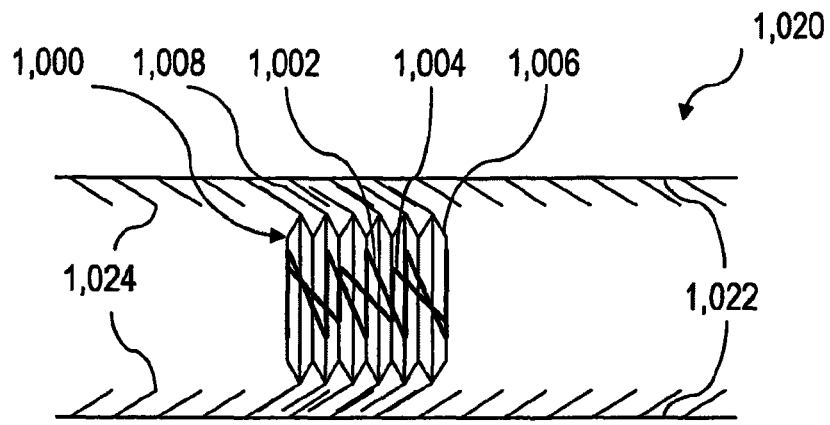
FIGS. 90, 91 and 92 are schematic side views of a shape memory material activated transport device with the thermally powered device in the initial position, with the forward end advanced, and with the aft end advanced, respectively.
Figure 91:
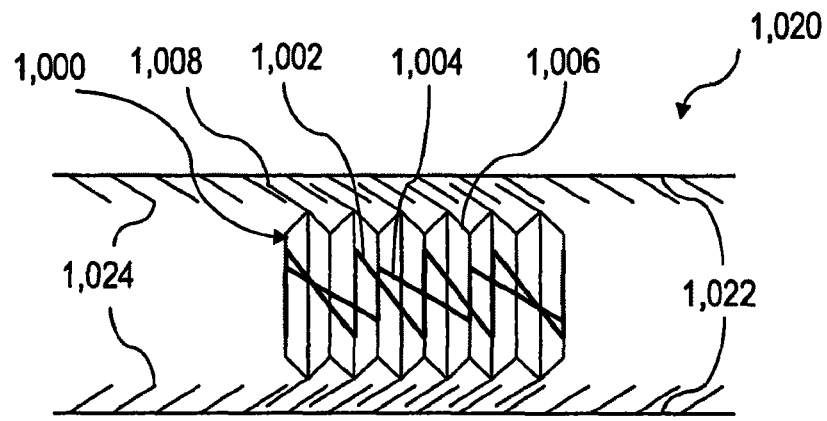
Figure 92:
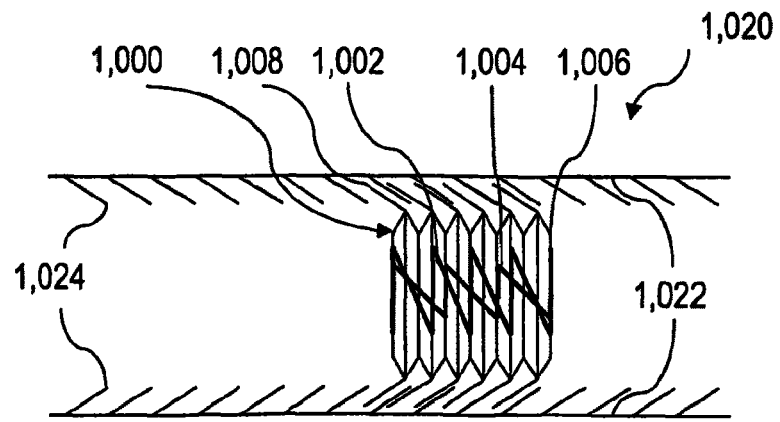

FIGS. 90, 91 and 92 illustrate an example of a shape memory material activated transport device 1,020 utilizing the thermally powered device 1,000 traveling on a plurality of tracks 1,022, each configured with a plurality of track fins 1,024. The fins 1008 of the variable length body 1,006 and the track fins 1,024 are oriented in the same direction, and are substantially flexible to allow movement of the variable length body in one direction but prevent the reverse movement by a locking action. The orientation of the fins is such that the variable length body fins are inclined toward the opposite direction of travel, while the track fins are inclined toward the travel direction with both sets essentially being parallel to each other. The shape memory material spring 1,002 and the bias spring 1,004 are housed inside the variable length body 1,006. As the temperature of the shape memory material spring 1,002 rises, it goes through shape recovery, overcomes the resistance offered by the bias spring 1,004 and in the process of expanding, forces the variable length body 1,006 to expand in one direction. FIG. 90 illustrates the embodiment of the shape memory material activated transport device 1,020 with the shape memory material spring 1,022 in the deformed martensitic state. FIG. 91 illustrates the forward advancement of the forward end of the thermally powered device 1,000 on the tracks. When the shape memory material spring 1,002 is heated above $A_s$ it undergoes shape recovery, overcomes the resistance force of the bias spring 1,004 and, as it expands, it increases the length of the variable length body 1,006. The length increase is prevented from taking place in the backward direction by the locking action of the biased fins while it is allowed in the forward direction. As the variable length body increases in length, the fins move past each other and accommodate each other by flexing toward their respective attachment points. They flex back to their original shape once they move past each other and they are no longer in contact with each other. FIG. 92 illustrates the forward advancement of the aft end of the thermally powered device 1,000 on the tracks. When the shape memory material spring 1,002 undergoes reverse recovery, the bias spring 1,004 forces the variable length body 1,006 to contract in length. During this half of the temperature cycle, by a similar locking and flexing action of the fins, the forward end is prevented from moving backward while the aft end is allowed to move forward. This movement allows the variable length body to return to is initial size at the completion of the temperature cycle. The interaction of the work enablers, fins in this case, provide the necessary traction means for the forward advancement of the thermally powered device. The spacing of the work enablers on both the track and the thermally powered device determine the precision of travel. With each half of the temperature cycle, the work enablers along the length of the thermally powered device move progressively from zero to the full distance of travel. By decreasing the spacing of the work enablers on the track side allows for better gripping as more work enables from both sides are able to mesh. The spacing of the work enablers does not have to be uniform. In can be random as in the case when irregular surface morphology is used as means for traction.

With the sequential advancement of one end followed by the other end, the thermally powered device 1,000, in one temperature cycle, travels a distance equal to the displacement produced by the shape memory material spring 1,002 in one half of the cycle. This way, the device is capable of traveling continuously with temperature cycling of the shape memory material spring. As a traveling vehicle, it is capable of performing multiple tasks. A few of these tasks are; carry a load from one location to another (in essence becoming a thermally activated transporter), release a substance along the travel path or at selected locations, push or pull on object, expand a tube or an opening, place on object at a specific location and, trigger an action as to activate a device by turning on a switch. The travel distance can be measured in whole temperature cycles or degrees of temperature per unit distance.

Figure 93:
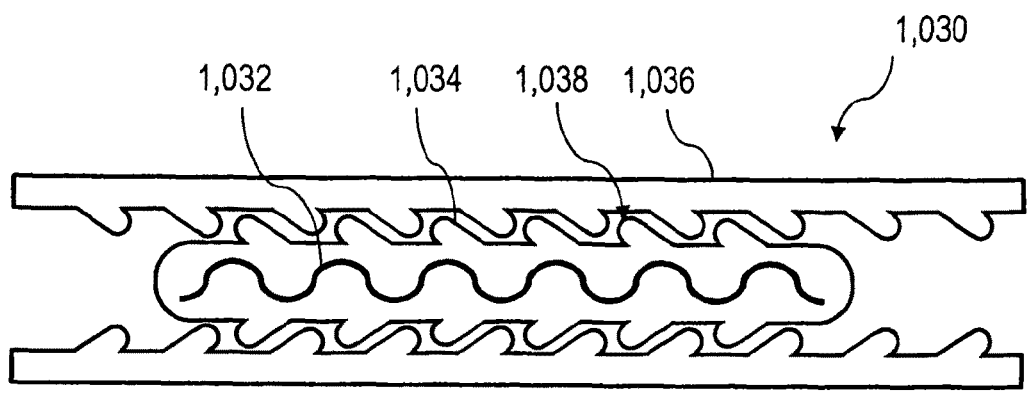
FIG. 93 is a schematic side view of a shape memory material activated transport device with the thermally powered device consisting of a shape memory material activator embedded in an elastomeric material.
Figure 94:
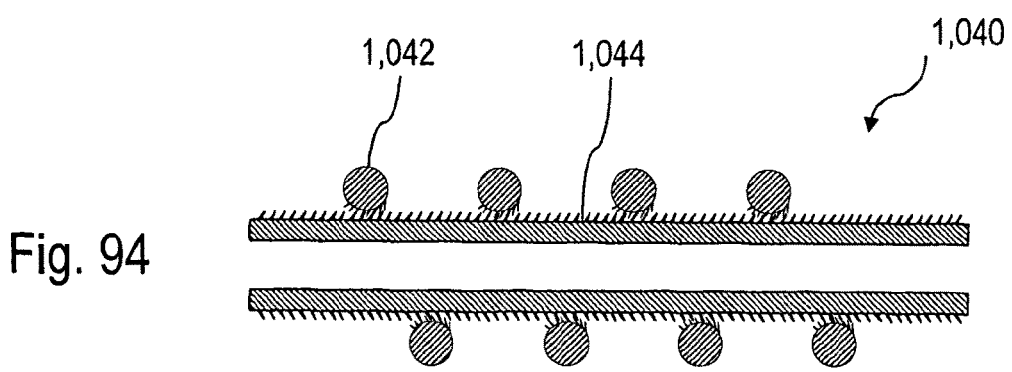
FIG. 94 is a schematic axial cross section of a shape memory material activated transport device with the thermally powered device consisting of a shape memory material activator, trained in a two way shape memory effect.

FIGS. 93 and 94 illustrate examples of a shape memory material activated transport devices 1,030 and 1,040, respectively. They are similar to the one illustrated in FIG. 90, but with the thermally powered devices utilizing a lower number of parts. The thermally powered device 1,038 of FIG. 93 consists of a shape memory material spring 1,032 in the form of a convoluted sheet or foil embedded in an elastomeric type material 1,034, configured with integral fins, that acts as a bias spring thereby eliminating the need for a variable length body. The shape memory material spring 1,032 has a convoluted shape in the martensitic state and assumes a straight shape upon shape recovery and in the process stretches the elastomeric bias spring. The fins of both the thermally powered device and of the track 1,036 have sufficient flexibility to allow the thermally powered device to advance in one direction but prevent it from moving in the opposite direction. When of a shape memory material spring in a convoluted shape is used, the track must accommodate any waviness in the elastomeric material caused by the shape recovery process. The waviness is caused by the fact that when the shape memory material obtains a straight shape, the elastomeric material contained in the concave side of each convolute is deformed elastically and bulges out. The bulging alternates between sides and follows the orientation of the convolutes resulting in a waviness along the length of the thermally powered device. The degree of waviness is influenced mostly by the radius and the arc length of the convolutes and the general shape of the elastomeric material. For an elastomeric material of constant thickness that resembles the shape of the shape memory material, the waviness decreases with the straightening of the shape memory material. With increased waviness, the thermally powered device forces the width or opening of the track to increase. This forced increase in the track opening provides opportunities for several applications that are described further below. The thermally powered device 1,040 is shown in FIG. 94 an axial cross sectional view. The device 1,040 consists of a shape memory material spring 1,042 trained in two way shape memory effect and configured with integral fins. This is a single part thermally powered device that travels on the outside surface of hollow tubular track 1,044 configured with fins. As the shape memory material spring 1,042 expands and contracts with temperature cycling, it advances forward similarly to the thermally powered devices illustrated in FIGS. 90 and 93.

Figure 95:
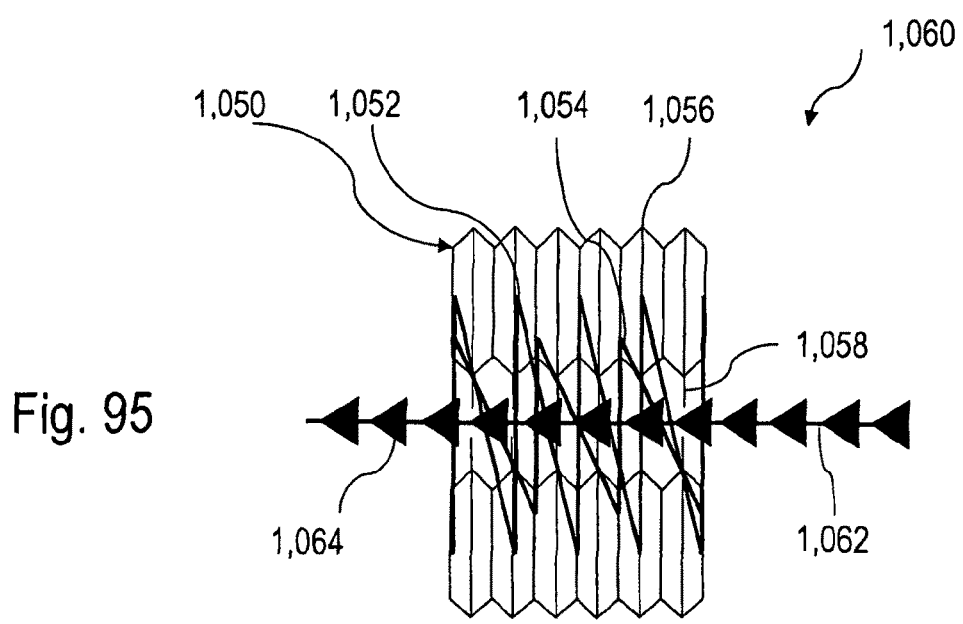
FIG. 95 is a schematic side view of a thermally powered device traveling on a single internal track.

FIG. 95 shows an alternative embodiment of a shape memory material activated transport device 1,060 utilizing a modified thermally powered device 1050. The device 1050 has a hollow variable length body 1,056 configured with a plurality of internal fins 1,058 and containing a shape memory material spring 1,052 coupled with a bias spring 1,054. The fins 1,058 facilitate the riding of device 1,050 on an internal "monorail" type single track guide rod 1,062 configured with a plurality of teeth 1,064 to allow travel in one direction only. The device operates the same way as the one illustrated in FIG. 90, with one end of the modified thermally powered device 1,050 advancing during the first half of the temperature cycle and the other end during the second half. The guide rod can also be a cylinder configured with fins or other frictional means as work enablers instead of teeth. Also, multiple internal tracks can be used instead of a single track. One advantage of the internal track is that is has a small profile and can be easily inserted in small tubes, body cavities or blood vessels and follow a treacherous path to guide the thermally powered device through it.

Figure 96:
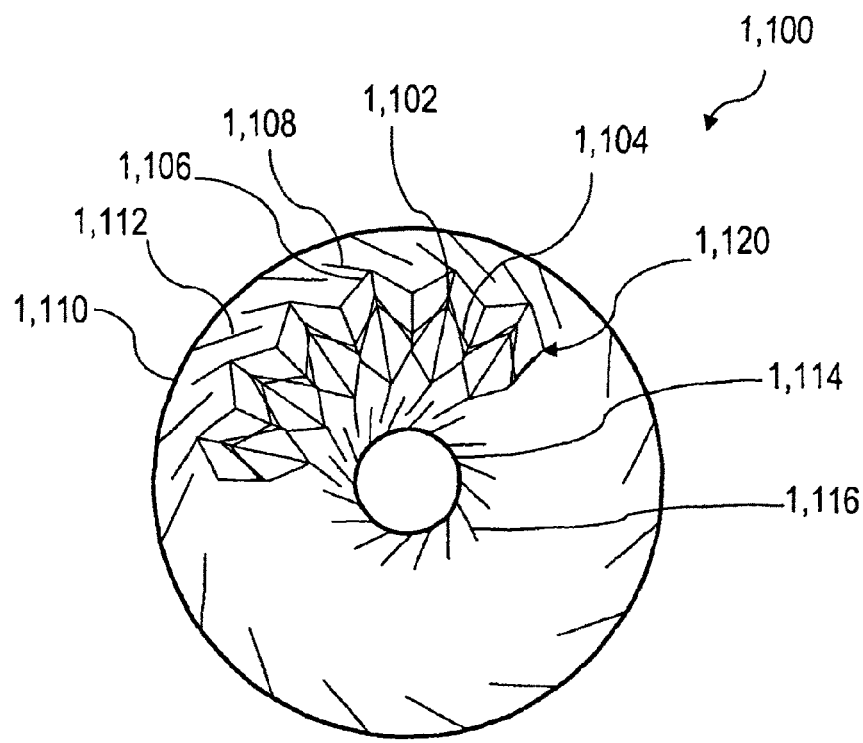
FIG. 96 is a schematic side view of a shape memory material activated circular transport device.

FIG. 96 illustrates an embodiment of a shape memory material activated circular transport device 1,100 comprising a circular outer track 1,110 configured with a plurality of inward fins 1,112, a circular inner track 1,114 configured with a plurality of outward fins 1,116 and a circular thermally powered device 1,120. The circular thermally powered device 1,120 comprises a curved variable length body 1,106 with a plurality of fins 1,108 that houses a shape memory material spring 1,102, and a bias spring 1,104. The fins 1108 of the variable length body 1,006 and those of the outer 1,112 and inner track 1,114 are skewed such as to allow movement of the variable length body in one circumferential direction but prevent the reverse movement by a locking action. During temperature cycling, the curved variable length body 1,106 expands and contracts while maintaining its curvature, thereby allowing the thermally powered device 1,120 to travel on a closed circular loop defined by the two tracks. The circular tracks may be comprised of a set of coaxial cylinders or simply a tube formed as a toroid that houses the thermally powered device. In the first case, the fins may be skewed and flat and in the second case, they may resemble conical surfaces. In both cases, they may be configured with additional features such as slots and variable thickness to increase their flexibility and to facilitate the travel process.

Figure 97:
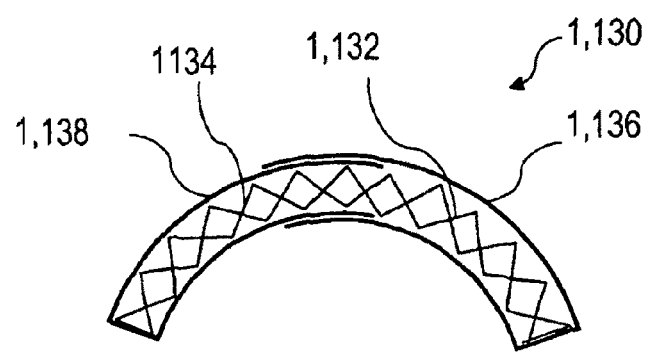
FIG. 97 is a schematic side view of shape memory material and bias springs housed in telescoping tubes.

The thermally powered device is capable of traveling on any two or three dimensional, open or closed loop, guided or unguided path. To avoid kinking of the shape memory material 1,132 and the bias 1,134 springs, they can be housed in telescoping tubes formed in circular segments as illustrated in FIG. 97. The outer 1,136 and the inner 1,138 tubes can be rigid to conform to a path of constant radius or flexible to providing lateral support and accommodate variable curvature paths. In addition, if the telescoping tubes are configured with work enablers such as fins that do not impede the expansion and contraction process, they can be used as a variable length body. Generally, the minimum number of fins required for any variable length body, including telescoping tubes, is one set of fins at each end of the variable length body.

Figure 98:
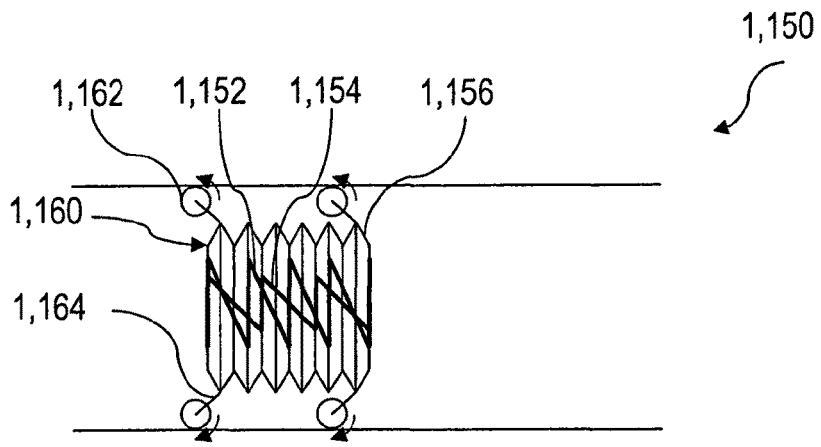
FIGS. 98, 99 and 100 are schematic side views of a shape memory material activated transport device with the thermally powered device traveling on wheels in the initial position, with the forward end advanced, and with the aft end advanced, respectively.
Figure 99:
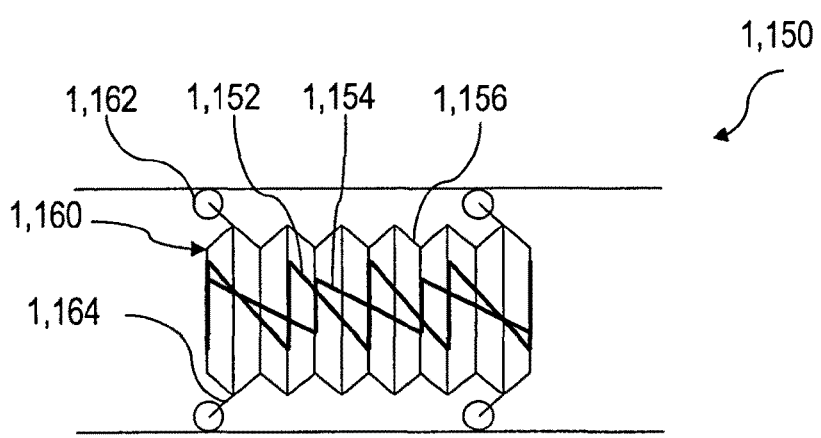
Figure 100:
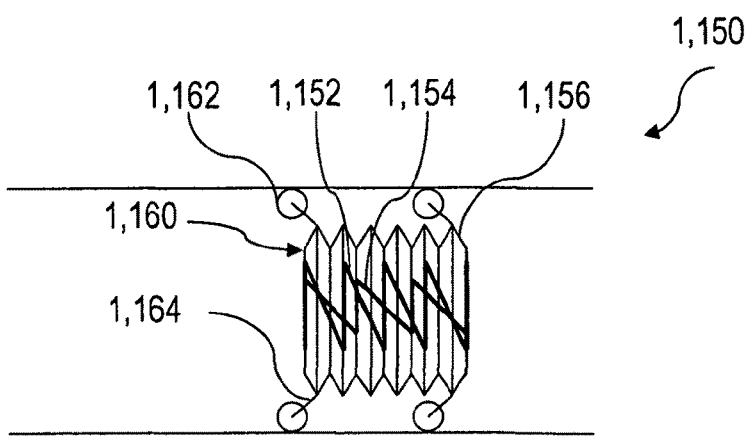

FIGS. 98 to 100 illustrate an embodiment of a shape memory material activated transport device 1,150 with a thermally powered device 1,160 traveling on wheels. The thermally powered device 1,160 is similar to device 1,000 illustrated in FIG. 89 but utilizes a plurality of wheels 1,162 attached to the variable length body with struts 1,162 instead of fins. The wheels 1,162 rotate only in one direction to prevent backward movement. Reverse rotation is prevented with detent and ratchet gear systems and the like. The struts can be single, rigid or flexible parts or multi-link spring-loaded assemblies that provide sufficient tension to hold the thermally powered device on the track, prevent backward sliding, and allow for travel on variable width tracks. Multi-part strut assemblies may allow for angular movement amongst their different parts to effectively render variable length to the struts. Variable length struts increase the agility of the thermally powered devices by allowing them to travel on variable size tracks. FIG. 98 illustrates the shape memory material activated transport device 1,150 with the shape memory material spring 1,152 in the deformed martensitic state. FIG. 99 illustrates the advancement of the forward end of the thermally powered device 1,160 during shape recovery of the shape memory material spring 1,152. During the shape recovery process the variable length body 1,156 increases in length in one direction. The length increase in one direction is afforded by the wheels 1,162 that can rotate only in one direction. The front wheels rotate to accommodate the length increase while the back wheels remain locked and prevent any length increase in the opposite direction. Friction between the wheel surface and the track prevents any movement by backward sliding. Depending on the application and the prevailing frictional conditions between the two surfaces, minor backward movement may be tolerated provided that there is a net forward movement with each full temperature cycle. FIG. 100 illustrates the forward advancement of the aft end of the thermally powered device 1,160. When the shape memory material spring 1,152 undergoes reverse recovery, the bias spring 1,154 shrinks the variable length body 1,156. During reverse recovery, the front wheels lock and prevent backward movement, the back wheels rotate to accommodate the shrinkage and to return the variable length body to its initial size, but in a new location.

Any type of work enablers such as fins, indentations, depressions, wheels, gear teeth, or spikes will advance the thermally powered device if matched it with the right track. The track provides the guiding path and can be comprised of a tube, two parallel surfaces, single or multiple rails, or a flat surface and the like. Also, fastener threads, male or female, can be used as a track for the thermally powered device to travel on. The ability to travel inside threaded holes provides opportunity for several applications such as plugging holes and securing fasteners in place.

Figure 101:
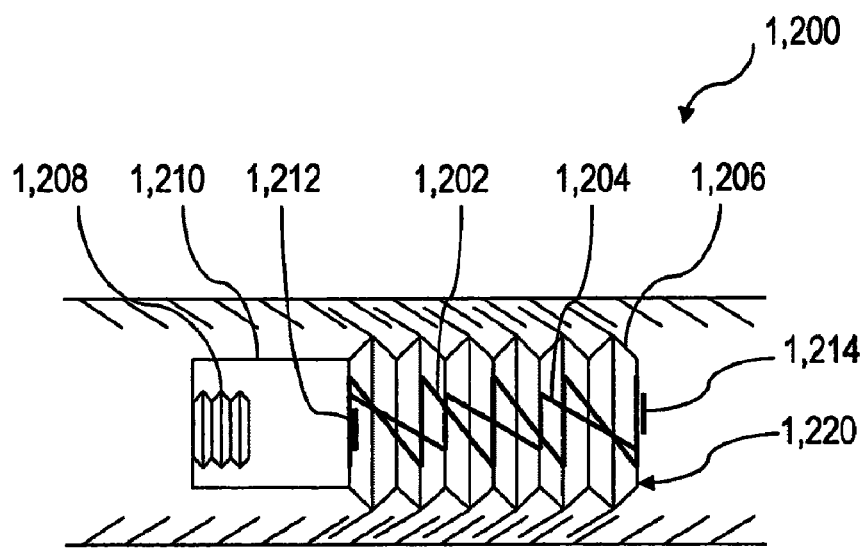
FIG. 101 is a schematic side view of a shape memory material activated transport device carrying a shell.

Applications of the shape memory material activated transport devices vary from toys to medical and industrial products to scientific instruments. One application is the release of a substance within a predetermined temperature range, while the temperature is either rising or falling, such that each release takes place at a different location along the traveled course. The release is independent of time as there is no release if the temperature stays constant. FIG. 101 shows a shape memory material activated transport device 1,200 where the thermally powered device 1,220 performs the dual function of a transporter and of a substance release device. The device 1,220 comprises a shell 1,206, also functioning as a variable length body, that houses a shape memory material spring 1,202, a bias spring 1,204, an inward one-way flow valve 1,212 and an outward one-way flow valve 1,214, and has a supply reservoir 1,210 containing a pressurant housing 1,208 attached to it. The device 1,220 carries its own supply reservoir as it travels. The pressurant housing 1,208 can contain a compressed fluid, a compressed spring such as one made of superelastic material, and the like whose function is to keep the substance contained in the reservoir under constant pressure. Pressurization is needed only in the cases where the reservoir substance is not pressurized by the surroundings. As the variable length body 1,206 expands, the forward end advances forward and at the same time it refills itself through the inward one-way flow valve 1,212. During cooling, the variable length body 1,206 contacts, the aft end advances forward, pressurizes the substance contained inside it and creates a path through the outward one-way flow valve 1,214 to release the substance. The release path can be a valve, a permeable wall or other means that will allow the substance to exit while under pressure.

Figure 102:
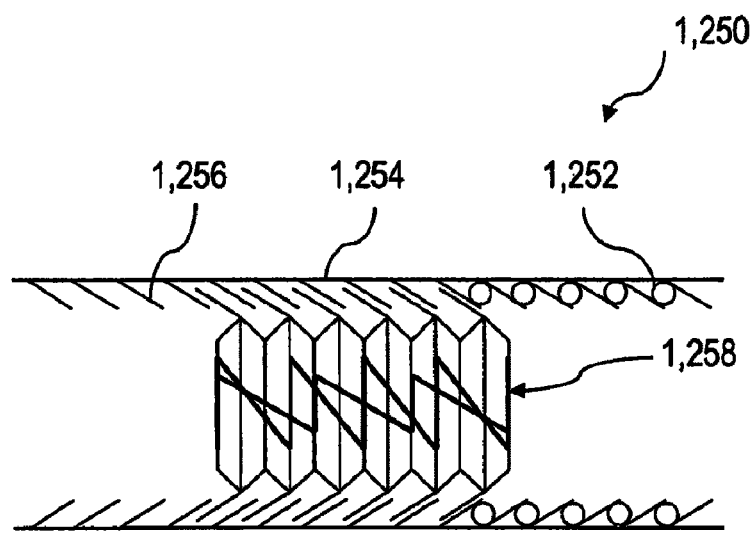
FIG. 102 is a schematic side view of a shape memory material activated transport device with shells located along the tracks.

FIG. 102 illustrates a concept of a shape memory material activated transport device 1,250 comprising a thermally powered device 1,258 that is similar to device 1,000 of FIG. 89, a set of tracks 1,254 each configured with a plurality of track fins 1,256 and a plurality of shells 1,252 containing a substance. The shells 1,252 are located along the path of the thermally powered device 1,258. They are placed strategically between the track fins such that as the thermally powered device advances, its fins compress the shells and create paths for the substances to be released. The paths through the shell walls can be in the form of permanent physical openings such as fractures and separations, or they can be microporous type paths. If the substance, instead of been encapsulated by the shells, is adhered to the track's fins in a granular form, the thermally powered device can release it to the environment by scarping it off while advancing forward. In this case, the track fins constitute the shells holding the substance in place. Further, the released substance may be in multiple states of matter such as a liquid or a gas contained in solid state casings.

In addition to integrating shells on the fins of the tracks, the fins of the thermally powered device can be made progressively longer, from front to back, such that the shells are increasingly squeezed as the thermally powered device goes by. With this concept, all fins contribute to the release of the substance both during the heating and the cooling of the shape memory material activator. Other fin modifications may include progressive adjustment of the fin angles and incorporation of variable stiffness fins. Further, the paths created through the wall of the shells may be through valves or permeable walls and the shells may be connected to supply reservoirs. Connecting the shells to supply reservoirs enhances the capabilities of the circular transport by enabling it to release one or more substances continuously as the thermally powered device travels around a loop. In another concept, the track fins can act as valves to create multiple paths and release a substance. In this case, the deflection of the fins caused by the advancement of the thermally powered device can create paths to release single or multiple substances by opening up valves connected to supply reservoirs.

Figure 103:
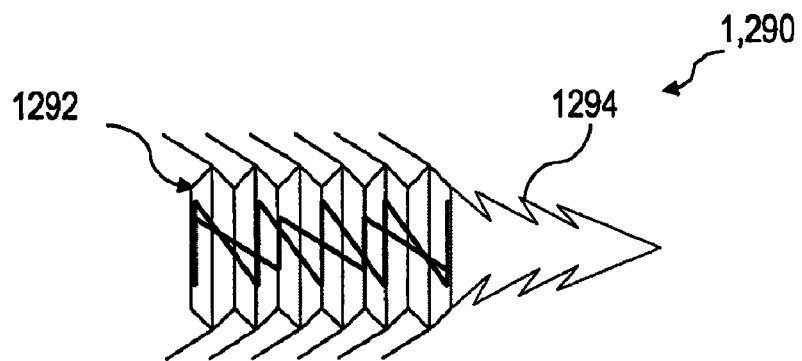
FIG. 103 is a schematic side view of a thermally powered device with a pointed nose.

FIG. 103 shows an example of a device 1,290 that uses a thermally powered device 1,292, that is similar to the device 1,000 illustrated in FIG. 89, with a pointed nose 1,294 mounted to the forward advancing end. By placing a series of balloon type shells inside the tracks, release paths can be created sequentially in shell after shell as each shell encounters the pointed nose 1,294 of the advancing thermally powered device 1,292. This concept has the advantage that each release is instantaneous and can be of a different substance. Instead of balloon type shells, other shells such as peelables can be used such that the thermally powered device can be equipped with hooks to grab their tabs as it goes by and peel them to release their substance.

Figure 104:
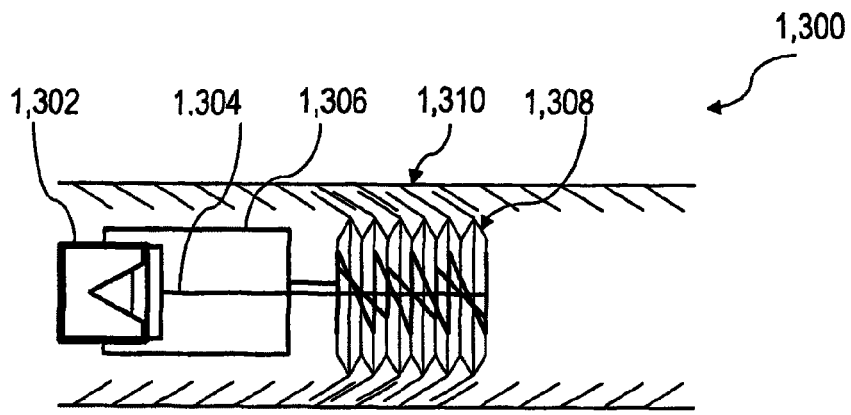
FIGS. 104, 105 and 106 are schematic side views of a shape memory material activated transport device carrying a time dependent release device in the initial position with the release device closed, with the forward end advanced and the release device open, and with the aft end advanced and the release device closed, respectively.
Figure 105:
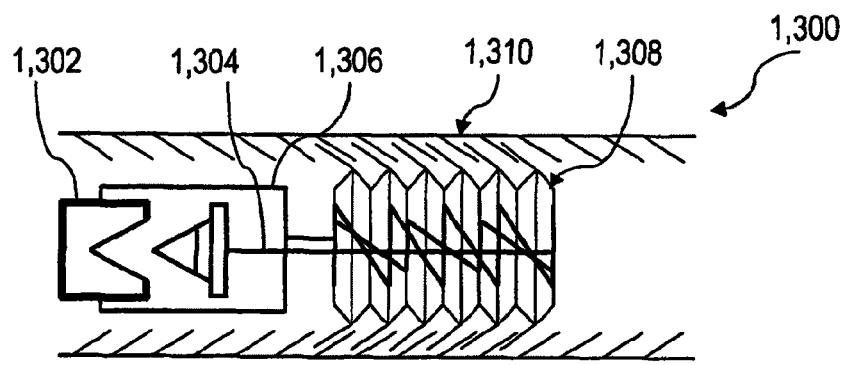
Figure 106:
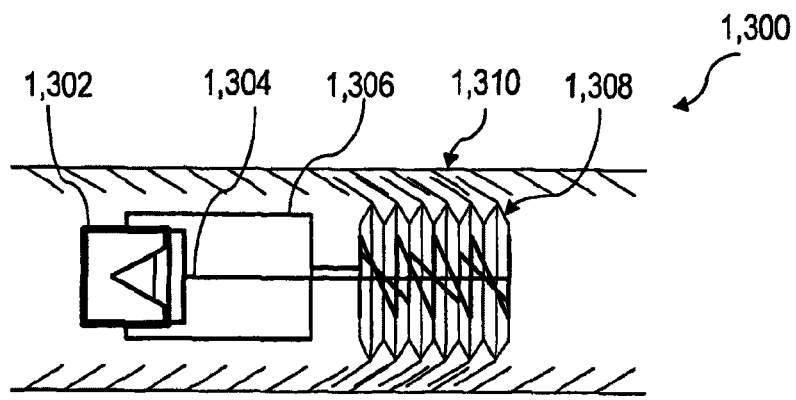

FIG. 104 illustrates an embodiment of a device 1,300 that combines a shape memory material activated transport device 1,310 with a time dependent release system 1,302 that is similar to the one illustrated in FIG. 61. In this case, the operation of the time dependent release system 1,302 is taken over by the thermally powered device 1,308. The source of the shell is attached to the forward end of thermally powered device 1,308 through a source bracket 1,304 and the sealer part of the shell is attached to the aft end through a sealer bracket 1,306. As the shape memory material spring undergoes shape recovery, FIG. 105, the forward end of the thermally powered device 1,308 advances forward and, in the process, pulls the source part with it, thereby creating a path for the substance to be released. The back end remains stationary and holds the sealer in its original position. During reverse shape recovery, FIG. 106, the forward end remains stationary and the aft end advances forward pulling the sealer part with it and closes the path once the martensitic temperature is reached. With this concept, the opening of the shell can be controlled by attaching the brackets holding the shell parts at different points along the length of the thermally powered device 1,308. As an example, by attaching the sealer bracket at the mid-point of the thermally powered device 1,308, the opening will be half as much as it is when both parts are attached to the ends of the shell. One of the advantages of this concept is the continuous release and integration of substance while the shell is advancing. The release path is fully closed while the shape memory material spring remains in the martensitic state. The same objective can be accomplished with the shape memory material spring contracting during shape recovery by simply reversing the order of the attachment points. Also, the path can be created during cooling of the shape memory material spring if the shell is closed at the austenitic temperature. In the latter case, the embodiment in FIG. 103 illustrates the austenitic condition with the shape memory material spring contracting during cooling. In this case, the release path is fully closed while the shape memory material spring remains in the austenitic state. An alternative way to mount the time dependent release system 1,302 to the thermally powered device 1,308 is to house it inside. In cases where an open track system is utilized, the time dependant system can travel outside the tracks while controlled by the traveling thermally powered device.

Figure 107:
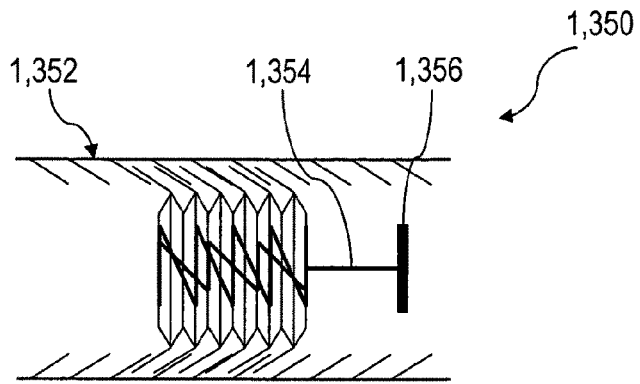
FIG. 107 is a schematic side view of a shape memory material activated transport device holding an element at the end of an extension arm.

Besides releasing a substance, the thermally powered device can perform other functions such as pushing or pulling an object to a predefined distance. This can be performed with the thermally powered device remaining on the tracks, extending a part out or using an extension arm. Applications for this concept include location identification and positioning of medical devices. One example is the placement of thermoseeds (magnetic rods) for the treatment of certain cancers. Anchoring the tracks in a mammalian body and utilizing the thermally powered device as a transporter for drug or medical delivery devices allows for a multitude of applications in the medical field. The thermally powered device can be used as means for the transfer or delivery of various objects, substances and the like. As an example, it may transport a shell containing a substance to a specific location to be released at a predetermined temperature or upon delivery. FIG. 107 shows a concept of a device 1,350 having a shape memory material activated transport device 1,352 holding an element 1,356 at the end of an extension arm 1,354. The element 1,356 may have any number or configurations of a single part or an assembly such as a tube, cable, fiber optic, medical or other device. In addition, it may be configured with work enablers. Once the thermally powered device advances sufficiently with thermal cycling, it can install or place the element 1,356 to different destinations such as an electrical terminal to provide an electric path, a fiber optic line to provide a light path, and terminals to provide an electric path. Further, it can be used to mechanically lock/unlock or to engage/disengage mechanical members such as fasteners, plugs, or quick disconnects. The shape memory material activated transport device or the thermally powered device alone can be used to create paths in all the shells presented herein. Depending on the nature of the element 1,356, any function requiring the application of a force such as assembly or disassembly, opening or closing can be accomplished with either the shape memory material activated transport device or the thermally powered device alone. Besides mounting the element 1,356 at the advancing end, it can be placed at the retreating end. In this case, it may be utilized to pull a tab to open a path to release a substance from a peelable shell or alternatively to create the path by pulling a plug from a different shell. In addition, it may be utilized to disconnect or deactivate a device by pulling a critical component such as a switch or a connector.

Means such as the element 1,356 and the extension arm 1,354 can be used to connect several thermally powered devices in series. With this arrangement, the shape memory material spring in each device can have a different hysteresis curve such that at least one device is changing length with a change in temperature within a given range. If the front end of this particular device is advancing forward; all devices ahead of it will be pushed forward without having to change their lengths. If on the other hand, the back end of this particular device is advancing forward, all devices behind it will be pulled forward without having to change their lengths. Thermally powered devices can be connected to each other with various methods such as pin or ball joints to accommodate travel on curved tracks and variable opening passages. In the case of the thermally powered devices, the sequence of activation depends on the arrangement of the hysteresis curves relative to the change in ambient heating. When the shape memory material springs are heated individually by external means such electric heating, a specific powering sequence can be achieved. Advantages of connecting several thermally powered devices in series include increase in the operating temperature range of the overall system and increased flexibility that allows travel along curved paths.

Figure 108:
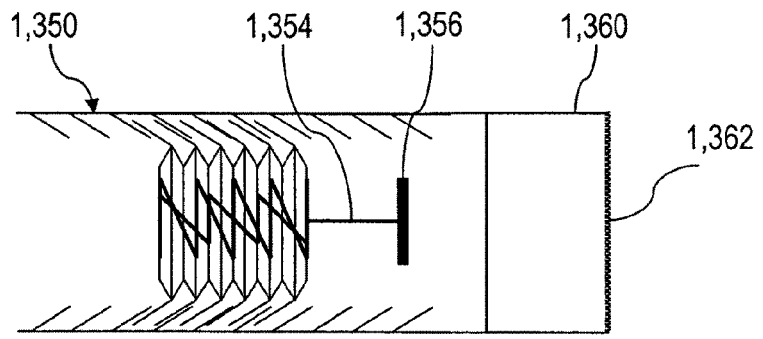
FIG. 108 is a schematic side view of the device of FIG. 107 with a shell.

FIG. 108 shows an example where the shape memory material activated transport device 1,350, illustrated in FIG. 107, is utilized to release a substance once the element 1,356 contacts a shell 1,360 placed at the end of the track. Contact takes place after the element 1,356 advances forward with temperature cycling. Release of the substance takes by pressurization of the shell 1,360 by the element 1,356. As the thermally powered device attempts to advance forward, when forced by the shape memory material spring, its progress is impeded by shell 1,360. The forward advancement compresses the shell and forces it to create a path and to release the substance. In this case the path is created through a permeable wall 1,362. The advantage of using a shape memory material activated transport device to release a substance is that the substance can be released after a predetermined number of temperature cycles of the shape memory material activator. Each cycle corresponds to a given distance traveled by the element 1,356. By knowing the required number of cycles, the total distance that the element 1,356 has to travel to contact the shell 1,360 can be calculated. Depending on the size of the shell, release can continue with temperature cycling until the shell is emptied. In an alternative embodiment to the one illustrated in FIG. 108, the element 1,356 may carry the shell until it encounters an object that prevents further travel. At this point, the thermally powered device attempts to advance and, in the process, pressurizes the shell and creates a path to release the substance on the surface of the contacted object. Release of a substance upon contact can be used in cases when there is a need to release a drug or chemical to the surface of an object to dissolve it in order to clear the pathway and the like.

Figure 109:
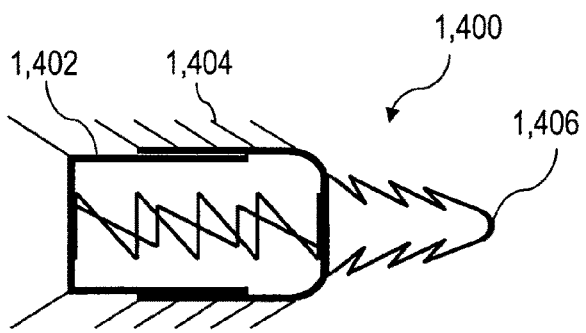
FIG. 109 is a schematic side view of an independent shape memory material activated transport device with a tubular telescoping body.

The thermally powered device can be used without tracks to travel in certain mediums that will sustain it and prevent it from sliding backwards. Such mediums include certain types of living mammalian matter, viscous substances and particulate media. As an example, when a thermally powered device travels in particulate media, the work enablers displace the particles of the media ahead of them as they advance forward. These particles flow to the space left behind by the work enablers to occupy it. Once this space is occupied, they provide traction for further advancement. The same principle applies to viscous substances. In a living mammalian matter or other elastic substance, with each advancement of the thermally powered device the substance needs time to relax and flow back to re-occupy the space left behind by the work enables before traction is available for further advancement. FIG. 103 illustrates an independent shape memory material activated transport device 1,290 that is similar to the previous ones with the exception that it travels without guiding tracks and it is equipped with a pointed nose 1,294 to allow it to minimize the drag resistance. FIG. 109 shows an alternative embodiment of an independent shape memory material activated transport device 1,400 comprising a tubular telescoping body 1,402 configured with variable length fins 1,404 and a rounded nose 1,406. The device 1,400 utilizes a telescoping body instead of a bellows type variable length body. In both concepts, the number of fins, their spacing, size, orientation and geometry must be optimized for the medium in which the device will travel. Preferably, the outside surfaces of the fins should be configured to minimize the frictional effects and drag during advancement and the inside or underside surfaces should be configured to maximize the frictional resistance and thrust. Both of these objectives are achieved through modifications in surface characteristics such as surface finish and the application of surface coatings. In addition, material properties and construction of the fins to produce selective flexibility will minimize drag and increase thrust.

Figure 110:
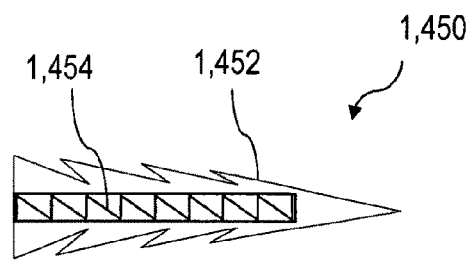
FIG. 110 is a schematic side view of an independent shape memory material activated transport device with a shape memory material body.
Figure 111:
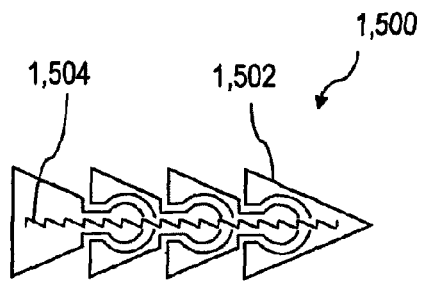
FIG. 111 is a schematic side view of an independent shape memory material activated transport device with a multi-part body.

FIG. 110 shows an independent shape memory material activated transport device 1,450 comprising a shape memory material body 1,452 that performs as a variable length body as well, and a bias spring 1,454 that forces it to return to martensitic shape upon cooling. The fins are integral with the body. The device 1,450 provides opportunities for applications requiring small advancements with temperature cycling and a minimum cross sectional area. FIG. 111 shows an independent shape memory material activated transport device 1,500 comprising a multi-part body 1,502 and a shape memory material spring trained in two way shape memory effect 1,404. The device 1,500 provides for flexibility in following a non-linear trajectory. This concept can be equipped with tracks as well to go around tight curves. Also, a bias spring may be added. To follow a curved course of a constant curvature, the variable length body of any thermally powered device can be made curved such that the curvature does not change with expansion and contraction.

An independent shape memory material activated transport device once deployed can be retrieved using a set of tracks. By placing the tracks in front of the device as it travels, it will be forced to enter the track. By withdrawing the track, the device is retrieved. In this case, the track act as a catcher.

Figure 112:
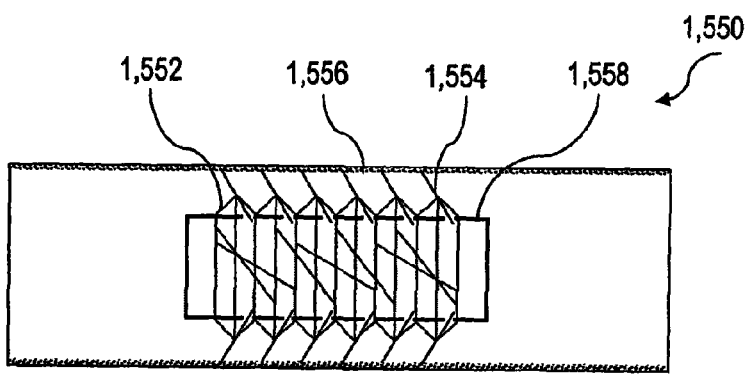
FIG. 112 is a schematic side view of a reversible fin-shape memory material activated transport device.

Fins for the thermally powered devices do not have to be fixed. They can be hinged to provide limited movement such as to minimize the drag resistance and increase the thrust. In addition, they can be made of multiple parts to allow for greater flexibility and travel on variable width or diameter tracks. Also, they can be reversible to allow for travel in both directions. FIG. 112 illustrates a reversible fin-shape memory material activated transport device 1,550 comprising a thermally powered device 1,552 with inwardly extended fins 1,554, a closed end track with a rough surface 1,556 and a shuttle bracket 1,558. The shuttle bracket 1,558 is configured with openings through which the fins are inserted. The inwardly extended fins 1,554 are hinged at the edges of the thermally powered device 1,552. The device 1,550 advances with temperature cycling, with the rough surface of the track proving traction, until the shuttle bracket 1,558 encounters the end of the track. At this point, the device attempts to overcome the resistance offered by the bracket and in the process the bracket forces the inwardly extended fins 1,552 to reverse direction by rotating about the hinge and allow the device to begin traveling in the opposite direction. The rotation is afforded by the flexibility of the fins that have to bend in order to allow the rotation to take place. When the device reaches the other end, the fins are forced to rotate to their initial position and travel begins in the initial direction. Rotation of the fins can also be achieved with different engagement-disengagement mechanisms that may incorporate clutches, cams, springs, ratchet gears, multi-link fins and the like. Reversible thermally powered devices provide an extended life for multiple release applications. In addition, release can take place at both ends of the track at a predetermined period of temperature cycles. By configuring this device with two elements one at each side, instead of single element 1,356 as illustrated in FIG. 108, its capability increases considerably since it can perform similar or different tasks at each end repeatedly as it shuttles back and forth. Reversibility of the thermally powered devices can be extended to devices containing non-fin type work enablers by incorporating mechanisms that are either available commercially or whose operation principles are well established. As an example, the wheels used as work enablers in FIGS. 98 to 100 can become reversible with the incorporation of reversing ratchets. These ratchets use a double end detent and by simply changing its position the wheel rotation can change direction. Actuation to change the position of the detent can be achieved by simple mechanical means with the detent connected to a shuttle type mechanical member via a linkage system. When the mechanical member is pushed against an obstacle or pulled externally, the detents of the wheels reverse their rotation and the thermally powered device begins advancing in the opposite direction.

Thermally powered devices, whether traveling on an open, closed or loop track, are capable of becoming temperature indicators and warning systems by releasing a substance. They can achieve the same function through their relative position on the tracks without having to release any substance. This position can be determined through direct visual observation of the device adjacent to a graduated scale. Preferably, the temperature record would be observed easier with a pointer attached to the thermally powered device pointing its exact position on the graduated scale.

Figure 113:
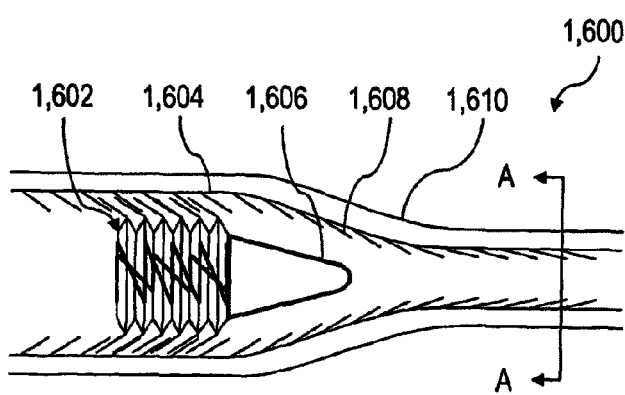
FIG. 113 is a schematic side view of tubular expansion device with a shape memory material activated transport device having a collapsible tubular track.
Figure 114:
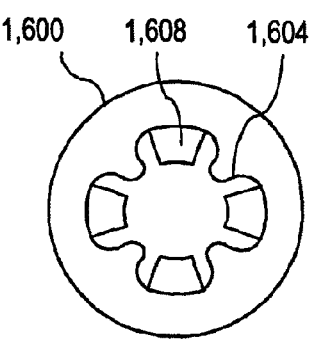
FIG. 114 is a cross sectional view taken along line A-A of FIG. 113.

The shape memory material activated transport devices can also be used to expand a closed conduit laterally such as a tubular passage or to increase the gap defined by the spacing of two surfaces. In addition, they can release a substance such as a drug or sealant to provide a curative agent or to seal the wall. Further, they can expand and place a retainer such as a stent or other support member to hold the conduit in the expanded position, to provide structural support or to form a sealed joint. Furthermore, they can transport diagnostic and detection equipment such as optical or acoustic devices for the inspection of pipes or the examination of cavities in mammalian bodies such as the colon. Samples of these devices are shown in FIG. 113 to 119. FIG. 113 illustrates a tubular expansion device 1,600 comprising a shape memory material activated transport device having a collapsible tubular track 1,604, configured with fins 1,608, inside of which the thermally powered device 1,602 configured with a nose 1,606 that aids the travel process. The purpose of this device is to expand another tube or lumen 1,610 to a larger diameter. FIG. 114 shows a circumferential cross sectional view of the track in the collapsed position at a location A-A indicated in FIG. 113. The tubular track 1,604 collapses between the fins 1,608 to form axial folds and to assume a smaller diameter. The diameter of the collapsed track is smaller than the diameter of the unexpanded portion of the tube 1,610. The difference in diameters allows the insertion of the tubular track 1,604, in the collapsed condition, into the unexpanded portion of the tube 1,610. As the thermally powered device 1,602 advances forward the collapsed tubular track 1,604 unfolds with the aid of the nose and the larger diameter of the thermally powered device and forces the tube 1,610 to expand. Expansion takes place only during one half of the temperature cycle with the advancement of the forward end. When the aft end advances, the forward end remains stationary. The track may remain in the expanded position or may revert back to the folded position once the thermally powered device goes by. An alternative concept to the folded track is to use a set of individual single tracks in a cluster form that opens up as the thermally powered device advances forward.

Figure 115:
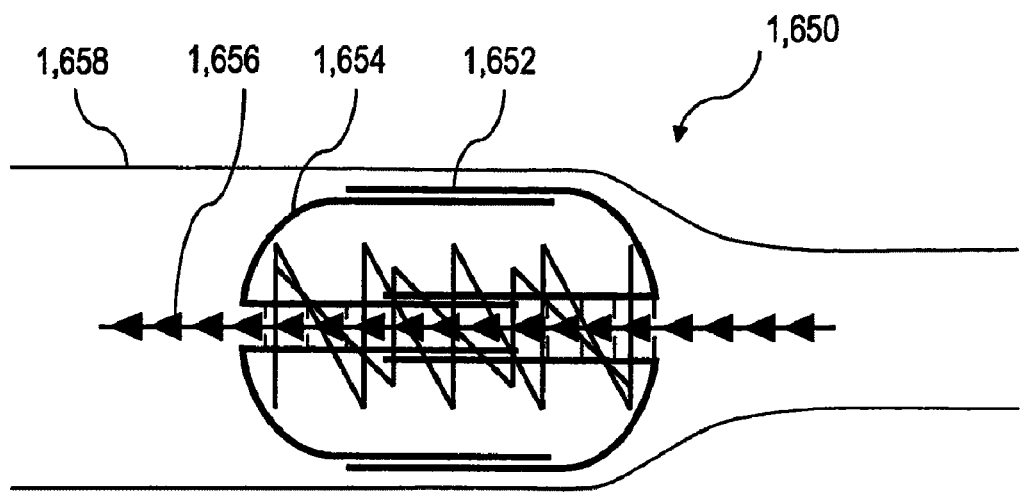
FIG. 115 is a schematic side view of a thermally powered device traveling on a single internal track with the variable length body made of two telescoping halves.

FIG. 115 shows a device 1,650 that is similar to the one shown in FIG. 113, except that the thermally powered device travels on a monorail track 1,656 and the variable length body consists of two telescoping halves, an outer one 1,652 and an inner one 1,654, forming a hollow cylindrical body that is able to expand and contract axially. The work enablers in the form of fins, or other configurations, are placed on the inside (hollow) surface. In order to allow expansion and contraction, there are no work enablers on the overlapping section of the outer half 1,652 of the variable length body. Typically, the monorail track 1,656 has a much smaller profile than the collapsed tubular track 1,604 of FIG. 113 and can be inserted in smaller diameter tubes 1,658 to guide the thermally powered device and to expand them.

Figure 116:
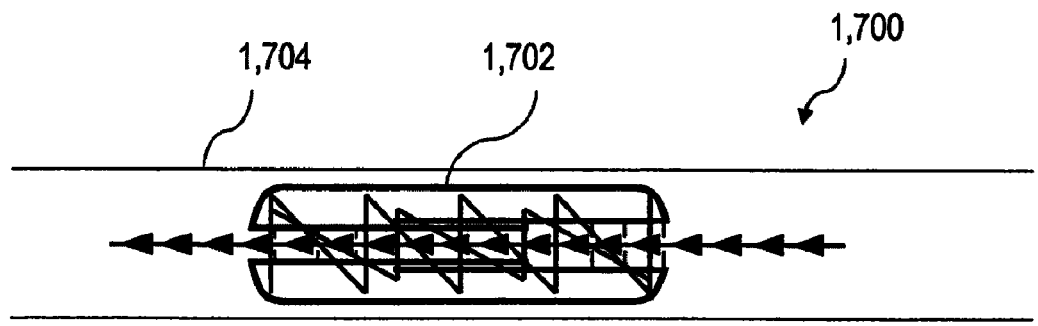
FIG. 116 is a schematic side view of a shape memory material activated collapsible tubular expansion device in the collapsed position.
Figure 116A:
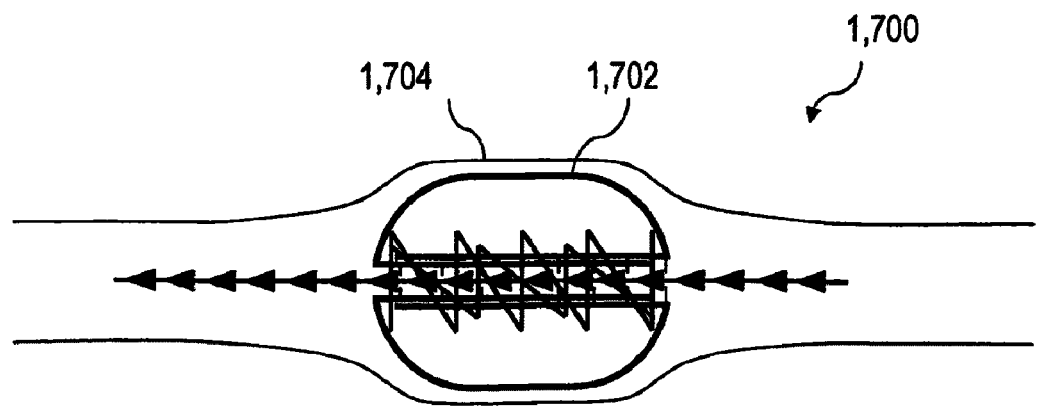
FIG. 116A is a schematic side view of the device in FIG. 116 in the expanded position.

The variable length body of any thermally powered device can become collapsible such that it expands while it travels with one temperature cycle and collapses while it travels with the second half. This allows for the selective or continuous expansion of passages. FIG. 116 illustrates a collapsible tubular expansion device 1,700 that is similar to the one illustrated in FIG. 115. In the present case, the two telescoping halves of the thermally powered device 1,702 are made of an elastically deformable material that has one shape in the free state and another one in the stressed state. FIG. 116 represents the free state of the variable length body while FIG. 116A represents the stressed state. In FIG. 116 the shape memory material spring is in the martensitic state while in FIG. 116A it is in the recovered austenitic shape. In FIG. 116A the aft end of the thermally powered device has advanced forward and its length has been shrunk. The forced axial shrinking of the thermally powered device applies a stress to the outside sections of the variable length body, causes a barreling effect, and forces it to increase its diameter. In turn, the increase in the diameter causes the tube 1,704 to expand. During the second half of the temperature cycle, when the shape memory material spring undergoes reverse recovery, the variable length body stretches forward, goes back to its free state and its diameter decreases to its original size. With the repeated contraction-expansion of the thermally powered device the tube 1,704 expands incrementally with expanded tube portions overlapping from cycle to cycle.

The same principle used to expand a tube diametrically can also be used to shrink a tube diametrically. For this to take place, the thermally powered device must have the work enablers on the outside and travel inside a track. In addition, it must have sufficient core clearance along its length for the tube, that is to be shrunk, to run through it. The tube is shrunk in a reverse manner to the one shown in FIG. 116A. The inner surface of the thermally powered device expands inwards, upon heating or cooling of the shape memory material, compresses the tube and shrinks it by a predetermined amount. The expandable type devices, can be axially segmented to allow for in-situ assembly. This requires that shape memory material springs, with the identical hysteresis curves and coupled with compatible bias springs, are incorporated in the different segments.

Figure 117:
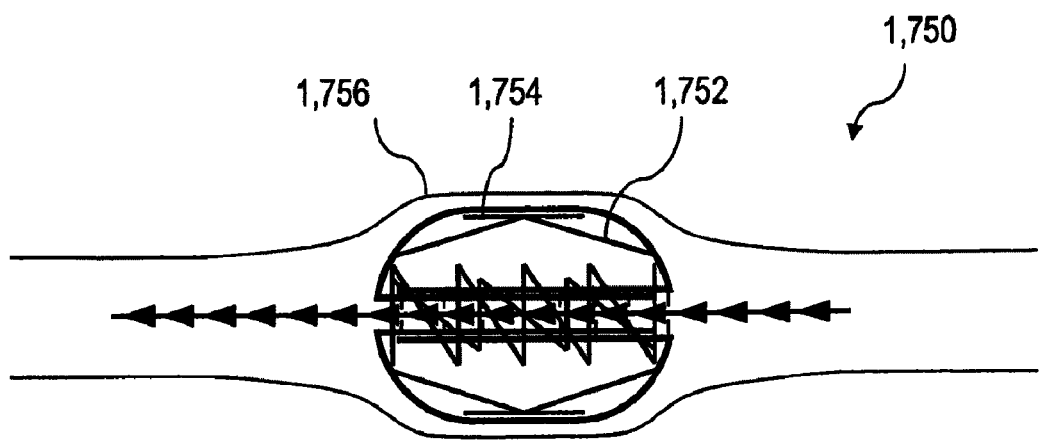
FIG. 117 is a schematic side view of a shape memory material activated lateral expansion device with a linkage system.

The variable length body made of an elastically deformable material can be utilized as a bias spring, thereby eliminating one element from the device. In addition, the variable length body can be made of a number of longitudinal leaf springs that collectively act as a bias spring. Further, a linkage can be incorporated to produce the lateral expansion. FIG. 117 shows an example of a lateral expansion device 1,750, where two identical links 1,752, each connected to one of the two halves of the variable length body, are both connected to another link 1,754 at a common point. The included angle between the two identical links 1,752 changes as the variable length body expands and contracts. During contraction, the included angle decreases and forces the third link 1,754 to move radially away from the axis of the thermally powered device and apply a stress to tube 1,756 and expand it. There are several types of linkage systems that can be used in conjunction with the tubular expansion device. However, the discipline of kinematics is well developed and this device can adopt any suitable linkage system.

Figure 118:
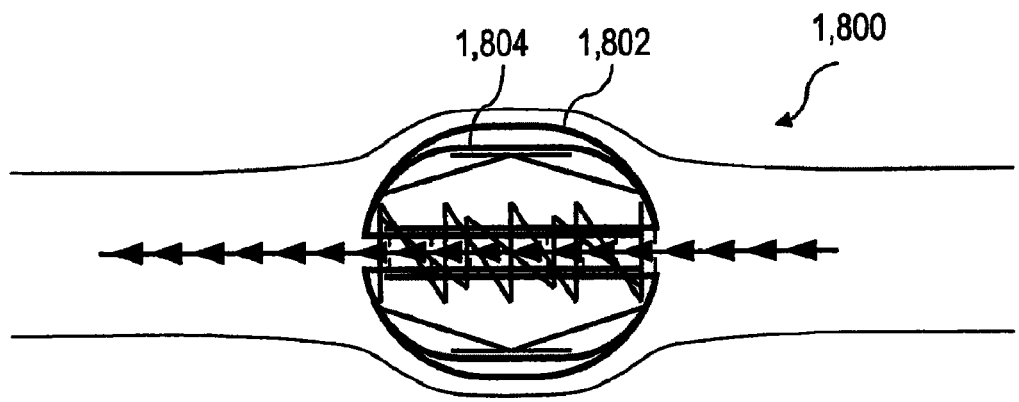
FIG. 118 is a schematic side view of a shape memory material activated lateral expansion device with a shell containing a substance.

The lateral expansion device can also release a substance during the tube expansion process. All substance release concepts presented herein can be used for this purpose. An additional concept of a lateral expansion device is shown in FIG. 118 where a device 1,800, that is similar to the one illustrated in FIG. 117, incorporates a shell 1,802 containing a substance on the outer layer of the variable length body. As the variable length body contracts axially during the circumferential expansion process, the shell shrinks, the substance contained in it is pressurized, the shell wall is converted into a permeable one and the substance is released through it. One of the advantages of this concept is the direct release of the substance to the tube surface upon contact. In addition, a shell of sufficient stiffness can be detached, in the expanded shape, from the thermally powered device upon shrinking and be left in place upon withdrawal of the device. The detached shell is left in the expanded position in contact with the wall of the conduit (tube, lumen or vessel) and with a path created to release its substance. The detached shell can perform multiple functions of releasing a substance, providing structural support to the conduit or sealing a leak at the wall. Prior to its expansion and subsequent detachment, the shell can be held on the surface of the thermally powered device by methods such dimensional interference or a low tack adhesives. The substance to be released on the contact surface may be contained in a shell or an expandable matrix that constitutes the shell or be held on the surface of the thermally powered device if it is in the solid form or substantially viscous. However, the substance released upon contact with the tube wall can be of any state of matter and its release rate can be controlled with similar means (permeable membranes, pressurants etc.) described herein. The substance may be dissolved or react with its surroundings upon release or stay inert. Typically dissolution or reaction is required for biological and chemical operations and inertness for mechanical operations where the released substance might be a sealant or an adhesive used to bond on internal ring to a tube. One advantage of the inner track is that while the device is in the expanded position, it can be pulled out and leave the device in place. This is possible due to the favorable orientation of the work enablers and the tendency of the expanded device to stay in place due to the hoop stresses that exist at the outside.

Besides expanding a tubular conduit and releasing a substance, any collapsible tubular expansion device can be used to expand an object such as a tube segment, ring, stent or a specific device and place it in its expanded form on the inner wall of a conduit such as a tube or a blood vessel. The purpose for the placement of such objects includes; to provide structural support, maintain the specific shape, seal a surface, monitor a the performance of a system and the like. This is achieved by producing an interference, snug, fit between the object to be expanded and the variable length body prior to inserting them in the tubular conduit or simply bonding the two together with low tack adhesive. The collapsible tubular expansion device along with its load, the object, are inserted inside the tubular conduit and at the proper location the temperature of the shape memory material spring is raised and it undergoes shape recovery. The shape recovery causes the variable length body to expand laterally and forces one of its ends to advance. Expansion of the variable length body forces the object to expand against the wall of the conduit and stay in place after the collapse of the variable length body. In addition to round objects, other non-round objects or partially round such as patches can also be placed provided they have the ability to stay in place by mechanical, adhesion or other means. Further, the expanded objects may be combined with a shell to perform the additional function of releasing a substance.

The shape memory material activator of the thermally powered device can be heated and cooled by changes in ambient temperature. In addition, it can be actively heated by direct contact, forced heating or resistance heating by an electric source, either induced or direct. In the case of the electric source, the shape memory material becomes part of the electric circuit and its relatively high electrical resistance produces the required heat to raise its temperature through the transformation range. The thermally powered device can travel and expand laterally in the same fashion as described herein without the utilization of a shape memory material. This requires the powering of the device with alternative means such as fluid pressure mechanical or electrical energy. The fluid pressure can be either hydraulic or pneumatic. By running supply lines to the device, the device expands and contracts following the pressurization-depressurization cycle, as in the case of the thermal cycle, and in the process advances forward similarly to the device that is configured with a shape memory material activator. Typically, for most applications, fluid pressurization, pneumatic or hydraulic, requires the sealing of the thermally powered device or a pressure chamber within the device to avoid leaks. Utilization of fluid pressure does not alleviate the need for a bias spring. The bias spring is required to aid the contraction process and to advance the aft end of the device. In addition to fluid pressure, the device can be operated by a cable release system that applies a force at one end of the device to expand it or contract it and, upon removal of the force, the process is reversed by the bias spring. Again, the device is able to travel with the repeated application and withdrawal of the force. One advantage of the cable release system is that it can be attached either to the internal or external surface of the device, at either the forward or aft end. Attachment to either end allows for the applied force to be either tensile or compressive and to either expand or contract the device. When there is no need to expand the device laterally, application of fluid pressure is restricted to devices whose variable length body can expand only axially with internal pressure. Examples of this are bellows and rigid telescoping tubes. The thermally powered device is also capable of traveling by the utilization of electrical energy to operate devices like motors or electromagnets. With these devices, the bias spring is needed only if the variable length body is actuated in one direction only.

Figure 119:
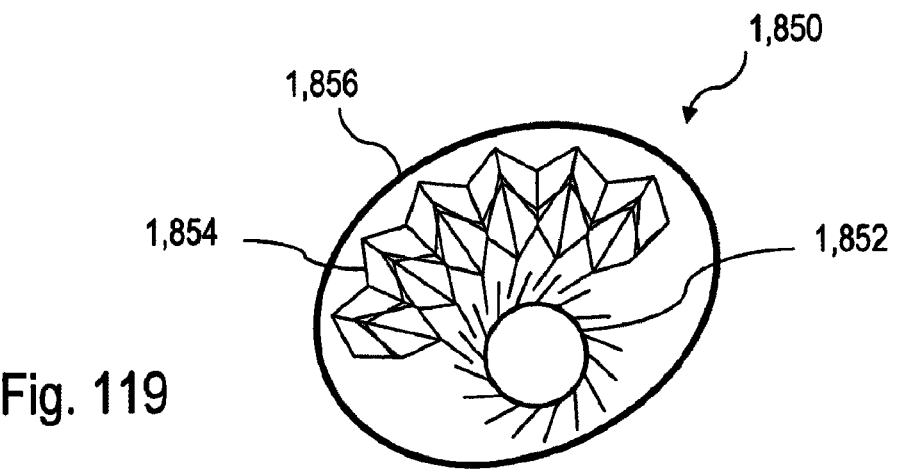
FIG. 119 is a schematic side view of a shape memory material activated eccentric tubular expansion device.

The variable length body in all tubular expansion devices can be made eccentric such as to expand tubes laterally to non-circular cross sections. This is achieved by placing the variable length body's axis at a distance from the track's axis or by making the variable length body non-symmetrical. The two axes may or may not be parallel to each other. FIG. 119 illustrates an alternative example of an eccentric tubular expansion device 1,850 that is similar to the shape memory material activated circular transport device, illustrated in FIG. 96. In this case, the thermally powered device 1,854 travels on the inside track 1, 852 only and the outside track is replaced with an outside housing 1,856. The outside housing 1,856 can be attached to the thermally powered device 1,854 to rotate with it or it can be made of a non-rotating flexible material that accommodates the thermally powered device 1,854 by stretching as it advances around the track. This device can also be used as a cam. When used as a cam, it becomes a self-generating motion device that, unlike mechanical cams that convert regular rotary motion to irregular rotary or reciprocating motion, converts thermal energy to irregular rotary or reciprocating motion. In addition to the asymmetric or the eccentric housing, eccentric motion can also be produced by utilizing a non-circular inner track.

Rotating devices, circular or eccentric, when equipped with abrasive means on their outside surfaces can be used to grind a shell's substance and release it by abrasion. Further, they can grind the inside wall of a conduit to abrade away any deposits such as corrosion products in a pipe or plaque in an blood vessel. In certain cases, depending on the nature of the deposits and the flexibility of the tube, the simple lateral expansion of the thermally powered device can be sufficient to break loose the deposits. By incorporating an adhesive layer on the outside surface of the thermally powered device, loose deposits will adhere to it and be carried away upon withdrawal of the device.

Thermally Driven Track

Figure 120:
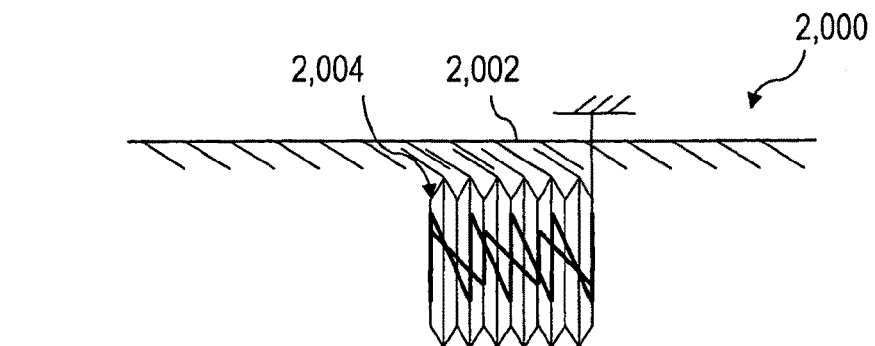
FIGS. 120, 121 and 122 are schematic side views of a thermally driven track device by a shape memory material activator with the thermally powered device anchored at the forward end, before shape recovery, after shape recovery, and after reverse shape recovery, respectively.
Figure 121:
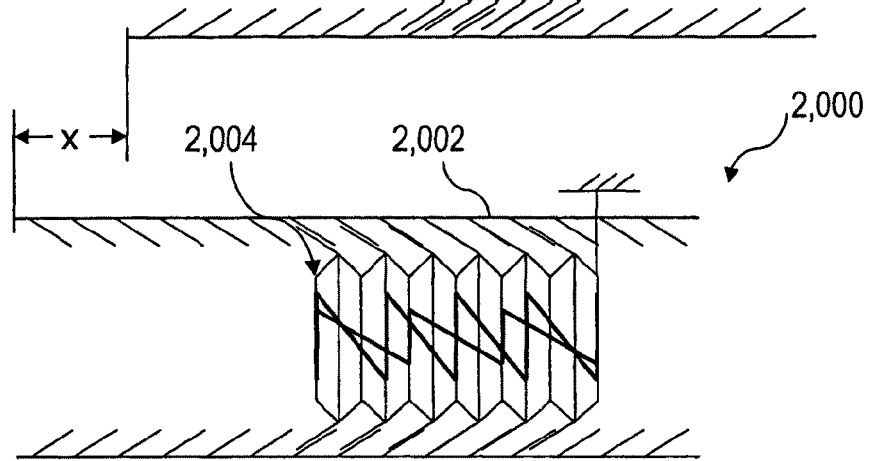
Figure 122:
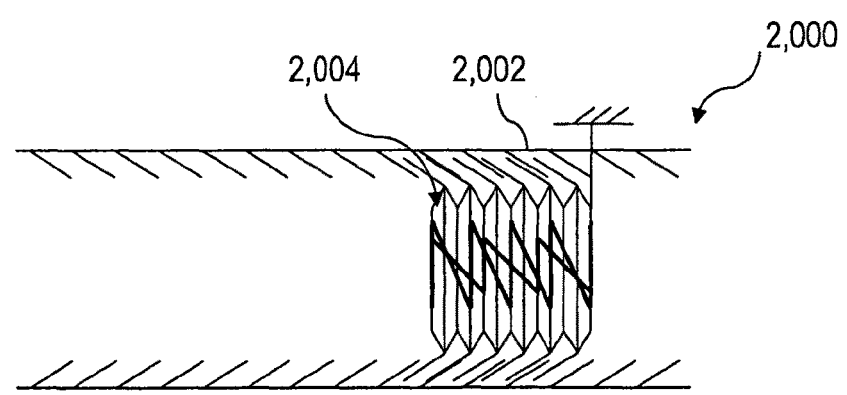

FIGS. 120 to 144 relate to devices that are similar to the shape memory material activated transport device illustrated in FIGS. 90 to 108, with the exception that the thermally powered device is not free to travel but it is anchored at one point along its body while the tract remains free to travel. With this concept, the thermally powered device becomes a self-powered device and acts as an engine to drive the track. FIGS. 120 to 122 illustrate a thermally driven track device 2,000 comprising a thermally powered device 2,004 mounted on an unrestrained track 2,002. This device is similar to the shape memory material activated transport device 1,020 illustrated in FIG. 90. In this case, the thermally powered device 2,004 is anchored at the forward end such that this end is restricted from expanding and the track is free to move. FIG. 120 illustrates the device 2,000 in its initial position with the shape memory material spring in the martensitic state. FIG. 121 illustrates the device 2,000 after shape recovery. During this process, the shape recovery force reacts against the anchored end and forces the thermally powered device 2,004 to expand in the reverse direction. Reverse expansion is possible only with the movement of the unrestrained track 2,002 due to interlocking of the fins. The track is forced to move a distance "x" which is equal to the expansion of the thermally powered device. Since one end of the thermally powered device remains fixed, its expansion is not uniform. The relative expansion along the length of the device is proportional to the distance from the fixed end. At this end expansion is 0% and at the other end it is 100%, which in absolute terms is equal to distance "x". Due to the proportional expansion, the fins along the length of the thermally powered device move by proportional amounts. On the other hand, all the track fins move by the same distance "x". To account for the proportionally unequal movement between the two sets of fins, one of the two sets or both must be flexible to accommodate one fin to move past the other by bending elastically. As a minimum only one set of fins at the free end of the device is required for functionality. FIG. 122 illustrates the device 2,000 in its final position after reverse shape recovery. During this process, the bias spring contracts and forces the thermally powered device 2,004 to contract by moving the aft end forward and returning it to its initial size. There is no movement of the track during this second half of the temperature cycle as the fins do not lock. They accommodate each other by bending elastically and slide past each other with minimal friction without engaging each other. In cases where work enablers other than fins are employed, whether they are wheels, gear teeth, surface effects such as grooves, rough surface finish, and the like, the frictional effects in the direction of contraction are minimal and allow the thermally powered device to contract freely.

Figure 123:
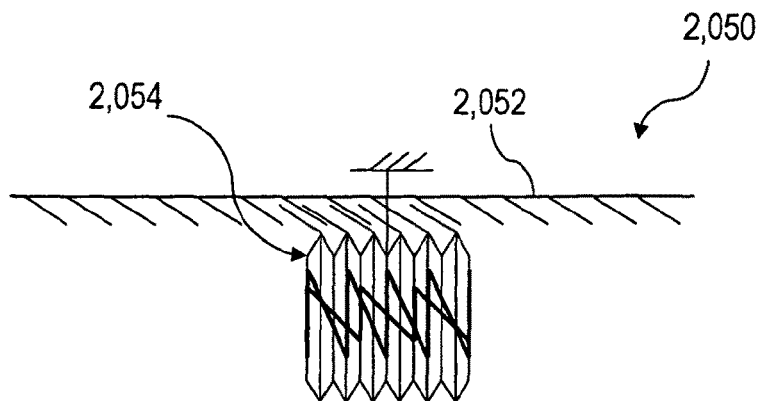
FIGS. 123, 124 and 125 are schematic side views of a thermally driven track device by a shape memory material activator with the thermally powered device anchored at the mid point, before shape recovery, after shape recovery, and after reverse shape recovery, respectively.
Figure 124:
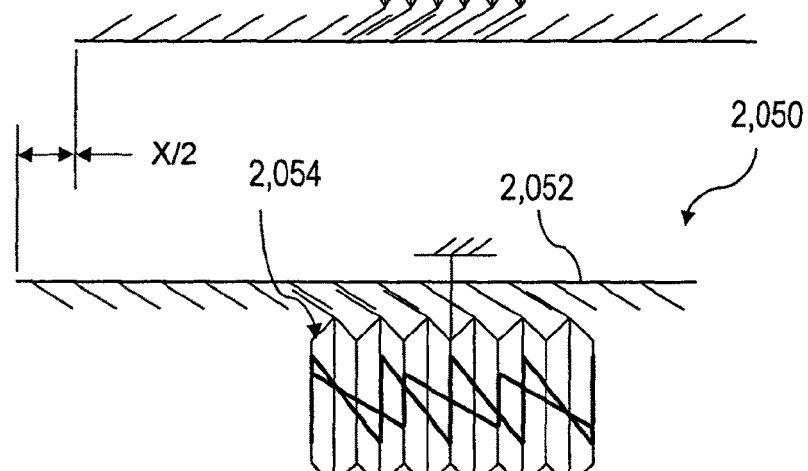
Figure 125:
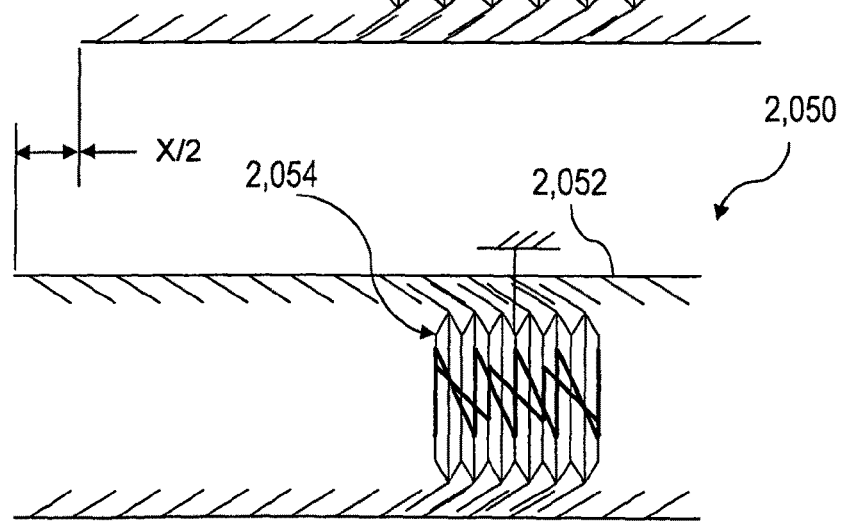

This concept forms the basis for a multitude of applications. Using the same concept as illustrated in FIGS. 120 to 122, but anchoring the thermally powered device 2,004 at the aft end, the unrestrained track travels the same distance. However, the track travels only during the second half of the temperature cycle when the shape memory material spring undergoes reverse shape recovery process. The anchoring point determines the portion of fins that would engage the track fins at each half of the temperature cycle. If the thermally powered device is anchored at mid-body, the track will travel equal distances during both halves of the temperature cycle. FIGS. 123 to 125 illustrate a thermally driven track device 2,050 with a thermally powered device 2,054 anchored at mid-body. In FIG. 123 the thermally powered device 2,054 is at its initial position with the shape memory material spring in the martensitic state. FIG. 124 illustrates the device 2,050 after shape recovery. During this process, the shape recovery force reacts against the anchored end and forces the thermally powered device 2,054 to expand in both directions. During this half of the temperature cycle, the unrestrained track travels one-half the distance "x/2" of the distance traveled when the thermally powered device was anchored at one end. This is due to the fact that during the expansion process only half of its fins engage the track's fins and apply a force to move it. FIG. 125 illustrates the device 2,050 in its final position after reverse shape recovery. During this process, the thermally powered device 2,054 contracts by moving both ends toward the anchor point and returns to its initial size. During contraction, the track travels a distance equal to the one traveled during expansion "x/2" and in the same direction. The fins that did not participate in the advancement of the track during the first half of the temperature cycle are the ones that lock with the fins of the track and advance it this time. The distance traveled with each half of the temperature cycle is proportional to the distance of anchor point from thermally powered device ends. For devices with same orientation fins, the determining factor as to which one will contribute 0% and which 100% is based on whether the shape memory material will expand or contract during the shape recovery process. By anchoring the thermally powered device at different points along its length, the relative distances traveled in each half cycle can be set.

Figure 126:
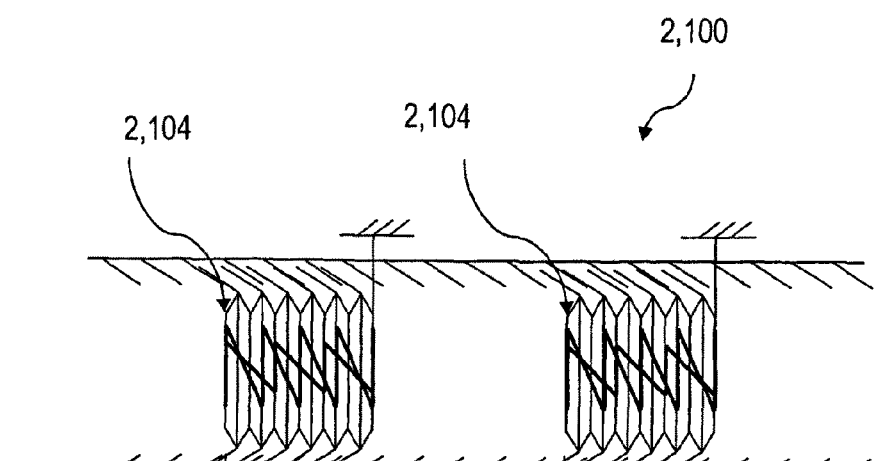
FIGS. 126 and 127 are schematic side views of thermally driven track device with multiple thermally powered devices activated by shape memory material, in the contracted and expanded positions, respectively.
Figure 127:
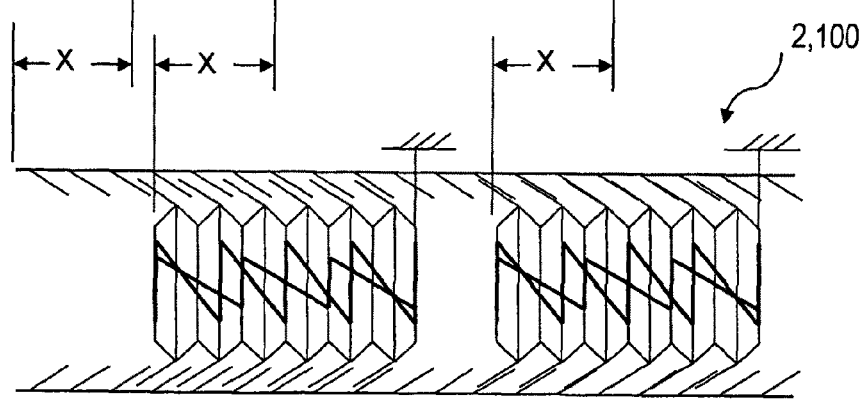

Multiple thermally powered devices can be utilized on the same track to produce additional travel or higher overall recovery forces. FIGS. 126 and 127 illustrate the martensitic and austenitic states, respectively, of a thermally driven track device 2,100 with two thermally powered devices 2,102 mounted on the same track and anchored at their forward ends. They are of the same size, both expand during shape recovery, and both have identical hysteresis curves. During the heating portion of the temperature cycle, both devices expand simultaneously by a distance "x". Because of the simultaneous expansion, the net distance traveled by the track is also "x". Had only one thermally powered device be employed, the total distance traveled by the track would be the same. However, had the track been constrained from traveling, the resultant constrained force would have been twice as large. If on the other hand, each thermally powered device is activated at a different temperature and there is no overlapping of the hysteresis curves, the total distance traveled would be twice as long. If the track is constrained from traveling, an initial constraining force will be developed, as the device with the lowest $A_s$ temperature is activated first will stop increasing in value once the $A_f$ temperature is reached. If the temperature increases further, the second device will be activated and begin to develop a constraining force. Again, this force will stop increasing once the $A_f$ temperature is reached. By adding multiple thermally powered devices to a track several objectives can be accomplished by the proper selection of shape memory material properties and track sizes. In one case, track travel can be extended with increasing temperature if the devices are activated sequentially with rising temperature. In another case, a high constraining force can be developed if the devices are activated in simultaneously with rising temperature. In other cases, by mixing and matching transformation temperatures, different profiles of displacement and constraining forces can be produced with rising and falling temperatures of the shape memory material activators.

By placing several thermally powered devices of different lengths and hysteresis curves anchored at different points along their lengths on the same track, various profiles of track travel with respect to temperature can be achieved. Such profiles include, but are not limited to: (a) Continuous travel if the $A_f$ temperature of one device is the same as the $A_s$ temperature of another device. (b) Discontinuous travel when the $A_s$ temperatures of one device is higher that the $A_f$ temperature of another device. (c) Continuous or discontinuous travel during heating and cooling of the shape memory material activators by anchoring the devices at different points along their lengths. In each case, the travel rate with respect to temperature can be varied by selecting shape memory material of different hysteresis slopes. In addition to employing thermally powered devices that expand with the rise in temperature, similar effects can be achieved with thermally powered devices that contract during the rise in temperature.

Figure 128:
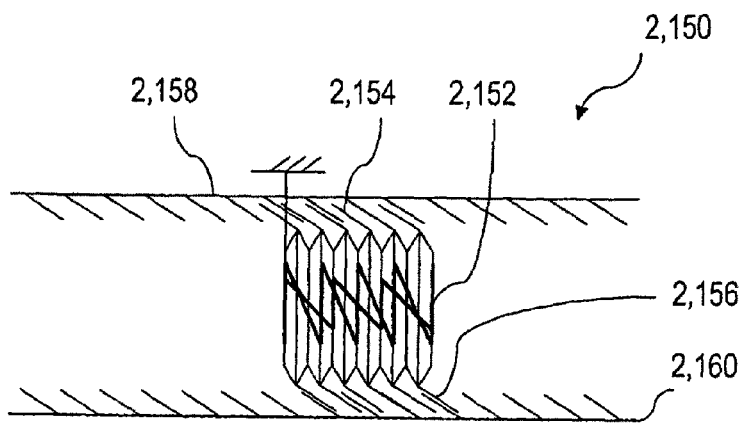
FIGS. 128, 129 and 130 are schematic side views of a thermally driven track device with a diverging fin-thermally powered device activated by a shape memory material and anchored at one end, before shape recovery, after shape recovery, and after reverse shape recovery, respectively.
Figure 129:
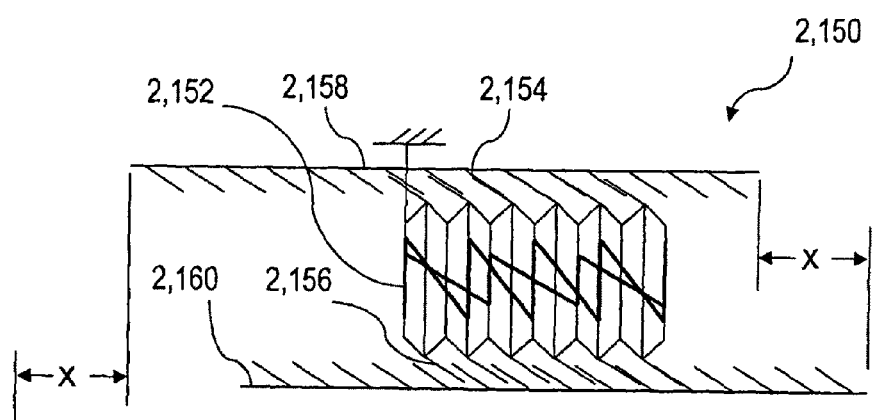
Figure 130:
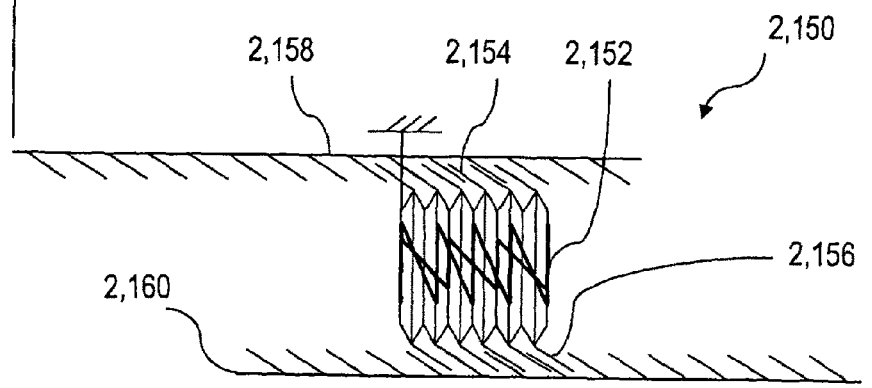

In addition to the design flexibility offered by choice of transformation temperatures and anchoring points, selection of tracks with opposing, non converging, fins offers one more degree of freedom. FIG. 128 illustrates a thermally driven track device 2,150 comprising a diverging fin thermally powered device 2,152 with a row of forwardly extending 2,156 and a row of backwardly extending 2,154 fins and, a set of track rails with opposing, non-converging, forwardly extending 2,158 and backwardly extending 2,160 fins. The fin direction of the track is determined in relation to the fin direction of thermally powered device 2,152. The tracks can move in opposite directions with temperature cycling. FIG. 128 shows the diverging fin thermally powered device 2,152 anchored at one end with the shape memory material spring compressed in the martensitic state. FIG. 129 shows the same device 2,152 in the expanded position after shape recovery. During the expansion process the fins 2,156 of the diverging fin-thermally powered device 2,152 and the fins of the track 2,160 engage and force the track to advance a distance "x" in the direction of expansion. FIG. 130 shows the diverging fin thermally powered device 2,152 in the contracted position after reverse shape recovery. During the contraction process the fins 2,154 of the diverging fin thermally powered device 2,152 and the fins of the track rail 2,158 engage and force the track rail to advance a distance "x" in the direction opposite to the expansion direction. The advantage of this system is that tracks integrated with a single diverging fin thermally powered device can travel in opposite directions with each temperature cycle. When the tracks are restrained from traveling, constraining forces of opposite directions are developed. Again, as with other concepts presented herein, instead of fins other work enables such as wheels, or gear teeth can be utilized.

Figure 131:
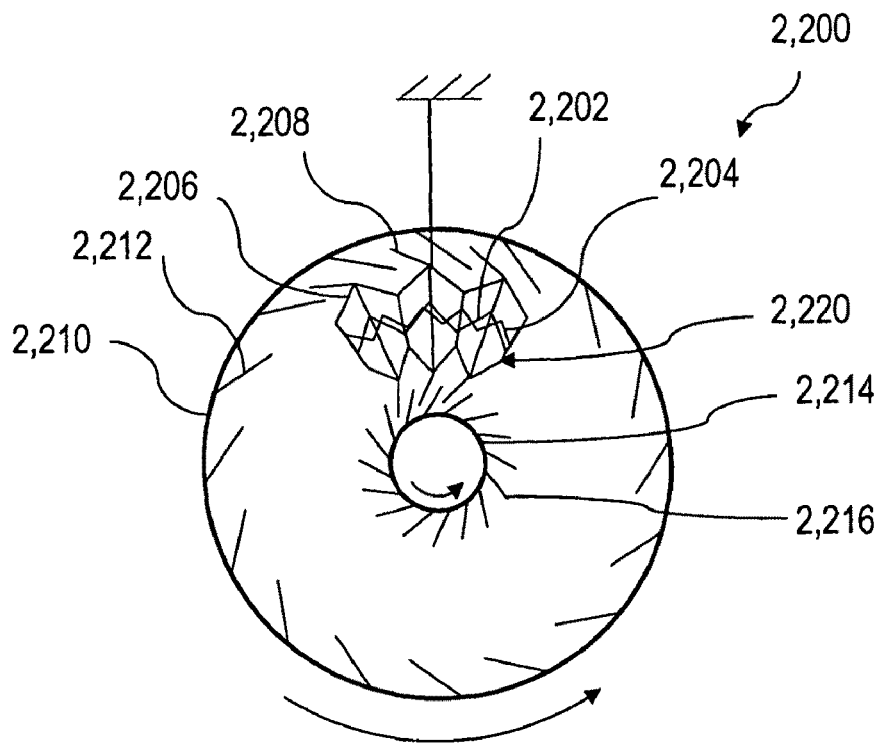
FIG. 131 is a schematic side view of a circular thermally driven track device with a shape memory material activator.

The thermally driven track does not necessarily have to be straight. It can be of any configuration that will advance with the application of shape recovery force. FIG. 131 shows a circular thermally driven track device 2,200 comprising a circular outer track 2,210 configured with a plurality of inward fins 2,212, a circular inner track 2,214 configured with a plurality of outward fins 2,216 and a circular thermally powered device 2,220 anchored at mid-body along its circumference. The circular thermally driven track device 2,200 is similar to the one illustrated in FIG. 96 with the circular thermally powered device 2,220 anchored at mid-body and the outer 2,210 and inner 2,214 tracks free to rotate. The circular thermally powered device 2,220 comprises a curved variable length body 2,206 with a plurality of fins 2,208 and houses a shape memory material spring 2,202, and a bias spring 2,204. The fins 2,208 of the variable length body 2,206 and those of the outer 2,212 and inner 2,214 tracks are skewed to lock the tracks in one direction and to allow them to rotate freely in the opposite direction by flexing and sliding past each other. With the circular thermally powered device anchored at mid-body, both the inner and outer tracks rotate during the heating and cooling cycle of the shape memory material spring by the same angle. One of the advantages of the circular thermally driven track devices is their ability to convert linear motion to rotary motion and to develop torque when the motion is restrained. They perform this function while the temperature changes within a predetermined temperature range.

The angular degree of rotation in each half cycle is half of the angular expansion of the circular thermally powered device. As was the case with the straight track, by anchoring the circular thermally powered device at different points along its body, the relative amounts of track rotation between heating and cooling can be adjusted. All thermally driven track systems presented herein can operate, as a minimum, with a single traveling track provided there is sufficient support to eliminate distortion of the thermally powered device and to keep it on track. As an example, the circular thermally powered device 2,200 can operate without the inner track fins 2,216 provided the inner track provides guiding support to the circular thermally powered device 2,200. Of course, with a monorail system as the one shown in FIG. 95, there is no need for a second track.

Figure 132:
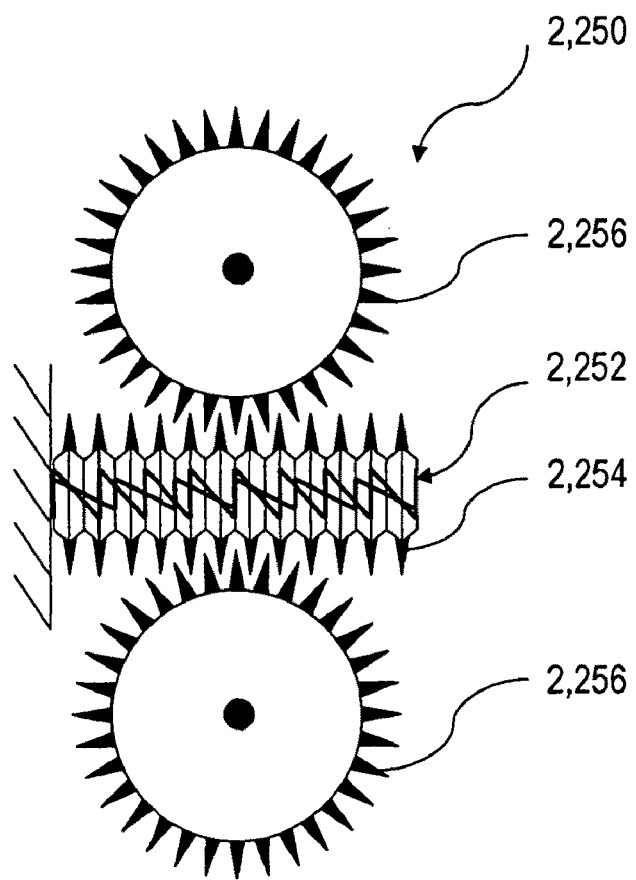
FIG. 132 is a schematic side view of a thermally powered device with a gear system.

Production of rotary motion is not limited to concentric tracks only. Other embodiments utilizing such means as gears, shafts, belts, or chains can be utilized. FIG. 132 illustrates the gear system 2,250 comprising a thermally powered device 2,252 with gear teeth 2,254 as work enablers, coupled with two gears 2,256. The thermally powered device 2,252 is anchored at one end and, as it expands and contacts with temperature cycling, it drives the gears 2,256 back and forth. In this case, the gear teeth geometry does not allow for bending and sliding, as was the case with fins, and the gears have to rotate back and forth. The thermally powered device can be coupled with other circular track systems to produce rotary motion. Instead of building a circular thermally driven system in a planar form, as is the case with the embodiments illustrated in FIGS. 131 and 132, the tracks and the thermally powered device can be integrated in a three dimensional manner for compactness and enhanced capabilities. For example, by powering two parallel circular tracks of equal size by a thermally powered device placed between them, the power will be distributed equally between the two. However, this is not the case with the planar arrangement of the concentric tracks (outer and inner tracks) shown in FIG. 131.

The thermally powered device's body does not have to be flexible in the form of a bellows, neither does it have to be made of one single part. It can be made of tubular telescoping parts requiring a minimum of only one set of fins at the aft end if the thermally powered device is anchored at the other end, or two sets (one at each end) if it is anchored elsewhere along the length of the body. Also, the thermally powered device's body can be an elastomer that performs as a bias spring and can encapsulate the shape memory material spring and become an integral part with it. In this case, the fins can be extensions that are molded or sculptured on the body. Further, the thermally powered device can have no body if the fins are attached to the shape memory material spring directly. The fin spacing on both the track and the body determine the precision of motion transferred from the thermally powered device to the tracks. Typically, the finer the spacing, the better the meshing between the two sets. Again, the shape memory material spring as well as the bias springs can have any configuration. They do not have to be coil springs. As long as the shape memory material can be deformed at one temperature and recover its shape at another temperature by producing a displacement when left unrestrained and a force when it is restrained, it will perform adequately in the devices presented herein. Also, for all the devices presented herein, functionality is independent of shape and size of shape memory material and bias springs. Further, functionality is independent of fabrication and assembly methods utilized to build the devices. The bias spring must have the ability to be deformed elastically by the shape memory material spring during the shape recovery process and produce, as a minimum, a force sufficient to aid the shape memory material spring in its reverse shape recovery process and return it to its deformed cold shape. For metallic shape memory materials such as the nickel-titanium based alloys, the martensitic condition is the cold shape.

Figure 133:
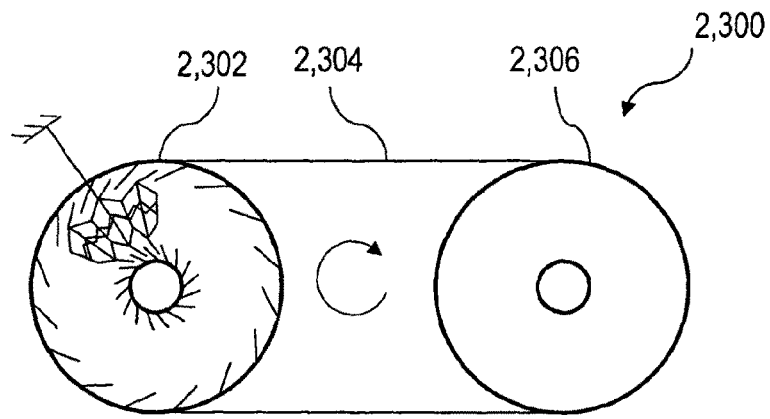
FIG. 133 is a schematic side view of a circular thermally driven power device with a belt transferring power to a wheel.

The energy generated by thermally powered devices can be utilized to create a path in a shell to release a substance. A linear or rotary thermally driven track device can be used for this purpose. Linear or rotary motion can be used to create a path in shell wall to release a substance by fracturing, exploding, imploding, puncturing, peeling, tearing, shearing, grinding, rupturing, splitting, twisting, stretching, squeezing, separating, debonding, grinding and the like, a shell. The path creation can take place with rising and/or falling of the shape memory activator's temperature. In addition, by adding several thermally powered devices to the same track system, a reversible type path can be created repeatedly over different temperature segments. The energy generated by thermally powered devices can be used for other purposes besides path creation. At times, it becomes beneficial if it is transferred to other devices by mechanical means. FIG. 133 Illustrates an example of a thermally driven power transmission device 2,300 comprising a circular thermally driven track device 2,302, and a wheel 2,306 connected to it with a belt 2,304. As the thermally driven track 2,302 rotates with changing temperature, the belt 2,304 transfers the motion to the wheel 2,306. The wheel 2,306 to which the circular thermally driven track device 2,302 is coupled can be of any size such as to either increase or decrease the angular rotation or the resulting torque. Besides the outer track, the inner track can also be used to transfer energy to another wheel. Instead of a belt, other flexible power transmission means such as chains, gears or shafts can be used to transfer motion. In both cases, several thermally powered devices can be incorporated on a single thermally driven track to produce motion over an extended temperature range, increase the torque, and produce motion in two directions during with the rise or fall of temperature.

Figure 134:
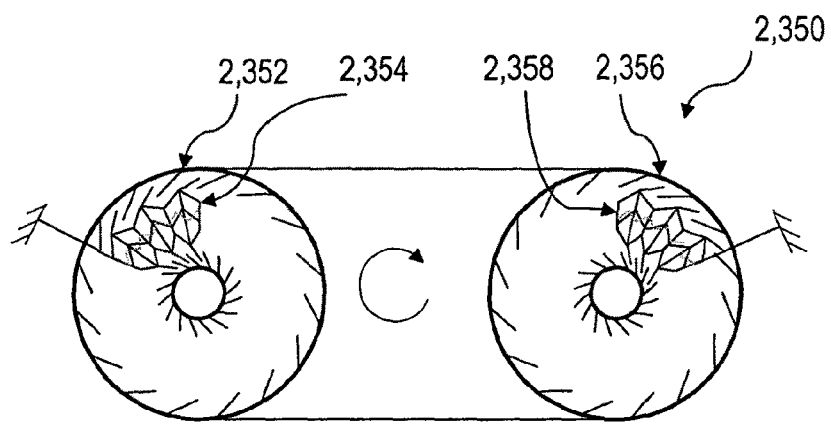
FIG. 134 is a schematic side view of two similar circular thermally driven track devices connected with a belt.

Instead of a free rotating wheel, two or more circular thermally driven track devices can be coupled together with a belt to produce devices with enhanced characteristics. Such a device 2,350 is shown in FIG. 134 where the fins of the outer and inner tracks of both thermally driven track devices 2,352 and 2,356 are oriented the same direction. Each of the thermally driven track devices 2,352 and 2,356 incorporates a single thermally powered device 2,354 and 2,358, respectively. Orientation of the fins in the same direction assures rotation of both devices 2,352 and 2,356 in the same direction. The thermally powered devices 2,354 and 2,358 are anchored at opposite ends such that if the shape memory material springs have identical hysteresis curves and both expand by the same amount during shape recovery, the thermally driven track device 2,352 will rotate clockwise during the shape recovery processes and the thermally driven track device 2,356 will rotate clockwise during the reverse shape recovery process following the path of the hysteresis curve. This way, the belt connecting the two devices will be advancing in the same direction by the same amount in both times. If the hysteresis curves are nested inside each other, overlap or are spaced apart, rotation will take place in the same manner. However, the temperature span between the two sequential advancements of the belt will change. In addition, if ambient heating is used, the temperature cycle must encompass the hysteresis curve width of both shape memory material springs and any span between them to assure complete recovery of both springs and return to martensitic state. If each shape memory material spring is heated individually such as by electric heating, their respective temperature cycles will based on their individual hysteresis curves. If the thermally powered devices illustrated in FIG. 134 are anchored at the same ends, both will rotate simultaneously with the rise in temperature if the hysteresis curves are identical or sequentially if they are different. If the hysteresis curves overlap, part of their shape recoveries may coincide and during this temperature segment, both devices will be rotate. Simultaneous rotation increases the torque of the system but not increase the advancement of the belt.

In the case where the fins of two coupled thermally driven track devices are oriented in opposite directions, the thermally powered devices will also rotate in opposite directions. Unless both shape memory material springs have similar or overlapping hysteresis curves, the thermally powered devices will not counter rotate simultaneously. By rotating at different temperatures, a back and forth rotation is generated. By selecting the shape recovery characteristics of each shape memory material spring, the temperature span between rotations and will be set. If there is simultaneous counter rotation, there will be no net rotation due to restrained motion, resulting in tensile stress in one span of the belt (or connecting member) and compressive stress on the other. Different combinations of fin orientation, anchoring points and shape memory material properties can be used to produce repeated motion with rising or falling temperatures within predefined temperature ranges. The resulting motion can be (a) unidirectional, where a set or tracks or a belt move in one direction, (b) bidirectional, where two tracks of the same track set move in opposite directions, or (c) oscillating, where a set of tracks or a belt go back a forth between two or more positions without making an overall net advancement. In all cases, when the motion is restrained, a force develops that can be converted into torque with rotary systems. These concepts can be used in applications such as; to create a path to release a substance, to accumulate torque, to apply a controlled force at given location, or generally to actuate or to power other devices.

When the shape memory material activators are actively heated, incorporation of multiple devices into one system enhances the system's output considerably. If heating is sequenced to allow one activator to cool to the martensitic state while another is heated to austenitic state such that at any time there is at least one activator powering the system, continuous rotation will be produced.

Figure 135:
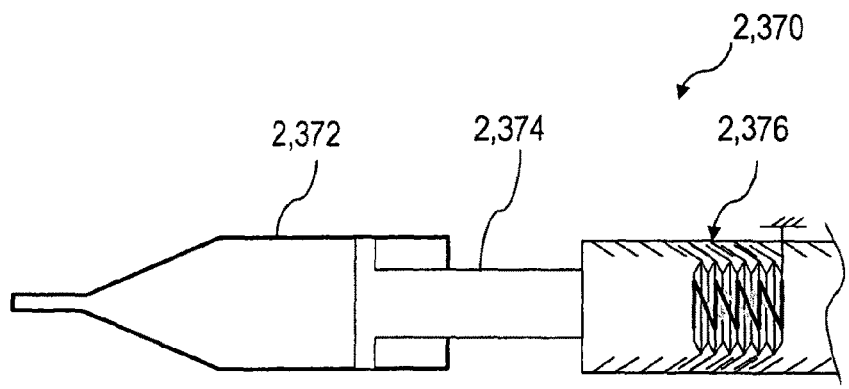
FIG. 135 is a schematic side view of a shape memory material activated extrusion type release device.

The concepts of thermally powered devices and thermally driven track devices can be used to create paths through shells to release substances. In addition, they enhance the path creation process in terms of release types, temperatures, repeated cycles, delayed cycles and the like. FIG. 135 shows an extrusion type release device 2,370, comprising a linear thermally driven track device 2,376, a shell 2,372 in the form of a syringe and a piston 2,374 connecting the two. As the thermally powered device expands during heating, the track applies pressure to the piston 2,374 that in turn transmits it to the substance contained in the shell 2,372 and creates the path to release it. Release takes place by extruding the substance through a nozzle, needle, valve or other opening that may contain a permeable membrane, filter, etc. With this concept, the substance is released only during the heating of the shape memory material spring. Once the $A_f$ temperature is reached, the release stops as there is no longer a force applied by the track. Path creation can also take place during cooling from the $M_s$ temperature simply by anchoring the thermally powered device 2,370 at the other (front) end. Anchoring between the two ends will take place both with rising and falling temperatures. However, the amount of substance released during the rising of the temperature will be a multiple of the fraction defined by the relative distance of the anchor point from the end to the total length of the thermally powered device. For a thermally powered device that expands and contracts linearly, the amount of substance released per degree of temperature change remains constant.

FIG. 136 shows a shape memory material based release device 2,380 that operates in a rolling fashion, but releases the substance similarly to the extrusion process concept. In this case, a circular thermally driven track device 2,384 is utilized and the path is created by a rolling process. The circular thermally driven track device 2,384 rotates as the temperature rises above $A_s$ and the shell 2,382 passes under it. The shell, as it becomes deformed by the rolling process, is forced to decrease volume, increase the internal pressure and to create a path to release the substance. In this process, a path is created by pressurizing the substance in a similar fashion as in the previous concept, FIG. 135. In the present example, the thermally driven track device 2,384 is anchored at its midbody and as such it rotates and creates paths both during heating and cooling.

FIG. 137 shows an example of a grinding release device 2,390. The thermally driven track device 2,394 applies an external compressive force to a shell 2,392 and as it rotates, during heating and cooling in this case, it grinds against the shell 2,392 that consists of a substance that is releasable by abrasion. The outer surface of the wheel may have a rough surface finish or may contain adhered abrasion particles to aid the grinding process.

FIG. 138 illustrates a shape memory material activated unrolling release device 2,400 that creates a series of paths by a peeling process. This device 2,400 comprises a circular thermally driven track device 2,408 that is utilized to peel off the peelable layer 2,404 from a series of shells 2,402 constructed sequentially on a tape spooled on a spring loaded reel 2,406. The reel 2,406 is spring loaded in order to provide tension during the peeling process. The expansion and contraction of the thermally powered device and the spacing of fins can be adjusted to correspond to the spacing and length of the shells, such that with a temperature change there is a predetermined number of shells that would release their substance. The change in length of the thermally powered device, along with its anchor point, determine the number of shells reeled off and thereby the number of paths created with each half of the temperature cycle, while the fin spacing determines the precision of the system. Advantages of this system include simultaneous creation of multiple paths in shells each containing a different substance when they are arranged in parallel to each other on the tape, and the predetermined number of path creations per degree of temperature change of the shape memory material activator.

Figure 139:
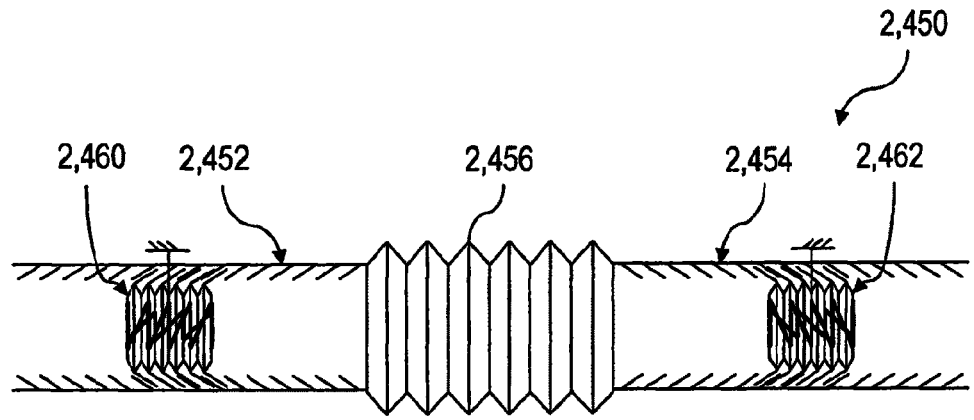
FIG. 139 is a schematic side view of shape memory material activated squeeze type release device with two thermally driven tracks and an accordion type shell.

FIG. 139 shows an example of a dual squeeze release device 2,450 comprising two linear thermally driven track devices 2,452 and 2,454, each containing a single thermally powered device 2,460 and 2,462, respectively, placed at either end of an accordion type shell 2,456. The two thermally driven track devices 2,452 and 2,454 are employed to create a path through the wall of the accordion type shell 2,456 by squeezing it. As the shape memory material springs undergo shape recovery, the thermally powered devices 2,460 and 2,462 force their respective tracks to move in the direction of the shell 2,456 and apply compressive stresses on it. These stresses result in the pressurization of the shell and the consequent release of the substance through a path creation process. The path can be created through increased wall permeability, incorporation of unidirectional flow valves, and the like. The thermally powered devices 2,460 and 2,462 are anchored at their respective midpoints such that they advance their tracks and release equal amounts of substance with each half of the temperature cycle. The pressure exerted by each thermally driven track on the shell is sufficiently large to release the substance but not to deform the thermally powered device of the other thermally driven track. Further, provisions can be made to prevent the force applied by one device form transmitting to the other. If heating and cooling of the shape memory material springs is independent of each other, substance release is independent of any relationship between hysteresis curves. On the other hand, if heating and cooling depend on ambient conditions, the relationship of the hysteresis curves influence the sequence of activation of the thermally driven track devices. If the hysteresis curves of different shape memory material springs have any portion of their $A_s$ to $A_f$ or $M_s$ to $M_f$ curves coincide with each other, both thermally driven track devices 2,452 and 2,454 will be squeezing the shell 2,456 simultaneously, resulting in twice the normal pressure. The increased pressure will result in an increased release rate with a higher overall release. By proper selection of the hysteresis curves, the sequence of substance release and the release rate can be controlled. By reversing the fin orientation of each thermally driven track, the shell will be pulled apart instead of being squeezed. Again, a path can be created to either release or admit a substance by the stretching the shell. Instead of an accordion type shell, other types of shells whose path is created by squeezing or stretching can be used with this device. Such shells include, but are not limited to, crushable and peelable shells. Incorporating two thermally driven tracks in a device extend the operational temperature range and provide for repeated releases with both increasing and decreasing temperatures.

Figure 140:
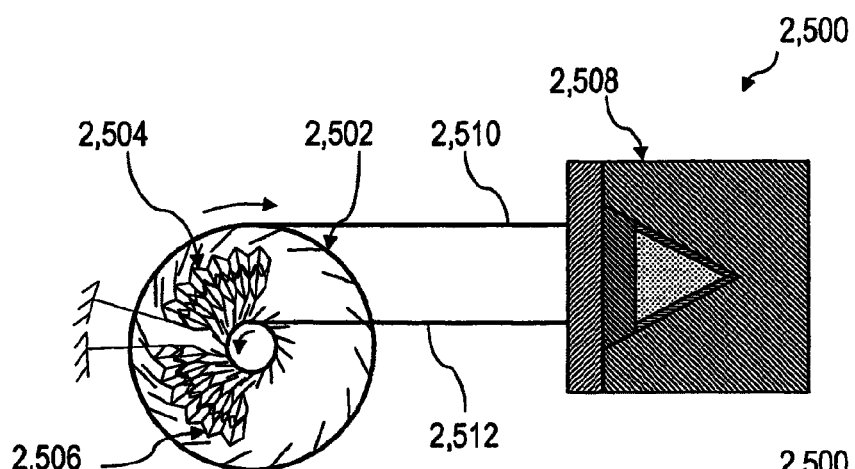
FIGS. 140 and 141 are schematic side views of a thermally driven track release device with two thermally powered devices and a time dependent release device in the closed and open position, respectively.
Figure 141:
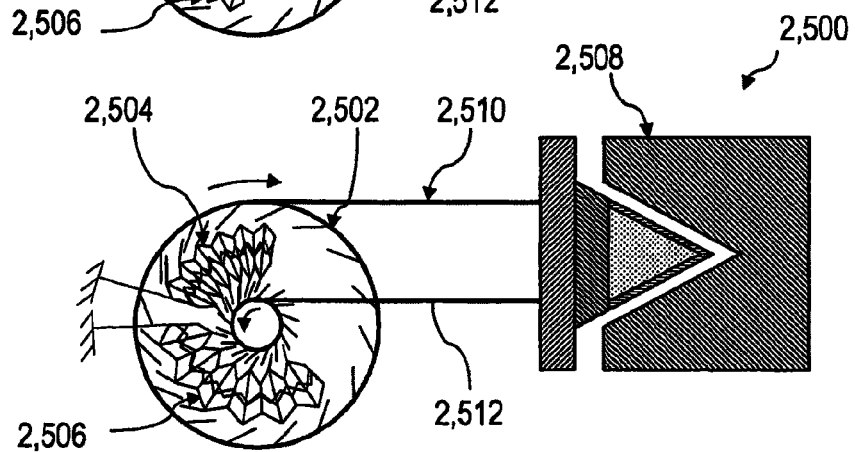

Multiple thermally powered devices can be integrated on a single thermally driven track to produce motion at different temperature ranges. FIGS. 140 and 141 illustrate a circular thermally driven track release device 2,500 comprising a fin diverging circular thermally driven track 2,502 with a pair of thermally powered devices 2,504 and 2,506 with both its outer and inner tracks connected to time dependent release device 2,508, similar to the one illustrated in FIG. 56, via extension members 2,510 and 2,512 respectively. The thermally powered devices 2,504 and 2,506 are anchored at adjacent ends and their fins are oriented in diverging directions to match those of the tracks. In the present embodiment, the hysteresis curves of the two thermally powered devices are spaced apart with the lower one 2,506 having the lowest $A_s$ temperature. As the temperature of the shape memory material spring of the lower thermally powered device is raised, it expands, as illustrated in FIG. 141, and in the process rotates the inner track counterclockwise and creates a path to release the substance. The path creation takes place by converting the rotary motion of the inner track to a linear one and transmitting it to the time dependent release device via the extension member 2,512. In turn, the extension member 2,512 pulls the closing member of the time dependent release device 2,508 open. During the path creation process, both extension members 2,510 and 2,512 retract. There are several established methods such as gearing systems and retractable tapes that can be used to achieve this. When the temperature of the shape memory material spring of the upper thermally powered device 2,504 is raised, it expands and rotates the outer track clockwise to close the path. When the shape memory material spring of the upper thermally powered device 2,504 undergoes reverse shape recovery with falling temperature, the device contracts and rotates the inner track counterclockwise to create the path. The lower thermally powered device 2,504 contracts and rotates the outer track clockwise to close the path when the shape memory material spring contained within it undergoes reverse shape recovery with falling temperature. To assure that expansion and contraction of the thermally powered devices result in equal displacements of the shell's closing member, the relative lengths of thermally powered device fins engaging the inner and outer tracks is adjusted. A larger length of fins is allowed to engage the inner track that the outer. The inner track, being of smaller diameter, requires additional angular rotation to produce the same amount of linear motion as the outer one.

The embodiment illustrated in FIGS. 140 and 141 demonstrates the capability of the circular thermally driven track device to integrate multiple thermally powered devices to create, and to close, a path to release a substance over multiple temperature ranges with repeated temperature cycles. In cases such as the present where a time dependent release device is utilized, the path remains open between temperature ranges. The path is created when one shape memory material spring undergoes shape recovery and it is closed when another shape memory material spring undergoes shape recovery. The release of a substance is only one of the capabilities of these devices. The production of motion and a force with temperature change, either ambient or induced, over multiple temperature ranges, can be utilized to power or actuate a multitude of devices. In addition to the device described above where the tracks are concentric and coplanar, equal or enhanced results can be achieved by arranging the different components in a three dimensional manner. Two or more thermally driven tracks can be arranged in parallel planes and be driven by multiple thermally powered devices placed between them.

Figure 142:
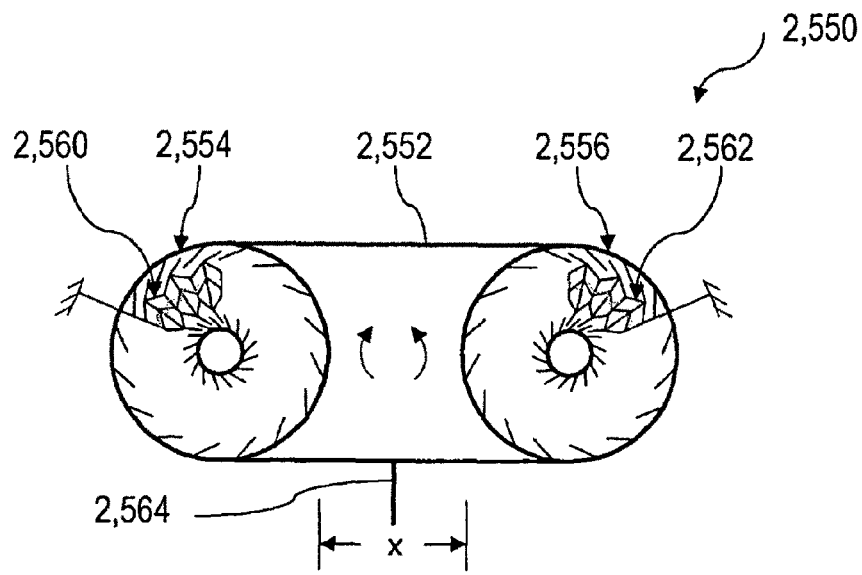

FIGS. 133 and 134 illustrated the production of linear, conveyor like, motion in one direction utilizing one or more thermally driven track devices. FIG. 142 shows an example of a counter-rotating device 2,550 with two thermally driven track devices 2,554 and 2,556 connected with a belt 2,552, having a lever 2,564 attached to it, and their respective thermally powered devices 2,560 and 2,562 anchored in opposite ends with their fins oriented in opposite directions. With the present arrangement, the thermally driven track devices rotate in opposite directions. Unless both shape memory material springs have similar or overlapping hysteresis curves, the thermally driven track devices 2,554 and 2,556 will not counter rotate simultaneously with ambient heating and cooling. By rotating at different temperatures, a back a forth motion is generated and the lever 2,564 oscillates within a distance "x" with each device advancing the belt 2,552 by the same amount, but in opposite direction. If there is a difference in this advancement, the lever will be moving back and forth by unequal amounts and as a result, with each device going through a full temperature cycle, it will be advancing by a net distance equal to the advancement difference between the two thermally powered devices. In cases where there is simultaneous counter rotation, there will be no rotation as a moment would be generated due to constrained motion that will result in tensile stress the lower part of the belt (or connecting member) and a compressive one on the upper. This device presents several opportunities for path creation and substance release applications. For example, the oscillating motion of the lever can be utilized to create a path repeatedly in several types of shells. Such shells include time dependent ones where part of the shell is withdrawn or slides to create a path. A sequential path can be created in several shells arranged in line, having a common sliding cover connected to the oscillating lever 2,564. The cover can be configured with an opening such that when it moves back and forth over the shells, by the action of the lever, a path is created every time the opening lines up with a specific shell. In a similar manner, a circular thermally driven track device can perform the same function by rotating a sliding cover, over a group of shells arranged in a circle.

Figure 143:
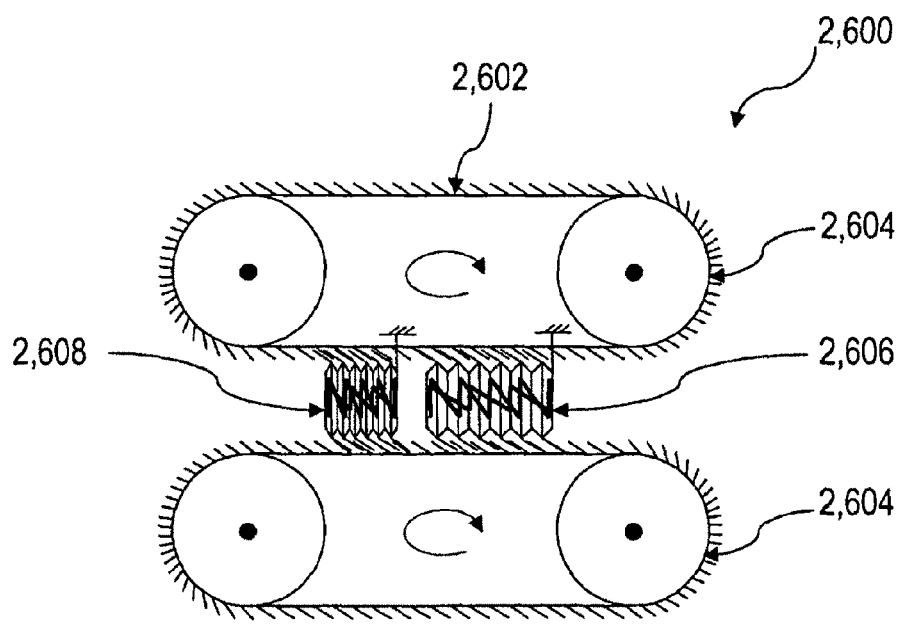

The thermally powered device constitutes an energy conversion machine. It utilizes thermal energy and converts it into mechanical energy. It is capable upon heating or cooling to produce motion and apply a force to perform work. When left unconstrained, it travels on a guided or unguided track. The thermally driven track device expands the capabilities of the thermally powered device in terms of providing the means for power transfer. When a circular thermally driven track device is utilized, the expansion and contraction of the thermally powered devices is converted into rotary motion that can easily be manipulated and transferred via mechanical power transfer mechanisms comprising gears, belts, chains, shafts and the like. The concept of the thermally driven track device is a modular one in that it allows for the integration of multiple devices, interconnected with mechanical power transfer means, to produce a system of increased work output. The modularity of the system is not restricted by the scale of the individual devices. This modularity provides a multitude of opportunities for expansion in both two and three dimensions. For example FIG. 143 illustrates an energy conversion system in the form of a planar thermally powered device 2,600 comprising two thermally powered devices 2,606 and 2,608 driving a set of two identical flexible tracks 2,602 with each track looping around two wheels 2,604. The fins of the thermally powered devices 2,606 and 2,608 are diverging such that the loops formed by the flexible tracks 2,602 rotate in the same direction. The thermally powered devices 2,606 and 2,608 are anchored at the same ends with the first one contracting with rising temperature and the second one expanding. With this arrangement, and identical hysteresis curves, both tracks rotate simultaneously with the rise and fall of the temperature. If the thermally powered devices are configured with continuous fins around their circumferences, more flexible tracks can be added to form a three dimensional system. In addition, the wheels 2,604 can be of different diameters in order to produce different values of speed or torque. Further, more thermally powered devices can be added to produce rotation over wider temperature ranges. Also, continuous rotation or higher torque values can be produced by heating and cooing individually the shape memory material springs of several thermally powered devices. One advantage of this device is that it converts linear motion to rotary motion. In addition, it can distribute the power generated by the shape memory material springs to different rotating members for further usage. One such usage is the path creation to release substances contained in multiple shells.

Figure 144:
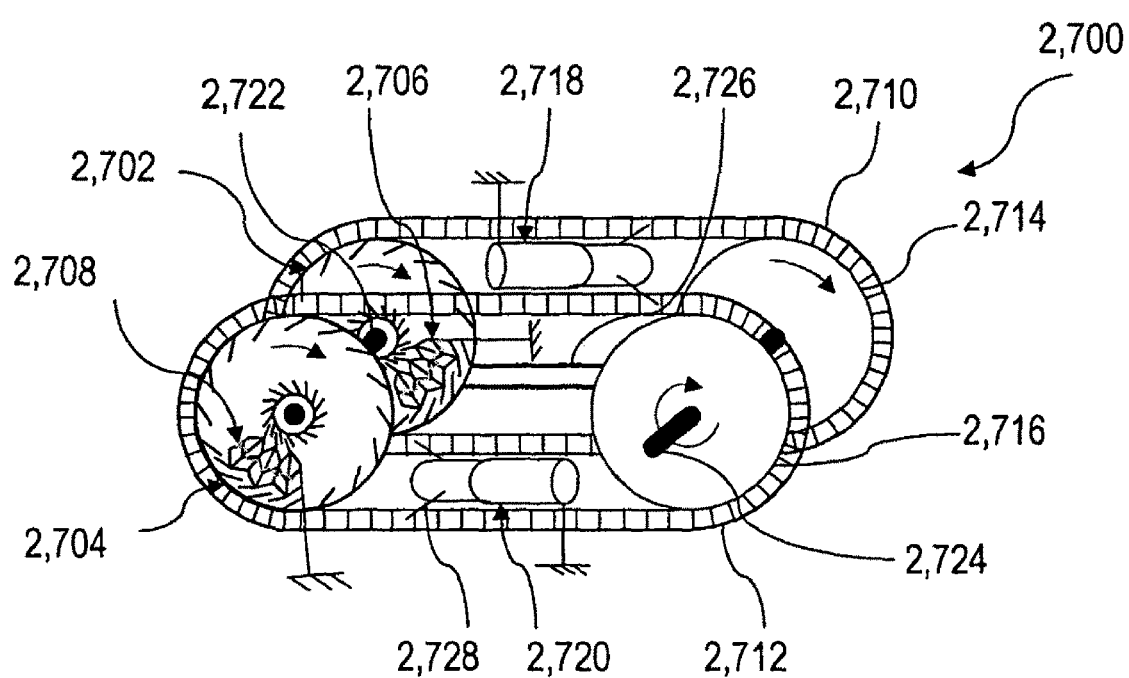

FIG. 144 illustrates an embodiment of an energy conversion system 2,700 in the form of a three dimensional thermally powered device comprising two circular thermally driven track devices 2,702 and 2,704. The first circular thermally driven track device 2,702 has a thermally powered device 2,706 mounted on its tracks and rotation from the outer track is transferred to a wheel 2,714 via a driving closed loop flexible track 2,710. The second circular thermally driven track device 2,704 has a thermally powered device 2,708 mounted on its tracks and rotation from the outer track is transferred to a wheel 2,716 via a driving closed loop flexible track 2,712. The two thermally driven track devices 2,702 and 2,704 are connected via a shaft 2,722 such that rotation from the inner track of one is transferred to the other. The two wheels 2,714 and 2,716 are connected via a shaft 2,724 such that rotation from both wheels is transferred to this shaft. The two shafts 2,722 and 2,724 are connected via a belt 2,726 such that rotation from the inner tracks of the thermally driven track devices 2,702 and 2,704 is transferred to shaft 2,724. The power generation is enhanced with the mounting of two telescoping type thermally powered devices 2,718 and 2,720 on the driving closed loop flexible tracks 2,710 and 2,712 respectively. The purpose of this device is to convert thermal energy into mechanical energy and concentrate it in a single shaft 2,724. It demonstrates the capability of thermally driven track devices to convert energy and build multi-component modular energy conversion systems. The system of FIG. 144 consists of four power conversion units; circular thermally driven track devices 2,702 and 2,704 and two telescoping type thermally powered devices 2,718 and 2,720 that utilize the driving closed loop flexible tracks 2,710 and 2,712 and belt 2,726 to transfer the generated motion to a single shaft. The work enablers, fins in this case, are oriented such that the direction of all rotating elements is clockwise. All thermally powered devices 2,706, 2,708, 2,718 and 2,720 are held stationary on one end and produce motion only during one-half of the temperature cycle of their respective shame memory material springs. The telescoping thermally powered devices 2,718 and 2,720 have only one set of fins 2,728 each, mounted at the free end. More fins can be added, however, one set is the minimum required for functionality. During expansion of their variable length bodies, telescoping tubes in this case, they force the driving closed loop flexible tracks 2,710 and 2,712 to rotate clockwise. An energy conversion system such as 2,700 offers the opportunity to add more thermally powered devices or modules to existing tracks or modules to increase the energy conversion capacity of the system. As a minimum, a module constitutes a thermally driven track device with means such as belts, chains, or gears to transfer motion to the system.

By integrating several modules comprised of thermally powered devices, tracks and connecting means, the energy conversion system can be expanded from a linear one to a planar one to a three dimensional system. Each module constitutes a subsystem that funnels the power generated to a single mechanical member such as rotating gear or shaft. There is no limit to the number of modules that can be combined to funnel their power output to a common mechanical member. This modularization provides the flexibility of increasing the capacity of the energy conversion system by the simple addition of more modules. By selecting the shape memory material springs to have different hysteresis curves, a continuous output motion can be produced with the rise and fall of the temperature. In addition, by selecting the shape memory material spring type and size along with the number of modules, different levels of energy output are achieved.

If the shape memory material springs are heated by ambient heat, energy conversion will take place during ambient temperature change. Depending on the hysteresis curves of the individual shape memory material springs, energy conversion may be extended continuously or intermittently from the lowest $A_s$ temperature to the highest $A_f$ of the hysteresis curves. Also, depending on the anchoring arrangements of the individual thermally powered devices, additional rotation can be produced during cooling from the highest $M_s$ to the lowest $M_f$ temperature. Any output during reverse shape recovery is attributed to either the bias springs or to the two way shape memory effect.

For a higher rate of energy conversion, heating of the shape memory material can be achieved by electric power. The electric resistance of the certain shape memory materials such as Nitinol is sufficiently high to allow them to be used as electric resistors. In this case, individual shape memory material springs are connected to a power source and heated resistively. Heating of the shape memory material springs can be simultaneous for maximum torque production with accompanied discontinuous motion, or sequential such as to allow one group of shape memory material springs to cool while another group is being heated up resulting in reduced torque but a continuous rotation. Increased energy output requires a rapid cooling rate in order to allow for fast cycling. A large system consisting of multiple modules of thermally driven track devices can be used to counter the effects of slow cooling. In this case, at any given time, different modules or group of modules will be at different stages of heating-cooling cycle such that there is motion produced continuously.

Figure 145:
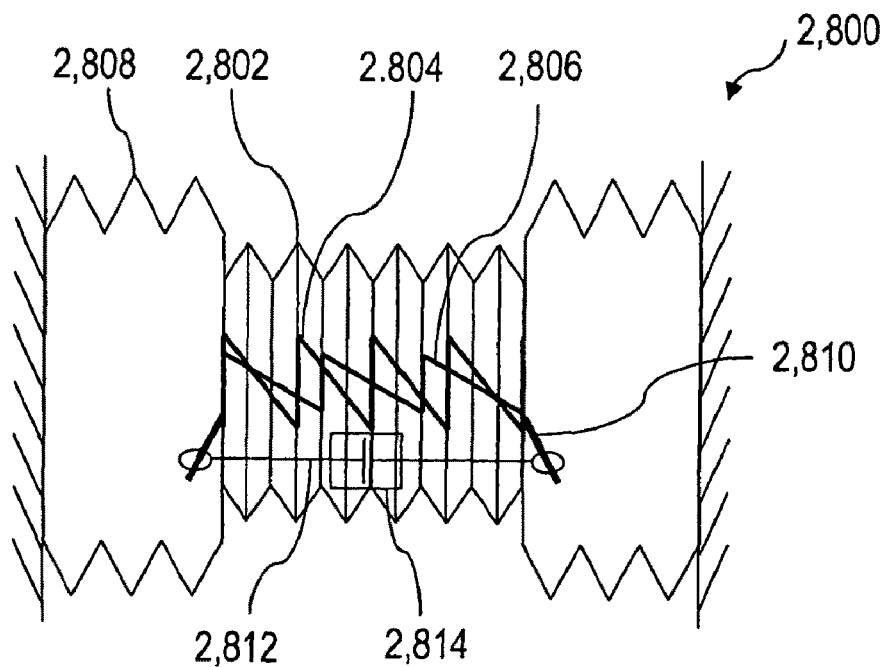

The shape memory material spring activators can be cooled with a moving fluid, gas or liquid, to accelerate the cooling rate. If the $M_f$ temperature is above ambient, forced ambient air can be used as a cooling medium. In cases where forced cooling is not possible or it is not considered optimum, the individual shape memory material spring activators can be cooled with a cooling fluid contained in individual reservoirs. Such a self cooling device 2,800 is illustrated in FIG. 145 and consists of a thermally powered device (work enablers not shown) and a cooling system. The variable length body 2,802 of the thermally powered device is capable of containing the cooling fluid and communicating with two cooling reservoirs The cooling system consists of two flexible body reservoirs 2,808, one at each end, that communicate with the variable lengthy body via two valves 2,810 that allow for in and out passage of the cooling fluid. The opening of two valves 2,810 is controlled by two links 2,812 that move apart from each other when the thermally powered device expands, opening the valves for the fluid to exit. The two links 2,812 move toward each other when the thermally powered device contracts, reversing the direction of the valves for the fluid to enter. The movement of the links 2,812, and in turn the total displacement of the valves, is controlled by a length restrainer 2,814. The total length of the device 2,800 is fixed such that when the thermally powered device expands by the shape recovery force, the reservoirs contract, and the fluid is forced to flow from the reservoirs to the variable length body.

Figure 146:
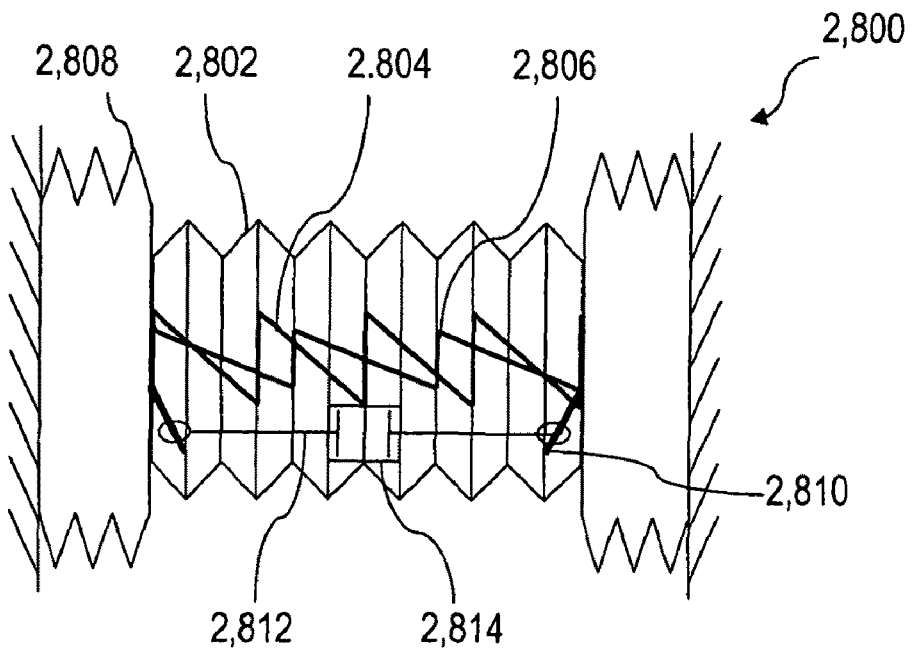

Prior to heating of the shape memory material spring 2,804, the variable length body is in the contracted position occupying a minimum volume while the two reservoirs 2,808 are in their expanded position occupying a maximum volume. The two valves 2,810 are open toward the reservoirs as shown in FIG. 145. Due to the volume differential between the variable length body and the reservoirs, sufficient fluid is drained into the reservoirs such the shape memory material spring 2,804 is not in contact with the fluid. During heating of the shape memory material spring 2,804, the variable length body expands as shown in FIG. 146, the two reservoirs 2,808 contract, the two valves 2,810 reverse direction and the fluid flows into the variable length body and begins to cool the shape memory material spring 2,804. As the cooling process progresses, the shape memory material spring undergoes reverse shape recovery and the bias spring 2,804 forces the variable length body to contract, the reservoirs to expand, and the valves to reverse direction. With the cooling process, the fluid flows back into the reservoirs, and the shape memory material spring no longer is in contact with the fluid. As the fluid in the reservoirs is heated up with temperature cycling, the heat can be transferred to ambient or be absorbed by another fluid in contact with the external surface of the reservoirs. Additionally, a fluid replenishing system can be put in place to provide a constant temperature fluid.

Figure 147:
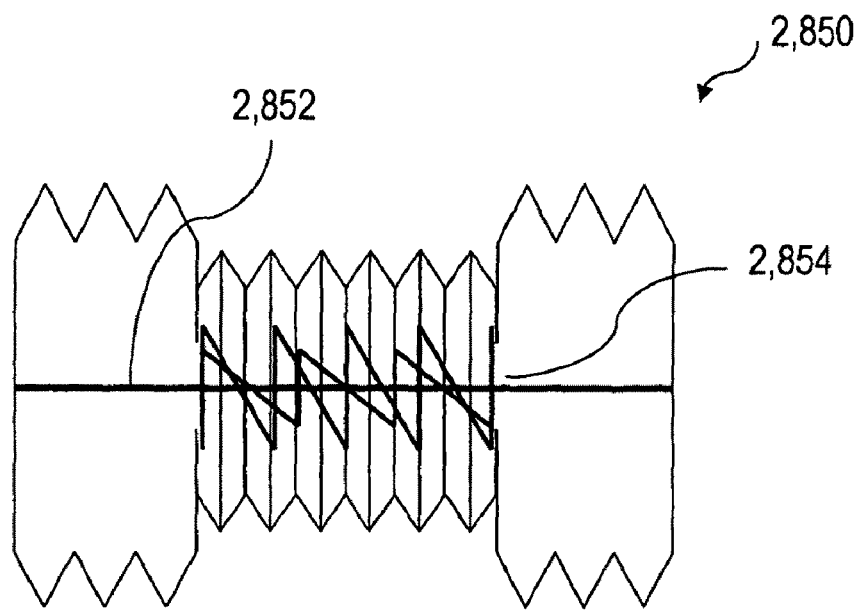
Figure 148:
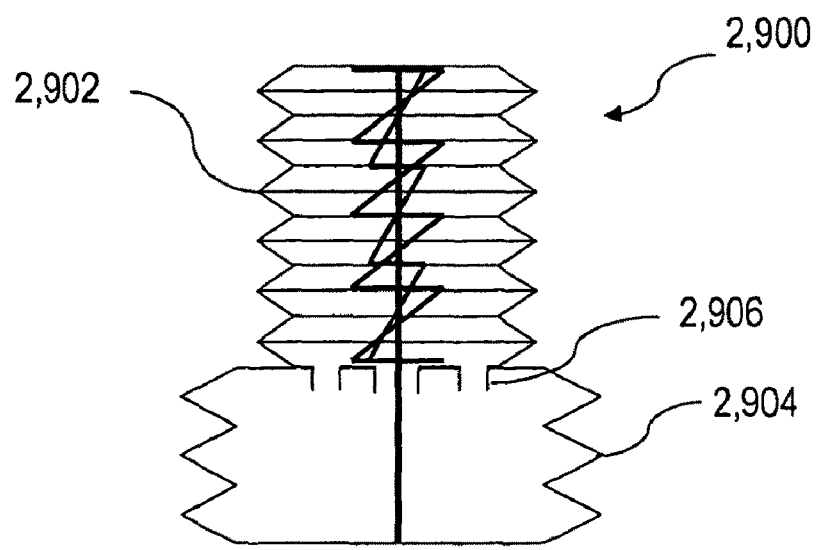

FIG. 147 illustrates a similar concept as the one illustrated in FIG. 145, with the exception that no valves are used. The device 2,850 of FIG. 147 utilizes a restraining rod 2,852 with two openings 2,854, one at each end of the variable length body, for the fluid to flow in and out of the reservoirs. The function of the restraining rod 2,852 is to keep the overall length of the device 2,850 constant such that when the variable length body expands, the reservoirs contract and the fluid flows into the variable length body. When the variable length body contracts, the reservoirs expand and the fluid flows into the reservoirs. The incorporation of two reservoirs allows the system to be orientation free. The relative sizes and shapes of the various components along with the location of the valves allow this device to operate at different orientations, from horizontal to vertical. A simpler version of device 2,850 is shown in FIG. 148, where a self cooled device 2,900 utilizes only one reservoir and the need for the valves is eliminated. In order for the fluid to flow in and wet the whole surface of shape memory material, the device 2,900 has to operate in the vertical position. Deviations from verticality are permitted as long as the ability to cool the shape memory material spring is not diminished. Openings 2,904 at the bottom of the variable length body 2,902 are adequate to allow the fluid to flow in and out with the expansion and contraction process of the variable length body, respectively.

When several modules of thermally powered devices are used, individual modules may be forced heated and cooled as groups by a circulating fluid system. By selecting the thermally powered devices in each module to have the same transformation temperatures, fluid used by one module for cooling can be used in another module for heating if the $M_f$ temperature of the first module is the same or higher than the $A_f$ temperature of the second module. In this system, the heat of transformation released by the shape memory material activators of one module during cooling is absorbed by the shape memory material springs of second one during the shape recovery process. This way, the temperature increase of the fluid attributed to austenite to martensite transformation in one module is reduced by the same relative amount in the second module by the heat absorbed during the martensite to austenite transformation. This type of closed recirculatory system tends to minimize the energy required to operate the system.

Certain materials suffer fatigue failures when subjected to cyclic loads. In many materials, including metallic shape memory ones, fatigue life is extended by frequent annealing treatments. To eliminate fatigue failures in thermally activated devices, the shape memory material springs can be partially or fully annealed in situ prior to developing permanent damage. Annealing removes the dislocations accumulated during cycling and in general rehabilitates the material. When the shape memory material springs are heated resistively for the operation of the device, the electric circuitry exists and can be used to anneal the spring resistively, in situ. The shape memory material springs already have their shape and since there is no need to re-set them, no restraining tooling is required for annealing. The annealing temperature to extend fatigue life should be kept at a level low enough not to alter the shape memory properties or the shape memory material spring. Typically, this level is below the temperature of the last heat treatment prior to placing the spring in service. When bias springs are used, it is preferable to decouple them from the shape memory material spring to eliminate the application of external stresses.

There are numerous applications for the energy conversion system. They range from the specific ones such as the creation of a path to open a shell or a group of shells to release a substance, to the general use of mechanical energy similar to the one produced by heat engines. Applications also include medical devices such as implants, or drug delivery systems. One of the main advantages of the energy conversion system is the ability to be scaled up and down by either adding modules of thermally powered devices together or by changing the size of the individual thermally powered devices. Both options allow for an extended range of sizes from large scale energy conversion industrial type applications to MEMS (micro electro-mechanical systems) and nano-scale applications. These options are available as the function of these devices is independent of their fabrication method.

Arming

A problem encountered by the industry of temperature activated devices is the requirement to keep them inactive, in a dormant state, during manufacturing, storage and transportation. The state of dormancy is maintained by keeping the devices at low temperatures until the beginning of their service life, mostly by refrigeration, in order to avoid premature activation by ambient heating. If the devices are designed to be activated at a temperature lower than the ambient, they must be kept heated at a temperature higher than ambient. A concept of a single action arming process, described herein, solves this problem by allowing the devices to remain dormant until usage time. In the dormant state, the devices are unable to create a path through the shell when exposed to various temperature environments. Upon arming, they are placed in an active state after which time they are ready to create a path through the shell once the shape memory material activator attains a predetermined temperature. This concept allows either the supplier or the user of the devices to arm them at anytime after their fabrication is completed. Arming, as defined herein, is the process of placing the device in an active state of readiness that enables the shape memory material activator to create a path through the shell once it attains a predetermined temperature. Prior to arming, the shape memory material activator can attain any temperature, and change phases accordingly, without being able to create a path to release the substance contained in the shell. Enabling is achieved by deforming the shape memory material activator in situ while in the martensitic state. Arming is performed with a single action involving one simple operation such as pushing, pulling, rotating, or bending. A second arming method involves the deformation of the shape memory material activator as well, but in addition it allows its coupling with the shell. In either case, the ability to arm the individual devices at any time before they are placed in service allows for their transportation and storage at any temperature. In the unarmed configuration there is no need to keep the devices below or above a specific temperature (refrigerated or heated) in order to avoid premature release. Besides the freedom of maintaining the devices at ambient temperature, this concept allows the user to set the release temperature, for a given shape memory material, by controlling the amount of deformation during arming that in turn controls the $A_s$ temperature. Of course, it is understood that a minimum amount of deformation is required to create a sufficiently large recovery force to create the path through the shell wall. In addition to arming substance release devices, the arming concept can also be used to place other devices in an active or inactive state.

Figure 149:
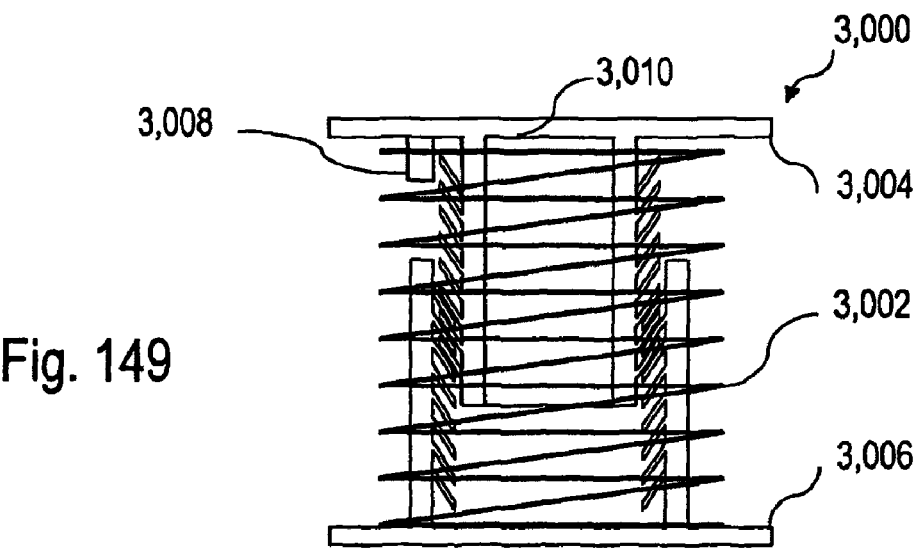
Figure 150:
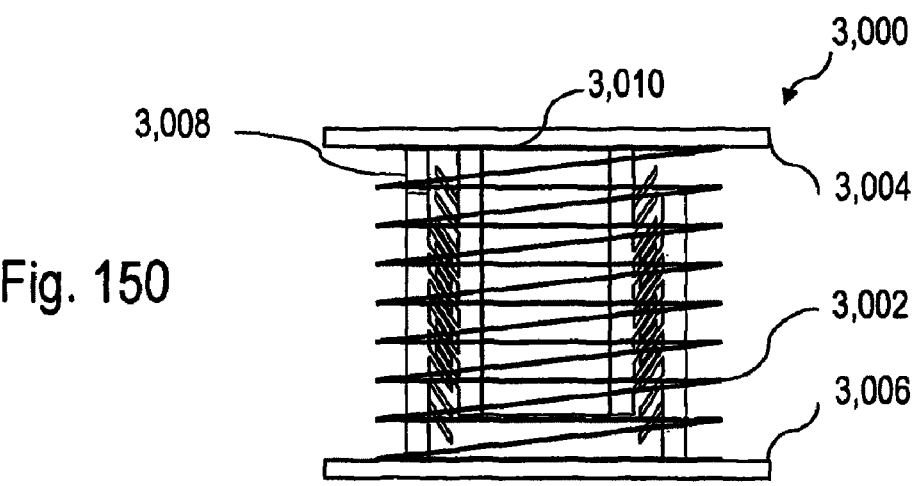
Figure 151:
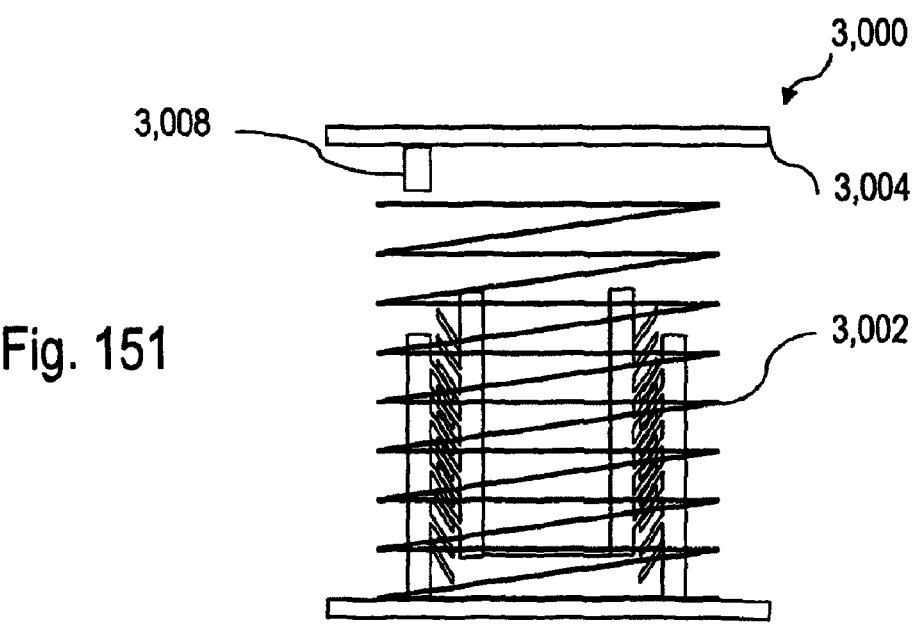

FIG. 149 illustrates a concept of an arming device 3,000 in which the shell is armed by simply pushing the two ends (top and bottom) together. The arming device 3,000 comprises a shape memory material spring 3,002 in a stress free and undeformed state, a shell 3,010 containing a substance and, an inner 3,004 and outer 3,006 frame with integral work enablers. The work enablers are similar to the ones described earlier that provide gripping and frictional means. In the present example they are configured as fins. The shape memory material spring 3,002 is allowed to expand and contract freely with fluctuations in temperature and to transform from one phase to another without undergoing shape recovery. The shell 3,010 can contain any substance. The two frames 3,004 and 3,006 are inserted inside each other and the orientation of their fins allows them to slide towards each other irreversibly. The frames are forced to overlap over a distance that will engage their fins but will not apply any stress to the shape memory material spring 3,002. In this position the device 3,000 can be maintained indefinitely at any temperature without the risk of releasing the substance prior to placement in service. Arming takes place by compressing the ends of the two frames, forcing them to slide past each other to deform the shape memory material spring as shown in FIG. 150. A stop 3,008 incorporated on the inner 3,006 frame allows for a maximum predetermined amount of deformation. Arming must take place while the shape memory material spring is in the martensitic state. Once armed, the device can be placed in service to release the substance contained in the shell 3,010 when the shape memory material spring undergoes shape recovery with rising temperature. Due to the interlocking nature of the fins, the force generated during shape recovery is insufficient to separate them. It forces the inner frame that forms part of the shell to fail structurally and create a path through the shell wall to release the substance as shown in FIG. 151. The path may be created in a predetermined separation joint, a weakened location or where the stresses attain their maximum value. Design means such as separation joints, material strength and reduced cross sections can be utilized to direct the path creation to a specific location. In addition, the path may be created by converting a shell to a permeable one by either stretching or unfolding, in which case, there is no need for the shell to fracture or separate. The frames can have any general shape that will allow them to slide past each other, such as round or square telescoping tubular shapes, or a multi post type structure.

Figure 152:
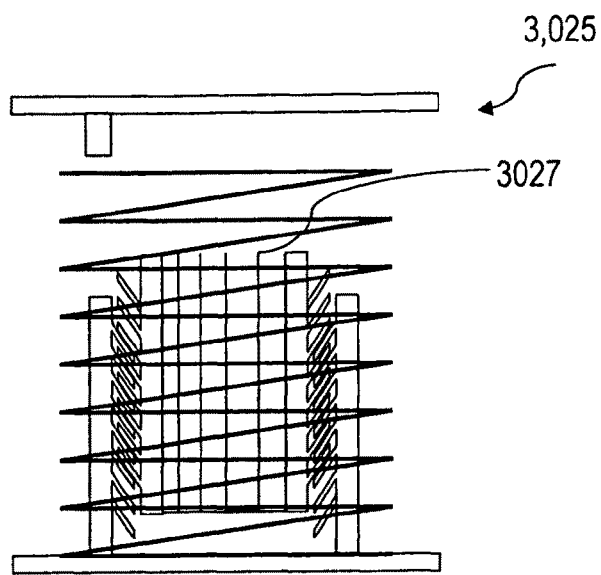
Figure 153:
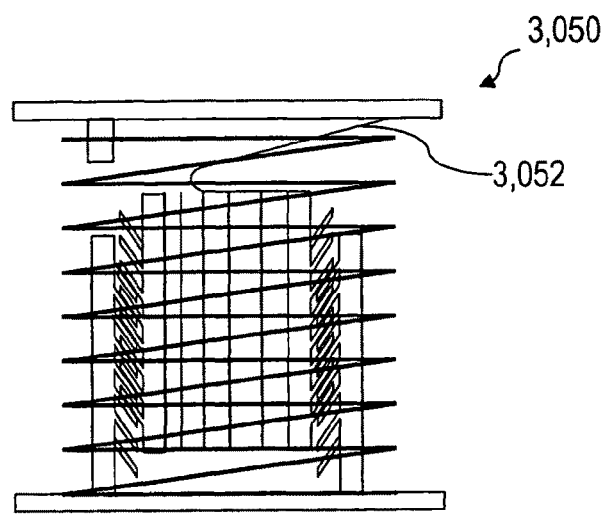
Figure 154:
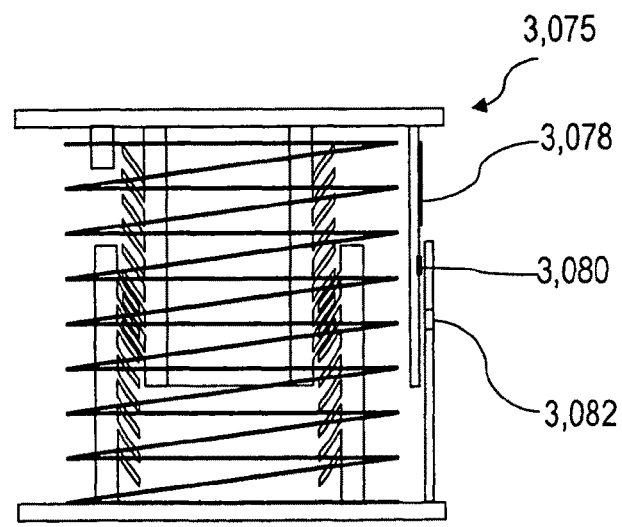

FIGS. 152 to 154 illustrate alternative embodiments of FIG. 149. FIG. 152 Illustrates an arming device 3,025 with multiple shells 3,027 arranged parallel to each other. The shells release their substances simultaneously upon activation of the shape memory material spring after arming. Path creation takes place instantaneously across all shells. FIG. 153 Illustrates an arming device 3,050 with multiple peelable shells. The path creation takes place by attaching the tab 3,052 of the peelable layer to the separable portion of the frame. When this portion of the frame is forced to separate and move away, it pulls the tab 3,052 with it and peels the peelable layer of the shells away to release their substances sequentially. FIG. 154 Illustrates an arming device 3,075 incorporating a witness window 3,082 in the outer frame to view a color change indicating the shape memory material has been deformed by the predetermined amount. The color change is produced when the device is compressed sufficiently for the two frames to overlap to the point that a color dot 3,084 placed on the inner frame aligns with the witness window. The witness window is useful for single temperature settings. For multiple temperature settings, a colored or graded strip indicator 3,078 can be employed. These indicators can be mounted directly on the two frames or indirectly on separate posts, as shown in FIG. 154.

Work enablers, such as fins that resemble featherboards, can be replaced with other means to restrict movement in one direction. Such means are similar to the ones used in the shape memory material activated transport devices that allow one way movement of thermally powered devices on tracks. They include ratchet gears with detents, ball detents, surface characteristics such as preferentially oriented features, one way rotating wheels and the like. These means rely primarily on mechanical locking, frictional and adhesion effects between the contact surfaces of two frames. One of the advantages of utilizing ratchet gears is that that the number of sound "clicks" produced during setting can be indicative of the temperature setting.

Figure 155:
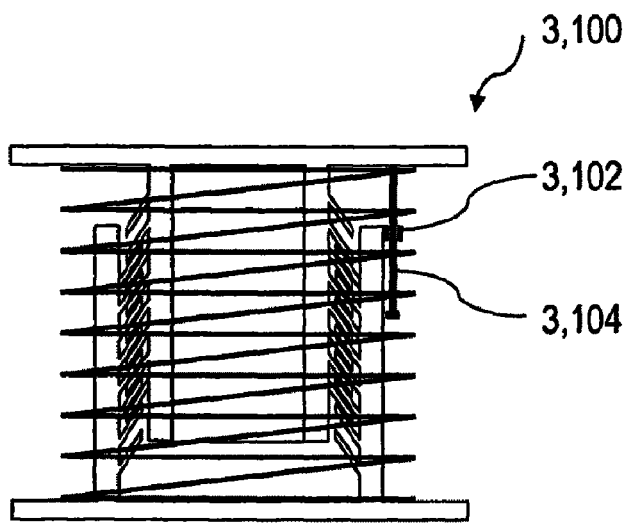
Figure 156:
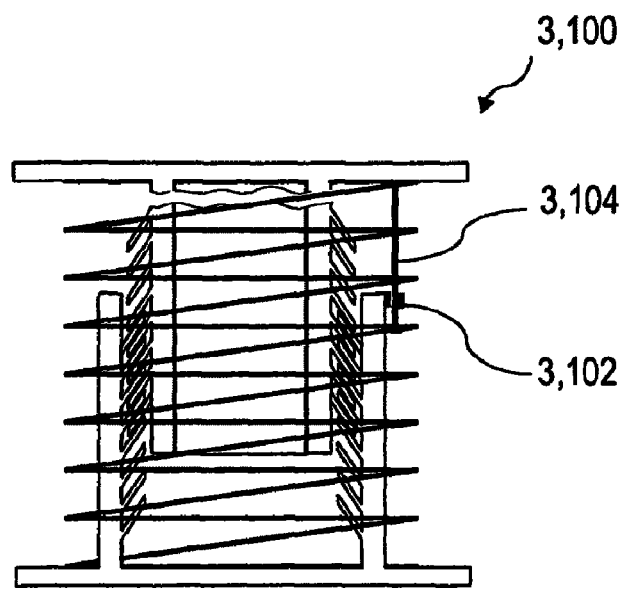

The same basic means, in a rearranged configuration, can be used to arm the device by pulling the two ends apart instead of pushing them together. This alternative concept is shown in FIG. 155 where the fins of an arming device 3,100 are oriented in the opposite direction to the fins of the device illustrated in FIG. 149. This allows the frames to move only in one direction, away from each other. In this concept, gripping and locking elements employed in the "push" type device are reversed to allow deformation of the shape memory material spring by a tensile force and prevent the reverse movement. Path creation is achieved by the compressive stress applied to the frames and to the shell that is generated during the shape recovery process. The substance can be released by any of the modes presented earlier such as fracturing of the shell, conversion of its walls to a permeable walls, or removal of a peelable layer. In the example shown in FIG. 156, the path is created by crushing the shell. Again, path creation can be directed to a specific location by employing design means similar to those mentioned above. In the pull-arming concept, the maximum amount of stretch of the shape memory material spring can be controlled by latch type restraining means. As an example, the increased diameter at the end of rod 3,104 serves as a stop once it reaches the hole of the restraining element 3,102.

Figure 157:
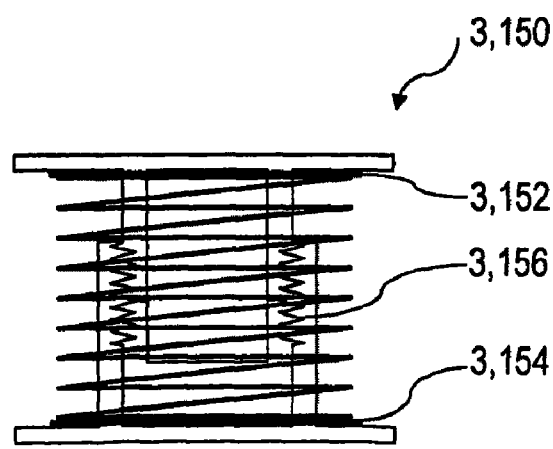

Arming can also be achieved by rotating the frames relative to each other. FIG. 157 shows an example of an arming device 3,150 where the two frames engage each other with threads 3,156. To avoid twisting the shape memory material spring due to friction generated by the ends of the frames, free rotating plates can be placed at the top end 3,152 and the bottom end 3,154 of the frames. To assure irreversibility of movement, a ratchet-detent gear can be placed between the inner and the outer frames. Again, the number of "clicks" can be indicative of the temperature setting. The rotating concept has the advantage of allowing for fine temperature setting when the frame members are engaged with fine threads. Fine threads produce small vertical movement per turn, thereby allowing for precise deformation of the shape memory material spring. As with the previous concepts, the rotating arming concept can be used to deform the shape memory material spring by stretching it or shrinking it. Rotary arming can also be accomplished with other rotary means besides threaded couplings.

The work enablers, that provide gripping and locking action, do not have to be placed on the frame sides. FIG. 158 shows an example of an arming device 3,200 in which arming takes place by pushing the ends of an inner 3,204 and an outer 3,210 frame together and locking them in position when the gripping element 3,208 is inserted into the locking element 3,206 as shown in FIG. 159. The shell is contained within the inner frame and during shape recovery of the shape memory material spring 3,202 the frame and the shell fracture and a path is created for the substance to be released as shown in FIG. 160. Instead of fracturing, the path can be created by stretching the shell to convert its walls to permeable ones, by peeling a peelable wall or by any other method that can result in path creation by the application of an external force on the shell.

FIGS. 161 and 162 show a concept for an arming device 3,250 used to create a path in a peelable shell. Arming takes place by pressing the two ends of the device. During the arming process a rod 3,252 with a gripping element is employed to engage a locking tab 3,254 that is part of the peeling layer while the shape memory material spring is deformed by compression. During the shape recovery process, the shape recovery force separates the inner frame's top and creates a path to release the substance by pulling the peeling layer 3,258 away from the shell 3,260. Instead of a single substance, multiple substances can be released if the shell is compartmentalized to smaller shells that are peeled sequentially with the same peelable layer.

There are cases, such as the ones where the frame parts are held together by friction, that do require the separation or the fracturing of the frame. In these cases, the shape memory material spring must stay deformed to the degree that shape recovery forces would be able to overcome the frictional forces and begin to move the two frames apart. For low pull forces, alternative gripping means such as fastening tape of loops and hooks can be used. In addition, other gripping means such as magnets can be used to replace the gripping element and the engaging tab. The rotating arming device can also be used with the peelable shell. In this case, the gripping element and the locking tab may be replaced with threaded parts (fastener and nut respectively) so that simultaneous engagement is achieved between the frame members and between these two parts during rotary arming. As with all the devices presented above, alternative one-way movement means and temperature indicators can be employed with peelable shells.

Mechanical arming can be achieved manually using finger pressure, hand tools such as pliers or automatically by a machine such as a press. The first two methods offer the advantage that the user can arm the devices in the field without the need of automated machines. The third method offers the advantage that devices can be armed individually or in groups and it is mostly conducive to mass arming. In all methods, arming takes place with a single action such as push, pull or rotation.

The basic concept of arming, can also be used as a force release device. FIGS. 163 and 164 show a force release device 3,300 prior to and after releasing a tensile force, respectively. This device is similar to device 3,000, except without the shell, as illustrated in FIG. 149. In the armed configuration, the device is capable of withstanding a tensile force, shown with arrows in FIGS. 163 and 164, of a given magnitude. During shape recovery, the shape memory material spring expands and generates a tensile shape recovery force internal to the device. The shape recovery force together with the externally applied force is capable of separating the device at a predetermined location and releasing the externally applied force. In essence this device acts as a mechanical fuse. By arming the device to different levels i.e. deforming the shape memory material spring by different amounts, the shape recovery force can be varied thereby allowing for release to take place at different magnitudes of applied forces. However, the amount of deformation influences the release temperature and, as such, the device becomes a temperature dependent force release device. The same concept used to release a tensile force can also be used to release a compressive force by simply reversing the orientation of the fins. Force release mechanisms as presented herein are useful for many purposes: (1) Create a path by impact to release a substance. The force release mechanisms can be incorporated in mechanisms such as those illustrated in FIGS. 80-83 for instantaneous release of a substance. (2) Improve the temperature release accuracy by controlling the amount of shape memory material deformation in the martensitic state for each individual device, thereby removing the uncertainties associated with chemistry inconsistency and processing variables. (3) Create the path to release the substance at a single temperature instead of a slowly developing force with increased temperature. In addition to mechanical fuses, the same devices can be used to activate or deactivate other devices at a predetermined temperature once they are armed. This is accomplished by utilizing the displacement and the associated force of separation to push, pull or turn a switch or to engage or disengage two mating parts such as of an electrical connector.

An alternative temperature dependent force release device 3,350, with enhanced capabilities, is shown in FIG. 165. This device 3,350 utilizes the thermally driven track device to release a force. The tensile force to be released is applied to thermally powered device 3,352, whose forward end advances on the track 3,354 during one half of the temperature cycle when the shape memory material spring expands. During the second half of the temperature cycle, the shape memory material spring contracts with the aid of the bias spring and the aft end of the thermally powered device 3,352 attempts to advance forward. The degree of advancement depends on the magnitude of the applied force. If the sum of the applied force and the reverse recovery force, as determined by the shape memory material and the bias springs, do not exceed the load carrying capability of the device, the aft end will move forward. However, if the load carrying capability of the device is exceeded the track will separate in a predetermined, structurally weakened, location and release the applied force. One of the advantages of this device is its capability to act as a thermally activated turnbuckle to link two objects together with a force and increase the magnitude of the force with temperature cycling until a maximum safe value is reached, at which point the force is released. A compressive force can also be released by simply reversing the orientation of the fins.

Arming examples so far have demonstrated the ability to arm a device by a single action that consists of the application of a tensile or compressive force or torque resulting in relative linear or rotary motion between parts of the device. FIG. 166 illustrates an embodiment of an arming device 3,400 in which the two parts of the frame 3,404 are pivoted at one end while the other ends are free to rotate about the pivot. One part of the frame holds the shell 3,408 that has a tab with a locking element 3,410 attached to it while the other part has a gripping element 3,406 attached to it. A shape memory material spring 3,402 is attached to both parts of the frame that can be deformed when the two parts are rotated towards each other. If the pressing continues, the two parts of the frame 3,404 lock together when the gripping element 3,406 is inserted in the locking element 3,410. When the shape memory material spring is compressed in the martensitic state, the device is armed and ready to release the substance contained in the shell when the shape memory material spring 3,402 is heated and undergoes shape recovery. During shape recovery, the shape memory material spring expands, forces the frame parts to counter rotate about the pivot, and creates a path to release the substance. Release takes place as the gripping element 3,406 pulls the tab with the locking element 3,410 and applies a force to the shell. This force results in the path creation by fracturing the shell, tearing it, peeling it, converting it into one with permeable walls and the like.

Single action arming is not limited to the methods of compression, tension and rotation. Other methods easily adaptable by the user of the device can be employed. In all cases, the objective is to deform the shape memory material during the arming process while it is in the martensitic state. One of these methods is to reposition the shell in the device at the time when the service life is to begin and at the same time deform the shape memory material spring in the martensitic state by a single action. The ability to reposition the shell at any time has several advantages: (1) Eliminates the need to transport and store the device at a safe temperature either by refrigeration or heating. (2) Permits the interchange of devices and shells. (3) Makes the device reusable. The third item is achieved by re-deforming the shape memory material at the martensitic state during the re-arming process. Re-arming is adaptable by many of the concepts described herein. FIG. 167 shows a single action arming device 3,450 where pressing on a shell 3,456 repositions it in the device and deforms the shape memory material spring 3,452 by bending it over a mandrel 3,454. FIG. 168 shows the shell in the new position after arming. The shell can be held in place securely by such means as adhesives pre-placed on the bottom of the device, interference fit, or frictional means 3,458. The shell is held in place prior to arming by similar means. In addition, a seal 3,460 that breaks during the arming process can be incorporated to assure the integrity of the device. The shape memory material spring in this case is either in a wire or strip form that is deformed at the martensitic state during the insertion of the shell. During shape recovery, the shape memory material spring straightens out and creates a path through the wall of the shell by puncturing it, as shown in FIG.

169, to release the substance. By varying the radius of the forming tool, the amount of deformation and in essence the $A_s$ temperature, can be varied.

An arming concept utilizing a deformable shell with the shape memory material inside the shell is shown in FIG. 170. In this concept a device 3,470 comprises a shape memory material spring 3,472 in the form of a wire or strip located inside a deformable shell 3,474. One end of the shell is fixed while the other one is free and contains frictional means 3,476 consisting of surface features such as fins or knurling marks that allow it to bend in one direction only and lock in position when it is rotated around an arc 3,480 containing similar frictional means 3,478. The different types of frictional means presented elsewhere are applicable in this case also. Prior to deformation, both the shell and the shape memory material spring have a straight shape and both are deformed simultaneously while in the martensitic state by a single action arming process of bending. The shell is restrained from moving back by the frictional means 3,476 and 3,478 as shown in FIG. 171. During shape recovery upon heating, the shape memory material spring attempts to recover its shape, while the shell is locked in place, and in the process creates a path through the shell wall by puncturing it from the inside to release the substance as shown in FIG. 172.

An alternative arming concept that utilizes a device 3,500 with a foldable shell 3,504 and a shape memory material spring 3,502 located inside the shell is shown in FIG. 173. The shell is prevented from expanding by the guide rods, but it is allowed to shrink when compressed. FIG. 174 shows the device 3,500 in the armed configuration. Arming of the foldable shell 3,504 is performed by compressing the shell and the shape memory material spring 3,502 simultaneously. Part of the shell may contain a compressible fluid to allow for volume reduction during arming. During compression, the ends of the folds are locked to prevent reversal of the deformation. A temperature indicator can be installed on the outside to indicate the release temperature based on the induced amount of deformation. During shape recovery, the shape memory material spring 3,502 expands, but the shell 3,504 is restrained from complying and the shape recovery force creates a path through the shell walls to release the substance. The resulting path can be a fracture in the shell as shown in FIG. 175, or conversion of the end of the shell to a permeable one by stretching. An alternative arming concept for the foldable shell is to place the shape memory material spring outside of the shell such that the two are in series.

The thermally powered device can be armed by a single action to become active with temperature cycling of the shape memory material spring in similar manner as the rest of the devices as shown in FIG. 176. This figure shows a thermally powered device 3,550 comprising a gripping element 3,552 and a locking element 3,554 that are incorporated in the variable length body 3,556 and the bias spring 3,558, respectively. One end of the bias spring 3,558 is attached to the one end of the variable length body while the other end remains free. The shape memory material spring 3,560, housed inside the variable length body, is attached to both ends of the body. In the unarmed state, the shape memory material spring is longer than the bias spring. During arming, the ends of the device are compressed along with the shape memory material spring 3,560. During this process, the gripping element 3,552 is inserted into the locking 3,554 element, both elements are locked together, and the free end of the bias spring becomes permanently attached to the end of the variable length body.

The thermally driven track device can also be armed by a single action to become active with temperature cycling. In this case, the beginning end of the track 3,584 of the thermally driven track device 3,580, shown in FIG. 177, contains no work enablers or frictional means. The thermally powered device 3,582 in this location expands and contacts with temperature cycling of the shape memory material spring but there is no traction to allow it to advance forward. Arming takes place by simple pushing the thermally powered device 3,582 to engage the fins of the track 3,580 a shown in FIG. 178 and begin the forward advancement. This method can also be used at the other end of the track when the travel of the thermally powered device is completed. In order to avoid having the thermally powered device apply a force to the end of the track or come out of the track if no barrier exists, elimination of a segment of work enablers or frictional means from the end of the track will keep the thermally powered device inside the track with no traction and unable to move out. This is a de-arming process that basically renders the device inactive.

A shape memory material based substance release device with a bias spring has the ability to produce a displacement during temperature rise from $A_s$ to $A_f$ and recover it with its from $M_s$ to $M_f$. Depending on the type of shell, this displacement and the associated constrained force can be used to create a path (a) with the temperature of the shape memory material spring either increasing or decreasing or (b) with the temperature increasing and close it with the temperature decreasing or vice versa. FIG. 179 illustrates an arming device 3,600 comprising a shape memory material spring 3,602 and a bias spring 3,604 with a restraining pin 3,606 holding the bias spring in a compressed state while the shape memory material spring is in the undeformed state. The device 3,600 is armed by a single action, shown in FIG. 180, by removing the restraining pin 3,606 while the shape memory material spring 3,602 is in the martensitic state. Upon removal of the pin, the bias spring expands and deforms the shape memory material spring an amount "x" until both springs come to equilibrium. During shape recovery, the shape memory material spring expands, compresses the bias spring and produces a displacement "y", shown in FIG. 181. During cooling from the austenitic to martensitic state, the resistive force of the shape memory material spring decreases and the bias spring is able to compress it an amount "−y". When the displacement "y" is constrained, a force is produced that can be utilized to open either a permanent path in a shell to release the substance contained in it or to open and close a path with temperature cycling for a repeated release. The two springs can be placed either in series or parallel to each other. Alternatively, the restraining pin 3,606 can be pushed in, or it can be replaced by a mechanical switch. This device is adaptable to many types of single or multiple release shells and can incorporate more than one shell as shown in FIG. 78. Advantages of this device include ease of arming and prevention of tampering, as the pin can not be re-inserted once the bias spring has been released.

Figure 182:
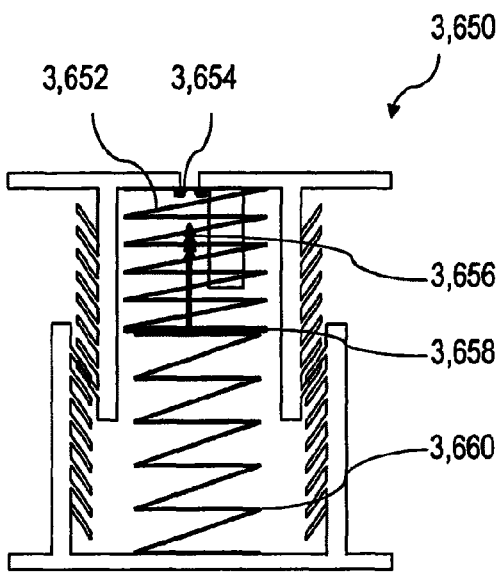
Figure 183:
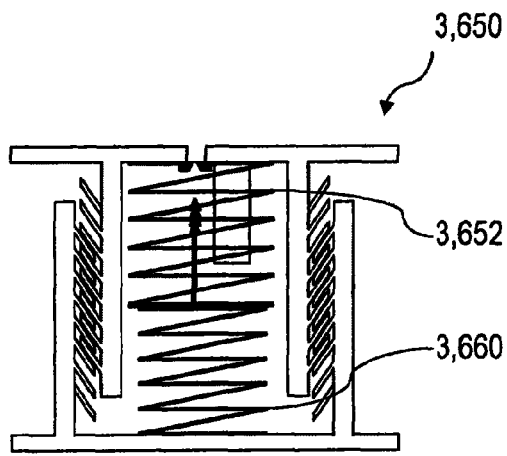
Figure 184:
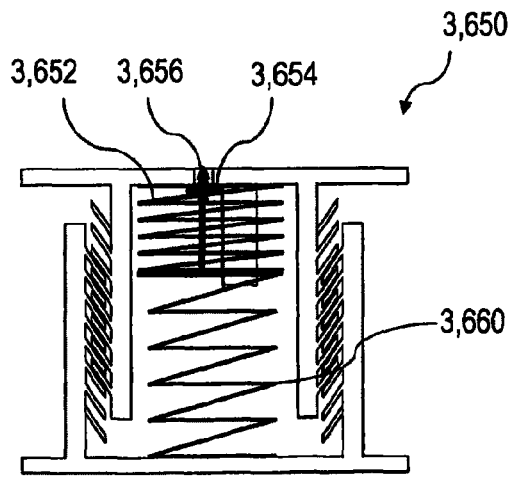
Figure 185:
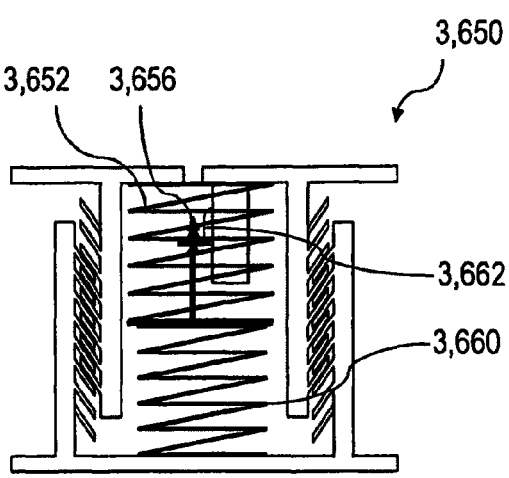

An alternative arming concept for a device that releases a substance with the fall of the temperature of the shape memory material spring is illustrated in FIG. 182. In this concept the device 3,650 is armed by a single action of pressing the two ends together, similar to the device illustrated in FIG. 149. The device 3,650 comprises a shape memory material spring 3,660 and a bias spring 3,652 in series, with an interface plate 3,658 between them. A gripping element 3,656 mounted on the interface plate 3,658 engages a locking element 3,654 mounted on the inside surface of the inner frame during the arming process. In this process the shape memory material spring 3,660 is compressed, as shown in FIG. 183, while in the martensitic state. With a rise in temperature the shape memory material spring 3,660 undergoes transformation, expands, compresses the bias spring 3,652 and engages the gripping 3,656 and locking 3,654 elements together, FIG. 184. With a fall in temperature the shape memory material spring 3,660 undergoes reverse transformation and shrinks as the bias spring 3,652 expands. During this process the interface plate 3,658 that holds the gripping element 3,656 withdraws and pulls the locking element 3,654 along with it. The locking element 3,654 is attached to the peelable layer 3,662 of the shell and peels it away, as shown in FIG. 185, creating the path to release the substance.

The single action arming concept is not limited to manual or mechanical arming. It can be extended to other single action methods such as hydraulic, pneumatic, electric, and magnetic. FIG. 186 illustrates a hydraulic arming device 3,700 that utilizes a flexible liquid fluid reservoir 3,710 to deform a shape memory material spring 3,708 in the martensitic state. This is accomplished by pressing on the reservoir and forcing the fluid though a one way outward flow valve 3,714 into a cylinder 3,704 through a connecting tube 3,718. The fluid pressure forces a piston 3,706, that is configured with a locking element on its front end, to move forward. As the piston 3,706 moves forward, it stretches the shape memory material spring 3,708 that is attached to its back end. This movement stretches the shape memory material spring and forces the locking element to engage the gripping element 3,720 attached to the tab 3,702 of the peelable shell. The device 3,700 in the armed position is shown in FIG. 187. During shape recovery, the shape memory material spring contracts, draws the piston with it and forces the fluid back into the reservoir through a one way inward flow valve 3,712 connected to the cylinder with a tube 3,716 and creates the path to release the substance by peeling the peelable layer of the shell. The device 3,700 with the path created is shown in FIG. 188.

The gripping process can produce an auditory signal (similar to a snapping action) that would be indicative of the completion of the arming process and can be utilized as a verification of the engagement. The number of sounds ("clicks" or "snaps") can be indicative of the degree of shape memory material spring deformation and the release temperature setting. This type of gripping verification applies to all mechanisms utilizing such engagement grips. Other advantages of this arming process include: (1) Faster activation in response to a changing outside temperature as the fluid surrounding the shape memory material spring acts as a heat transfer medium. (2) The tubes connecting the device with the reservoir can be of any length such that arming can take place remotely.

The hydraulically arming device can also be used to arm shells that create and close a path with temperature cycling when a bias spring is coupled with the shape memory material spring. Once the device is armed, the fluid flows in and out of the reservoir with temperature cycling as the piston oscillates back and forth. Optionally, the fluid can be drained out after the second half temperature cycle instead of returning to the reservoir. Hydraulic arming is not limited to peelable shells. Other types of shells whose path can be created with the application of an external force can be incorporated in this device.

The hydraulic arming concept of FIG. 186 can be adapted to arm a device mechanically by using a flexible mechanical elements such as cable release systems to apply pressure to the piston and advance it to engage the gripping element. In addition the cable may, upon completion of expanding the shape memory material, engage it with a bias spring to allow the device to release a substance repeatedly with temperature cycling after it is armed. As with the hydraulic arming, the cable release constitutes a single action arming process.

Instead of hydraulic arming, the same device can be armed pneumatically. A gas, like air, can be used for this process. The gas can be supplied under pressure by a reservoir or it can be pumped atmospheric air. Advantages of gas arming are that the reservoir used for hydraulic arming can become a gas reservoir or it can be replaced with a manually operated air pump. In either case, the gas does not have to be collected back during shape recovery.

FIG. 189 illustrates an alternative arming device 3,750 that utilizes vacuum for the arming process. This device 3,750 comprises a mechanically arming device 3,752 similar to the one illustrated in FIG. 149 whose inner and outer frames constitute telescoping tubes and a housing 3,754 sealed around the bottom of the outer frame that contains an opening. Arming takes place by pulling vacuum through the opening of the bottom of the outer frame. During this process, a pressure differential is maintained between the volume defined by the space between the exterior of the device 3,752 and the interior of the housing 3,754, and the volume defined by the interior space of the device 3,752. This pressure differential forces the inner frame of the device 3,752 to slide down, compress the shape memory material spring and arm the device. The two frames of the device 3,752 are engaged with fins on the inner side and surface roughness on the outer side to aid the development of the differential pressure. The advantage of this concept is the ability to arm multiple units by single action, in their storage or transportation containers, by pulling vacuum directly through the containers. For individual arming, the housing can be eliminated and vacuum can be pulled from the opening of the bottom of the outer frame. In this case, the arming differential pressure exists between ambient atmosphere and the inner volume of the device.

In addition to the methods mentioned above, a magnetic force can also be utilized to arm the device 3,800 by a single action as illustrated in FIG. 190. The device 3,800 is similar to the one illustrated in FIG. 149 with magnetic material 3,802 attached to the bottom of the inner frame such that when the bottom of the device is in close proximity to a magnet, the attractive magnetic force pulls the upper frame downward and arms the device. The magnetic material can be incorporated in the device by several methods such as separate parts attached to it, plated on its components and the like. For mass arming, a large magnetic table can be used to arm the units inside their storage or transportation containers provided the units are properly oriented and the container construction materials do not interfere with the magnetic forces.

Optionally, all devices can be armed by electrical energy sources. Such sources include batteries and electric power. Electric arming has the advantage that it eliminates the need for manual arming, especially in cases where either a substantial force is required or manual accessibility does not exist. For arming to take place, the electric energy must be converted to other forms of energy such as mechanical or magnetic to produce a force along with motion to deform the shape memory material spring. With the addition of microprocessors, fine motion control can be achieved that can result in increased arming precision. Single action arming with electrical energy involves a simple operation such as pushing a button. The push of a button may activate an electromagnet, such as a solenoid, to apply a force and arm one or more devices.

In addition to single action arming method, a multi-action method can be adopted to arm the devices. This method typically involves two or more sequentially and separate operations such as the bending of the shape memory material spring and its installation of it in the device. Such a concept is illustrated in FIGS. 191 to 195 where, as part of the arming process, the device is armed by coupling the shell with the shape memory material spring. In this concept the shell is in the form of a hollow straight cylindrical shape as shown in FIG. 191. The core opening of the shell is large enough to accommodate a shape memory material spring in the form of a wire or strip. The initial austenitic shape of the shape memory material is curved, FIG. 192. It is deformed to a straight shape, FIG. 193, in the martensitic state and loaded into the shell, FIG. 194. During shape recovery, the shape memory material spring goes back to the curved shape and, in the process, creates a path (single or multiple) through the shell wall to release the substance, FIG. 195. One of the advantages of this concept is the ability to mix and match shape memory material springs of various $A_s$ temperatures with shells containing different substances. In addition, the release temperature can be adjusted by deforming the shape memory material springs to various levels.

Devices incorporating the arming concept can become reusable. For devices whose path creation is permanent, a new shell must be inserted after each release. Reuse of the device provides the advantage of having to replace only the shell or its contents and avoids the expense of using a new device each time.

Besides the spring presented herein, other springs configurations can be used to arm the device and create a path through the shell wall. "ASME Y14.13M (ANSI Y14.13M-1981) Mechanical Spring Representation" presents springs that can be used for this purpose. Any shape memory material of any configuration that can produce work during temperature change is capable of being used as an activator to create a path though a shell wall.

The release accuracy of the devices can be improved by fine-tuning the arming process. This might be necessary due to of the large influence of chemical composition and processing parameters on the shape recovery characteristics of the shape memory materials, especially the nickel-titanium based alloys. Major influencing processing parameters include cold work and heat treating. Shape recovery characteristics include transformation temperatures and shape recovery forces. Fine-tuning involves certain adjustments that result in a consistent path creation temperature with the minimum required force within the same lot or different lots of materials. It also allows for a "dial-in" path creation temperature for an individual device. Fine-tuning is accomplished by the methods described herein but it is not limited to these methods.

The first fine tuning method is the arming process itself. It controls the shape memory material spring deformation, which in turn controls the relative position of the $A_s$ to $A_f$ curve, and, in general, the hysteresis curve with respect to temperature. The greater the induced deformation, the greater the shift of the curve to higher temperatures, resulting in increased release temperatures. Typically, once deformation exceeds a certain level, the width of the hysteresis begins to expand, usually by shifting the $A_s$ to $A_f$ portion of the curve to higher temperatures. With this method, inconsistencies in the shape memory material behavior can be minimized among the different devices. Further, the shape recovery forces, required to create the path, increase with deformation but tend to level off above a certain level that is of the order of 1.5% strain and begin to slowly decrease above 8%. This way, deformation above a minimum level produces consistent path creation forces while shifting the release temperature to higher levels. However, the variation of the shape recovery force is not important as long as the minimum force required to create the path and release the substance is generated.

Figures 196, 197:
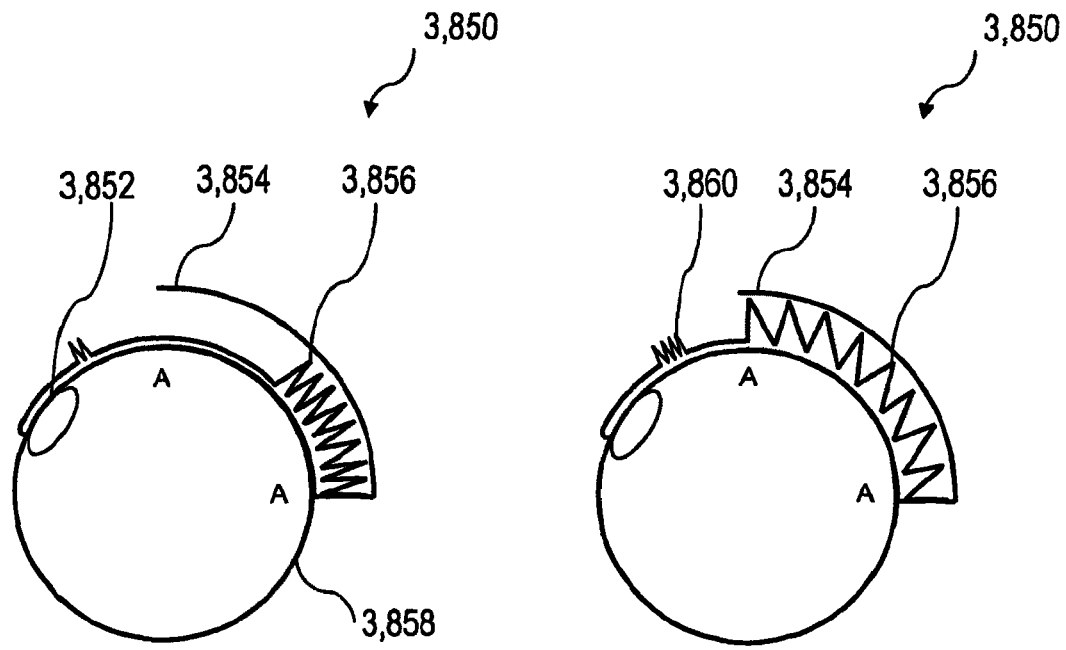
Figures 198, 199:
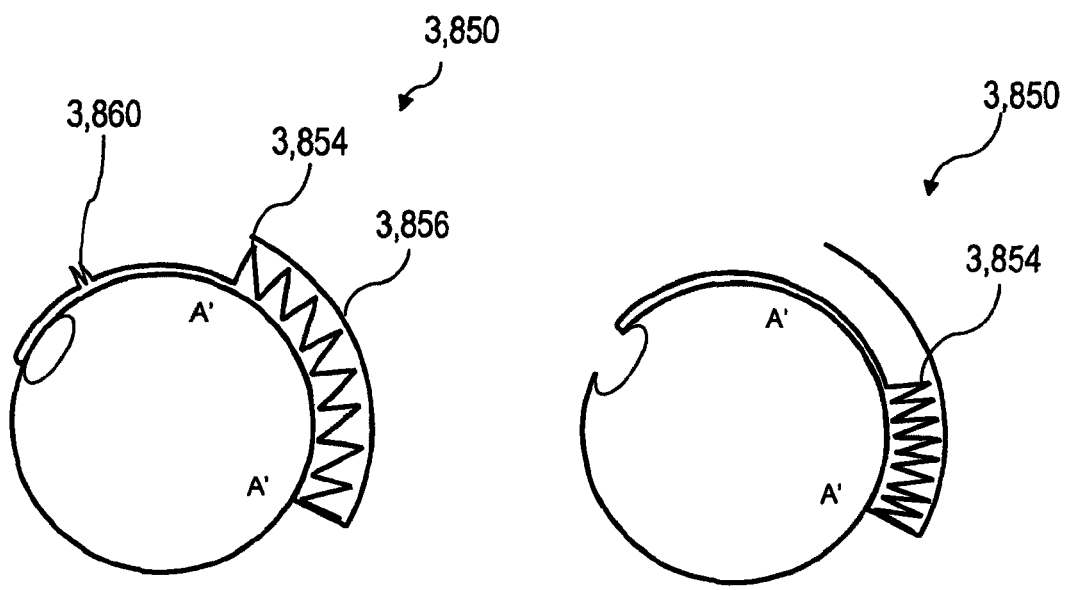

The second fine tuning method is the control of the temperature above $A_s$ at which the shape recovery force begins to develop. Ignoring compliance factors that tend to be device specific, this temperature is controlled by the gap or the slack allowed between the deformed shape memory material spring and the shell. This can be the gap between the shape memory material spring and the shell in the case that path creation takes place by expansion of the shape memory material spring, or the extra tab length allowed on a peelable shell. FIG. 196 shows an example of device 3,850 in the unarmed state with a peelable shell 3,852 mounted on a round substrate 3,858 and a shape memory material spring 3,856 inside a housing 3,854 that is capable of rotating in one direction along the circumference of the substrate via a ratchet mechanism (not shown). FIG. 197 shows the device 3,850 in the armed state with the shape memory material spring 3,856 in the martensitic state. Arming can take place with any of the methods presented in this document. Arming results in expansion of the shape memory material spring 3,856 and increases the slack that exists in the length of the tab 3,860. Fine tuning involves the rotation of the housing assembly, FIG. 198, from position A-A to A'-A' such that a calculated amount of extra tab 3,860 length remains behind. Once shape recovery begins, the shape memory material spring will begin to contract but will not exert a force on the shell until all the slack is taken up and the tab is snug. It is at this temperature that the shape recovery force will begin to develop and start the path creation process and release of the substance, FIG. 199. While the first method controls the position of the transformation temperature curve, the second method controls the temperature at which release takes place within the transformation curve. The sequence of the two methods is interchangeable.

An alternative fine tuning method consists of a combination of the first and second method. This involves the adjustment of both the amount deformation induced in the shape memory material and the length of the deformed section. It is applicable to devices, similar to the ones illustrated in FIGS. 4 and 14, where a shape memory material hook is used to restrain a non-shape memory material containing stored mechanical energy. Fine tuning of the release temperature is achieved by varying the bend radius of the hook of the shape memory material spring and/or the arc length of the hook. Another alternative method, applicable to the force limited release systems similar to the one illustrated in FIG. 88, consists of varying either the bias angle of the restraining non-shape memory material leaf spring and/or its length. A large angle requires larger recovery forces for release and thereby higher release temperatures. Also, a longer length, results in higher release temperatures.

Release of Substances

All devices presented herein are capable of releasing substances that can stimulate the senses; vision, smell, taste, touch and hearing or be undetected by the senses. Applications for release of visible substances was described earlier under temperature indicators. Applications for release of substances that stimulate the rest of the senses are described in this section. Typically, any released substance may be detected by more than one sense and release of a single substance may effectively serve multiple purposes.

Any of the devices described herein are capable of releasing a substance to produce an odor. This odorous substance can be of any type, from objectionable to fragrant. When used in temperature warning devices, the odor may be objectionable to indicate that a safe temperature limit has been exceeded. The device may release the odorous substance directly onto the product that it is protecting. The product may be a type of food such as ground meat that has been exposed to an unsafe temperature. Release of the substance effectively transfers the source of the odor to the product and renders it unusable. Alternatively, the substance can be released into a reservoir. Release of the substance can also take place when a sensor, such as a biological one, detects increased or undesirable microbe activity and commands the release of the odorous substance. In this case, activation requires an external heat source such as a battery to provide the necessary heat to activate the shape memory material. When the odorous substance is released on a product, olfaction based devices not only act as warning devices, they also act as decision makers and inspection devices determining product acceptability and assuring that a rejected product can not be used. When released into a reservoir, the wall of the reservoir must be sufficiently permeable to allow the volatile odor compounds to permeate through and be released to the surroundings. The release rate can be controlled through the permeability and physicochemical properties of the reservoir wall in relation to the properties of the substance. In releasing the substance into the reservoir, the osmotic principle can be used to restrict the flow direction across a surrounding membrane and avoid dilution of the substance inside the shell. Optionally, the substance may be combined with another substance in the reservoir to produce a new odor. If the release rate of the substance into the reservoir is continuous, the type and strength of released odor will change with time due to continuous change in the mix ratio of the two substances.

The release rate of the odor can be controlled either by the permeability of the reservoir walls or the substance can be contained in a permeable or semi-permeable membrane within the shell, such that when the path is created through the shell wall, the substance, and in essence the odor, is released through the membrane. Further, the substance can be pressurized in the shell to provide additional means for release rate control. Use of time dependent and time-temperature dependent release devices to release odor-producing substances enhances the capabilities of the olfactory devices. The release can be integrated once a predetermined temperature is exceeded such that the odor changes in strength and type with either time alone or time and temperature. The features of vision and olfaction based temperature warning devices can be combined to produce one device that would provide a dual indication, a color change and odor. This is achieved by the release of an odorous substance that is also a dye. The reservoir to which such a substance is released must have a transparent window for the color detection and part of its wall must be sufficiently permeable to allow the odorant's volatile compounds to be released to the environment. Control of the permeability and the release area of the wall provide more degrees of freedom to control the release rate of the odor.

Temperature activated olfaction based devices can be used as fire alarms to provide a warning once a predetermined temperature is exceeded. In this concept, the shape memory material creates a path through the shell wall to release a substance containing strong and objectionable odorant components. The substance can be released directly into environment were the odor will be emitted to the atmosphere at a rate controlled by the properties of the substance and the volatility of the odorous compound itself.

For fire alarms, a characteristic odor can be selected such that upon detection it will be associated with the danger of a fire. When multiple shells are incorporated in one device, the path in the shells can be created sequentially with increased temperature. As more substances are being released, the type and strength of the odor can change to indicate the increased danger. These devices can be installed in buildings as wall units, in areas where there is a potential for a fire such as electrical cabinets, on the outside surface of stove hoods etc., and in the heating and air-conditioning ducts of buildings where the released odor can be distributed throughout the building by the re-circulated air. Temperature activated odorous safety devices have several advantages over conventional fire alarms. They are maintenance free as they can operate without external energy sources such a batteries. They can be placed in areas such as the kitchen because they are unaffected by humidity, steam and volatile products generated by cooking. Since they detect temperature, they can be activated and provide a warning by releasing an odor before there are any combustion products in the air. In addition to being able to replace or complement existing alarm systems, they offer warning to visually and auditory challenged people for whom present fire alarm systems may not be beneficial.

Olfaction based devices can also be used as fragrance delivery devices. In this capacity, the released odor produces a pleasant scent. The substance can be released directly to the environment, to a reservoir for mixing with another substance prior to release to the environment, to a mammalian body through a transdermal (patch) device or to an absorbent material that would further control its release to the environment. In all cases, all the devices described herein are capable of delivering the fragrance. However, when the substance is released to an enclosure such as the reservoir mentioned above, means must be provided to allow the fragrant volatile compounds to be released from the enclosure to the surroundings. Such means include permeable or semi-permeable barriers such as membranes or walls. The transdermal drug delivery devices, can be used to deliver a fragrance to a mammalian body when the body temperature exceeds a predetermined level. These devices can be designed to deliver the fragrance to both the environment and to a mammalian body simultaneously. This is achieved by converting part of the top layer of the transdermal device into a permeable or semi-permeable wall. In this case, upon activation of the shape memory material the fragrance is released into a reservoir prior to delivery. If desired, more than one release device can be incorporated in one patch that would either extend the temperature release range, upwards or downwards, or complement the fragrance of the others. Alternatively, the transdermal devices can be used to release the fragrance to the environment only but use the body's heat for activation. Transdermal fragrance delivery devices have distinct advantages over manually applied fragrances such as perfumes. They can provide on-demand perfume delivery once the body temperature exceeds a predetermined level. The need for such situations arises during physical activity such as exercise and emotional changes. In addition, they can be placed strategically in the body to counter any localized sources of odor. Further, they are capable of changing the strength and type of fragrance with time or with time and temperature.

Instead of being body temperature activated, transdermal fragrance delivery devices can also be configured to be activated with changes in ambient temperature. Simply, the shape memory material is thermally isolated from the body, by being worn an a piece of clothing, such that it responds the ambient temperature fluctuations. Since ambient temperature fluctuates more than body temperature these devices are capable of producing fragrances of various types and strengths at higher frequencies as a person moves from place to place.

All the devices with their features described herein can be used as delivery systems to introduce, enhance and in general alter the taste or flavor of foods and drinks exposed above or below a predetermined temperature. These devices can be activated during cooking to release spice flavors to the food once a predetermined temperature is reached without actually releasing the spice seeds and leaves themselves. Utilizing the same principle, instead of spices the shell may contain tea leaves or coffee. The device is immersed in water while it is being heated and when the predetermined temperature is reached, the shape memory material creates the path to allow the hot water to enter the shell and extract the tea and coffee flavor. Using the reversible shell, the path is closed once the temperature drops below a predetermined level thereby stopping the extraction process to avoid extracting unpleasant flavors. For repeated usage, the devices can be modified to allow the opening and closing of the shell to insert new substances.

In addition to being used as gustation delivery systems, these devices can also be used as taste alarms to alert one that the a food product has exceeded a predetermined safe temperature. Taste can be altered by directly releasing a substance that may be safe for consumption but renders the food uneatable due to its objectionable flavor, texture or other attributes intolerable by the sense of taste. In addition, the substance in these alarms can be combined with odor generating substances and or dyes to provide a double or triple alarm. Food and drink alarms that stimulate the sight and especially the smell and taste senses are useful for the general population and provide a great benefit to children whose instinct of safety is not well develop, to elderly and mentally challenged people that can not rely on visual means or slightly altered taste to determine food safety.

Any shape memory material activated device based on the concepts presented herein is capable of releasing substances that can be perceived by the sense of touch. Such devices, among other things, can be used as warning devices for food and pharmaceutical products. Once a predetermined temperature has been reached, the shape memory material creates a path though the shell wall to release a tactile substance that serves as an indication that the product has been exposed to an unsafe temperature. Release substances can be of any type that can be felt by touch and act as warning indicators. Preferred candidate types of substances include the ones that will drastically alter the touch feeling of the product container. Candidates include substances such as adhesives that will produce a sticky feeling, greases that will produce a slippery feeling. The released substance, in addition to being tactile, may contain ingredients to provide visual, olfaction and gustation indications.

In all substance release device concepts presented herein, auditory means can be incorporated to generate an acoustic signal upon release of the substance. This feature complements the stimulation of the senses used to detect the release of the substance such as vision, smell, taste and touch. This feature is incorporated by utilizing stored mechanical energy to release the substance. With this concept, the shape memory material releases an elastically deformed spring whose stored mechanical energy is used to create the path by applying an impact force to the shell. During the path creation process, upon impact with the shell wall, a "snap" type auditory signal is produced that can be utilized as verification process. Besides the concepts in which stored mechanical energy is utilized to create the path, other devices are capable of producing an acoustic signal upon release of the substance. They include devices with brittle shells and/or shape memory materials whose shape recovery curves have a steep slope such that shape recovery takes place within a narrow temperature range. Narrow temperature ranges effectively result in the rapid generation of shape recovery forces that can produce auditory signals especially when they fracture brittle shells. Another way to produce a auditory signal upon release of a substance is to seal the contents of the shell in vacuum or to pressurize them. During the path creation process a "popping" sound will be generated, as the pressure equilibrium is achieved, indicating the initiation of the release process.

Release of sense stimulating type substances once a predetermined temperature is attained can be extended to toys that encompasses many of the perceptible substances. A doll can be made to cry or perspire once a predetermined temperature is reached. This is achieved by incorporating shape memory material activated devices to release substances that simulate sweat, tears or other bodily substances. Each substance can have its own color, smell, taste and touch feeling to resemble reality. The path creation can take place though valves resembling the tear glands in case of crying simulation or the though permeable walls in case of sweat.

Any number of substance release devices presented herein can be grouped together to perform as a system and to produce a combined effect. Devices performing collectively as a system have the capacity to produce results different and of a larger scale that no single device by itself can produce. The systems behave differently than their individual components. The release temperatures of the individual devices can be selected such that the system as a whole will produce any release profile with respect to either time, or time and temperature. The system may be designed to begin releasing at temperature "A" and finish releasing at temperature "B". However, the release rate can be kept constant within the "A"-"B" range or it can be variable. In addition, the system may be designed to release substances at more than one temperature range such that a group of devices may be activated within a temperature range of "A"-"B" and another group within a range of "C"-"D". One temperature range may encompass the other, the two ranges may overlap or they may be distanced such that there is no release between them. There is no limit to the number of devices that can participate in a group or groups to form the system. This is truly a flexible and variable scale release system. It can consist of any number of release devices, of any type, with each shell containing the same or a different substance. The substances released by an individual device upon activation and path creation may change state, such as liquid to solid, with either direct release to the surroundings or release to a reservoir first. Further, the physical distances between devices can be variable and depend only on the purpose of the system.

Variable scale release systems can be used in either indoor or odor gatherings such as theaters, concerts, sport events etc. Shape memory material activated release devices containing fragrant producing substances can be placed in inconspicuous places in the gathering area. Activation of the shape memory material materials and creation of the paths can take place with a rise or fall of the temperature. Where there is climatic control such as air-conditioning or heating, release can be programmed to coincide with special timings by increasing or decreasing the temperature. In outdoor gatherings, release will depend on changes in the outside temperature. Different fragrances or combination of fragrances can be produced in different sections of the gathering area simply by selecting the shell substances that would produce the desired fragrances. Also, different devices can be activated at different temperatures to produce different fragrances and to enhance the effectiveness of the special events. The distribution density of the devices can be adjusted to produce the optimum fragrance strength for a given space and population. By combining the release devices with microprocessors and a battery for activation, the release time can be preprogrammed.

The same concept used for the fragrance mass delivery systems can also be used to deliver pharmaceutical products such as vaccines, immunizations and in general prophylactic type drugs to large numbers of people. The people may be city dwellers, villagers or military personnel in the battlefield. Large scale drug delivery systems can be used in emergency cases such as imminent chemical or biochemical terrorist attracts where the affected population must be immunized as soon as possible or an antidote or curative drug must be delivered as soon as possible after such an attract. Besides chemical and biochemical terrorist or war disasters, the same systems can be used to deliver prophylactic drugs to large populations in other types of calamities such as infectious epidemic diseases having the potential for rapid propagation. The devices can be used to deliver drugs to large populations spread over large areas where there is no time to distribute and administer the drugs by conventional means or no distribution system exists at all.

These systems can release drugs that are in the gas, liquid or solid state but volatize and become airborne upon release. The drugs are delivered to humans primarily by the inhalation process. The shell may contain means to volatize or atomize the substance upon release to further aid the delivery process. The mass delivery drug systems offer the advantages of being able to produce slow releases over long times such that the danger of overdosing are minimized. They can be distributed at one ambient temperature and be activated at a different temperature for optimum delivery and to allow maximum exposure to affected population. The devices can be distributed by; airplane, launch rockets or other remote launch systems. The devices can be stored and transported at any temperature and for any length of time as long as the shell contents remain unaffected. They can be armed prior to distribution time i.e. upon dropping from an airplane. If there is rapid depressurization of the devices at this time, such as when they are dropped from a airplane, it can be used advantageously to arm them pneumatically upon exposure to a lower pressure environment. They can be selected to have different activation temperatures and be able to release the substance instantaneously, continuously, with changing temperature or with repeated temperature cycling.

Variable scale release systems can be used as non-lethal weapon delivery systems. The purpose of these delivery systems is to minimize or eliminate lethality, act as deterrent systems and, in general, to replace land mines. They offer a substantial improvement over land mines whose results are probabilistic in nature and are associated with long lasting effects far beyond the end of war conflicts. Their intent is to be used for such operations as warfare, riot control, containment and to deny ground. These systems are similar to the drug mass delivery systems and they are distributed by similar means. The main difference is that the shell may contain any substance that upon release may discomfort or incapacitate the recipients.

Capabilities and advantages of these delivery devices both individually and as a system include: (1) They are not restricted to a particular substance. Shells can contain any substance without affecting the device design. (2) They can be stored indefinitely at any temperature without the risk of accidental activation. Since they are maintained unarmed, there are no stressed parts to undergo stress relaxation or creep and, if shape memory material such as Nitinol is used as the activator, the material remains corrosion free. (3) The shells can be made of material that would degrade with time to release their contents. This provides and added feature to assure that there are no long term effects with these type of non-lethal delivery systems. (4) Use of multi-release device can extend the release for multiple day-night temperature cycles.

There are multiple applications for systems of substance release devices. They include release of substances to remotely sterilize, fumigate, or decontaminate an area or structure. Another application is insect repellant systems in which case the path is created below a certain temperature (typically in the evening) to release the repellant. A nearly insect free area can be created by placing several devices with path reversal in strategic locations. Path reversal is required only if the devices are expected to function daily at a given temperature.

Drug Delivery

The following is an explanation of some of the applications of the embodiments described herein for use in drug delivery systems. On demand drug delivery system applications are subdivided into four general categories as follows:

(1) A first application is a transdermal system that is activated by rising body temperature. In this application the patch is applied when fever is anticipated due to upcoming flu symptoms, a disease or a drug side effect etc. However, there is no need for the drug until the fever rises to a critical temperature. With this device, although the patch may be worn, the drug is not released until the critical temperature is reached. The advantage of this application is the elimination of orally administered drugs, elimination of temperature measurement, and the fact that the drug is used only if and when it is needed. More, background, information on transdermal systems is presented below.

(2) A second application involves transdermal systems used to deliver drugs but not activated by rising body temperature. In this case, the device must be activated with an external energy source when the need for the drug arises. For automatic activation the energy source has to be stored electrical energy (batteries) while for manual activation heat applied directly to the device, such as by a hot compress, will suffice. One example of this case is insulin delivered drugs.

(3) A third application involves implantable drug delivery systems. Again, for an automatic operation, a self-contained energy source is required. For manual operation an external heat source is required. In this case heat is conducted through the body to raise the temperature of the shape memory material and activate the device.

(4) A fourth application involves mixing of predetermined quantities of two or more drugs. This is a useful application when there is a need to mix two or more drugs without having to measure them. This need may arise from field work where it is not convenient to measure or when the shelf life of a drug is extended when mixing takes place at the time of application.

Activation Energy Sources

Various energy sources can be used to heat the shape memory material in order to undergo shape recovery. The choice of energy source depends on the particular application. For most applications, ambient thermal energy is the ideal candidate. This includes mostly temperature warning and alarm systems as well a temperature indicators. For all ambient heating applications the heating source can be substituted with others ones such as electric heating. For drug delivery applications the choices depend on the particular application. Transdermal drug delivery systems can utilize the body temperature for activation or an external source such as batteries. In the second case, a temperature sensor, other than the shape memory material, is required to detect the rise in body temperature and activate the device. When a separate temperature sensor is used, the shape memory material acts as the actuator to create the path and release the drug. For remote heating applications such as in the case of implant drug delivery devices, the primary choices are; body heat, direct application of heat, electric heating, and magnetic induction heating. Body heat can be due to fever caused by ailments or it can be due to induced fever with the objective to activate the shape memory material based implant. Direct application of heat using sources such as hot pads requires the transfer of heat through the body to reach the shape memory material. Electric heating requires stored energy sources such as batteries. Electric heating is achieved by utilizing the shape memory material as a resistor and heating it by passing electric current through it. Magnetic heating of the shape memory material is achieved by conduction from a ferromagnetic material that is heated by magnetic heat induction. All energy sources used for substance release devices can also be used for thermally powered devices, whether they are releasing a substance or not. Thermally powered devices can also be powered hydraulically, pneumatically or mechanically without the incorporation of a shape memory material activator.

For greater flexibility, a more accurate temperature activation system, and better time response, the shape memory material, coupled with a separate temperature sensor and the appropriate controls to activate the device, can be used as the means to generate the force to fracture the shell. Types of temperature sensors that can be used are: thermocouples, resistive temperature devices (RTDs and thermistors), IC temperature sensors etc. Irrespective of the sensor type, an energy source such as a battery or other energy source will be required to provide heat to the shape memory material in order to undergo the phase transformation and create a path through the shell. With this system, means must be provided to connect the shape memory material to the power source and electrically insulate it to avoid short circuits and energy leaks. One advantage of this system is the ability to have the temperature sensor and the enclosure placed in to two different locations, as long as they are connected together. The controls (microprocessor, solenoid, switch etc.) can be placed either inside the enclosure or outside. Because, in this case, the shape memory material is no longer the temperature sensor, its $A_s$ temperature has to be higher than the activation temperature of the system in order to avoid premature activation. With an electrically activated system, activation does not have to be due to local temperature. Different parameters can be used for activation. This enhances the system considerably when it is used as a drug delivery system. Sensors can be used to detect parameters such as biological activity and concentrations of different substances and to command the activation of substance release device once a predetermined parameter has been exceeded.

In many applications where the drug delivery device is implanted deep in the body such that direct heating is not applicable, magnetic induction heating offers an alternative in terms of minimizing the size of the device. In this concept, a ferromagnetic material is placed in physical contact with the shape memory material. While the ferromagnetic material is being heated by external magnetic induction, it transfers thermal energy to the shape memory material and heats it up. Once the ferromagnetic material reaches the Curie temperature, it becomes paramagnetic (nonmagnetic) and it stays at this temperature as long as the external magnetic field is applied. The concept of heating by magnetic induction is similar to the one used to treat tissue at elevated temperatures by hyperthermia or thermal therapy with the purpose of destroying cancerous tissue selectively or to necrose all cells. The Curie temperature imposes a self-limit as to how hot the material will get before it becomes paramagnetic and loses its magnetism. Magnetic induction heated materials are based on alloys such as; Co—Pd, Ni—Cu, Ni—Pd, Ni—Co, Ni—Si and magnetic stainless steels. The heating of the magnetic material and consequently of the shape memory material is controlled by the selection of magnetic material with the appropriate Curie temperature.

Physical contact between the magnetic material and the shape memory material can be achieved by methods such as physical interference, filling the space around the shape memory material with the magnetic material in a powder form, and coating the shape memory material with the magnetic material. Issues with biocompatibility of the magnetic material do not exist as long as it is placed inside the device and does not come in contact with the device's surroundings.

Insulation

To add a time delay at temperature the shape memory material and/or the enclosure can be insulated. The level of insulation will depend on the time delay desired. This feature will delay the triggering of the device until thermal equilibrium between the shape memory material and ambient is reached. The delayed trigger will be more representative of the product temperature in the case where the device is used for temperature warning. Insulation can be in the form of a jacket similar to the insulation used for electrical wires. Space can be left between the jacket and the shape memory material to be filled with thermally insulating material to further delay the shape recovery process. In no case should the insulation impede the performance of the device.

While the invention has been described in detail with reference to the preferred embodiments thereof, it will be apparent to one skilled in the art that various changes and modifications can be made and equivalents employed, without departing from the present invention.

Deformation

In the description of the preferred embodiments, for optimum performance, the shape memory material activator is deformed at a temperature in which the material is in the martensitic state. However, certain types of shape memory materials, such as the nickel-titanium based alloys, can be deformed at a higher temperature provided that the temperature at which martensite can be stress-induced is not exceeded. This is known as $M_d$ temperature. Generally, strain induced martensitic deformation results in permanent strains after shape recovery and it is not applicable to devices that require temperature cycling of the shape memory material.

While the invention has been described in detail with reference to the preferred embodiments thereof, it will be apparent to one skilled in the art that various changes and modifications can be made and equivalents employed, without departing from the present invention.

What is claimed is:

1. A temperature activated device to provide actuation, comprising:
    an activator made from a shape memory material, the shape memory material being deformable at a first temperature, then recovers its original, undeformed shape upon heating above a second, higher temperature, defining an active state of readiness of the activator, the shape memory material activator having an undeformed shape incapable of undergoing shape recovery and being normally unresponsive to temperature changes and defining a dormant state thereby maintaining the undeformed shape regardless of the temperature changes; and
    means for deforming the activator in situ by only a single irreversible action, whereby the device is transformed from the dormant state to an active state of readiness, thereby the shape memory material activator is enabled to undergo shape recovery wherein the activator responds to temperature changes and the device becomes a functioning actuator.

2. A method for arming a temperature activated device, the method comprising the steps of:
providing an activator made from a shape memory material, wherein the shape memory material deforms at a first temperature, then recovers its original, undeformed shape upon heating above a second, higher temperature, defining an active state of readiness of the activator, the shape memory material activator having an undeformed shape incapable of undergoing shape recovery and being normally unresponsive to temperature changes and defining a dormant state thereby maintaining the undeformed shape regardless of the temperature changes; and
deforming the activator in situ by only a single irreversible action, whereby the device is transformed from the dormant state to an active state of readiness, thereby the shape memory material activator is enabled to undergo shape recovery wherein the activator responds to temperature changes.

3. An extended temperature responding shape memory material device, comprising:
an initially variably deformed shape memory material element having unequally deformed locations thereby responding to different shape recovery temperatures, wherein the non-uniformly deformed locations define least deformed locations and most deformed locations, wherein the shape memory material element undergoes non-uniform shape recovery within a predetermined extended temperature range beginning from the least deformed locations and proceeding to the most deformed locations with increasing temperature.

* * * * *